US010669537B2

(12) United States Patent
Nyerges et al.

(10) Patent No.: US 10,669,537 B2
(45) Date of Patent: Jun. 2, 2020

(54) MUTAGENIZING INTRACELLULAR NUCLEIC ACIDS

(71) Applicant: BIOLOGICAL RESEARCH CENTRE, Szeged (HU)

(72) Inventors: Akos Jozsef Nyerges, Székesfehérvár (HU); Csaba Pal, Szeged (HU); Balint Csorgo, Szeged (HU); Balint Kintses, Budapest (HU)

(73) Assignee: BIOLOGICAL RESEARCH CENTRE, Szeged (HU)

( * ) Notice: Subject to any disclaimer, the term of this patent is extended or adjusted under 35 U.S.C. 154(b) by 0 days.

(21) Appl. No.: 16/469,140

(22) PCT Filed: Dec. 13, 2017

(86) PCT No.: PCT/EP2017/082574
§ 371 (c)(1),
(2) Date: Jun. 12, 2019

(87) PCT Pub. No.: WO2018/108987
PCT Pub. Date: Jun. 21, 2018

(65) Prior Publication Data
US 2020/0017850 A1 Jan. 16, 2020

(30) Foreign Application Priority Data

Dec. 14, 2016 (EP) .................... 16204081

(51) Int. Cl.
C12N 15/10 (2006.01)
C12N 15/90 (2006.01)
(Continued)

(52) U.S. Cl.
CPC .......... *C12N 15/1024* (2013.01); *A61K 48/00* (2013.01); *C12N 15/1031* (2013.01);
(Continued)

(58) Field of Classification Search
CPC ............ C12N 15/1024; C12N 15/1082; C12N 15/902; C12N 15/1031; C40B 40/02; A61K 48/00
See application file for complete search history.

(56) References Cited

U.S. PATENT DOCUMENTS 6,391,640 B1    5/2002  Minshull et al.

FOREIGN PATENT DOCUMENTS

WO    0042561 A2    7/2000
WO    0168803 A2    9/2001
(Continued)

OTHER PUBLICATIONS

Amiram M. et al. "Evolution of translation machinery in recoded bacteria enables mulit-site incorporation of nonstandard amino acids", Nature Biotechnology, vol. 33, No. 12, pp. 1272-1279 (Dec. 2015).
(Continued)

*Primary Examiner* — Jeremy C Flinders
(74) *Attorney, Agent, or Firm* — Loza & Loza, LLP; Michael F. Fedrick

(57) ABSTRACT

A method of in vivo mutagenesis of a preselected target region (PTR) of an intracellular DNA within a cell culture, which PTR comprises at least one sequence of interest (SOI) which is at least 60 nucleobases long, the method comprising: a) providing a pool of partially overlapping single stranded DNA (ssDNA) oligonucleotides which upon alignment form a continuous sequence that is complementary to the SOI, wherein the pool contains a diversity of mutagenizing oligonucleotides covering nucleobase mismatches at every position of said SOI and combination of said nucleobase mismatches, wherein each mutagenizing oligonucleotide is hybridizing with the PTR and comprises at least one mismatching nucleobase up to 20% mismatching nucle-
(Continued)

Figure 1:

obases, compared to the SOI; b) integrating the pool into said intracellular DNA by homologous recombination and inducing in vivo mutagenesis of the intracellular DNA through hybridizing the oligonucleotides to the PTR, thereby producing a cell library comprising a repertoire of variant cells covering point mutations at every position and combinations of said point mutations within said PTR.

26 Claims, 50 Drawing Sheets

Specification includes a Sequence Listing.

(51) Int. Cl.
C40B 40/02 (2006.01)
A61K 48/00 (2006.01)
(52) U.S. Cl.
CPC ....... *C12N 15/1082* (2013.01); *C12N 15/902* (2013.01); *C12N 15/907* (2013.01); *C40B 40/02* (2013.01)

(56) References Cited

FOREIGN PATENT DOCUMENTS

WO 0214495 A2 2/2002
WO 2014102688 A1 7/2014

OTHER PUBLICATIONS

Csörgö, B. et al. "System-Level genome editing in mircobes", Current Opinion in Microbiology, vol. 33, pp. 113-122 (2016).
Biedenbach D. J. et al. "In Vitro Activity of Gepotidacin, a Novel Triazaacenaphthylene Bacterial Topoisomerase Inhibitor, against a Broad Spectrum of Bacterial Pathogens", Antimicrobial Agents and Chemotherapy, vol. 60, No. 3, pp. 1918-1923 (2016).
Bloom J. D. et al. "In the light of directed evolution: Pathways of adaptive protein evolution", Proceedings of the National Academy of Science, vol. 106, (Supplement 1), pp. 9995-10000 (2009).
Bonde M. T. et al. "Direct Mutagenesis of Thousands of Genomic Targets Using Microarray-Derived Oligonucleotides", ACS Synthetic Biology, vol. 4, No. 1, pp. 17-22 (2014).
Coussement P. et al. "One step DNA assembly for combinatorial metabolic engineering", Metabolic Engineering, vol. 23, pp. 70-77 (2014).
Dai Z. et al. "Yeast synthetic biology for high-value metobolites", FEMS Yeast Research, vol. 15, No. 1, pp. 1-11 (2015).
Dicarlo J. E. et al. "Yeast Oligo-mediated Genome Engineering (YOGE)", ACS Synthetic Biology, vol. 2, No. 12, pp. 741-749 (2013).
Diner E. et al. "Recombineering reveals a diverse collection of ribosomal proteins L4 and L22 that confer resistance to macrolide antibiotics Journal of Molecular Biology", vol. 386, No. 2, pp. 300-315 (2009).
Farrell D. J. et al. "In Vitro Activity of Gepotidacin (GSK2140944) against Neisseria gonorrhoeae", Antimicrobial Agents and Chemotherapy, vol. 61, No. 3, e02047-16 (2017).
Farzadfard F. et al. "Genomically Encoded Analog Memory with Precise In vivo DNA Writing in Living Cell Populations", Science, vol. 346, No. 6211, pp. 1256272 (2014).
Flensburg J. et al. "Massive overproduction of dihydrofolate reductase in bacteria as a response to the use of trimethoprim", European Journal of Biochemistry, vol. 162, No. 3, pp. 473-476 (1987).
Gallagher R. et al. "Rapid editing and evolution of bacterial genomes using libraries of synthetic DNA Nature Protocols", vol. 9, No. 10, pp. 2301-2316 ( 2014).
Gao X. et al. "A flexible light-directed DNA chip synthesis gated by deprotection using solution photogenerated acids", Nucleic Acids Research, vol. 29, No. 22, pp. 4744-4750 (2001).
Hacia J.G. "Mutational analysis using oligonucleotide microarrays", J Med Genet, vol. 36, pp. 730-736 (1999).
Hermes J. D. et al. "A reliable method for random mutagenesis: the generation of mutant libraries using spiked oligodeoxyribonucleotide primers", Gene, vol. 84, No. 1, pp. 143-151 (1989).
Hooper D. C. et al. "Mechanisms of Action of and Resistance to Ciprofloxacin", The American J of Medicine, vol. 82, No. 4A, pp. 12-20 (1987).
Hooper D. C. et al. "Mechanisms of drug resistance: quinolone resistance", Annals of the New York Academy of Sciences, vol. 1354, pp. 12-31 (2015).
Houlleberghs H. et al. "Oligonucleotide-directed mutagenesis screen to identify pathogenic Lynch syndrome-associated MSH2 DNA mismatch repair gene variants", Proceedings of the National Academy of Sciences of the USA, vol. 113, No. 15, pp. 4128-4133 (2016).
Khodursky A. B. et al. "Topoisomerase IV is a target of quinolones in *Escherichia coli*", Proceedings of the National Academy of Sciences of the USA, vol. 92, No. 25, pp. 11801-11805 (1995).
Kow Y. W. "Oligonucleotide transformation of yeast reveals mismatch repair complexes to be differentially active on DNA replication strands", Proceedings of the National Academy of Sciences of the USA, vol. 104, No. 27, pp. 11352-11357 (2007).
Leproust E M. et al. "Synthesis of high-quality libraries of long (150mer) oligonucleotides by a novel depurination controlled process", Nucleic Acids Research, vol. 38, No. 8, pp. 2522-2540 (2010).
Li X. et al."Bacterial DNA polymerases participate in oligonucleotide recombination", Molecular Microbiology, vol. 88, No. 5, pp. 906-920 (2013).
McArthur Andrew G.et al. "The Comprehensive Antibiotic Resistance Database", Antimicrobial Agents and Chemothearpy, vol. 57, No. 7, pp. 3348-3357 (2013).
Moerschell R. P. et al. "Transformation of yeast with synthetic oligonucleotides", Proceedings of the National Academy of Sciences of the USA, vol. 85, No. 2, pp. 524-528 (1988).
Neuner P. et al. "Codon-based mutagenesis using dimer-phosphoramidites", Nucleic Acids Research, vol. 26, No. 5, pp. 1223-1227 (1998).
Nordwald E. M. et al. "Accelerated protein engineering for chemical biotechnology via homologous recombination", Current Opinion in Biotechnology, vol. 24, No. 6, pp. 1017-1022 (2013).
Nyerges A. et al. "Conditional DNA repair mutants enable highly precise genome engineeering", Proceedings of the National Academy of Sciences, vol. 113, No. 9, pp. 2502-2507 (2016).
Nyerges A. et al. "A highly precise and portable genome engineering method allows comparison of mutattional effects across bacterial species", Nucleic Acids Research, vol. 42, No. 8, e62 (2014).
Piddock, L. "Mechanisms of Fluoroquinolone Resistance: An Update 1994-1998", Drugs, vol. 58, No. 2, pp. 11-18 (1999).
Richardson S. M. et al. "Design of a synthetic yeast genome", Science, vol. 355, No. 6329, pp. 1040-1044 (2017).
Rios X. et al. "Stable Gene Targeting in Human Cells Using Single-Strand Oligonucleotides with Modified Bases", PLoS ONE, vol. 7, No. 5, e36697 (2012).
Savage V. J. et al. "Biological profiling of novel tricyclic inhibitors of bacterial DNA gyrase and topoisomerase IV", The Journal of Antimicrobial Chemotherapy, vol. 71, No. 7, pp. 1905-1913 (2016).
Sawitzke J. A. et al. "Probing cellular processes with oligo-mediated recombination; using knowledge gained to optimize recombineering", J Mol. Biol., 407(1), 45-59 (2011).
Sondek J. et al. "A general strategy for random insertion and substitution mutagenesis: Substoichiometric coupling of trinucleotide phosphoramidites", Proceedings of the National Academy of Sciences, vol. 89, No. 8, pp: 3581-3585 (1992).
Szamecz B. et al. "The Genomic Landscape of Compensatory Evolution", PLOS Biology, vol. 12, No. 8, e1001935 (2014).
Toprak, E. et al. "Evolutionary paths to antibiotic resistance under dynamically sustained drug stress", Nature Genetics, vol. 44, No. 1, pp. 101-105 (2011).
Vickers C. E. "The minimal genome comes of age", Nature Biotechnology, vol. 34, No. 6, pp. 623-624 (2016).

(56) References Cited

OTHER PUBLICATIONS

Wang H. H. and Church G. M. "Multiplexed Genome Engineering and Genotyping Methods: Applications for Synthetic Biology and Metabolic Engineering", In Methods in Enzymology, vol. 498, pp. 409-426 (2011).

Wang H. H. et al. "Programming cells by multiplex genome engineering and accelerated evolution", Nature, vol. 460, No. 7257, pp. 894-898 (2009).

Watson M. et al. "Directed evolution of trimethoprim resistance in *Escherichia coli*", The FEBS Journal, vol. 274, No. 10, pp. 2661-2671 (2007).

Wisell K. T. et al. "Trimethoprim and enterococci in urinary tract infections: new perspectives on an old issue", The Journal of Antimicrobial Chemotherapy, vol. 62, No. 1, pp. 35-40 (2008).

Yu D. et al. "Recombineering with overlapping single-stranded DNA oligonucleotides: Testing a recombination intermediate", Proceedings of the National Academy of Sciences, vol. 100, No. 12, pp. 7207-7212 (2003).

Written Opinion for International Patent Application No. PCT/EP2017/082574, 6 pages (dated May 3, 2018).

Extended European Search Report for Euopean Patent Application No. 16204081.0, 8 pages, dated May 8, 2017.

International Preliminary Report on Patentability for International Patent Application No. PCT/EP2017/082574, 7 pages (dated Jan. 3, 2019).

International Search Report for International Patent Application No. PCT/EP2017/082574, 6 pages (dated May 3, 2018).

PCT Notification Concerning Informal Communication with the Applicant for International Patent Application No. PCT/EP2017/082574, 3 pages (Nov. 5, 2018).

Demand under Article 31 of the Patent Cooperation Treaty Request for International Patent Application No. PCT/EP2017/082574, 8 pages (Nov. 9, 2018).

Fig. 2

| Indicator | Value (%) | Standard Deviation (SD) |
|---|---|---|
| A→N, T→N (%) | 41.6 | 2.8 |
| G→N, C→N (%) | 58.4 | 2.8 |
| A→G, T→C (%) | 14.0 | 1.3 |
| G→A, C→T (%) | 25.0 | 2.7 |
| A→T, T→A (%) | 14.8 | 1.7 |
| A→C, T→G (%) | 12.8 | 0.6 |
| G→C, C→G (%) | 13.7 | 1.3 |
| G→T, C→A (%) | 19.6 | 0.7 |

Fig. 6

| Indicator | Value (%) | Standard Deviation (SD) |
|---|---|---|
| A→N, T→N (%) | 45.6 | 2 |
| G→N, C→N (%) | 54.4 | 2 |
| AT→GC (%) | 28.7 | 1.3 |
| GC→AT (%) | 39.6 | 1.8 |
| A→G, T→C (%) | 14.7 | 1.1 |
| G→A, C→T (%) | 21.4 | 1.5 |
| A→T, T→A (%) | 16.9 | 1.6 |
| A→C, T→G (%) | 14 | 0.7 |
| G→C, C→G (%) | 14.8 | 1.5 |
| G→T, C→A (%) | 18.2 | 1 |

Figure 7:
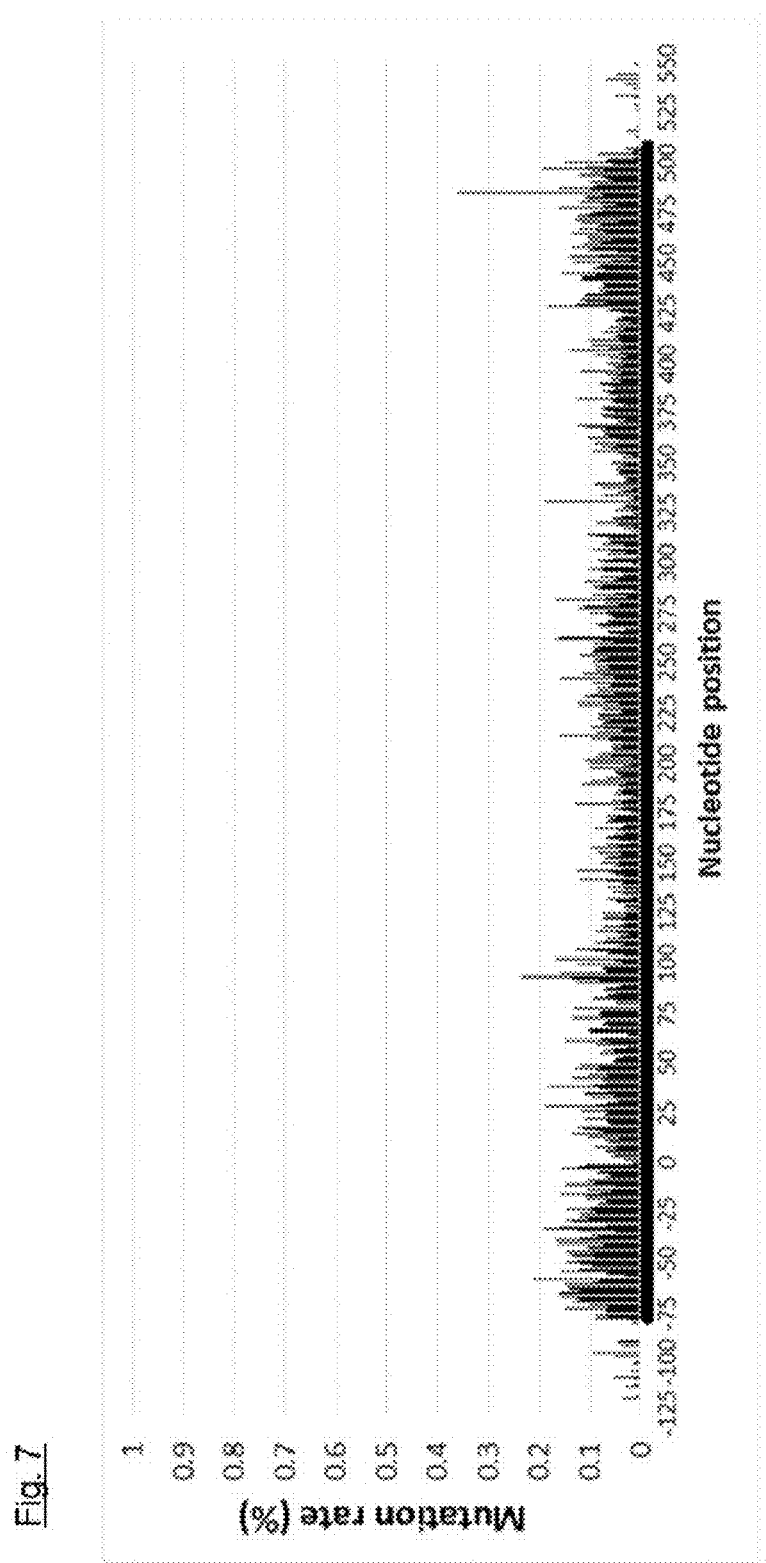

Fig. 7 continued: Table 2

| Clone | DNA mutation | Number_of_DNA_mutations | Number_of_Amino_Acid_mutations |
|---|---|---|---|
| 1 | G269A;C458G;A540T;T778A;A796C;G798C;G803T | 7 | 3 |
| 2 | G488C;C496G;G499A;C507T;G547T;G685C | 6 | 5 |
| 3 | G657A;C676T;G679A;T707C;T794C | 5 | 3 |
| 4 | C464G;T673A;C689T;G706C;A748T | 5 | 5 |
| 5 | C232T;C361A;C369A;A761C;T783A | 5 | 3 |
| 6 | C243G;A526G;A540C;T596A;C604G | 5 | 4 |
| 7 | C518A;C669T;G705A;G768C;C797A | 5 | 1 |
| 8 | G372A;G376A;G442C;C573A;A651G | 5 | 2 |
| 9 | A293G;C342A;C356T;A465T | 4 | 1 |
| 10 | C382T;C386T;G426T;A436G | 4 | 4 |
| 11 | C236T;C238T;T261A;T284A | 4 | 0 |
| 12 | A295T;C306A;A626C;G649A | 4 | 2 |
| 13 | A223G;G235T;T285A;A295C | 4 | 0 |
| 14 | C238T;G247C;T260G;G809A | 4 | 0 |
| 15 | T533A;A748T;G755T;G774C | 4 | 3 |
| 16 | T230G;G269T;A330C;A516C | 4 | 0 |
| 17 | A277C;T281C;C373A;A665C | 4 | 2 |
| 18 | C238T;T267A;T642C;C648T | 4 | 1 |
| 19 | T254A;G274C;T281C;T393A | 4 | 1 |
| 20 | G235A;C246T;T253G;T709A | 4 | 1 |
| 21 | T682G;G755T;T757A;G768C | 4 | 3 |
| 22 | C246A;C249A;T375C;C548T | 4 | 1 |
| 23 | C370G;T423A;G508C;G799A | 4 | 2 |
| 24 | C243G;G390C;C432G;G593C | 4 | 2 |
| 25 | C234T;A506C;C518T;G586C | 4 | 3 |
| 26 | T439A;G459A;G514A | 3 | 2 |
| 27 | C669T;G678T;A692T | 3 | 1 |
| 28 | C239G;G762A;T795A | 3 | 0 |
| 29 | C231T;C736A;T793G | 3 | 1 |
| 30 | T309G;G312T;C369T | 3 | 1 |
| 31 | T254A;T259C;C263A | 3 | 0 |
| 32 | T391A;A396T;T435G | 3 | 3 |
| 33 | A237C;T260G;T610A | 3 | 1 |
| 34 | A667C;C669T;T793C | 3 | 1 |
| 35 | A671G;G705C;T718G | 3 | 2 |
| 36 | C317T;T598C;G657A | 3 | 2 |
| 37 | T682G;C688A;G700C | 3 | 3 |
| 38 | A351C;A540T;A571G | 3 | 3 |
| 39 | C234T;C711T;T732C | 3 | 0 |
| 40 | T279C;A473C;A478T | 3 | 2 |
| 41 | G589A;T611G;C640G | 3 | 3 |
| 42 | T359C;A667T;T681C | 3 | 2 |
| 43 | T697G;A722C;G730A | 3 | 3 |
| 44 | C669T;T697A;A702T | 3 | 2 |
| 45 | T261C;A295C;G774A | 3 | 0 |
| 46 | G250T;G500T;A516C | 3 | 1 |
| 47 | T545A;G579C;G590A | 3 | 2 |
| 48 | A408T;T453G;A660G | 3 | 1 |
| 49 | C548A;G587A;A740C | 3 | 3 |
| 50 | G328C;C666T;C745T | 3 | 2 |

Figure 9:
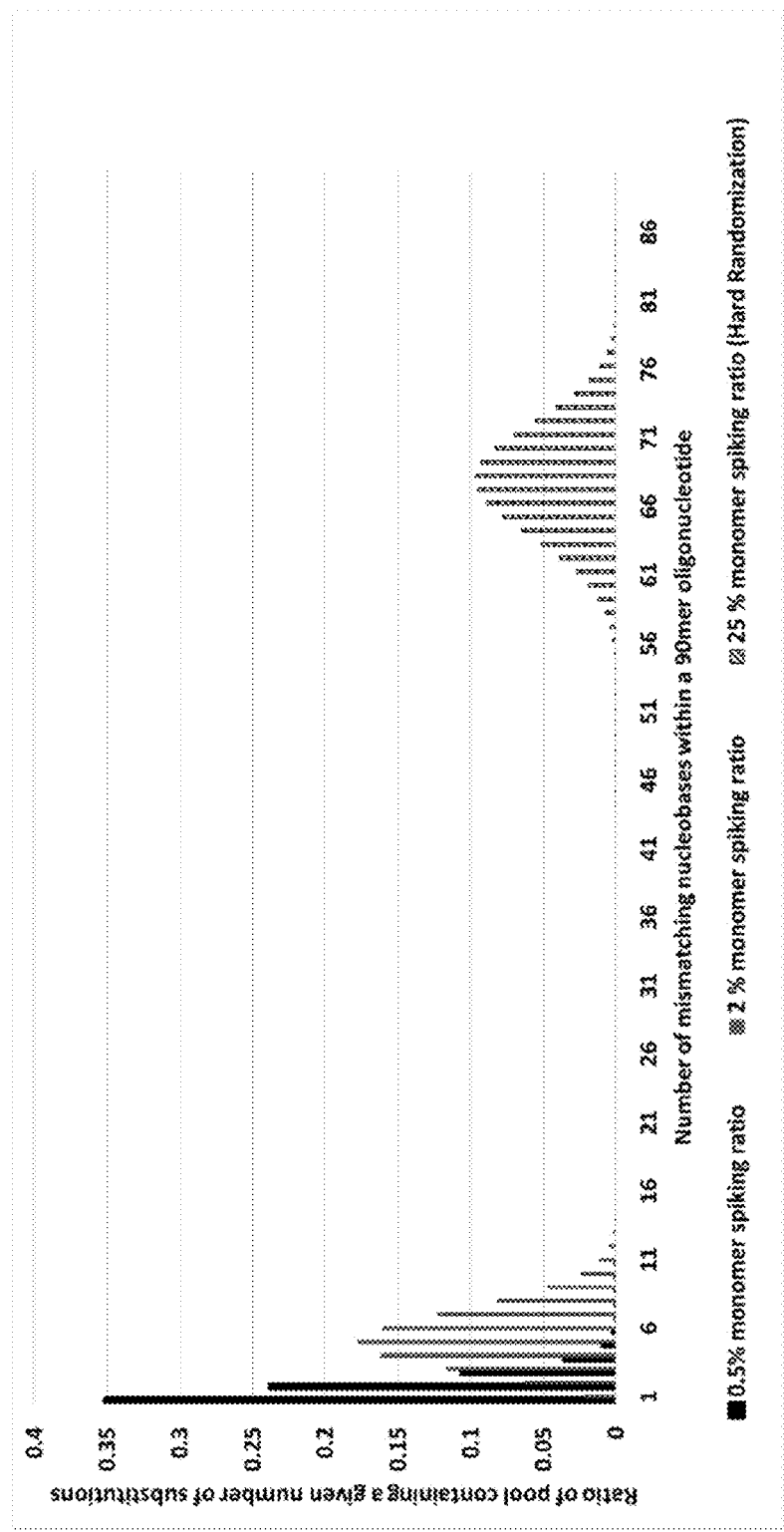

Fig. 9 continued: Table 1

|  |  | Percentage (%) of oligonucleotides within the oligonucleotide pool, with the corresponding number of mismatches | | |
|---|---|---|---|---|
|  |  | Monomer spiking ratio: 0.5 % | Monomer spiking ratio: 2 % | Monomer spiking ratio: 5 % |
| Number of mismatches within a 90 nucleotide-long oligonucleotide, compared to the PTR | 0 | 25.66 | 0.38 | 0.00 |
| | 1 | 35.17 | 2.19 | 0.00 |
| | 2 | 23.83 | 6.23 | 0.01 |
| | 3 | 10.65 | 11.66 | 0.03 |
| | 4 | 3.53 | 16.18 | 0.11 |
| | 5 | 0.92 | 17.77 | 0.33 |
| | 6 | 0.20 | 16.06 | 0.84 |
| | 7 | 0.04 | 12.30 | 1.77 |
| | 8 | 0.01 | 8.15 | 3.24 |
| | 9 | 0.00 | 4.74 | 5.21 |
| | 10 | 0.00 | 2.45 | 7.45 |
| | 11 | 0.00 | 1.14 | 9.56 |
| | 12 | 0.00 | 0.48 | 11.10 |
| | 13 | 0.00 | 0.18 | 11.75 |
| | 14 | 0.00 | 0.06 | 11.41 |
| | 15 | 0.00 | 0.02 | 10.20 |
| | 16 | 0.00 | 0.01 | 8.44 |
| | 17 | 0.00 | 0.00 | 6.48 |
| | 18 | 0.00 | 0.00 | 4.64 |
| | 19 | 0.00 | 0.00 | 3.10 |
| | 20 | 0.00 | 0.00 | 1.94 |
| | 21 | 0.00 | 0.00 | 1.14 |
| | 22 | 0.00 | 0.00 | 0.63 |
| | 23 | 0.00 | 0.00 | 0.33 |
| | 24 | 0.00 | 0.00 | 0.16 |
| | 25 | 0.00 | 0.00 | 0.08 |
| | 26 | 0.00 | 0.00 | 0.03 |
| | 27 | 0.00 | 0.00 | 0.01 |
| | 28 | 0.00 | 0.00 | 0.01 |
| | 29 | 0.00 | 0.00 | 0.00 |
| | 30 | 0.00 | 0.00 | 0.00 |
| | 31 | 0.00 | 0.00 | 0.00 |
| | 32 | 0.00 | 0.00 | 0.00 |
| | 33 | 0.00 | 0.00 | 0.00 |
| | 34 | 0.00 | 0.00 | 0.00 |
| | 35 | 0.00 | 0.00 | 0.00 |

Fig. 13: Table 3

| Identified DHFR mutations | Number within the pool | % within the pool |
|---|---|---|
| T383G=Leu28Arg | 379 | 12.5083 |
| C243T=NA;T383G=Leu28Arg | 232 | 7.6568 |
| G376A=Ala26Thr;T383G=Leu28Arg | 148 | 4.8845 |
| C243T=NA | 126 | 4.1584 |
| G269A=NA;T383G=Leu28Arg | 65 | 2.1452 |
| G247A=NA;T383G=Leu28Arg | 37 | 1.2211 |
| C243T=NA;G376A=Ala26Thr;T383G=Leu28Arg;C416G=Pro39Arg | 31 | 1.0231 |
| G247A=NA;C258A=NA;T383G=Leu28Arg | 30 | 0.9901 |
| C243T=NA;G376A=Ala26Thr;T383G=Leu28Arg | 23 | 0.7591 |
| C243T=NA;G593C=Arg98Pro | 23 | 0.7591 |
| A237G=NA;C243T=NA;G250C=NA;T282A=NA;T383G=Leu28Arg | 20 | 0.6601 |
| C243T=NA;T282C=NA;T383G=Leu28Arg;G440T=Trp47Leu;A444T=Glu48Asp | 20 | 0.6601 |
| C225G=NA;T285A=NA;T383G=Leu28Arg;G593C=Arg98Pro | 19 | 0.6271 |
| C243A=NA;T383G=Leu28Arg | 18 | 0.5941 |
| C243T=NA;T347G=Met16Arg;T383G=Leu28Arg;A410C=Asn37Thr | 18 | 0.5941 |
| C377T=Ala26Val;T383G=Leu28Arg | 17 | 0.5611 |
| G241C=NA;C377T=Ala26Val;T383G=Leu28Arg | 16 | 0.5281 |
| C263T=NA;C377T=Ala26Val;T383G=Leu28Arg;G418C=Val40Leu | 14 | 0.462 |
| G269A=NA;A275C=NA;A293G=NA;T383G=Leu28Arg;G389T=Trp30Leu | 14 | 0.462 |
| T383G=Leu28Arg;G593C=Arg98Pro | 13 | 0.429 |
| C263G=NA;T383G=Leu28Arg | 12 | 0.396 |
| G247A=NA;A275T=NA;T383G=Leu28Arg | 12 | 0.396 |
| G269A=NA | 12 | 0.396 |
| C231G=NA;C243A=NA;C377A=Ala26Asp;T383G=Leu28Arg | 10 | 0.33 |
| C243T=NA;T254A=NA;T383G=Leu28Arg;G390C=Trp30Cys | 10 | 0.33 |
| G593C=Arg98Pro | 10 | 0.33 |
| C225A=NA;A229C=NA;G235C=NA;G247A=NA;T383G=Leu28Arg;T492A=Ser64Arg;T795A=NA | 9 | 0.297 |
| C243T=NA;G355T=Ala19Ser;T383G=Leu28Arg;A716G=Glu139Gly | 9 | 0.297 |
| C243T=NA;T279G=NA;T383G=Leu28Arg | 9 | 0.297 |
| C243T=NA;T383G=Leu28Arg;C416G=Pro39Arg | 9 | 0.297 |
| C243T=NA;T383G=Leu28Arg;T485A=Leu62His;G508C=Asp70His | 9 | 0.297 |
| T383G=Leu28Arg;G389T=Trp30Leu | 9 | 0.297 |
| C243T=NA;G247T=NA;T383G=Leu28Arg | 8 | 0.264 |
| C243T=NA;T338A=Val13Asp;T383G=Leu28Arg | 8 | 0.264 |
| C243T=NA;T383G=Leu28Arg;A409G=Asn37Asp;A413G=Lys38Arg | 8 | 0.264 |
| C263T=NA;C377T=Ala26Val;T383G=Leu28Arg | 8 | 0.264 |
| T383G=Leu28Arg;G390C=Trp30Cys | 8 | 0.264 |
| A262C=NA;G274A=NA;C377T=Ala26Val;T383G=Leu28Arg | 7 | 0.231 |
| C243T=NA;T260A=NA;T281A=NA;T383G=Leu28Arg;C566A=Pro89Gln;G590C=Gly97Ala | 7 | 0.231 |
| C243T=NA;T383G=Leu28Arg;G508C=Asp70His | 7 | 0.231 |
| G247A=NA;T283A=NA;T383G=Leu28Arg | 7 | 0.231 |
| G269C=NA;T383G=Leu28Arg | 7 | 0.231 |
| A255T=NA;G257A=NA;G269A=NA;C299G=NA;T383G=Leu28Arg | 6 | 0.198 |
| C263T=NA;T383G=Leu28Arg | 6 | 0.198 |
| G247A=NA;C377A=Ala26Asp;T383G=Leu28Arg | 6 | 0.198 |
| G272A=NA;T284C=NA;G376A=Ala26Thr;T383G=Leu28Arg | 6 | 0.198 |
| G376A=Ala26Thr | 6 | 0.198 |
| G376A=Ala26Thr;T383G=Leu28Arg;C416G=Pro39Arg | 6 | 0.198 |
| T227A=NA;C243T=NA;T383G=Leu28Arg | 6 | 0.198 |
| T227A=NA;C243T=NA;T383G=Leu28Arg;A739G=Asn147Asp | 6 | 0.198 |
| T260A=NA;G269A=NA;G790T=NA | 6 | 0.198 |
| C225A=NA;A229C=NA;G235C=NA;G247A=NA;T383G=Leu28Arg | 5 | 0.165 |
| C225A=NA;A229C=NA;G235C=NA;G247A=NA;T383G=Leu28Arg;T492A=Ser64Arg | 5 | 0.165 |
| C225G=NA;T285A=NA;T383G=Leu28Arg | 5 | 0.165 |
| C231A=NA;T254G=NA;G269A=NA;A294G=NA;T383G=Leu28Arg;T406A=Leu36Ile | 5 | 0.165 |
| C231G=NA;T383G=Leu28Arg | 5 | 0.165 |
| C243T=NA;T282C=NA;T383G=Leu28Arg | 5 | 0.165 |
| C243T=NA;T383G=Leu28Arg;C721G=His141Asp | 5 | 0.165 |
| G241C=NA;T383G=Leu28Arg | 5 | 0.165 |

Fig. 14: Table 6.

| Escherichia coli K-12 MG1655 | | | | |
|---|---|---|---|---|
| Position | Reference nucleotide | Detected mutation | IC75 (Trimethoprim) µg / ml | IC75 (-fold change compared to wild-type) |
| -58 | C | T | 16.7 | 11.9 |
| -54 | G | A | 8.0 | 5.7 |
| -32 | G | C | 8.9 | 6.3 |
| -32 | G | A | 6.9 | 4.9 |
| Position | Reference Amino-acid | Detected missense mutation | IC75 (Trimethoprim) µg / ml | IC75 (-fold change compared to wild-type) |
| 5 | I | F | 3.5 | 2.5 |
| 7 | A | T | 4.2 | 3.0 |
| 20 | M | I | 5.1 | 3.6 |
| 20 | M | V | 6 | 4.3 |
| 21 | P | T | 5.1 | 3.6 |
| 21 | P | Q | 5.1 | 3.6 |
| 21 | P | L | 6.9 | 4.9 |
| 27 | D | E | 6.9 | 4.9 |
| 28 | L | R | 93.8 | 67.0 |
| 30 | W | C | 6.9 | 4.9 |
| 30 | W | G | 9.6 | 6.9 |
| 30 | W | R | 6.9 | 4.9 |
| 30 | W | S | 6 | 4.3 |
| 94 | I | L | 9.6 | 6.9 |
| 97 | G | S | 1.5 | 1.1 |
| 98 | R | P | 16.8 | 12.0 |
| 153 | F | S | 11.4 | 8.1 |

Fig. 15: Table 7.

| Identified GyrA mutation | Number within the pool | % within the pool |
|---|---|---|
| C248T=Ser83Leu | 1320 | 49.9244 |
| C248G=Ser83Trp | 46 | 1.7398 |
| T256A=Tyr86Asn;C248T=Ser83Leu | 21 | 0.7943 |
| G259T=Asp87Tyr | 19 | 0.7186 |
| G259A=Asp87Asn | 18 | 0.6808 |
| G244A=Asp82Asn | 17 | 0.643 |
| T1001C=Met334Thr;C248T=Ser83Leu | 16 | 0.6051 |
| G2354A=Gly785Asp;C248T=Ser83Leu | 14 | 0.5295 |
| G250C=Ala84Pro | 10 | 0.3782 |
| G241T=Gly81Cys | 9 | 0.3404 |
| C261G=Asp87Glu;C248T=Ser83Leu | 8 | 0.3026 |
| G2354A=Gly785Asp | 7 | 0.2648 |
| A265C=Ile89Leu;C248T=Ser83Leu | 7 | 0.2648 |
| G2356A=Ala786Thr | 5 | 0.1891 |
| G242A=Gly81Asp | 4 | 0.1513 |
| A260G=Asp87Gly | 4 | 0.1513 |
| C283T=Pro95Ser;C248T=Ser83Leu | 3 | 0.1135 |
| T256A=Tyr86Asn | 3 | 0.1135 |
| C284T=Pro95Leu;C248T=Ser83Leu | 3 | 0.1135 |
| G427A=Val143Ile | 2 | 0.0756 |
| G1467C=Leu489Phe;G259T=Asp87Tyr | 2 | 0.0756 |
| A607C=Ile203Leu | 2 | 0.0756 |
| A2621T=Glu874Val | 2 | 0.0756 |
| C248T=Ser83Leu;G242A=Gly81Asp | 2 | 0.0756 |
| G259T=Asp87Tyr;G250C=Ala84Pro | 2 | 0.0756 |
| G250A=Ala84Thr;C248T=Ser83Leu | 2 | 0.0756 |
| G250C=Ala84Pro;C248G=Ser83Trp | 2 | 0.0756 |
| G863A=Gly288Asp | 2 | 0.0756 |
| G259C=Asp87His;T247G=Ser83Ala | 2 | 0.0756 |
| A2467C=Ile823Leu;C248T=Ser83Leu | 2 | 0.0756 |
| G2356A=Ala786Thr;C248T=Ser83Leu | 2 | 0.0756 |
| G1467C=Leu489Phe | 2 | 0.0756 |
| C248T=Ser83Leu;C216A=Asp72Glu | 2 | 0.0756 |

Fig. 18: Table 7:

| Identified URA3 mutation | Number within the pool | % within the pool |
|---|---|---|
| G622T=Gly108Cys | 1687 | 34.1015 |
| C490A=Leu64Ile;G622T=Gly108Cys | 209 | 4.2248 |
| G622T=Gly108Cys;G677T=Gly126Val | 113 | 2.2842 |
| G622T=Gly108Cys;G1045T=Glu249* | 91 | 1.8395 |
| G622T=Gly108Cys;G1001T=Gly234Val | 80 | 1.6171 |
| G622T=Gly108Cys;T899A=Met200Lys | 61 | 1.2331 |
| G622T=Gly108Cys;G866A=Gly189Asp | 50 | 1.0107 |
| G622T=Gly108Cys;G1004T=Arg235Ile | 48 | 0.9703 |
| G622T=Gly108Cys;G985T=Asp229Tyr | 45 | 0.9096 |
| G622T=Gly108Cys;A1076C=Tyr259Ser;G1080C=Leu260Phe;G1085T=Arg262Ile | 41 | 0.8288 |
| A380T=Glu27Val;T395C=Leu32Ser;C422T=Thr41Ile;G622T=Gly108Cys | 36 | 0.7277 |
| C479A=Thr60Lys;G622T=Gly108Cys | 36 | 0.7277 |
| G622T=Gly108Cys;A685T=Ile129Phe | 36 | 0.7277 |
| G575A=Arg92Lys;G622T=Gly108Cys;G709A=Ala137Thr | 34 | 0.6873 |
| G622T=Gly108Cys;A1052C=Tyr251Ser | 33 | 0.6671 |
| T560G=Leu87*;G622T=Gly108Cys | 31 | 0.6266 |
| G622T=Gly108Cys;G1085C=Arg262Thr | 29 | 0.5862 |
| T466A=Cys56Ser;A478G=Thr60Ala;G622T=Gly108Cys | 28 | 0.566 |
| T318A=Tyr6*;G622T=Gly108Cys | 26 | 0.5256 |
| A572T=Asp91Val;A576C=Arg92Ser;G622T=Gly108Cys | 24 | 0.4851 |
| G622T=Gly108Cys;A725C=Lys142Thr | 24 | 0.4851 |
| G622T=Gly108Cys;T743C=Leu148Ser | 23 | 0.4649 |
| G622T=Gly108Cys;G927T=Lys209Asn | 22 | 0.4447 |
| A598C=Thr100Pro;C610T=Gln104*;G622T=Gly108Cys;G1039C=Glu247Gln | 21 | 0.4245 |
| C329A=Ala10Asp;G622T=Gly108Cys | 21 | 0.4245 |
| C490A=Leu64Ile;A572C=Asp91Ala;G622T=Gly108Cys;T990G=Ile230Met | 21 | 0.4245 |
| G622T=Gly108Cys;G709A=Ala137Thr | 21 | 0.4245 |
| T550G=Tyr84Asp;G622T=Gly108Cys;A1052C=Tyr251Ser | 21 | 0.4245 |
| G622T=Gly108Cys;A1058G=Lys253Arg;A1076G=Tyr259Cys;G1080C=Leu260Phe;G1085T=Arg262Ile | 20 | 0.4043 |
| G622T=Gly108Cys;G1001C=Gly234Ala | 20 | 0.4043 |
| C573A=Asp91Glu;G622T=Gly108Cys;G677T=Gly126Val | 19 | 0.3841 |
| G568T=Glu90*;G609T=Leu103Phe | 18 | 0.3639 |
| G622T=Gly108Cys;T916A=Leu206Ile;A923T=Asp208Val;T937A=Leu213Met | 18 | 0.3639 |
| T395G=Leu32Trp;G622T=Gly108Cys | 18 | 0.3639 |
| G575A=Arg92Lys;G622T=Gly108Cys | 17 | 0.3436 |
| A471C=Leu57Phe;G622T=Gly108Cys;C752A=Ala151Glu | 16 | 0.3234 |
| A478C=Thr60Pro;C490A=Leu64Ile;G622T=Gly108Cys;A1046C=Glu249Ala;A1052C=Tyr251Ser | 15 | 0.3032 |
| A478G=Thr60Ala;C490A=Leu64Ile;A524G=Lys75Arg;G622T=Gly108Cys | 15 | 0.3032 |
| G622T=Gly108Cys;A860T=Asp187Val | 15 | 0.3032 |
| G622T=Gly108Cys;A887T=Asp196Val | 15 | 0.3032 |
| G622T=Gly108Cys;G1039T=Glu247* | 15 | 0.3032 |
| G622T=Gly108Cys;G676T=Gly126Cys | 15 | 0.3032 |
| T466A=Cys56Ser;G622T=Gly108Cys | 15 | 0.3032 |
| A441T=Leu47Phe;G622T=Gly108Cys | 14 | 0.283 |
| A461C=Lys54Thr;C490A=Leu64Ile;A533C=Lys78Thr;G622T=Gly108Cys | 14 | 0.283 |
| G322C=Glu8Gln;G622T=Gly108Cys | 14 | 0.283 |
| G622T=Gly108Cys;T776G=Leu159Arg | 14 | 0.283 |
| G622T=Gly108Cys;T812A=Ile171Asn | 14 | 0.283 |
| A478G=Thr60Ala;G622T=Gly108Cys | 13 | 0.2628 |

Fig. 19:
1
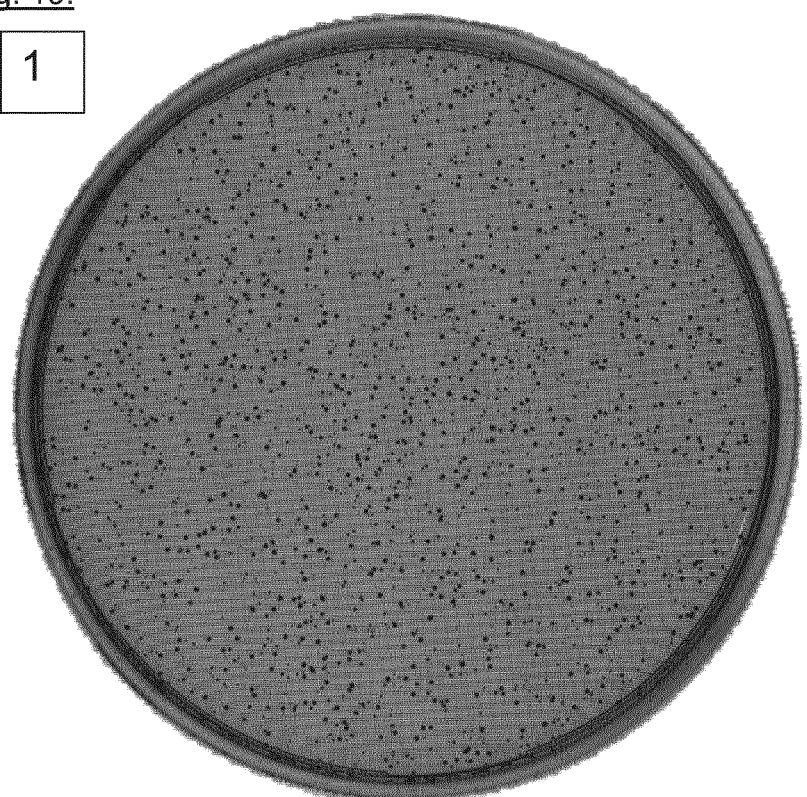
2
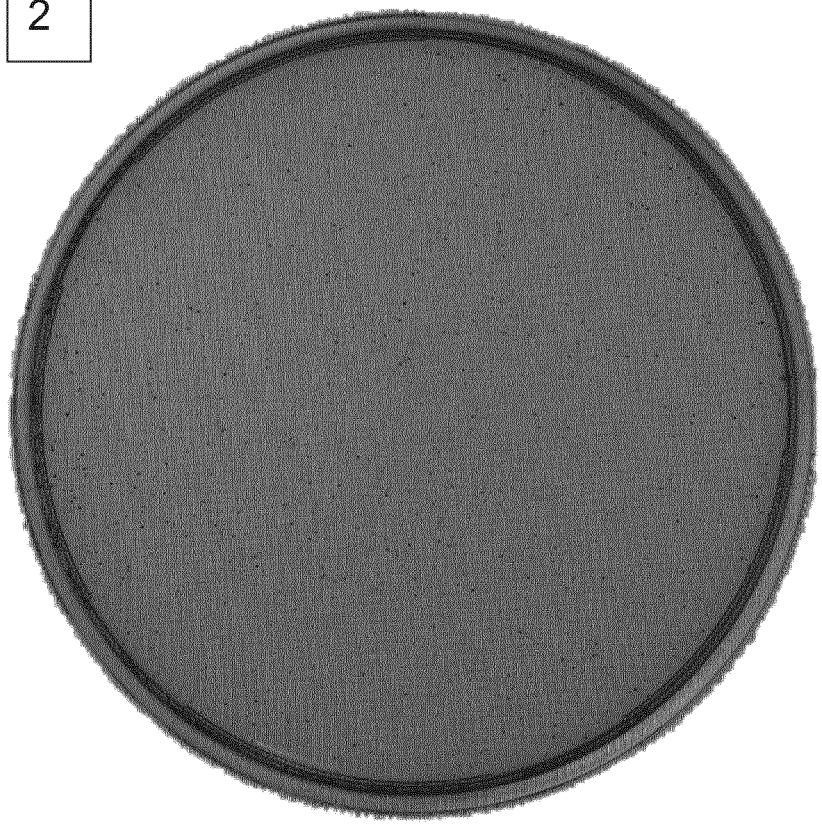

Fig. 20:

SEQ ID NO:1
CAGCTGTCTCTTATACACATCTCCGCTGTGCTTTCAGTGGATTTCGGATAACAGAA
AGGCCGGGAAATACCCAGCCTCGCTTTGTAACGGAGTAGACGAAAGTGATTGCG
CCTACCCGGATATTATCGTGAGGATGCTCATCGCCATTTCACTCATCTTTCAGGG
CTTTTATCGCCGGATGTAAATCAACAGATTGTAACAGACCACCCGGCGGCGTTTT
CACAAGTTGCGGACATAACCGTTCCACGTCCGCCAGCAGGGTTATGGCCTGTGC
CATTGACCACTGCGCATGTTCGCTCATCAGATTTCGTGCAATCCACTGCGCAATAT
TGCCAGGTTCGAATACGGACTGCTTCGCCAGGTAGCCATCAGTTCAGGAATCAA
GATTTGTAAATTTTGTTGGCGTAAGGGTAAAGGCACTGCCCTGATGGTCACATGC
TGTGCATCTGACTGGAAATCAATACCCAATTCCGCCAGGGCAGACTGCGCTTTTT
CTAATGCCGATTTTTCTTCGGCAGAAACTTTTAGCCGCAACGGAATCAGCAGCGG
CTGGGCGCAAACGGGCGCTTCACCCGGCGTCAATTGTGCCTGACGCAGCCAACG
TTCTGCCACTGGCAAGGATAAAGTGAAATGTTGCCGTCGCGCTCCAGCAACGCA
CAGTCGGAATGGACGATAGTCAGTACCCGACCAAAACTCTGACTGTTCGCCGCAA
GTGCAGGTTCCTGCGGTTCCGGCGCTTTTAATTTTTGCATCGGCGCGGGCGTTTG
CAAAAGCTGGCGATACACTTCACCTTGCTGTTTCTGGTAGCCTGGCTGCGCATTC
GGCCAGGGGGCAGCCGGACGACTGCCTGATGCTGGCGCAGGAGTGTAGCGCG
GAGCTACCGGCTCACGAGCTGCCGGTTCTGCAAAGTGATTGCGCCCCGCCGCCA
CGCGGTTTTCCGGAATGGAACGCGGTGCAGGTTGGGGTTCATCGTCCAGCGGTA
GCGGCGTTTCCAGTTGCTGTTGTAGCACGCTCAGCACGCCCTGATAGATAAAATC
ATGCACCAGACGCGACTGATGGAAACGCACTTCGTGTTTGGCGGGGTGCACGTT
GACGTCCACCTGATGTGGGTCGATCTCCAGATACAACACAAATGCCGGTTGCTGA
TCGGCCCCAGTTTGTCTTCGCAGGCCTGGCGGATCGCGTGATTGATCAGGCGA
TCGCGCATCATGCGACCGTTCACGTAGCAATACTGAATTTCTGCCAGTGCGGGCG
TGGTGTGATTTGGATCGGCCACCCAGCCGCGTAGCGTGAGATCGCCGTGTTGCC
ATTCAATCGCCAGCGCTTGTTCAAGAAAGCGGTGCCGCAAATCGCGCCTAAGC
GCCGTTCTTTTTGCCCGCCTTCCGGCACTGCGCGGTACTGACGCACAATTTTACC
GTTATGCGACAGGTTGATCGTGACGTCGAAACGCGCCAGCGCAATGCGGCGGAT
GATCTCATCAATGTGGTTAAATTCGGTTTTCTCGGTGCGCAGGAATTTGCGCCGC
GCCGGGGTGTTGTAGAACAGATCCAGCACCTCCAGCGTCGTCCCCACAGGATGC
GCCGCCGGTTTTACCGTCACGTTCATATCGCGCCCTTCGGCATAGGCCTGCCAG
GCTTCCTGCTGTTCTGCGGTGCGTGAAGTGAGCGTCAGGCGGGAAACCGAACTG
ATACTCGCCAGCGCCTCACCGCGAAAGCCCAGGCTGATAATGGCTTCGAGATCG
TCCAGAGAGGCGATTTTACTGGTGGCATGACGAGCCAGCGCCAGCGCCAGCTCA
TCTTTTTTGATACCGCAGCCGTTATCACGAATGCGGATAAGTTTCGCCCCACCGC
GTTCGATATCAATATCGATACGCGTCGCACCTGCATCGAGGCTGTTTTCACTAGT
TCTTTGACTACCGACGCAGGTCGCTCGACCACCTCACCTGCGGCAATCTGGTTCG
CCAGTTGTGGCGGTAAGACCTGAATTGGCATTTTGTAATCCTCCTCTCTCATCGC
CATTGCTCCCCAAATACAAAACCAATTTCAGCCAGTGCCTCGTCCATTTTTTCGAT
GAACTCCGGCACGATCTCGTCAAAACTCGCCATGTACTTTTCATCCCGCTCAATC
ACGACATAATGCAGGCCTTCACGCTTCATACGCGGGTCATAGTTGGCAAAGTACC
AGGCATTTTTTCGCGTCACCCACATGCTGTACTGCACCTGGGCCATGTAAGCTGA
CTTTATGGCCTCGAAACCACCGAGCCGGAACTTCATGAAATCCCGGGAGGTAAAC
GGGCATTTCAGTTCAAGGCCGTTGCCGTCACTGCATAAACCATCGGGAGAGCAG
GCGGTACGCATACTTTCGTCGCGATAGATGATCGGGGATTCAGTAACATTCACGC
CGGAAGTAAATTCAAACAGGGTTCTGGCGTCGTTCTCGTACTGTTTTCCCCAGGC
CAGTGCTTTAGCGTTAACTTCCGGAGCCACACCGGTGCAAACCTCAGCAAGCAG
GGTGTGGAAGTAGGACATTTTCATGTCAGGCCACTTCTTTCCGGAGCGGGGTTTT

Fig. 20 continued

GCTATCACGTTGTGAACTTCTGAAGCGGTGATGACGCCGAGCCGTAATTTGTGCC
ACGCATCTTCCCCCTGTTCGACAGCTCTCACATCGATCCCGGTACGCTGCAGGAT
AATGTCCGGTGTCATGCTGCCACCTTCTGCTCTGCGGCTTTCTGTTTCAGGAATC
CAAGAGCTTTTACTGCTTCGGCCTGTGTCAGTTCTGACGATGCACGAATGTCGCG
GCGAAATATCTGGGAACAGAGCGGCAATAAGTCGTCATCCCATGTTTTATCCAGG
GCGATCAGCAGAGTGTTAATCTCCTGCATGGTTTCATCGTTAACCGGAGTGATGT
CGCGTTCCGGCTGACGTTCTGCAGTGTATGCAGTATTTTCGACAATGCGCTCGGC
TTCATCCTTGTCATAGATACCAGCAAATCCGAAGGCCAGACGGGCACACTGAATC
ATGGCTTTATGACGTAACATCCGTTTGGGATGCGACTGCCACGGCCCCGTGATTT
CTCTGCCTTCGCGAGTTTTGAATGGTTCGCGGCGGCATTCATCCATCCATTCGGT
AACGCAGATCGGATGATTACGGTCCTTGCGGTAAATCCGGCATGTACAGGATTCA
TTGTCCTGCTCAAAGTCCATGCCATCAAACTGCTGGTTTTCATTGATGATGCGGGA
CCAGCCATCAACGCCCACCACCGGAACGATGCCATTCTGCTTATCAGGAAAGGC
GTAAATTTCTTTCGTCCACGGATTAAGGCCGTACTGGTTGGCAACGATCAGTAAT
GCGATGAACTGCGCATCGCTGGCATCACCTTTAAATGCCGTCTGGCGAAGAGTG
GTGATCAGTTCCTGTGGGTCGACAGAATCCATGCCGACACGTTCAGCCAGCTTCC
CAGCCAGCGTTGCGAGTGCAGTACTCATTCGTTTATACCTCTGAATCAATATCAA
CCTGGTGGTGAGCAATGGTTTCAACCATGTACCGGATGTGTTCTGCCATGCGCTC
CTGAAACTCAACATCGTCATCAAACGCACGGGTAATGGATTTTTGCTGGCCCCG
TGGCGTTGCAAATGATCGATGCATAGCGATTCAAACAGGTGCTGGGGCAGGCCT
TTTTCCATGTCGTCTGCCAGTTCTGCCTCTTTCTCTTCACGGGCGAGCTGCTGGT
AGTGACGCGCCCAGCTCTGAGCCTCAAGACGATCCTGAATGTAATAAGCGTTCAT
GGCTGAACTCCTGAAATAGCTGTGAAAATATCGCCCGCGAAATGCCGGGCTGATT
AGTAATCCGGAATCGCACTTACGGCCAATGCTTCGTTTCGTATCACACACCCCAA
AGCCTTCTGCTTTGAATGCTGCCCTTCTTCAGGGCTTAATTTTAAGAGCGTCACC
TTCATGGTGGTCAGTGCGTCCTGCTGATGTGCTCAGTATCACCGCCAGTGGTATT
TATGTCAACACCGCCAGAGATAATTTATCACCGCAGATGGTTATCTGTATGTTTTT
TATATGAATTTATTTTTTGCAGGGGGGCATTGTTTGGTAGGTGAGAGATCTGAATT
GCTATGTTTAGTGAGTTGTATCTATTTATTTTTCAATAAATACAATTGGTTATGTGTT
TTGGGGGCGATCGTGAGGCAAAGAAAACCCGGCGCTGAGGCCGGGTTAAGAGTT
GGTAGCTCTTGATCCGGCAAACAAACCACCGCTGGTAGCGGTGGTTTTTTTGTTT
GCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTC
ATGAGATTATCAAAAAGGATCTTCACCTAGATCCTTTTAAATTAAAAATGAAGTTTT
AAATCAATCTAAAGTATATATGAGTAAACTTGGTCTGACAGTTACCAATGCTTAATC
AGTGAGGCACCTATCTCAGCGATCTGTCTATTTCGTTCATCCATAGTTGCCTGACT
CCCCGTCGTGTAGATAACTACGATACGGGAGGGCTTACCATCTGGCCCCAGTGC
TGCAATGATACCGCGAGACCCACGCTCACCGGCTCCAGATTTATCAGCAATAAAC
CAGCCAGCCGGAAGGGCCGAGCGCAGAAGTGGTCCTGCAACTTTATCCGCCTCC
ATCCAGTCTATTAATTGTTGCCGGGAAGCTAGAGTAAGTAGTTCGCCAGTTAATAG
TTTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCCC
CCATGTTGTGCAAAAAGCGGTTAGCTCCTTCGGTCCTCCGATCGTTGTCAGAAG
TAAGTTGGCCGCAGTGTTATCACTCATGGTTATGGCAGCACTGCATAATTCTCTTA
CTGTCATGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAATACGG
GATAATACCGCGCCACATAGCAGAACTTTAAAAGTGCTCATCATTGGAAAACGTTC
TTCGGGGCGAAAACTCTCAAGGATCTTACCGCTGTTGAGATCCAGTTCGATGTAA

Fig. 20 continued

```
CCCACTCGTGCACCCAACTGATCTTCAGCATCTTTTACTTTCACCAGCGTTTCTGG
GTGAGCAAAAACAGGAAGGCAAAATGCCGCAAAAAAGGGAATAAGGGCGACACG
GAAATGTTGAATACTCATACTCTTCCTTTTTCAATATTATTGAAGCATTTATCAGGG
TTATTGTCTCATGAGCGGATACATATTTGAATGAATTCAACCATTTACTATGTTATG
TTCTGAGGGGAGTGAAAATTCCCCTAATTCGATGAAGATTCTTGCTCAATTGTTAT
CAGCTATGCGCCGACCAGAACACCTTGCCGATCAGCCAAACGTCTCTTCAGGCC
ACTGACTAGCGATAACTTTCCCCACAACGGAACAACTCTCATTGCATGGGATCATT
GGGTACTGTGGGTTTAGTGGTTGTAAAAACACCTGACCGCTATCCCTGATCAGTT
TCTTGAAGGTAAACTCATCACCCCCAAGTCTGGCTATGCAGAAATCACCTGGCTC
AACAGCCTGCTCAGGGTCAACGAGAATTAACATTCCGTCAGGAAAGCTTGGCTTG
GAGCCTGTTGGTGCGGTCATGGAATTACCTTCAACCTCAAGCCAGAATGCAGAAT
CACTGGCTTTTTTGGTTGTGCTTACCCATCTCTCCGCATCACCTTTGGTAAAGGTT
CTAAGCTCAGGTGAGAACATCCCTGCCTGAACATGAGAAAAACAGGGTACTCAT
ACTCACTTCTAAGTGACGGCTGCATACTAACCGCTTCATACATCTCGTAGATTTCT
CTGGCGATTGAAGGGCTAAATTCTTCAACGCTAACTTTGAGAATTTTTGTAAGCAA
TGCGGCGTTATAAGCATTTAATGCATTGATGCCATTAAATAAAGCACCAACGCCTG
ACTGCCCCATCCCCATCTTGTCTGCGACAGATTCCTGGGATAAGCCAAGTTCATT
TTTCTTTTTTTCATAAATTGCTTTAAGGCGACGTGCGTCCTCAAGCTGCTCTTGTGT
TAATGGTTTCTTTTTTGTGCTCATACGTTAAATCTATCACCGCAAGGGATAAATATC
TAACACCGTGCGTGTTGACTATTTTACCTCTGGCGGTGATAATGGTTGCATGTACT
AAGGAGGTTGTATGGAACAACGAGATGTGTATAAGAGACAGCTGGCCTGCCCCT
CCCTTTTGGTGTCCAACCGGCTCGACGGGGGCAGCGCAAGGCGGTGCCTCCGG
CGGGCCACTCAATGCTTGAGTATACTCACTAGACTTTGCTTCGCAAAGTCGTGAC
CGCCTACGGCGGCTGCGGCGCCCTACGGGCTTGCTCTCCGGGCTTCGCCCTGC
GCGGTCGCTGCGCTCCTTGCCAGCCCGTGGATATGTGGACGATGGCCGCGAG
CGGCCACCGGCTGGCTCGCTTCGCTCGGCCCGTGGACAACCCTGCTGGACAAG
CTGATGGACAGGCTGCGCCTGCCCACGAGCTTGACCACAGGGATTGCCCACCGG
CTACCCAGCCTTCGACCACATACCCACCGGCTCCAACTGCGCGGCCTGCGGCCT
TGCCCCATCAATTTTTTTAATTTTCTCTGGGGAAAAGCCTCCGGCCTGCGGCCTG
CGCGCTTCGCTTGCCGGTTGGACACCAAGTGGAAGGCGGGTCAAGGCTCGCGC
AGCGACCGCGCAGCGGCTTGGCCTTGACGCGCCTGGAACGACCCAAGCCTATG
CGAGTGGGGGCAGTCGAAGGGCGAAGCCCGCCCGCCTGCCCCCCGAGCCTCAC
GGCGGCGAGTGCGGGGGTTCCAAGGGGGCAGCGCCACCTTGGGCAAGGCCGA
AGGCCGCGCAGTCGATCAACAAGCCCCGGAGGGGCCACTTTTTGCCGGAGGGG
GAGCCGCGCCGAAGGCGTGGGGGAACCCCGCAGGGGTGCCCTTCTTTGGGCAC
CAAAGAACTAGATATAGGGCGAAATGCGAAAGACTTAAAAATCAACAACTTAAAAA
AGGGGGGTACGCAACAGCTCATTGCGGCACCCCCGCAATAGCTCATTGCGTAG
GTTAAAGAAAATCTGTAATTGACTGCCACTTTTACGCAACGCATAATTGTTGTCGC
GCTGCCGAAAAGTTGCAGCTGATTGCGCATGGTGCCGCAACCGTGCGGCACCCC
TACCGCATGGAGATAAGCATGGCCACGCAGTCCAGAGAAATCGGCATTCAAGCC
AAGAACAAGCCCGGTCACTGGGTGCAAACGGAACGCAAAGCGCATGAGGCGTG
GGCCGGGCTTATTGCGAGGAAACCCACGGCGGCAATGCTGCTGCATCACCTCGT
GGCGCAGATGGGCCACCAGAACGCCGTGGTGGTCAGCCAGAAGACACTTTCCAA
GCTCATCGGACGTTCTTTGCGGACGGTCCAATACGCAGTCAAGGACTTGGTGGC
CGAGCGCTGGATCTCCGTCGTGAAGCTCAACGGCCCCGGCACCGTGTCGGCCTA
CGTGGTCAATGACCGCGTGGCGTGGGCCAGCCCCGCGACCAGTTGCGCCTGT
CGGTGTTCAGTGCCGCCGTGGTGGTTGATCACGACGACCAGGACGAATCGCTGT
TGGGGCATGGCGACCTGCGCCGCATCCCGACCCTGTATCCGGGCGAGCAGCAA
```

Fig. 20 continued

CTACCGACCGGCCCCGGCGAGGAGCCGCCCAGCCAGCCCGGCATTCCGGGCAT
GGAACCAGACCTGCCAGCCTTGACCGAAACGGAGGAATGGGAACGGCGCGGGC
AGCAGCGCCTGCCGATGCCCGATGAGCCGTGTTTTCTGGACGATGGCGAGCCGT
TGGAGCCGCCGACACGGGTCACGCTGCCGCGCCGGTAGCACTTGGGTTGCGCA
GCAACCCGTAAGTGCGCTGTTCCAGACTATCGGCTGTACCGCCTCG

SEQ ID NO:2
TTGAGATGTTAGATAGGCACCATACTCACTTTTGCCCTTTAGAAGGGGAAAGCTG
GCAAGATTTTTTACGTAATAACGCTAAAAGTTTTA

SEQ ID NO:3
TTAGATAAAAGTAAAGTGATTAACAGCGCATTAGAGCTGCTTAATGAGGTCGGAAT
CGAAGGTTTAACAACCCGTAAACTCGCCCAGAAG

SEQ ID NO:4
ATCGGCAGGCAGGTTCCACGGCATGGCGTTTTCCATGCCGATAACGCGATCTAC
CGCTAACGCCGCAATCAGACTGATCATTGAGATTTC

SEQ ID NO:5
ACCGATTGATTCCCAGGTATGGCGGCCCATAATCACGGGTTTATTTAAGGTGTTG
CGTTTAAACCAGGCGAGATCGGCAGGCAGGTTCCA

SEQ ID NO:6
CACCCACGTTACGCGATCGTCCGTACCCGGTTGACTGCTGAGGATAATATTTTTG
CGTCCTGGCAACGGACGACCGATTGATTCCCAGGT

SEQ ID NO:7
AACGCGACCGCCGCCAATCACCATGATTTCTGGTACGTCACCACACGCCGCGAT
GGCTTCATCCACCGACTTCACCCACGTTACGCGATC

SEQ ID NO:8
GGTGTCGCCTTCCACTTCTGCGTCGATATGCGTCAGATACAGTTTTTGCGCTTTTG
GCAAGAACTGTTCATAAACGCGACCGCCGCCAAT

SEQ ID NO:9
GTTCTGCGCATCAGCATCGTGGAATTCGCTGAATACCGATTCCCAGTCATCCGGC
TCGTAATCCGGGAAATGGGTGTCGCCTTCCACTTC

SEQ ID NO:10
GCATCCGGCGCTAGCCGTAAATTCTATACAAAATTACCGCCGCTCCAGAATCTCA
AAGCAATAGCTGTGAGAGTTCTGCGCATCAGCATC

SEQ ID NO:11
ACTGATCATTGAGATTTCCCGATAAAAAAAATTGTCGCCACTATACGTAAAGCGTA
AACCGTCGTCGACTGGTGCGAGGATGATGTTGAG

Fig. 20 continued

SEQ ID NO:12
ATCGGCAGGCAGGTTCCACGGCATGGCGTTTTCCATACCGATGACGCGATCCAC
CGCTAACGCCGCAATCAGACTGATCATTAATTATTT

SEQ ID NO:13
TCCGATGGACTCCCAGGTGTGACGTCCCATGACGACAGGTTTATTTAACGTGTTA
CGTTTAAACCAGGCGAGATCGGCAGGCAGGTTCCA

SEQ ID NO:14
CACCCACTGCACGCGATCGTCGGTGCCTGGCTGGCTGCTGATAACAATATTTTTA
CGTCCCGGTAAGGGGCGTCCGATGGACTCCCAGGT

SEQ ID NO:15
CACGCGCCCGCCGCCAATGACCATAATTTCCGGCGCATCGCCGCAAGCGGCAAT
CGCCTCATCGACAGACTTCACCCACTGCACGCGATC

SEQ ID NO:16
GGTATCGCCTTCGACTTCCGCATCAATATGCGTCAGATAAAGCTTCTGCGCCTTT
GGCAGGAACTGCTCGTACACGCGCCCGCCGCCAAT

SEQ ID NO:17
ATTCTGCGCGTCGGCATCGTGAAACTCACTGAATACCGATTCCCAGTCATCCGGT
TCATAATCCGGAAAATGGGTATCGCCTTCGACTTC

SEQ ID NO:18
TAAGGCGTTTCGCCGCCATCCGGCACTACAGCGTTAACGACGCTCCAGAATCTC
GAAACAATAGCTGTGAGAATTCTGCGCGTCGGCATC

SEQ ID NO:19
ACTGATCATTAATTATTTCCTGATACAAAAAAAATTGCCGCCACTATACGTAAAGC
GCAATCTTTCGTCGACTGACGAAAAGAGGATGAG

SEQ ID NO:20
ATCGGCAGGCAGGTTCCACGGCATGGCGTTTTCCATGCCGATAACGCGATCTAC
CGCTAACGCCGCAATCAGACTGATCATTGAGATTTC

SEQ ID NO:21
ACCGATGGATTCCCAGGTATGGCGGCCCATAATCACGGGTTTATTTAAAGTGTTG
CGTTTAAACCAGGCGAGATCGGCAGGCAGGTTCCA

SEQ ID NO:22
CACCCACGTTACGCGATCGTCCGTACCCGGTTGACTGCTGAGGATAATATTTTTG
CGTCCTGGCAACGGACGACCGATGGATTCCCAGGT

SEQ ID NO:23
AACGCGACCGCCGCCAATCACCATGATTTCTGGTACGTCACCACACGCCGCAAT
GGCTTCATCCACCGACTTCACCCACGTTACGCGATC

Fig. 20 continued

SEQ ID NO:24
GGTGTCGCCTTCCACTTCCGCGTCGATATGCGTCAGATACAGTTTTTGCGCTTTC
GGCAGGAACTGCTCATAAACGCGACCGCCGCCAAT

SEQ ID NO:25
GTTCTGCGCATCGGCATCGTGGAATTCGCTGAATACCGATTCCCAGTCATCCGGC
TCGTAATCCGGGAAATGGGTGTCGCCTTCCACTTC

SEQ ID NO:26
GTATCAGTGATGCCGGAATTCTAATATACAAAATTACCGCCGCTCCAGAATCTCAA
AGCAATAGCTGTGAGAGTTCTGCGCATCGGCATC

SEQ ID NO:27
ACTGATCATTGAGATTTCCCGATAAAAAAATTGTCGCCACTATACGTAAAGCGTA
AACCGTCGTCGACTGGTGCGAGGATGATGTTGAG

SEQ ID NO:28
GGACCGCGAACATCTGTCATTAATTCAACGACATGGCTGGCAGGGAACCGAAGA
AGGTAAACATACCGGCAACATGGCGGATGAACCGGAAACGAAACCCTCATCCTAA
TAAAGAGTGACGTAAATCACACTTTACAGCTAACTGTTTGTTTTTGTTTCATTGTAA
TGCGGCGAGTCCAGGGAGAGAGCGTGGACTCGCCAGCAGAATATAAAATTTTCC
TCAACATCATCCTCGCACCAGTCGACGACGGTTTACGCTTTACGTATAGTGGCGA
CAATTTTTTTTATCGGGAAATCTCAATGATCAGTCTGATTGCGGCGTTAGCGGTAG
ATCGCGTTATCGGCATGGAAAACGCCATGCCGTGGAACCTGCCTGCCGATCTCG
CCTGGTTTAAACGCAACACCTTAAATAAACCCGTGATTATGGGCCGCCATACCTG
GGAATCAATCGGTCGTCCGTTGCCAGGACGCAAAAATATTATCCTCAGCAGTCAA
CCGGGTACGGACGATCGCGTAACGTGGGTGAAGTCGGTGGATGAAGCCATCGC
GGCGTGTGGTGACGTACCAGAAATCATGGTGATTGGCGGCGGTCGCGTTTATGA
ACAGTTCTTGCCAAAAGCGCAAAAACTGTATCTGACGCATATCGACGCAGAAGTG
GAAGGCGACACCCATTTCCCGGATTACGAGCCGGATGACTGGGAATCGGTATTC
AGCGAATTCCACGATGCTGATGCGCAGAACTCTCACAGCTATTGCTTTGAGATTC
TGGAGCGGCGGTAATTTTGTATAGAATTTACGGCTAGCGCCGGATGCGACGCCG
GTCGCGTCTTATCCGGCCTTCCTATATCAGGCTGTGTTTAAGACGCCGCCGCTTC
GCCCAAATCCTTATGCCGGTCGACGGCTGGACAAAATACTGTTTATCTTCCCAG
CGCAGGCAGGTTAATGTACCACCCCAGCAGCAGCCGGTATCCAGCGCGTATATA
CCTTCCGGCGTACCTTTGCCCTCCAGCGATGCCCAGTGACCAAAGGCGATGCTG
TATTCTTCAGCGACAGGGCCAGGAATCGCAAACCACGGTTTC

Fig. 20 continued

SEQ ID NO:29
AGACCGTGAACATCTGTCATTAATTCAACGACATGGCTGGCAGGGAACCGAAGAA
GGGAAACATACTGGCAATATGGCGGATGAACCGGAAACGAAGCCCTCATCCTAAT
AAAGAGTGACGTAAATCACGCTTTACAGCTAACTGTTTGTTTTTGTTTCATTGTAAT
GCGGCGAGTCCAGGGAGAGAGCGTGGACTCGCCAGCAGAATATAAAATTTTCCT
CAACATCATCCTCGCACCAGTCGACGACGGTTTACGCTTTACGTATAGTGGCGAC
AATTTTTTTTATCGGGAAATCTCAATGATCAGTCTGATTGCGGCGTTAGCGGTAGA
TCGCGTTATCGGCATGGAAAACGCCATGCCGTGGAACCTGCCTGCCGATCTCGC
CTGGTTTAAACGCAACACTTTAAATAAACCCGTGATTATGGGCCGCCATACCTGG
GAATCCATCGGTCGTCCGTTGCCAGGACGCAAAAATATTATCCTCAGCAGTCAAC
CGGGTACGGACGATCGCGTAACGTGGGTGAAGTCGGTGGATGAAGCCATTGCG
GCGTGTGGTGACGTACCAGAAATCATGGTGATTGGCGGCGGTCGCGTTTATGAG
CAGTTCCTGCCGAAAGCGCAAAACTGTATCTGACGCATATCGACGCGGAAGTG
GAAGGCGACACCCATTTCCCGGATTACGAGCCGGATGACTGGGAATCGGTATTC
AGCGAATTCCACGATGCCGATGCGCAGAACTCTCACAGCTATTGCTTTGAGATTC
TGGAGCGGCGGTAATTTTGTATATTAGAATTCCGGCATCACTGATACGTGCAGAT
ATCCGTGTATACTAGACGTATAAATTGTACAGGAGCACGAGATCATGACTGCAAAA
CGTACCACACAAAGTGTGACCGTCACCGTCGACCGTGAGTTAGTCAATCGCGCTC
GTGATGCAGGCTTAAA

SEQ ID NO:30
GAGCATCTGTCGTTGATTCAGCGCCACGGCTGGCAGGGAACGGCTGAGGGCAAA
CATTCCGGGGAGGTCGCCGATGAACCCGAGGTCAAACCGTCAATCTAAAGTAAAA
AATGTGATGTTCTGCAAACTTTACTGCTAATTGGCTGTTTTGAACTACTGTAATGC
TGGCGCTCCACATCAAATGAGTGGCGTCGCCAGCAGAACGAAAAATTTTCGTGCT
CATCCTCTTTTCGTCAGTCGACGAAAGATTGCGCTTTACGTATAGTGGCGGCAATT
TTTTTTGTATCAGGAAATAATTAATGATCAGTCTGATTGCGGCGTTAGCGGTGGAT
CGCGTCATCGGTATGGAAAACGCCATGCCGTGGAACCTGCCTGCCGATCTCGCC
TGGTTTAAACGTAACACGTTAAATAAACCTGTCGTCATGGGACGTCACACCTGGG
AGTCCATCGGACGCCCCTTACCGGGACGTAAAAATATGTTATCAGCAGCCAGCCA
GGCACCGACGATCGCGTGCAGTGGGTGAAGTCTGTCGATGAGGCGATTGCCGCT
TGCGGCGATGCGCCGGAAATTATGGTCATTGGCGGCGGGCGCGTGTACGAGCA
GTTCCTGCCAAAGGCGCAGAAGCTTTATCTGACGCATATTGATGCGGAAGTCGAA
GGCGATACCCATTTTCCGGATTATGAACCGGATGACTGGGAATCGGTATTCAGTG
AGTTTCACGATGCCGACGCGCAGAATTCTCACAGCTATTGTTTCGAGATTCTGGA
GCGTCGTTAACGCTGTAGTGCCGGATGGCGGCGAAACGCCTTATCCGGCCTACT
CTTGAGCCAGATGTCGCCAGATGTAGGCCTGATAAGCGTAGCGCCATCAGGCAT
AAACCTATCAGGCGTTGACCGCTTCGCCTTCGCCCATATCCATCTGGCGGTTTGA
CGGCTGCACAAAATACTGTTTATCTTCCCAGCGTAAACAGGTCAACTCCCCGCCC
CAGCAGCAGCCGGTATCCAGCGCGTAAATACCTTCCGGCGTCCCTTTCCCTTCCA
GCGACGCCCAGTGCCCGAACGCAATACTGTAAGCCTC

SEQ ID NO:31
TCATTGTAATGCGGCGAGTCCA

Fig. 20 continued

SEQ ID NO:32
AAGCGGCGGCGTCTTAAACA

SEQ ID NO:33
ACCCGAGGTCAAACCGTCAATC

SEQ ID NO:34
CGCTACGCTTATCAGGCCTACA

SEQ ID NO:35
GATGAACCGGAAACGAAACCC

SEQ ID NO:36
TGCAGTCATGATCTCGTGCTCCT

SEQ ID NO:37
GTCGCTCATCTAACCGCTATCCCTCTACTGTATCCCGGATTCAAAGGTCGCAAATT
ATAACACAGCCGCGCAGTTTGAGGTAAACCTATA

SEQ ID NO:38
CGACATCGCATAATCCAGATAGGAGCTCTTCAGCTCTTCCTCAATGTTGACCGGT
GTAATTTCTCTCGCAAGGTCGCTCATCTAACCGCT

SEQ ID NO:39
GGCGTAAAGTACGCGACGGTGTACCGGCTTCAGGCCATCTCGGACATCTGGCAG
CGCACGGCCAACAATGACCGACATCGCATAATCCAG

SEQ ID NO:40
ACCGATTACGTCACCAACGACACGGGCAGATTTTTTATAGGCTTTGTTCCAGTCAT
TGCCTAGTACGTTCATGGCGTAAAGTACGCGACG

SEQ ID NO:41
ACGCAGCGAGAATGGCTGCGCCATGCGGACGATCGTGTCATAGACCGCCGAGTC
ACCATGGGGATGGTATTTACCGATTACGTCACCAAC

SEQ ID NO:42
CGTATAACGCATTGCCGCCGCAGAGTCGCCGTCGATAGAACCGAAGTTACCCTG
ACCGTCTACCAGCATATAACGCAGCGAGAATGGCTG

SEQ ID NO:43
ATCAACGAAATCGACCGTCTCTTTTTCGAGATCGGCCATCAGTTCATGGGCAATTT
TCGCCAGACGGATTTCCGTATAACGCATTGCCGC

SEQ ID NO:44
AGAACCGTTCACCAGCAGGTTAGGAATTTTGGTTGGCATGACGTCCGGAATTTTT
TCCGTGCCGTCATAGTTATCAACGAAATCGACCGT

Fig. 20 continued

SEQ ID NO:45
CAGACAACCGTTGATGACTTCCGTCAGGTTGTGCGGCGGGATGTTGGTTGCCATA
CCTACGGCGATACCGGAAGAACCGTTCACCAGCAG

SEQ ID NO:46
CGTCGGGAAGTCCGGCCCCGGGATGTGTTCCATCAGCCCTTCAATGCTGATGTC
TTCATCATCAATATACGCCAGACAACCGTTGATGAC

SEQ ID NO:47
GCGGATATACACCTTGCCGCGACCGGTACGGTAAGCTTCTTCAATACCGCGACG
ACCGTTAATGATTGCCGCCGTCGGGAAGTCCGGCCC

SEQ ID NO:48
CTGATACGGAATTTCGTGGACGATAATGGTTTCACGACCGGTTTTGGCGTCAACT
TCCACTTCTGCGCGAGCGCGGATATACACCTTGCC

SEQ ID NO:49
CGCGCTGATGCCTTCCACGCGTTTTCTTTTACCAGTTCCGCAATCTTCTCGATCA
GGCGCGCTTTGTTTACCTGATACGGAATTTCGTG

SEQ ID NO:50
AACTTCACCGACCGCATCGCGTTTCACTTCAATCACGATGCGCATACCGTCTTTGT
CAGACTCGTCACGCAGCGCGCTGATGCCTTCCAC

SEQ ID NO:51
ATGGTGCAATGCCACCATGTTGATACCGAAAGAAACCTGCAACTGGGTCTGGGAG
TAGAGGTTGTTGAGCACAACTTCACCGACCGCATC

SEQ ID NO:52
GGTCACCACTTCACGGCGGTGACGAACAAACGCCGCGATGATGTCTTTCAGGTT
CATGATCTTCGGCTGACCATGGTGCAATGCCACCAT

SEQ ID NO:53
CAGCGCCACGGCTAATGCTTCAAGGATATGAGCACGATCGCGAGCTTTACGCAG
TTCGAAAATAGTACGACGGGTCACCACTTCACGGCG

SEQ ID NO:54
AACCAGCGCAGTTTTCGCTTCTGCAGGCGTCGGCGCATGACGGATCAGTTCGAT
GATCGGGTCGATGTTCGCCAGCGCCACGGCTAATGC

SEQ ID NO:55
TTCCGGACGCGCAGCATCGTCGCCAGCACGTTCGAGCATCGCGGCAACGTTGCC
CAGCTGCCACGGATTAGCAACCAGCGCAGTTTTCGC

SEQ ID NO:56
CAGAATCGCCTGAGCTTGCTGTTCGGTCAGGTAGTACAGACCATCACGCACGCC
GAACTCTGGCTCCAGCCATTCCGGACGCGCAGCATC

Fig. 20 continued

SEQ ID NO:57
ATCCAGCAGCTCTTTGTATTCGTCGAGCAGTTTTCGTGCTCAAGACCGGTCAGTT
TCTGCAAACGCAGATCCAGAATCGCCTGAGCTTG

SEQ ID NO:58
CTCCAGCTCTTCACGGATCACTTCCATCAGACGATCGGCGCTACCAAGAATACGC
AACAGTTCCGCGATCTGATCCAGCAGCTCTTTGTA

SEQ ID NO:59
TTCCAGGTTGATGTCTGCGCTGTTGGCGGTGATTTCAGTACGACGTTTGTCACCG
AACTGTTCACGAACCAGCTCCAGCTCTTCACGGAT

SEQ ID NO:60
AGAAAGCGGCTGATACTTAACGTAGCCCTGGTGAGAGAGCGTCACGACCACATC
TTCCTGGGTGATCAGATCTTCCAGGTTGATGTCTGC

SEQ ID NO:61
GTCGATAAAGTCTTCTTCTTTAATACGTGCGGCAGATTTACCTTTCCCGCCACGAC
GCTGCGCTTCGTATTCAGAAAGCGGCTGATACTT

SEQ ID NO:62
TTTCATCGAATAGACGCGACCACGGCTGGAGAAGCACAGAATATGGTCGTGAGT
GTTCGCCACCAGCAGTCGGTCGATAAAGTCTTCTTC

SEQ ID NO:63
CTGCTCCAGCGGCAGCAGGTTGACGATCGGACGACCGCGCGCGCCACGAGTGG
CTTCCGGCAACTGATAAACTTTCATCGAATAGACGCG

SEQ ID NO:64
AGCGGTCGCCATGAAGACTTTCACGCCTTCTTCAAACTCGGTCACTGGCAGGATC
GCAGTGATACGTTCGTCCTGCTCCAGCGGCAGCAG

SEQ ID NO:65
TTTGATCGCCACTTTACCGGCGGTACGCAGACGGTTGAACTCGGTGAGGACAGTT
TTCTTCACGGTACCGTTAGCGGTCGCCATGAAGAC

SEQ ID NO:66
AGCGGAGAACAGCATTACTTCGTCTTCGCCGCTGGTCAGGTCAACGCCGATCAG
CTCATCGCCGTCAACCAGTTTGATCGCCACTTTACC

SEQ ID NO:67
ACCGCGAACACCGGTGGTGTTGCAGCCCATCGCACGGACAGAAGACTCTTTAAA
GCGCACCACTTTACCTTCAGCGGAGAACAGCATTAC

SEQ ID NO:68
TGCGGTGAGGATTGCGCCATCGCCACGAGGCACGATCAGAGAGACGACTTTATC
GCCTTCACCTAAGCGAATACCGCGAACACCGGTGGT

Fig. 20 continued

SEQ ID NO:69
AACCCCTTTCGTCGCACGCGACTTGGTTGGGTATTCCGCCACTGCGGTACGTTTA
CCGTAACCGTTTTGCGTTGCGGTGAGGATTGCGCC

SEQ ID NO:70
GATCTGGTCGCAGTCATCTACCTGTACCGCGCCAACAACTAAACCGTTACGTTCG
GTAACCTTGATGGAGATAACCCCTTTCGTCGCACG

SEQ ID NO:71
GGTGTTACGGCCCACGATGCTGATTTCCGAAACGCGAGTACGTACCAGCGTACC
GGCATCGGTGATCATCATGATCTGGTCGCAGTCATC

SEQ ID NO:72
AACCGGTTCAGCAACACGTTGCAGACCCACTACGTTTTCATCTTCCGCAGTACGG
ATGAGGATCACGCCCTGGGTGTTACGGCCCACGAT

SEQ ID NO:73
GTCCACTTCCGGAGCGATTTCATCGTCCCCTTCCGCGGCACTGCCGTCGATGGT
ATCCAGATCTTCCTCGTCAACCGGTTCAGCAACACG

SEQ ID NO:74
ATTCAAACAAGGGAGATAGCTCCCTTTTGGCATGAAGAAGTAAAATTATTCTTCTT
CTGGCTCGTCGTCAACGTCCACTTCCGGAGCGAT

SEQ ID NO:75
TTACGCACCGCATCCAGCCCTTTCAGGACTTTGATACTGGAGGAGTCATAAGAAT
TCGACATCAACGTTTCTCGCTCATTTATACTTGGG

SEQ ID NO:76
TCTACCACCTCGAATACCATGTGGTGCAGACCGGTGCCGTCATCCGTGTCGCCG
ATATACATACCCGGGCGCTTACGCACCGCATCCAGC

SEQ ID NO:77
ACAGAGTTATCGGCGTGAATGGTGACGATAATTTCTTTACAGTGACCCGCGAGCG
CTTCGTCGATAGCGTTATCTACCACCTCGAATACC

SEQ ID NO:78
ACTTCCGCCGCCGATACGCCCTCTTCCGGGTGAATACCGGTCGGAATGCCGCGC
CCGTCATCCTGTACAGAGACAGAGTTATCGGCGTGA

SEQ ID NO:79
CCGTGCAGACCGCCGGACACTTTATAGGAGTTATCGTCAAATTTACCGCCTGCGT
GCAGAACGGTCATGATCACTTCCGCCGCCGATACG

SEQ ID NO:80
TGAATTTTACCCTCGCGCTGGATAACCAGCTCCAGTTTTTGCGACAGGGCGTTTA
CTACCGAAACACCAACGCCGTGCAGACCGCCGGAC

Fig. 20 continued

SEQ ID NO:81
GTGCCGGTTTTTCAGTCTCGCCGGTAACCGCCAGCGGGGCCTGCGGTACACCG
TGTTCGTAGATCTGACGGTGAATTTTACCCTCGCGC

SEQ ID NO:82
TTCGCCAGAATTTCATATTCGAACTCGGTCACATTGGTGAAGGTTTCGAGGCTGG
GCCAGAAACGCACCATGGTGCCGGTTTTTCAGTC

SEQ ID NO:83
TCTTTGCCGTCGCGCTTGTCGCGCAGACGAATGGAAACGCCGGAGTTGAGGAAC
GACAACTCACGCAGACGTTTCGCCAGAATTTCATAT

SEQ ID NO:84
TGGATCGGCGTTTTGTTCTTGTTCAGATATTCAACGAACGCCTTGATGCCGCCTTC
ATAGTGGAAGTGGTCTTCTTTGCCGTCGCGCTTG

SEQ ID NO:85
CCATCGTTCCACTGCAACGCCACTTCGACGCCAATACCGTCTTTTTCAGTGGAGA
AGTAGAAGATATTCGGGTGGATCGGCGTTTTGTTC

SEQ ID NO:86
AAGCCTGCCAGGTGAGTACCGCCGTCACGCTGCGGAATGTTGTTGGTAAAGCAG
TAGATGTTTTCCTGGAAGCCATCGTTCCACTGCAAC

SEQ ID NO:87
CTGACTTTGGCTTTTTTGCTGTAGCCTTCTTTGTCCATGTAGGCGTTCAGGGTACG
GGTCATCGCCGCACGGAAGCCTGCCAGGTGAGTA

SEQ ID NO:88
GAGAATTTCGGGTCCGGCACTTTCACGGAAACGACCGCAATCAGGCCTTCACGC
GCATCGTCACCGGTGGCGCTGACTTTGGCTTTTTTG

SEQ ID NO:89
AGCAGTTCGTTCATCTGCTGTTCAACCGCCGATTTCACCTCAGAAGAAACCAGTTT
GTCTTTGGTCTGGGAGGAGAATTTCGGGTCCGGC

SEQ ID NO:90
GCACGGGCAGCATCGATAATTTTGCCAACCACGATTTTCGCGTCGGTTGGGTTTT
CCAGCAGGTATTCTGCCAGCAGTTCGTTCATCTGC

SEQ ID NO:91
CCCGGCAGGCCCGCTAAGTCGAGCGCACCTTTACGGCGGGTCATTTCACGCGCG
CGACGCGCCGCTTCACGGGCACGGGCAGCATCGATA

SEQ ID NO:92
CCCGCGGAGTCCCCTTCCACCAGGTACAGTTCGGAAAGCGCCGGATCGCGTTCC
TGGCAGTCTGCCAGTTTGCCCGGCAGGCCCGCTAAG

Fig. 20 continued

SEQ ID NO:93
ACGTTGAGGATTTTACCCTTCAGCGGCAGAATCGCCTGGTTCTTGCGGTTACGCC
CCTGCTTCGCAGAGCCGCCCGCGGAGTCCCCTTCC

SEQ ID NO:94
CCACAGCCAAGCGCGGTGATAAGCGTCGCCACTTCCTGAGAAGAGAGCATCTTA
TCGAAGCGCGCTTTCTCGACGTTGAGGATTTTACCC

SEQ ID NO:95
ACGTCCGCATCGGTCATGATGATGATGCTGTGATAACGCAGTTTGTCCGGGTTGT
ACTCGTCACGACCGATACCACAGCCAAGCGCGGTG

SEQ ID NO:96
CCGCGTTCAACGATTTCCGGCATCTGACGATAGAAGAAGGTCAACAGCAGCGTAC
GAATGTGCGAGCCGTCGACGTCCGCATCGGTCATG

SEQ ID NO:97
TCGTCTTTAATGTACTGTTCCTGCTTGCCTTTCTTCACTTTGTACAGCGGCGGCTG
AGCGATGTAGACGTGACCGCGTTCAACGATTTCC

SEQ ID NO:98
GGTGCACTGGCGTTGGTGTGCAGCGTTGCGCCGTCCAGCGCGATAGAGATCTGG
TACTGATCCATCGCTTCGTCGTCTTTAATGTACTGT

SEQ ID NO:99
ATACGATTGATCATTTTCTGCGTCGCGTTGTACTCAGATACCAGTTTCTCTAACGC
TTCGCCAGCCAATGCCGGTGCACTGGCGTTGGTG

SEQ ID NO:100
GAAAGGTCAGCTTCCGTCAACGTCGGCTGATAGATAAGCTCTTTCAGCATTGCTT
TCGGATAACGACGCTCCATACGATTGATCATTTTC

SEQ ID NO:101
CTGCCGTGCTGTTCTTTGTCGTTCAGTTCGCTGACCAGCGCGTTCACCCAGCGG
GTAACGGTCTGCTCATCAGAAAGGTCAGCTTCCGTC

SEQ ID NO:102
TGGGTACGCACGCGAACAATCGGCTCGAACAGGTTTTGCTCAGCATTGGTGTGAA
CATCAAACTTCCACTGGCTGCCGTGCTGTTCTTTG

SEQ ID NO:103
AGCGTGCAGATACGACGATATTCGCCACCGGTGATAAACTCGTGATCCAGCGGAT
AGTCAGTATCCACACCGTGGGTACGCACGCGAACA

SEQ ID NO:104
GCTACCGGCTGACGACGCTCGCCACGTTCGATAAACGCATCTTCTTCCAGCAAGC
CACGCAGTTTCTCACCCAGCGTGCAGATACGACGA

Fig. 20 continued

SEQ ID NO:105
CCTTTATAACGCTGGATGGAGAGGCCGCGACGGGACTCTTTCACCAGCCAGTCC
AGCGCCTGCTCGAAGCTGGCTACCGGCTGACGACGC

SEQ ID NO:106
ACGCGCAGCATACGACGACTTTCCGGGTCCATAGTGGTTTCCCACAGCTGTTCCG
GGTTCATCTCGCCCAGACCTTTATAACGCTGGATG

SEQ ID NO:107
CGGCGCGGTTCAACGGCGTCGCCCATCAGCGTGGTGAACAACTGGTCGGCAGC
AATCGCATCTTTAACGGTAACGCGCAGCATACGACGA

SEQ ID NO:108
GCACGCTCGCATGGTTAGCGCCATTAAATATCGATATTCGCCGCTTTCAGGGCGT
TCTCTTCAATAAACGCACGGCGCGGTTCAACGGCG

SEQ ID NO:109
GTAGTTTAAGTAGGCGTTTTCCGTAAATTCATGTAGCGCAAGGCGCTCTGCCATAT
CGCTCATTAATTCTGATTCCTCAACTTATTCGCC

SEQ ID NO:110
AATGCGGCGCTGAACAGGTTTCAGACCATCACCAATAAACGGCAACGCACGGTC
CATGATCACGTACATGGAGTAGTTTAAGTAGGCGTT

SEQ ID NO:111
GTCACCGACGGTACGGGCCGATTTTTTAAATTTGGCGCTGGCATTCAGGCCCAGT
TCAGACATCGCATACACAATGCGGCGCTGAACAGG

SEQ ID NO:112
GAACGGTTGCGCCATCAGGACCATCGCTTCATAACAGGCGCTATCGCCGTGCGG
ATGGTATTTACCCAGTACGTCACCGACGGTACGGGC

SEQ ID NO:113
TGCCGCGAACGATTTCGGATCGTCCGGCGCGCCCCAGTTCCCCTGACCATCAAC
CAGCGGATAACGGTAAGAGAACGGTTGCGCCATCAG

SEQ ID NO:114
AGCCGTCCCCTGCCCCAGCTCGCTCAATAGCAGCTCGGAATATTTCGACAACCG
GGATTCGGTGTAACGCATTGCCGCGAACGATTTCGG

SEQ ID NO:115
CAAAATGTTTGGCAGACGGGCAGGTAGCATTTTCGGCTCCTGCAAAGTGCCGTC
GAAGTTTGGCACCCAGTCAGCCGTCCCCTGCCCCAG

SEQ ID NO:116
AGCCACTTCACGCAGGTTATGCGGTGGAATATCGGTCGCCATGCCGACGGCAAT
ACCGGTGGTGCCGTTAAGCAAAATGTTTGGCAGACG

Fig. 20 continued

SEQ ID NO:117
CGGCCCCTGCACGATATCCAGCAGCTGATCGAGCGTGGTTTTCGGCTGGTCGAT
TAATGCGATTGCCGCCTGAGCCACTTCACGCAGGTT

SEQ ID NO:118
ACCACGTCCGTTCTCGTAGATTTTACGGATCTCGGCGCGCGAAGTGATAATTTCC
GCTTCAGTCGGATAATCCGGCCCCTGCACGATATC

SEQ ID NO:119
AACCTGATGCGGCAATGCGCTGATAACCACCGCGCCATCTTCTTTCTTCCACACC
GCGCGCATACGCACTGAACCACGTCCGTTCTCGTA

SEQ ID NO:120
AGATCGTCAACCATCGGCAGCTTTTGTTGCGCATTTGCGCAGCAATTTGCTCCA
GTACGCGCGCACCTGAAACCTGATGCGGCAATGCG

SEQ ID NO:121
TCCATATCCACGCGGTTGGAACGCGGCACAATCACCAGGCGGGTCGGGTTCTCG
TGGTCAGATTCATCGCGCAGATCGTCAACCATCGGC

SEQ ID NO:122
CCGATCATATTAAGGTTAATACGATAGCTCTTTTCCAGATCGGTGGTAGCGAAGA
GGTGGTTCATCACCTGATCCATATCCACGCGGTTG

SEQ ID NO:123
GTATCGCGGCGGAACACCAGCCATTCGGAGAGGATTTCCAGCAGGTTTTTCACC
GCCGGACGACCATCCAGACCGATCATATTAAGGTTA

SEQ ID NO:124
ACCAGCAAACCTTCGAGGATATGCAGGCGCTTGAGGACTTTCTCCAGACGATAGT
TCAGTCGGCGGCGCACGGTATCGCGGCGGAACACC

SEQ ID NO:125
GACATCAGCGCCGGTTTCGGTTCATCTTCATTACGAATGATCTCAATCACTTCGTC
GATATTGAGAAACGCCACCAGCAAACCTTCGAGG

SEQ ID NO:126
TCCAGTTTGGCAAGATGACGCAGTTTCAGTTCGAGGATCGCTTCCGCCTGGGTTT
CCGTAAGGCCAAACCGCGACATCAGCGCCGGTTTC

SEQ ID NO:127
GAAGCCAAAATGCCCTGCAACTGGTCGCGCTCTTTTTCCAGTTCACTCTGCTCAC
CGCGAATCTTCATCTCTTCCAGTTTGGCAAGATGA

SEQ ID NO:128
CGACGATCGTCACCGTAGGCTTGCGCGTCTGCCTGCAGTTCTTTCTTCAGCAGGT
TATTCATTTTACGCTCGGAAGCCAAAATGCCCTGC

Fig. 20 continued

SEQ ID NO:129
GTGACAGGTTCAGACGGCAGCATGTCGTGCTCGCTCATCGCTTTCGCTTCTTCGC
GTTCCTGCAACGGCGAACGACGATCGTCACCGTAG

SEQ ID NO:130
TAATTCAGGCCCGGCGCGTCGATATCATGGCCTTTAGCGCTGCGTACCCAGCCC
ATCTGCGACAGCACAATGGTGACAGGTTCAGACGGC

SEQ ID NO:131
GTGGAATCAACAAACACTACCGGTTGGTTGCTCTTACCTTTCACCGCCGCTTTGA
AGCTATCACCCGCTTTATAATTCAGGCCCGGCGCG

SEQ ID NO:132
TTGCCGGTGAGCGGCTCGCCCTGACCACGCGCCGACGGCAGCGTAATCGGGTC
AATGGCATAGCTACGACCGGTGGAATCAACAAACACT

SEQ ID NO:133
GCCATCAGCAGTTTCTGATCGTCGCTTTCCATCAGCATATGGTCAACGGTCGCCC
CAGGCGGCAACGTTAATTTGCCGGTGAGCGGCTCG

SEQ ID NO:134
AAAGCCTTACCTGCACGGTTACGCGCCACCAGATCGTTAAAGGTGCAGACGAAAC
CGTAACCCGCATCGGAAGCCATCAGCAGTTTCTGA

SEQ ID NO:135
GCCAGCAGCATATCGGAAGCATCTTCAATCACCACCGGCGGCATAACATGGGCA
TTTTCCGGTAAGGTGATCAAAGCCTTACCTGCACGG

SEQ ID NO:136
TTGCCTTTGCCCTTCGACAGCTGCGGCAGATCACTTACCGGGAACATCAACATAC
GGCCTGCCTGAGTGATTGCCAGCAGCATATCGGAA

SEQ ID NO:137
GGCAGAACGTACAATTGCGCCAGACCATCTTCTCCACGCGCGGCTTCTGCCGAT
GGAATGTTGATAATCTTGTTGCCTTTGCCCTTCGAC

SEQ ID NO:138
ACTTTCTGTAACTCTTCCGGGCGCAGTTTAATTTTGCGTTTCCCAACATGAATGGT
CAGCGTGCTTTGCGGCGGCAGAACGTACAATTGC

SEQ ID NO:139
GAGTCGATCTCAACACGATCGATACGCTGCAAACCGCGCATCAACGTACCGCGG
CGTCCACGTTCGCCAGTGACTTTCTGTAACTCTTCC

SEQ ID NO:140
TGCAAGCGGGAGGAAACAGCGCCCTCCCCGGCATATTACTCTTCGCTATCACCG
CTGCTGGCACGGCGAGGAGAGTCGATCTCAACACGA

Fig. 20 continued

SEQ ID NO:141
CGGCGAACCGGCTCAAGCCCGGTGAGTACCTCAATGGCATCAGCGTTATAAGTTT
GCGTCATGGTTTAAGTTAGTAATTCGAGTTGATCG

SEQ ID NO:142
TCCACACTGTTATCAATGACTTCTTGCCCCAAATGGTTAGGGCGAGTGGTATCGG
TATACATCCCCGGACGGCGGCGAACCGGCTCAAGC

SEQ ID NO:143
TCAATAACTTCTAACGACTGGTCAGCATGTAAAATAACGTCCACGCGTTTTGCGTG
ACCCGCCAGTGCTTCATCCACACTGTTATCAATG

SEQ ID NO:144
CGGCAAAGAATCAGTTCAACCGCCGGTACACCCTCTTCCGGGTGAATATCCACCG
GCATCCCGCGCCCATCGTCAATAACTTCTAACGAC

SEQ ID NO:145
GAAATCCCCACGCCATGCAGGCCGCCAGAGAACTGGTAATTTTTGTTAGAGAATT
TACCGCCTGCATGCAGACGGCAAAGAATCAGTTCA

SEQ ID NO:146
AAGGCGATGTTATAAACCTGACCATCGCGGCGCACGTTAACTTCTACGCGCTTCG
ACAGGGCGTTAACCACCGAAATCCCCACGCCATGC

SEQ ID NO:147
ACACTGGTACCAGTATTGCGTTTACCGCAAGTGCCGACAACCTGTAAATCCTGCA
CCTTTTCGCCATTTTCAAAGGCGATGTTATAAACC

SEQ ID NO:148
TTCAGCACATGCGTCAGGCGTGAAACAGAAAATCGCGGGCTGTCAAAGAAGGTTT
CATCCGGCCAGAAGTGCACACTGGTACCAGTATTG

SEQ ID NO:149
CAGCGTTGTTCGGTATTGTTGATCTCATCTTTAAAAGTGATCTCAACGCCAGGGCA
CAATACCGCTTTGGCTTTCAGCACATGCGTCAGG

SEQ ID NO:150
GGTTTTTCCGGCAGCGTCGGCAGACCATTTACCGCTTCCGCCAGGTAATCATTCA
GACCGTCCTGATAGCACCAGCGTTGTTCGGTATTG

SEQ ID NO:151
TCACCGCCTTCCGGCAGCCACAGTAGCGCCCAGTCCACAGCTTCAGTATCACCA
GCGAAATTACCGATAAACGGTTTTTCCGGCAGCGTC

SEQ ID NO:152
TGACGCAGACCATTAACATGGGTACCGCCCTGCATCGTTGGGATAAGGTTGACGT
AGCTTTCGGTCAGCAGTTCACCGCCTTCCGGCAGC

Fig. 20 continued

SEQ ID NO:153
GCCGACAGCTTTACACCGCGCGGCAGAATATTGCGGTATTCACAGAACTCACGCATCGCGTCCAACAGGCCCTGACGCAGACCATTAACA

SEQ ID NO:154
GTCTGCCCGGCAAACTGCGGATCCTGCATTTTACTGACAGCACATAGGCGCAGCGATCCCAGATATCTTCCGCCGACAGCTTTACACCG

SEQ ID NO:155
CACAGGATAAAGGCATCTTTCACCACGCCAGAAACGAATGCCGCGCATTGACGCGAAGAGAGACGCTCTTTCGTCTGCCCGGCAAACTGC

SEQ ID NO:156
CGCATACGGCGCTGGGCGCTGGAAATCGCCATCTCCGCCAGCAGTTCAGCCGCCTGAACGTTCTGGTTCAGCCACAGGATAAAGGCATCT

SEQ ID NO:157
GTACAATCAGCCAGTTTGCCAGGCAACGCCGGGCCGCTGGTCAGCTTTTTACGCACCACTTTTTTGGCCGCACGCATACGGCGCTGGGCG

SEQ ID NO:158
GCCTGCTTGGCAGATCCGCCTGCGGAGTCACCTTCCACAAGGAACAGCTCGGTACGGTTAAGGTCCTGCGCGGTACAATCAGCCAGTTTG

SEQ ID NO:159
TCGGAAGAGACTTCCCAGGTGTTAAGGATCTTACCTTTCAGTGGCATGATCGCCTGATATTCGCGATCGCGCGCCTGCTTGGCAGATCCG

SEQ ID NO:160
AGATCGTCGCTGTCAGGATCGATACCGATCGCTACCGAAATATCGTGCACTTCCTGCGAAGCCAGCACTTCGTCGGAAGAGACTTCCCAG

SEQ ID NO:161
AGCGTGGCAATGTGCAGACCATCAGAGTCCGCATCCGCGAGGATACAGATTTTGCCATAACGAAGCTGGCTCAGATCGTCGCTGTCAGGA

SEQ ID NO:162
GGTGGCAGTGCGACGTAAACGTGACCGTGTTTCACCAACGCGCGGAAATGTTTTACGAACAAAGCGCAGAGCAGCGTGGCAATGTGCAGA

SEQ ID NO:163
TCAAGTACGCCCTCTTTCTCTTCTTCCGTCAGCGCGTAATAAACCTCTTTCCCGAGATCAATACGGTAGAGCGGTGGCAGTGCGACGTAA

SEQ ID NO:164
TGCATCGGGTTCATTTCCCCCAGACCTTTAAAACGCTGGACGTTCGGCTTGCCTTTCTTGCGTTTTAATTGCTCAAGTACGCCCTCTTTC

Fig. 20 continued

SEQ ID NO:165
TGATCGTCTTCATCATCGATAGTCAACTGCACCAGACGGCGAGTGTTCGGATCAAGCGTGGTTTCGCGCAATTGCATCGGGTTCATTTCC

SEQ ID NO:166
TCTTGCAACCAGTTGCGGCGATCTTCCGAGCGTTTCTTCGCCAGCAGCATATCCATCATCGCGTCAGTACGCTGATCGTCTTCATCATCG

SEQ ID NO:167
CTTGTTTGCCCGGCCATCCTGACCGGGCAATGTTCTTTCCTTTAAACCTCAATCTCCGCCATGTCGCCTTTCTCTTGCAACCAGTTGCGG

SEQ ID NO:168
GTCGAGTTGATCCATGGTCTTGCGAGCGACTCTATCGGCACTTCTACTCCGTAATTGG

SEQ ID NO:169
TGACACAGACGCATAGGATCGATAGAGTCGCTCGCAAGCGGAAAGCAGTGCTATTG

SEQ ID NO:170
GTCGAGTTGATCCATGGTCTTGCGAGCGACTCTATCGGCACTTCTACTCCGTAATTGG

SEQ ID NO:171
TGACACAGACGCATAGGATCGAGCGCAGATGCTGTCAGCGGAAAGCAGTGCTATTG

SEQ ID NO:172
GTCGAGTTGATCCATGGTCTCTGCGCAGTACGTGCAGGCACTTCTACTCCGTAATTGG

SEQ ID NO:173
TGACACAGACGCATAGGATCATGTAGTAGTGAGCATAGCGGAAAGCAGTGCTATTG

SEQ ID NO:174
GTCGAGTTGATCCATGGTCTGAGATACGCTGCAGTCGGCACTTCTACTCCGTAATTGG

SEQ ID NO:175
TGACACAGACGCATAGGATCGAGCGCAGATGCTGTCAGCGGAAAGCAGTGCTATTG

SEQ ID NO:176
GTCGAGTTGATCCATGGTCTTGCGAGCGACTCTATCGAATATGCTGAGGTGCTGGAAC

Fig. 20 continued

SEQ ID NO:177
TGACACAGACGCATAGGATCGATAGAGTCGCTCGCACGGGATGATAATTGCGGATTGC

SEQ ID NO:178
GTCGAGTTGATCCATGGTCTTGCGAGCGACTCTATCGAATATGCTGAGGTGCTGGAAC

SEQ ID NO:179
TGACACAGACGCATAGGATCGAGCGCAGATGCTGTCCGGGATGATAATTGCGGATTGC

SEQ ID NO:180
GTCGAGTTGATCCATGGTCTCTGCGCAGTACGTGCAGAATATGCTGAGGTGCTGGAAC

SEQ ID NO:181
TGACACAGACGCATAGGATCATGTAGTAGTGAGCATCGGGATGATAATTGCGGATTGC

SEQ ID NO:182
GTCGAGTTGATCCATGGTCTGAGATACGCTGCAGTCGAATATGCTGAGGTGCTGGAAC

SEQ ID NO:183
TGACACAGACGCATAGGATCGAGCGCAGATGCTGTCCGGGATGATAATTGCGGATTGC

SEQ ID NO:184
GTCGAGTTGATCCATGGTCTTGCGAGCGACTCTATCGCACCGCTGATTCCTATCTAC

SEQ ID NO:185
TGACACAGACGCATAGGATCGATAGAGTCGCTCGCAGTTCGATGCTGTCACCATGTC

SEQ ID NO:186
GTCGAGTTGATCCATGGTCTTGCGAGCGACTCTATCGCACCGCTGATTCCTATCTAC

SEQ ID NO:187
TGACACAGACGCATAGGATCGAGCGCAGATGCTGTCGTTCGATGCTGTCACCATGTC

SEQ ID NO:188
GTCGAGTTGATCCATGGTCTCTGCGCAGTACGTGCAGCACCGCTGATTCCTATCTAC

Fig. 20 continued

SEQ ID NO:189
TGACACAGACGCATAGGATCATGTAGTAGTGAGCATGTTCGATGCTGTCACCATGTC

SEQ ID NO:190
GTCGAGTTGATCCATGGTCTGAGATACGCTGCAGTCGCACCGCTGATTCCTATCTAC

SEQ ID NO:191
TGACACAGACGCATAGGATCGAGCGCAGATGCTGTCGTTCGATGCTGTCACCATGTC

SEQ ID NO:192
GTCGAGTTGATCCATGGTCTTGCGAGCGACTCTATCCATCACCCTGACGTTGAGATG

SEQ ID NO:193
TGACACAGACGCATAGGATCGATAGAGTCGCTCGCACTGGAACGCACCAATGGAAG

SEQ ID NO:194
GTCGAGTTGATCCATGGTCTTGCGAGCGACTCTATCCATCACCCTGACGTTGAGATG

SEQ ID NO:195
TGACACAGACGCATAGGATCGAGCGCAGATGCTGTCCTGGAACGCACCAATGGAAG

SEQ ID NO:196
GTCGAGTTGATCCATGGTCTCTGCGCAGTACGTGCACATCACCCTGACGTTGAGATG

SEQ ID NO:197
TGACACAGACGCATAGGATCATGTAGTAGTGAGCATCTGGAACGCACCAATGGAAG

SEQ ID NO:198
GTCGAGTTGATCCATGGTCTGAGATACGCTGCAGTCCATCACCCTGACGTTGAGATG

SEQ ID NO:199
TGACACAGACGCATAGGATCGAGCGCAGATGCTGTCCTGGAACGCACCAATGGAAG

SEQ ID NO:200
AGATAAATCATGTCGAAAGCTACATATAAGGAACGTGCTGCTACTCATCCTAGTCCTGTTGCTGCCAAGCTATTTAATATCATGCACGAA

Fig. 20 continued

SEQ ID NO:201
TTTAATATCATGCACGAAAAGCAAACAAACTTGTGTGCTTCATTGGATGTTCGTAC
CACCAAGGAATTACTGGAGTTAGTTGAAGCATTA

SEQ ID NO:202
GAGTTAGTTGAAGCATTAGGTCCCAAAATTTGTTTACTAAAAACACATGTGGATAT
CTTGACTGATTTTTCCATGGAGGGCACAGTTAAG

SEQ ID NO:203
ATGGAGGGCACAGTTAAGCCGCTAAAGGCATTATCCGCCAAGTACAATTTTTTACT
CTTCGAAGACAGAAAATTTGCTGACATTGGTAAT

SEQ ID NO:204
TTTGCTGACATTGGTAATACAGTCAAATTGCAGTACTCTGCGGGTGTATACAGAAT
AGCAGAATGGGCAGACATTACGAATGCACACGGT

SEQ ID NO:205
ATTACGAATGCACACGGTGTGGTGGGCCCAGGTATTGTTAGCGGTTTGAAGCAG
GCGGCGGAAGAAGTAACAAAGGAACCTAGAGGCCTT

SEQ ID NO:206
AAGGAACCTAGAGGCCTTTTGATGTTAGCAGAATTGTCATGCAAGGGCTCCCTAG
CTACTGGAGAATATACTAAGGGTACTGTTGACATT

SEQ ID NO:207
AAGGGTACTGTTGACATTGCGAAGAGCGACAAAGATTTTGTTATCGGCTTTATTGC
TCAAAGAGACATGGGTGGAAGAGATGAAGGTTAC

SEQ ID NO:208
GGAAGAGATGAAGGTTACGATTGGTTGATTATGACACCCGGTGTGGGTTTAGATG
ACAAGGGAGACGCATTGGGTCAACAGTATAGAACC

SEQ ID NO:209
GGTCAACAGTATAGAACCGTGGATGATGTGGTCTCTACAGGATCTGACATTATTAT
TGTTGGAAGAGGACTATTTGCAAAGGGAAGGGAT

SEQ ID NO:210
TTTGCAAAGGGAAGGGATGCTAAGGTAGAGGGTGAACGTTACAGAAAAGCAGGC
TGGGAAGCATATTTGAGAAGATGCGGCCAGCAAAAC

SEQ ID NO:211
GCTCGTCGCGCGCACAGTTGAAGAAACATGAAATTGCCCAG

SEQ ID NO:212
TGTGCGCGCGACGAGCCGAGATTCCCGGGTAATAACTGAT

SEQ ID NO:213
ACACACAGACTGTGAGGTTGAAGAAACATGAAATTGCCCAG

Fig. 20 continued

SEQ ID NO:214
CTCACAGTCTGTGTGTCGAGATTCCCGGGTAATAACTGAT

SEQ ID NO:215
MPIQVLPPQLANQIAAGEVVERPASVVKELVKNSLDAGATRIDIDIERGGAKLIRIRDNG
CGIKKDELALALARHATSKIASLDDLEAIISLGFRGEALASISSVSRLTLTSRTAEQQEA
WQAYAEGRDMNVTVKPAAHPVGTTLEVLDLFYNTPARRKFLRTEKTEFNHIDEIIRRIA
LARFDVTINLSHNGKIVRQYRAVPEGGQKERRLGAICGTAFLEQALAIEWQHGDLTLR
GWVADPNHTTPALAEIQYCYVNGRMMRDRLINHAIRQACEDKLGADQQPAFVLYLEI
DPHQVDVNVHPAKHEVRFHQSRLVHDFIYQGVLSVLQQQLETPLPLDDEPQPAPRSI
PENRVAAGRNHFAEPAAREPVAPRYTPAPASGSRPAAPWPNAQPGYQKQQGEVYR
QLLQTPAPMQKLKAPEPQEPALAANSQSFGRVLTIVHSDCALLERDGNISLLSLPVAE
RWLRQAQLTPGEAPVCAQPLLIPLRLKVSAEEKSALEKAQSALAELGIDFQSDAQHVT
IRAVPLPLRQQNLQILIPELIGYLAKQSVFEPGNIAQWIARNLMSEHAQWSMAQAITLLA
DVERLCPQLVKTPPGGLLQSVDLHPAIKALKDE

Fig. 20 continued

SEQ ID NO:216
ATGATCAGTCTGATTGCGGCGTTAGCGGTAGATCGCGTTATCGGCATGGAAAACG
CCATGCCGTGGAACCTGCCTGCCGATCTCGCCTGGTTTAAACGCAACACCTTAAA
TAAACCCGTGATTATGGGCCGCCATACCTGGGAATCAATCGGTCGTCCGTTGCCA
GGACGCAAAAATATTATCCTCAGCAGTCAACCGGGTACGGACGATCGCGTAACGT
GGGTGAAGTCGGTGGATGAAGCCATCGCGGCGTGTGGTGACGTACCAGAAATCA
TGGTGATTGGCGGCGGTCGCGTTTATGAACAGTTCTTGCCAAAAGCGCAAAAACT
GTATCTGACGCATATCGACGCAGAAGTGGAAGGCGACACCCATTTCCCGGATTAC
GAGCCGGATGACTGGGAATCGGTATTCAGCGAATTCCACGATGCTGATGCGCAG
AACTCTCACAGCTATTGCTTTGAGATTCTGGAGCGGCGGTAA

SEQ ID NO:217
ATGAGCGACCTTGCGAGAGAAATTACACCGGTCAACATTGAGGAAGAGCTGAAG
AGCTCCTATCTGGATTATGCGATGTCGGTCATTGTTGGCCGTGCGCTGCCAGATG
TCCGAGATGGCCTGAAGCCGGTACACCGTCGCGTACTTTACGCCATGAACGTACT
AGGCAATGACTGGAACAAAGCCTATAAAAATCTGCCCGTGTCGTTGGTGACGTA
ATCGGTAAATACCATCCCCATGGTGACTCGGCGGTCTATGACACGATCGTCCGCA
TGGCGCAGCCATTCTCGCTGCGTTATATGCTGGTAGACGGTCAGGGTAACTTCG
GTTCTATCGACGGCGACTCTGCGGCGGCAATGCGTTATACGGAAATCCGTCTGG
CGAAAATTGCCCATGAACTGATGGCCGATCTCGAAAAGAGACGGTCGATTTCGT
TGATAACTATGACGGCACGGAAAAATTCCGGACGTCATGCCAACCAAAATTCCT
AACCTGCTGGTGAACGGTTCTTCCGGTATCGCCGTAGGTATGGCAACCAACATCC
CGCCGCACAACCTGACGGAAGTCATCAACGGTTGTCTGGCGTATATTGATGATGA
AGACATCAGCATTGAAGGGCTGATGGAACACATCCCGGGGCCGGACTTCCCGAC
GGCGGCAATCATTAACGGTCGTCGCGGTATTGAAGAAGCTTACCGTACCGGTCG
CGGCAAGGTGTATATCCGCGCTCGCGCAGAAGTGGAAGTTGACGCCAAAACCGG
TCGTGAAACCATTATCGTCCACGAAATTCCGTATCAGGTAAACAAAGCGCGCCTG
ATCGAGAAGATTGCGGAACTGGTAAAAGAAAAACGCGTGGAAGGCATCAGCGCG
CTGCGTGACGAGTCTGACAAAGACGGTATGCGCATCGTGATTGAAGTGAAACGC
GATGCGGTCGGTGAAGTTGTGCTCAACAACCTCTACTCCCAGACCCAGTTGCAG
GTTTCTTTCGGTATCAACATGGTGGCATTGCACCATGGTCAGCCGAAGATCATGA
ACCTGAAAGACATCATCGCGGCGTTTGTTCGTCACCGCCGTGAAGTGGTGACCC
GTCGTACTATTTTCGAACTGCGTAAAGCTCGCGATCGTGCTCATATCCTTGAAGCA
TTAGCCGTGGCGCTGGCGAACATCGACCCGATCATCGAACTGATCCGTCATGCG
CCGACGCCTGCAGAAGCGAAAACTGCGCTGGTTGCTAATCCGTGGCAGCTGGGC
AACGTTGCCGCGATGCTCGAACGTGCTGGCGACGATGCTGCGCGTCCGGAATGG
CTGGAGCCAGAGTTCGGCGTGCGTGATGGTCTGTACTACCTGACCGAACAGCAA
GCTCAGGCGATTCTGGATCTGCGTTTGCAGAAACTGACCGGTCTTGAGCACGAAA
AACTGCTCGACGAATACAAAGAGCTGCTGGATCAGATCGCGGAACTGTTGCGTAT
TCTTGGTAGCGCCGATCGTCTGATGGAAGTGATCCGTGAAGAGCTGGAGCTGGT
TCGTGAACAGTTCGGTGACAAACGTCGTACTGAAATCACCGCCAACAGCGCAGAC
ATCAACCTGGAAGATCTGATCACCCAGGAAGATGTGGTCGTGACGCTCTCTCACC
AGGGCTACGTTAAGTATCAGCCGCTTTCTGAATACGAAGCGCAGCGTCGTGGCG
GGAAAGGTAAATCTGCCGCACGTATTAAAGAAGAAGACTTTATCGACCGACTGCT
GGTGGCGAACACTCACGACCATATTCTGTGCTTCTCCAGCCGTGGTCGCGTCTAT
TCGATGAAAGTTTATCAGTTGCCGGAAGCCACTCGTGGCGCGCGGTCGTCCG
ATCGTCAACCTGCTGCCCGCTGGAGCAGGACGAACGTATCACTGCGATCCTGCCA
GTGACCGAGTTTGAAGAAGGCGTGAAAGTCTTCATGGCGACCGCTAACGGTACC

Fig. 20 continued

GTGAAGAAAACTGTCCTCACCGAGTTCAACCGTCTGCGTACCGCCGGTAAAGTG
GCGATCAAACTGGTTGACGGCGATGAGCTGATCGGCGTTGACCTGACCAGCGGC
GAAGACGAAGTAATGCTGTTCTCCGCTGAAGGTAAAGTGGTGCGCTTTAAAGAGT
CTTCTGTCCGTGCGATGGGCTGCAACACCACCGGTGTTCGCGGTATTCGCTTAG
GTGAAGGCGATAAAGTCGTCTCTGATCGTGCCTCGTGGCGATGGCGCAATCC
TCACCGCAACGCAAAACGGTTACGGTAAACGTACCGCAGTGGCGGAATACCCAA
CCAAGTCGCGTGCGACGAAAGGGGTTATCTCCATCAAGGTTACCGAACGTAACG
GTTTAGTTGTTGGCGCGGTACAGGTAGATGACTGCGACCAGATCATGATGATCAC
CGATGCCGGTACGCTGGTACGTACTCGCGTTTCGGAAATCAGCATCGTGGGCCG
TAACACCCAGGGCGTGATCCTCATCCGTACTGCGGAAGATGAAAACGTAGTGGG
TCTGCAACGTGTTGCTGAACCGGTTGACGAGGAAGATCTGGATACCATCGACGG
CAGTGCCGCGGAAGGGGACGATGAAATCGCTCCGGAAGTGGACGTTGACGACG
AGCCAGAAGAAGAATAA

SEQ ID NO:218
ATGTCGAATTCTTATGACTCCTCCAGTATCAAAGTCCTGAAAGGGCTGGATGCGG
TGCGTAAGCGCCCGGGTATGTATATCGGCGACACGGATGACGGCACCGGTCTGC
ACCACATGGTATTCGAGGTGGTAGATAACGCTATCGACGAAGCGCTCGCGGGTC
ACTGTAAAGAAATTATCGTCACCATTCACGCCGATAACTCTGTCTCTGTACAGGAT
GACGGGCGCGGCATTCCGACCGGTATTCACCCGGAAGAGGGCGTATCGGCGGC
GGAAGTGATCATGACCGTTCTGCACGCAGGCGGTAAATTTGACGATAACTCCTAT
AAAGTGTCCGGCGGTCTGCACGGCGTTGGTGTTTCGGTAGTAAACGCCCTGTCG
CAAAAACTGGAGCTGGTTATCCAGCGCGAGGGTAAAATTCACCGTCAGATCTACG
AACACGGTGTACCGCAGGCCCCGCTGGCGGTTACCGGCGAGACTGAAAAAACCG
GCACCATGGTGCGTTTCTGGCCCAGCCTCGAAACCTTCACCAATGTGACCGAGTT
CGAATATGAAATTCTGGCGAAACGTCTGCGTGAGTTGTCGTTCCTCAACTCCGGC
GTTTCCATTCGTCTGCGCGACAAGCGCGACGGCAAAGAAGACCACTTCCACTATG
AAGGCGGCATCAAGGCGTTCGTTGAATATCTGAACAAGAACAAAACGCCGATCCA
CCCGAATATCTTCTACTTCTCCACTGAAAAAGACGGTATTGGCGTCGAAGTGGCG
TTGCAGTGGAACGATGGCTTCCAGGAAAACATCTACTGCTTTACCAACAACATTCC
GCAGCGTGACGGCGGTACTCACCTGGCAGGCTTCCGTGCGGCGATGACCCGTA
CCCTGAACGCCTACATGGACAAAGAAGGCTACAGCAAAAAAGCCAAAGTCAGCG
CCACCGGTGACGATGCGCGTGAAGGCCTGATTGCGGTCGTTTCCGTGAAAGTGC
CGGACCCGAAATTCTCCTCCCAGACCAAAGACAAACTGGTTTCTTCTGAGGTGAA
ATCGGCGGTTGAACAGCAGATGAACGAACTGCTGGCAGAATACCTGCTGGAAAA
CCCAACCGACGCGAAAATCGTGGTTGGCAAAATTATCGATGCTGCCCGTGCCCG
TGAAGCGGCGCGTCGCGCGCGTGAAATGACCCGCCGTAAAGGTGCGCTCGACTT
AGCGGGCCTGCCGGGCAAACTGGCAGACTGCCAGGAACGCGATCCGGCGCTTT
CCGAACTGTACCTGGTGGAAGGGGACTCCGCGGGCGGCTCTGCGAAGCAGGGG
CGTAACCGCAAGAACCAGGCGATTCTGCCGCTGAAGGGTAAATCCTCAACGTC
GAGAAAGCGCGCTTCGATAAGATGCTCTCTTCTCAGGAAGTGGCGACGCTTATCA
CCGCGCTTGGCTGTGGTATCGGTCGTGACGAGTACAACCCGGACAAACTGCGTT
ATCACAGCATCATCATCATGACCGATGCGGACGTCGACGGCTCGCACATTCGTAC
GCTGCTGTTGACCTTCTTCTATCGTCAGATGCCGGAAATCGTTGAACGCGGTCAC
GTCTACATCGCTCAGCCGCCGCTGTACAAAGTGAAGAAAGGCAAGCAGGAACAG
TACATTAAAGACGACGAAGCGATGGATCAGTACCAGATCTCTATCGCGCTGGACG
GCGCAACGCTGCACACCAACGCCAGTGCACCGGCATTGGCTGGCGAAGCGTTAG
AGAAACTGGTATCTGAGTACAACGCGACGCAGAAAATGATCAATCGTATGGAGCG

Fig. 20 continued

TCGTTATCCGAAAGCAATGCTGAAAGAGCTTATCTATCAGCCGACGTTGACGGAA
GCTGACCTTTCTGATGAGCAGACCGTTACCCGCTGGGTGAACGCGCTGGTCAGC
GAACTGAACGACAAAGAACAGCACGGCAGCCAGTGGAAGTTTGATGTTCACACC
AATGCTGAGCAAACCTGTTCGAGCCGATTGTTCGCGTGCGTACCCACGGTGTG
GATACTGACTATCCGCTGGATCACGAGTTTATCACCGGTGGCGAATATCGTCGTA
TCTGCACGCTGGGTGAGAAACTGCGTGGCTTGCTGGAAGAAGATGCGTTTATCG
AACGTGGCGAGCGTCGTCAGCCGGTAGCCAGCTTCGAGCAGGCGCTGGACTGG
CTGGTGAAAGAGTCCCGTCGCGGCCTCTCCATCCAGCGTTATAAAGGTCTGGGC
GAGATGAACCCGGAACAGCTGTGGGAAACCACTATGGACCCGGAAAGTCGTCGT
ATGCTGCGCGTTACCGTTAAAGATGCGATTGCTGCCGACCAGTTGTTCACCACGC
TGATGGGCGACGCCGTTGAACCGCGCCGTGCGTTTATTGAAGAGAACGCCCTGA
AAGCGGCGAATATCGATATTTAA

SEQ ID NO:219
ATGAGCGATATGGCAGAGCGCCTTGCGCTACATGAATTTACGGAAAACGCCTACT
TAAACTACTCCATGTACGTGATCATGGACCGTGCGTTGCCGTTTATTGGTGATGG
TCTGAAACCTGTTCAGCGCCGCATTGTGTATGCGATGTCTGAACTGGGCCTGAAT
GCCAGCGCCAAATTTAAAAAATCGGCCCGTACCGTCGGTGACGTACTGGGTAAAT
ACCATCCGCACGGCGATAGCGCCTGTTATGAAGCGATGGTCCTGATGGCGCAAC
CGTTCTCTTACCGTTATCCGCTGGTTGATGGTCAGGGGAACTGGGGCGCGCCGG
ACGATCCGAAATCGTTCGCGGCAATGCGTTACACCGAATCCCGGTTGTCGAAATA
TTCCGAGCTGCTATTGAGCGAGCTGGGGCAGGGGACGGCTGACTGGGTGCCAA
ACTTCGACGGCACTTTGCAGGAGCCGAAAATGCTACCTGCCCGTCTGCCAAACAT
TTTGCTTAACGGCACCACCGGTATTGCCGTCGGCATGGCGACCGATATTCCACCG
CATAACCTGCGTGAAGTGGCTCAGGCGGCAATCGCATTAATCGACCAGCCGAAA
ACCACGCTCGATCAGCTGCTGGATATCGTGCAGGGGCCGGATTATCCGACTGAA
GCGGAAATTATCACTTCGCGCGCCGAGATCCGTAAAATCTACGAGAACGGACGT
GGTTCAGTGCGTATGCGCGCGGTGTGGAAGAAAGAAGATGGCGCGGTGGTTATC
AGCGCATTGCCGCATCAGGTTTCAGGTGCGCGCGTACTGGAGCAAATTGCTGCG
CAAATGCGCAACAAAAAGCTGCCGATGGTTGACGATCTGCGCGATGAATCTGACC
ACGAGAACCCGACCCGCCTGGTGATTGTGCCGCGTTCCAACCGCGTGGATATGG
ATCAGGTGATGAACCACCTCTTCGCTACCACCGATCTGGAAAAGAGCTATCGTAT
TAACCTTAATATGATCGGTCTGGATGGTCGTCCGGCGGTGAAAAACCTGCTGGAA
ATCCTCTCCGAATGGCTGGTGTTCCGCCGCGATACCGTGCGCCGCCGACTGAAC
TATCGTCTGGAGAAAGTCCTCAAGCGCCTGCATATCCTCGAAGGTTTGCTGGTGG
CGTTTCTCAATATCGACGAAGTGATTGAGATCATTCGTAATGAAGATGAACCGAAA
CCGGCGCTGATGTCGCGGTTTGGCCTTACGGAAACCCAGGCGGAAGCGATCCTC
GAACTGAAACTGCGTCATCTTGCCAAACTGGAAGAGATGAAGATTCGCGGTGAGC
AGAGTGAACTGGAAAAGAGCGCGACCAGTTGCAGGGCATTTTGGCTTCCGAGC
GTAAAATGAATAACCTGCTGAAGAAAGAACTGCAGGCAGACGCGCAAGCCTACG
GTGACGATCGTCGTTCGCCGTTGCAGGAACGCGAAGAAGCGAAAGCGATGAGCG
AGCACGACATGCTGCCGTCTGAACCTGTCACCATTGTGCTGTCGCAGATGGGCT
GGGTACGCAGCGCTAAAGGCCATGATATCGACGCGCCGGGCCTGAATTATAAAG
CGGGTGATAGCTTCAAAGCGGCGGTGAAAGGTAAGAGCAACCAACCGGTAGTGT
TTGTTGATTCCACCGGTCGTAGCTATGCCATTGACCCGATTACGCTGCCGTCGGC
GCGTGGTCAGGGCGAGCCGCTCACCGGCAAATTAACGTTGCCGCCTGGGGCGA
CCGTTGACCATATGCTGATGGAAAGCGACGATCAGAAACTGCTGATGGCTTCCGA
TGCGGGTTACGGTTTCGTCTGCACCTTTAACGATCTGGTGGCGCGTAACCGTGCA

Fig. 20 continued

GGTAAGGCTTTGATCACCTTACCGGAAAATGCCCATGTTATGCCGCCGGTGGTGA
TTGAAGATGCTTCCGATATGCTGCTGGCAATCACTCAGGCAGGCCGTATGTTGAT
GTTCCCGGTAAGTGATCTGCCGCAGCTGTCGAAGGGCAAAGGCAACAAGATTAT
CAACATTCCATCGGCAGAAGCCGCGCGTGGAGAAGATGGTCTGGCGCAATTGTA
CGTTCTGCCGCCGCAAAGCACGCTGACCATTCATGTTGGGAAACGCAAAATTAAA
CTGCGCCCGGAAGAGTTACAGAAAGTCACTGGCGAACGTGGACGCCGCGGTAC
GTTGATGCGCGGTTTGCAGCGTATCGATCGTGTTGAGATCGACTCTCCTCGCCGT
GCCAGCAGCGGTGATAGCGAAGAGTAA

SEQ ID NO:220
ATGACGCAAACTTATAACGCTGATGCCATTGAGGTACTCACCGGGCTTGAGCCGG
TTCGCCGCCGTCCGGGGATGTATACCGATACCACTCGCCCTAACCATTTGGGGC
AAGAAGTCATTGATAACAGTGTGGATGAAGCACTGGCGGGTCACGCAAAACGCG
TGGACGTTATTTTACATGCTGACCAGTCGTTAGAAGTTATTGACGATGGGCGCGG
GATGCCGGTGGATATTCACCCGGAAGAGGGTGTACCGGCGGTTGAACTGATTCT
TTGCCGTCTGCATGCAGGCGGTAAATTCTCTAACAAAAATTACCAGTTCTCTGGC
GGCCTGCATGGCGTGGGGATTTCGGTGGTTAACGCCCTGTCGAAGCGCGTAGAA
GTTAACGTGCGCCGCGATGGTCAGGTTTATAACATCGCCTTTGAAAATGGCGAAA
AGGTGCAGGATTTACAGGTTGTCGGCACTTGCGGTAAACGCAATACTGGTACCAG
TGTGCACTTCTGGCCGGATGAAACCTTCTTTGACAGCCCGCGATTTTCTGTTTCAC
GCCTGACGCATGTGCTGAAAGCCAAAGCGGTATTGTGCCCTGGCGTTGAGATCA
CTTTTAAAGATGAGATCAACAATACCGAACAACGCTGGTGCTATCAGGACGGTCT
GAATGATTACCTGGCGGAAGCGGTAAATGGTCTGCCGACGCTGCCGGAAAAACC
GTTTATCGGTAATTTCGCTGGTGATACTGAAGCTGTGGACTGGGCGCTACTGTGG
CTGCCGGAAGGCGGTGAACTGCTGACCGAAAGCTACGTCAACCTTATCCCAACG
ATGCAGGGCGGTACCCATGTTAATGGTCTGCGTCAGGGCCTGTTGGACGCGATG
CGTGAGTTCTGTGAATACCGCAATATTCTGCCGCGCGGTGTAAAGCTGTCGGCG
GAAGATATCTGGGATCGCTGCGCCTATGTGCTGTCAGTAAAAATGCAGGATCCGC
AGTTTGCCGGGCAGACGAAAGAGCGTCTCTCTTCGCGTCAATGCGCGGCATTCG
TTTCTGGCGTGGTGAAAGATGCCTTTATCCTGTGGCTGAACCAGAACGTTCAGGC
GGCTGAACTGCTGGCGGAGATGGCGATTTCCAGCGCCCAGCGCCGTATGCGTG
CGGCCAAAAAAGTGGTGCGTAAAAAGCTGACCAGCGGCCCGGCGTTGCCTGGCA
AACTGGCTGATTGTACCGCGCAGGACCTTAACCGTACCGAGCTGTTCCTTGTGGA
AGGTGACTCCGCAGGCGGATCTGCCAAGCAGGCGCGCGATCGCGAATATCAGG
CGATCATGCCACTGAAAGGTAAGATCCTTAACACCTGGGAAGTCTCTTCCGACGA
AGTGCTGGCTTCGCAGGAAGTGCACGATATTTCGGTAGCGATCGGTATCGATCCT
GACAGCGACGATCTGAGCCAGCTTCGTTATGGCAAAATCTGTATCCTCGCGGATG
CGGACTCTGATGGTCTGCACATTGCCACGCTGCTCTGCGCTTTGTTCGTAAAACA
TTTCCGCGCGTTGGTGAAACACGGTCACGTTTACGTCGCACTGCCACCGCTCTAC
CGTATTGATCTCGGGAAAGAGGTTTATTACGCGCTGACGGAAGAAGAGAAAGAG
GGCGTACTTGAGCAATTAAAACGCAAGAAAGGCAAGCCGAACGTCCAGCGTTTTA
AAGGTCTGGGGGAAATGAACCCGATGCAATTGCGCGAAACCACGCTTGATCCGA
ACACTCGCCGTCTGGTGCAGTTGACTATCGATGATGAAGACGATCAGCGTACTGA
CGCGATGATGGATATGCTGCTGGCGAAGAAACGCTCGGAAGATCGCCGCAACTG
GTTGCAAGAGAAAGGCGACATGGCGGAGATTGAGGTTTAA

Fig. 20 continued

SEQ ID NO:221
ATGTCGAAAGCTACATATAAGGAACGTGCTGCTACTCATCCTAGTCCTGTTGCTG
CCAAGCTATTTAATATCATGCACGAAAAGCAAACAAACTTGTGTGCTTCATTGGAT
GTTCGTACCACCAAGGAATTACTGGAGTTAGTTGAAGCATTAGGTCCCAAAATTTG
TTTACTAAAAACACATGTGGATATCTTGACTGATTTTTCCATGGAGGGCACAGTTA
AGCCGCTAAAGGCATTATCCGCCAAGTACAATTTTTTACTCTTCGAAGACAGAAAA
TTTGCTGACATTGGTAATACAGTCAAATTGCAGTACTCTGCGGGTGTATACAGAAT
AGCAGAATGGGCAGACATTACGAATGCACACGGTGTGGTGGGCCCAGGTATTGT
TAGCGGTTTGAAGCAGGCGGCGGAAGAAGTAACAAAGGAACCTAGAGGCCTTTT
GATGTTAGCAGAATTGTCATGCAAGGGCTCCCTAGCTACTGGAGAATATACTAAG
GGTACTGTTGACATTGCGAAGAGCGACAAAGATTTTGTTATCGGCTTTATTGCTCA
AAGAGACATGGGTGGAAGAGATGAAGGTTACGATTGGTTGATTATGACACCCGGT
GTGGGTTTAGATGACAAGGGAGACGCATTGGGTCAACAGTATAGAACCGTGGAT
GATGTGGTCTCTACAGGATCTGACATTATTATTGTTGGAAGAGGACTATTTGCAAA
GGGAAGGGATGCTAAGGTAGAGGGTGAACGTTACAGAAAAGCAGGCTGGGAAG
CATATTTGAGAAGATGCGGCCAGCAAAACTAA

MUTAGENIZING INTRACELLULAR NUCLEIC ACIDS

CROSS-REFERENCE TO RELATED APPLICATIONS

This application is the U.S. national stage of International Patent Application No. PCT/EP2017/082574, filed on Dec. 13, 2017 and entitled MUTAGENIZING INTRACELLULAR NUCLEIC ACIDS, which claims the benefit of priority under 35 U.S.C. § 119 from European Patent Application No. 16204081.0, filed Dec. 14, 2016. The disclosures of the foregoing applications are incorporated herein by reference in their entirety.

SEQUENCE LISTING

The entire content of a Sequence Listing titled "Sequence_ Listing.txt," created on May 23, 2019 and having a size of 86 kilobytes, which has been submitted in electronic form in connection with the present application, is hereby incorporated by reference herein in its entirety.

The invention refers to a method of in vivo mutagenesis of a preselected target region (PTR) of intracellular DNA by single stranded DNA oligonucleotide integration.

BACKGROUND

Large-scale mutational analysis and accelerated evolution of genes of microorganisms or other cells has been aided by in vitro mutagenesis in combination with epichromosomal expression in model organisms followed by analysis of these site-specific changes in the model systems.

However, techniques for random mutagenesis of extended genomic regions in their native genetic context suffer from serious limitations. Currently there are four different ways to elevate the in vivo mutation rate in extended regions of the cellular DNA.

The first type of protocols takes advantage of chemical mutagens, ultraviolet light or hypermutator strains and introduces mutations everywhere into the cellular DNA in an untargeted way. These methodologies lead to the accumulation of numerous undesired, off-target modifications outside a PTR posing detrimental side effects for the organism to be evolved.

The second type of mutagenesis protocols targets mutations to a PTR, but introduces them in vitro using error-prone PCR or site-saturation mutagenesis and recombines the resulting genetic repertoire into cellular DNA subsequently using CRISPR-Cas9-mediated engineering. Basically, these methods demand prior genomic modification of the host organism or time-consuming mutagenic donor template generation.

The third type of mutagenesis protocol introduces a double strand DNA break into cellular DNA and harnesses the natural increase in the mutation rate (up to 800 fold) during the break repair. With this technique there is very little control over the type and location of mutations around a break.

The fourth type of protocols applies targeted, enzymatically-induced DNA damage to achieve mutagenesis on a short PTR (<100 consecutive nucleotides).

These methods lack the ability to provide bias-free and off-target-effect free mutagenesis on extended genomic loci.

Recent progress has been made in single stranded DNA (ssDNA) recombineering, broadening the toolset for in vivo bacterial mutagenesis techniques.

Most promising among these is MAGE (Multiplex Automated Genome Engineering) which enables the efficient recombination of ssDNA oligonucleotides (oligonucleotides or oligos) into the cellular DNA (inducing in vivo synthesis of the cellular DNA through hybridizing the oligonucleotides to the PTR) and has been applied to introduce vast combinatorial mutational diversity (Wang et al. 2009). With good control over the mutational spectra and the PTR, MAGE has allowed the specific in vivo mutagenesis of short sequences such as ribosome binding sites or directed evolution of certain residues in protein coding sequences (Diner and Hayes 2009; Amiram et al. 2015). In these experiments, however, the maximum number of mutagenized neighboring nucleobase positions was always less than 30 residues. MAGE has never been demonstrated for longer continuous sequences. This is due to the fact that MAGE's efficiency is largely dependent on oligo interaction with the target sequence (Wang and Church 2011; Gallagher et al. 2014), Specifically, the efficiency of oligonucleotide integration decreases with the increasing number of mutagenized positions in the PTR, putting a practical limit to the number of positions that can be randomized with a single oligo. Additionally, efficient integration of the oligo requires strict sequence identities to the PTR at the extremities of the oligos. Thus, the PTR undergoing mutagenesis must be positioned to the center of single ssDNA oligonucleotides. The net result of these constraints is that diversification of every positions of a PTR longer than ~30 bps is not feasible using a conventional oligo design strategy.

Norwald et al. propose a tool for multiplexed DNA synthesis and homologous recombination to construct rational libraries (Nordwald et al. 2013). Recombineering is described as a method for producing genetic diversity and creating sequence-to-activity mapping libraries for protein engineering. In this method, each single amino acid substitution is introduced by a separate, rationally designed ssDNA oligo, limiting the number of possible nucleobase alterations. Reference is made to a multi-step strategy using MAGE for parallel combinatorial optimization of proteins.

U.S. Pat. No. 6,391,640 B1 discloses the evolution of genes or metabolic pathways by recursive sequence recombination (U.S. Pat. No. 6,391,640 B1: Methods and compositions for cellular and metabolic engineering). Initial substrates for recombination are cloned into a plasmid vector. A diversity of substrates may be used. Such diversity can be produced by mutagenesis.

WO 00/42561 A2 discloses oligo mediated nucleic acid recombination for in vitro DNA shuffling, thereby producing a diversity of nucleic acids (WO 00/42561 A2: Enzymes, pathways and organisms for making a polymerizable monomer by whole cell bioprocess).

Coussement et al. describe a one-step DNA assembly for combinatorial metabolic engineering. Two promoter libraries were simultaneously introduced in front of two target genes (Coussement et al. 2014).

Daiguan Yu et al. describe recombineering in *E. coli* using overlapping DNA oligonucleotides (Yu et al. 2003). Multiple overlapping oligos are described to be useful for making complex constrcuts in vivo without the need for restriction enzymes or DNA ligase.

DiCarlo et al. describe yeast oligo-mediated genome engineering for allelic replacement in yeast for short sequences (DiCarlo et al. 2013).

WO2014/102688A1 discloses a donor matrix to perform homologous recombination in cells wherein said matrix is made of single stranded oligonucleotides that partially hybridize with each other over a complementary sequence.

According to an example, the matrix is used for targeted genetic modification by homologous recombination, introducing an exogenous sequence into a genomic locus.

WO02/14495A2 discloses enhanced homologous recombination mediated by lambda recombination proteins. The DNA used in the method is a single oligonucleotide sequence, or may be two or more overlapping sequences.

There is a need for new cost effective methods for in vivo cellular mutagenesis which could cover a large PTR.

SUMMARY OF THE INVENTION

It is the objective of the invention to provide methods for in vivo intracellular DNA mutagenesis and respective libraries which cover a diversity of mutants characterized by nucleobase alterations and combinations of said nucleobase alterations throughout a predetermined region.

The objective is solved by the subject matter as claimed and further described herein.

The invention provides for a method of in vivo mutagenesis of a preselected target region (PTR) of an intracellular DNA within a cell culture, which PTR comprises at least one sequence of interest (SOI) which is at least 60 nucleobases long, the method comprising:

a) providing a pool of partially overlapping single stranded DNA (ssDNA) oligonucleotides which upon alignment form a continuous sequence that is complementary to the SOI, wherein the pool contains a diversity of mutagenizing oligonucleotides covering nucleobase mismatches at every position of said SOI and combination of said nucleobase mismatches, wherein each mutagenizing oligonucleotide is hybridizing with the PTR and comprises at least one mismatching nucleobase and up to 20% mismatching nucleobases, compared to the SOI;

b) integrating the pool into said intracellular DNA by homologous recombination and inducing in vivo mutagenesis of the intracellular DNA through hybridizing the oligonucleotides to the PTR, thereby producing a cell library comprising a repertoire of variant cells covering point mutations at every position and combinations of said point mutations within said PTR.

Specifically, the single stranded DNA oligonucleotides are provided as linear oligonucleotides without a plasmid carrier. Specifically, said ssDNA are not in the form of a plasmid.

Specifically, the diversity of the mutagenizing oligonucleotides covers at least one mismatch at every position in the nucleotide sequence of the SOI and/or a combination of two or more different mismatches at the same positions. Mutagenizing oligonucleotides specifically align to a continuous sequence which may be less than 100% complementary to the SOI, by a series of nucleobase mismatches. In the pool of oligonucleotides the diversity of mutagenizing oligonucleotides particularly provides for a certain mutation rate at every position of the SOI, thereby producing a large repertoire of variant cells which differ in the PTR sequence even at positions where the oligonucleotide overlaps were hybridizing to the PTR to induce the in vivo mutagenesis. Thereby, point mutations throughout the respective PTR (herein also referred to as the "SOI region of the PTR", i.e. the region within the PTR which is characterized by the nucleotide sequence identical to the SOI or its complementary sequence), e.g., covering mutations at every position may be introduced.

Such diversity of the mutagenizing oligonucleotides specifically produces a repertoire of variant cells which covers at least one point mutation at every position within said SOI and combination of said nucleobase mismatches, and practically a distribution of point mutations throughout said SOI, at least at one or more positions corresponding to the overlapping section of the mutagenizing oligonucleotides. Such variation of intracellular DNA at a low level is herein understood as a pattern of accelerated cellular evolution, also referred to as evolutionary pattern.

Specifically, the pattern of evolution encompasses point mutations at every position within said PTR, in particular at every position within the SOI region of said PTR, generally without any exception, but optionally except for one or more specific positions in the library which remain unchanged in the cellular repertoire (e.g. due to ssDNA oligo incorporation incompatibilities). Specifically, the evolutionary pattern may include clustering of point mutations, e.g. at predefined loci, wherein the frequency of point mutations is higher than the frequency besides a cluster. Specifically, the evolutionary pattern includes a uniform increase in the rate of ssDNA oligo mediated point mutations along the PTR. Uniform is herein understood as an average frequency of the oligonucleotide mediated mutations that is at least $10^{-7}$, $10^{-6}$, $10^{-5}$, $10^{-4}$, $10^{-3}$, $10^{-2}$ or higher within any five consecutive nucleobase positions within the PTR, in particular within the SOI region of said PTR.

Specifically, the repertoire of variant cells covers point mutations which are randomly distributed within the PTR, in particular within the SOI region of said PTR.

Specifically, the probability of point mutations at each position of the PTR can vary on a position-to-position basis, e.g. between 0 and 50%, such as at a maximum of 0.1%, 1%, 5%, 25% or 50%.

Specifically, the probability of point mutations at each position of the PTR can vary during one or more consecutive cycles of oligonucleotide pool integration and recombination, thereby the evolutionary pattern can be independently dynamic for each sequence position.

Specifically, the cells are viable cells which can be cultured in vitro in a suitable culture medium or cultivated in vivo in a host organism. Amongst suitable host organisms are model organisms, including e.g., *Caenorhabditis elegans, Drosophila melanogaster, Arabidopsis thaliana, Physcomitrella patens, Danio rerio, Fundulus heteroclitus, Nothobranchius furzeri, Anolis carolinensis, Mus musculus, Xenopus laevis* or *X. tropicalis*, or non-model vertebrates, plants, or their diseased or engineered (artificial) variants. However, it is specifically understood that the method of in vivo mutagenesis is not carried out in a human being.

Specifically, the variant cells are mutants which exhibit improved viability, survival and/or growth under a selected growth condition or show an improved functional characteristic or phenotype. Specifically, the selected growth condition comprises the presence of any of an environmental contaminant, an industrial waste product, a medical waste product, a drug or candidate drug, any nutrient, chemical substance or a selected carbon source, or one or more other organisms, such as pathogens or viruses. In other specific embodiments, the desired phenotype may be any measurable cellular trait, such as conferred by the activity or concentration of any biomolecule or cellular metabolite.

Specifically, the variant cells produced by the method are of a different phenotype associated with the variant genotype, e.g. as determined by the expression of a different type of one or more proteins, or by at least one altered functionality or drug-resistance of the cell.

Specifically, the targeted SOI region of the PTR is a contiguous region within the PTR, wherein mutations are introduced and distributed throughout the SOI region. Specifically, said repertoire of variant cells covers point mutations which are distributed throughout said SOI region of said PTR, meaning the repertoire includes variants, wherein the point mutations are found in at least one of the variants of the repertoire.

Specifically, the distribution of point mutations within the repertoire of cells or intracellular DNA is uniform. Specifically, the distribution is considered uniform, if upon statistical analysis of the mutations of said intracellular DNA, or the SOI region of the PTR in said variant cells, the repertoire covers an about equal distribution of point mutations on the population level. In this regard, a distribution is considered about equal if the average frequency of oligonucleotide mediated mutations is at least $10^{-7} 10^{-6}$, $10^{-5}$, $10^{-4}$, $10^{-3}$, $10®^2$ or higher within every five consecutive nucleobase position within the PTR, in particular within the SOI region of said PTR.

According to specific embodiments, the average number of point mutations produced in each member of the library of cells or the library of the intracellular DNA, is any of 0, 1, 2, 3, 4 or 5, or up to 20 per 100 nucleobases, preferably 0, 1, 2, 3, 4 or 5, or up to 10 per 100 nucleobases of the SOI region of the PTR. Specifically, the average number of point mutations is determined not just by the number of mismatches in the mutagenizing oligos (e.g. any of 1-20 per 100 nucleobases), but also by the content of mutagenizing oligonucleotides in the pool of oligonucleotides or the ratio of mutagenizing and non-mutagenizing oligos in the pool. Therefore, the mutation rate can even be lower than 1 point mutation per 100 base pairs.

Specifically, the continuous sequence formed upon aligning the pool of oligonucleotides with their overlaps is complementary to the SOI except for the mismatches introduced by the mutagenizing oligonucleotides. Typically, there is a region within a mutagenizing oligonucleotide, which is the core region, which is flanked at its 5' end and 3' end by the respective 5'- and 3'-terminal regions that may at least partly overlap with other mutagenizing oligonucleotides of the pool. Specifically, the continuous sequence of the SOI spans at least one overlap of two oligonucleotides, and optionally at least one or two core regions of the overlapping oligonucleotides. The core region is typically designed for aligning and hybridizing with the PTR and to introduce mutations into the PTR, in particular into the SOI region of the PTR. The 5'- and 3'-terminal sequences typically have a length of e.g. 1 to 5 or 10 nucleobases, which align and hybridize with the SOI without introducing mutations.

Figure 4:
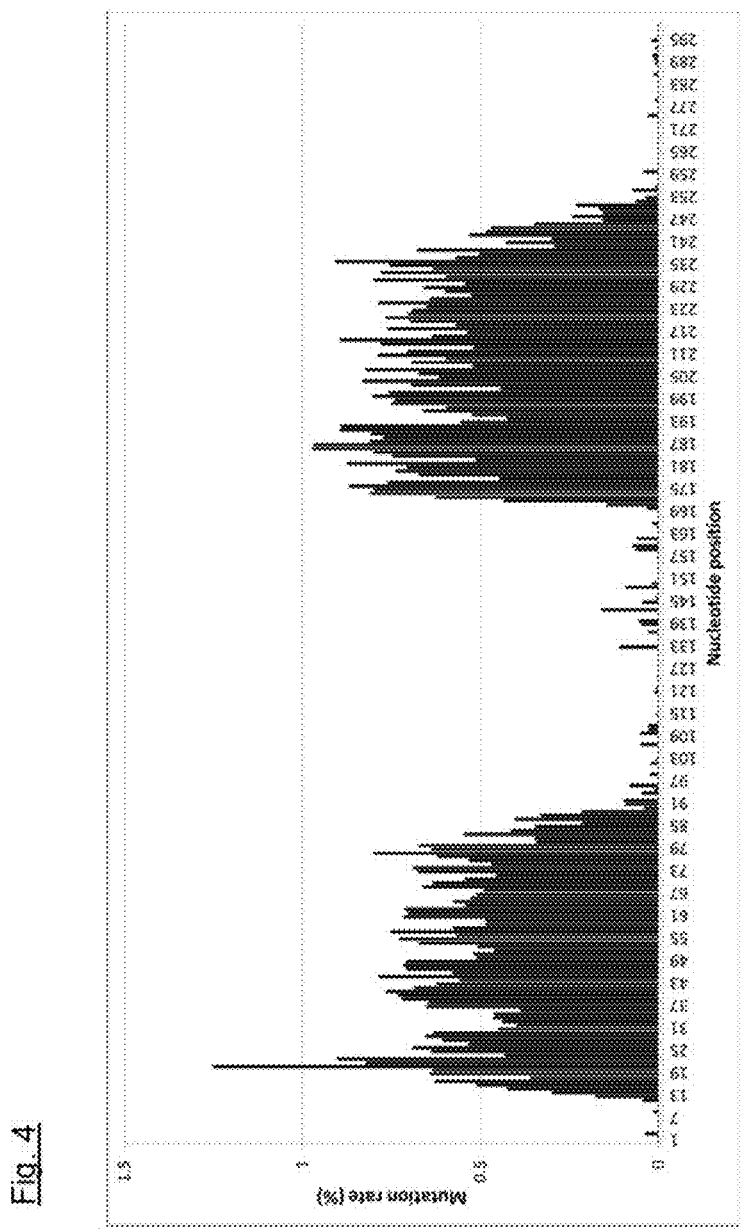

According to a specific example, a set of mutagenizing oligonucleotides of about 90 nucleotides length or the respective pool can integrate mutations (mutagenize) into a 60-80 nucleobases-long SOI (FIG. 4). In this case, the core region is 60-80 nucleobases-long. Typically, the overlapping regions of the oligonucleotides are at least one of the 5' and 3'-terminal regions of the oligonucleotides.

Unexpectedly, by using serially overlapping oligonucleotides, the oligonucleotides are even mutagenizing the SOI in the hybridizing area of the overlaps, thus supporting the uniform distribution of nucleobase alterations and point mutations throughout the continuous sequence and the SOI.

Specifically, the SOI has a length corresponding to at least 60, 70, 90, 100, 140, 250, 300, 500, 1000 or at least 2000 nucleobases. The minimal length of the SOI is calculated based on the minimum length of the oligonucleotide (e.g. 40 nt) and the minimum length of the overlap (e.g. 5 nt). Certain embodiments refer to a SOI which spans a whole gene or even a larger genomic area, e.g. of at least 1.000 nucleobases, or 2.000 nucleobases, 10.000 nucleobases, or even longer.

Specifically, each of the overlapping oligonucleotides comprises an overlap which is up to any of 50%, 25%, 10% or 5% of the oligonucleotide length, preferably at least any of 3, 5, 10, 20, 50, or 100 nucleotides long.

Specifically, each of the overlapping oligonucleotides comprises an overlap of at least 5 up to 20 nucleotides at the 5' and/or 3' ends.

Specifically, the overlaps are non-complementary, such that hybridization of the overlapping parts to a double stranded nucleic acid molecule is avoided. In particular, overlapping ssDNA oligonucleotides as used herein are characterized by regions having the same sequence. Thus, two overlapping ssDNA oligonucleotides cannot form a short double-stranded region when two ssDNA oligonucleotides meet. Specifically, each of the oligonucleotides has a length of 40-200 nucleotides, preferably 50-110 nucleotides, e.g. 90 nucleotides, and the overlaps of two oligonucleotides in the pool are up to any of 50%, 25%, 10% or 5% of the oligonucleotide length, preferably at least any of 3, 5, 10, 20, 50, or 100 nucleotides at the 5' and/or 3' ends.

Specifically, the pool of oligonucleotides comprises mutagenizing and non-mutagenizing oligonucleotides. The non-mutagenizing oligonucleotides have 100% sequence identity to the corresponding sequence within the SOL. In specific cases, at least any of 0.1%, 1%, 10%, 50%, 75%, up to 100% of the oligonucleotides contained in said pool are mutagenizing oligonucleotides.

Specifically, a majority of the mutagenizing oligonucleotides comprises less than 20 e.g., less than 15, 10, 7, 5, 4, 3, or 2, mismatching nucleobases, or less than 6 e.g., less than 5, 4, 3, or 2, codon substitutions per 100 nucleobases.

Specifically, the pool of oligonucleotides comprises mutagenizing oligonucleotides, which comprise a combination of mismatching nucleobases, thus more than one mismatching nucleobases. For example, the pool may contain more than one repertoire of mutagenizing oligonucleotides, e.g. at least i) a repertoire, wherein each mutagenizing oligonucleotide comprises one mismatching nucleobase, and
ii) a repertoire, wherein each mutagenizing oligonucleotide comprises a combination of 2 or more mismatching nucleobases, in particular mismatches at different positions within the oligonucleotide.

Specifically, the pool contains a diversity of mutagenizing oligonucleotides covering nucleobase mismatches at every position of said SOI and combinations of said nucleobase mismatches corresponding to the same position of said SOI or different positions, wherein said combinations of nucleobase mismatches are through combination of mutagenizing oligonucleotides, which are oligonucleotides each characterized by any of 1, 2, or more mismatching nucleobases, or preferably by a mixture of oligonucleotides each characterized by any of 1, 2, or more mismatching nucleobases, preferably wherein the mismatching nucleobases correspond to different positions within said SOI.

Specifically, the majority of the oligonucleotides (>50%) or each of the oligonucleotides has a length of 40-200 nucleotides, preferably 60-100 nucleotides, e.g. at least any of 70, 80, 89, 90 or 100 nucleotides, and the overlaps are up to any of 50%, 25% or 10% of the oligonucleotide length, preferably at least any of 3, 5, 10, 20, 50, or 100 nucleotides at the 5' and/or 3' ends.

Specifically, the mutagenizing oligonucleotide is hybridizing to the PTR and in particular hybridizing to the SOI region of the PTR, thereby mutagenizing the SOI region of the PTR by integrating the mismatches into the SOI e.g. by homologous recombination, if the cell is any that enables homologous recombination through endogenous or heterologous enzymes present in the cells. Specifically, homologous recombination provides an integration of homologous polynucleotide segments along the length of the oligonucleotide and the cellular DNA which results in the replacement of the corresponding region within the SOI region of the PTR, which is serving as a substitute for the previous or original SOI region.

Specifically, each of the non-mutagenizing oligonucleotides is characterized by a sequence identity of about 100% compared to the SOI and PTR, respectively.

Specifically, each of the mutagenizing oligonucleotides is characterized by a sequence identity of at least any of 80%, 90%, 95%, or even higher, compared to the PTR. Specifically, each of the mutagenizing oligonucleotides hybridizes to the PTR under physiological conditions, or at least has a region within the oligonucleotide that hybridizes under physiological conditions.

Specifically, the mutagenizing oligonucleotide is hybridizing with the respective sequence within the PTR, in particular the SOI region of the PTR, thereby inducing integration of the oligonucleotide at the corresponding position within the SOI region of the PTR. The degree of sequence identity necessary for hybridizing homologous sequences varies, e.g. depending on the type of cell and its mismatch repair system, or the media and culture conditions used. Specifically, homologous recombination can be carried out under stringent conditions.

Specifically, the oligonucleotide integration technique employs any of ssDNA-binding protein mediated recombination, MAGE, bacterial homologous recombination, yeast homologous recombination, mammalian homologous recombination, plant homologous recombination, ssDNA-mediated recombineering, Lambda Red recombineering, pORTMAGE recombineering, CRISPR/Cas9, BuDs, ZFNs, TALEs, and TALENs or natural competence or any alternative methods of in vivo mutagenesis using ssDNA as a template.

Specifically, the oligonucleotide is a linear polymer of nucleotide monomers and comprises "A" denoting deoxyadenosine, "T" denoting deoxythymidine, "G" denoting deoxyguanosine, and "C" denoting deoxycytidine or besides conventional bases (A, G, C, T) can comprise nucleotide-analogs e.g., inosine and 2'-deoxyinosine and their derivatives (e.g. 7'-deaza-2'-deoxyinosine, 2'-deaza-2'-deoxyinosine)azole- (e.g. benzimidazole, indole, 5-fluoroindole) or nitroazole analogues (e.g. 3-nitropyrrole, 5-nitroindole, 5-nitroimidazole, 4-nitropyrazole, 4-nitrobenzimidazole) and their derivatives, acyclic sugar analogues (e.g. those drived from hypoxanthine- or indazole derivatives, 3-nitroimidazole, or imidazole-4,5-dicarboxamide), 5'-triphosphates of universal base analogues (e.g. derived from indole derivatives), isocarbostyril and its derivatives (e.g. methylisocarbostyril, 7-propynylisocarbostyril), hydrogen bonding universal base analogues (e.g. pyrrolopyrimidin), and other chemically modified bases (such as diaminopurine, 5-methylcytosine, isoguanine, 5-methyl-isocytosine, K-2'-deoxyribose, P-2'-deoxyribose) or e.g. others modified bases which can have different base-pairing preferences and can pair with more than one natural nucleobase with similar stringency/probability. The monomers are linked by phosphodiester linkage or in certain cases, by peptidyl linkages or by phosphorothioate linkages or by any of the other types of nucleotide linkages.

Specifically the ssDNA oligonucleotide (herein simply referred to as oligonucleotide) is or comprises natural nucleosides (e.g. adenosine, thymidine, guanosine, cytidine, uridine, deoxyadenosine, deoxythymidine, deoxyguanosine, and deoxycytidine); nucleoside analogs (e.g., inosine, or 5-methylisocytosine, or 3-nitropyrrole, 5-nitroindole, pyrrolidine, 4-nitroimidazole, 4-nitropyrazole, 4-nitrobenzimidazole, 4-aminobenzimidazole, 5-nitroindazole, 3-nitroimidazole, 5-aminoindole, benzimidazole, 5-fluoroindole, indole, methylisocarbostyril, pyrrolopyrimidine 7-propynylisocarbostryril, 2-aminoadenosine, 2-thiothymidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-amino-adenosine, 7-deaza-adenosine, 7-deaza-guanosine, 8-oxoadenosine, 8-oxoguanosine, 0(6)-methylguanine, and 2-thiocytidine); chemically or biologically modified bases (including methylated bases); intercalated bases; modified sugars (e.g., ribose, 2'-deoxyribose, arabinose, and hexose); and/or modified phosphate groups (e.g., phosphorothioates and 5'-N-phosphoramidite linkages).

Specifically, the single stranded oligonucleotide pools can be produced by any of the chemical polynucleotide (oligonucleotide) synthesis methods, including the H-phosphonate, phosphodiester, phosphotriester or phosphite triester synthesis methods or any of the massively parallel oligonucleotide synthesis methods, e.g. microarray or microfluidics-based oligonucleotide synthesis (e.g. as described in References (Gao et al. 2001) (LeProust et al. 2010) (Bonde et al. 2014)).

Specifically, the single stranded oligonucleotide pools can be produced by any of the enzymatic polynucleotide (oligonucleotide) synthesis methods, including ssDNA synthesis by DNA polymerase proteins or by reverse transcriptase proteins, which produce hybrid RNA-ssDNA molecules. Specifically, the enzymatic polynucleotide synthesis reaction can occur in vivo or in vitro.

Specifically, the oligonucleotides are produced by synthesizing the oligonucleotide sequence from nucleotide building blocks by any of the polynucleotide synthesis methods, wherein the building blocks are comprised of "A" denoting deoxyadenosine, "T" denoting deoxythymidine, "G" denoting deoxyguanosine, or "C" denoting deoxycytidine or other natural nucleosides (e.g. adenosine, thymidine, guanosine, cytidine, uridine), nucleotide-analogs e.g., inosine and 2'-deoxyinosine and theirs derivatives (e.g. 7'-deaza-2'-deoxyinosine, 2'-deaza-2'-deoxyinosine), azole- (e.g. benzimidazole, indole, 5-fluoroindole) or nitroazole analogues (e.g. 3-nitropyrrol, 5-nitroindol, 5-nitroimidazole, 4-nitropyrazole, 4-nitrobenzimidazole) and their derivatives, acyclic sugar analogues (e.g. those drived from hypoxanthine- or indazole derivatives, 3-nitroimidazole, or imidazole-4,5-dicarboxamide), 5'-triphosphates of universal base analogues (e.g. derived from indole derivatives), isocarbostyril and its derivatives (e.g. methylisocarbostyril, 7-propynylisocarbostyril), hydrogen bonding universal base analogues (e.g. pyrrolopyrimidine), or any of the other chemically modified bases (such as diaminopurine, 5-methylcytosine, isoguanine, 5-methyl-isocytosine, K-2'-deoxyribose, P-2'-deoxyribose). The building blocs are linked by phosphodiester linkage or peptidyl linkages or by phosphorothioate linkages or by any of the other types of nucleotide linkages.

Specifically, the single stranded oligonucleotide pools are produced by synthesizing the oligonucleotide sequence from monomer-building blocks, dimer-building blocks (Neuner, Cortese, and Monaci 1998) or trimer-building blocks (Sondek and Shortle 1992), (e.g. natural dimer-nucleotide building blocks, including 5'-dA-dC-3', 5'-dA-dG-3', 5'-dA-dT-3', 5'-dA-dA-3', 5'-dT-dC-3', 5'-dT-dG-3', 5'-dT-dT-3', 5'-dT-dA-3', 5'-dG-dC-3', 5'-dG-dG-3', 5'-dG-dT-3', 5'-dG-dA-3', 5'-dC-dC-3', 5'-dC-dG-3', 5'-dC-dT-3', 5'-dC-dA-3' or their derivatives; or natural trimer-nucleotide building blocks, including 5'-dA-dC-dA-3', 5'-dA-dG-dA-3', 5'-dA-dT-dA-3', 5'-dA-dA-dA-3', 5'-dT-dC-dA-3', 5'-dT-dG-dA-3', 5'-dT-dT-dA-3', 5'-dT-dA-dA-3', 5'-dG-dC-dA-3', 5'-dG-dG-dA-3', 5'-dG-dT-dA-3', 5'-dG-dA-dA-3', 5'-dC-dC-dA-3', 5'-dC-dG-dA-3', 5'-dC-dT-dA-3', 5'-dC-dA-dA-3', 5'-dA-dC-dT-3', 5'-dA-dG-dT-3', 5'-dA-dT-dT-3', 5'-dA-dA-dT-3', 5'-dT-dC-dT-3', 5'-dT-dG-dT-3', 5'-dT-dT-dT-3', 5'-dT-dA-dT-3', 5'-dG-dC-dT-3', 5'-dG-dG-dT-3', 5'-dG-dT-dT-3', 5'-dG-dA-dT-3', 5'-dC-dC-dT-3', 5'-dC-dG-dT-3', 5'-dC-dT-dT-3', 5'-dC-dA-dT-3', 5'-dA-dC-dG-3', 5'-dA-dG-dG-3', 5'-dA-dT-dG-3', 5'-dA-dA-dG-3', 5'-dT-dC-dG-3', 5'-dT-dG-dG-3', 5'-dT-dT-dG-3', 5'-dT-dA-dG-3', 5'-dG-dC-dG-3', 5'-dG-dG-dG-3', 5'-dG-dT-dG-3', 5'-dG-dA-dG-3', 5'-dC-dC-dG-3', 5'-dC-dG-dG-3', 5'-dC-dT-dG-3', 5'-dC-dA-dG-3', 5'-dA-dC-dC-3', 5'-dA-dG-dC-3', 5'-dA-dT-dC-3', 5'-dA-dA-dC-3', 5'-dT-dC-dC-3', 5'-dT-dG-dC-3', 5'-dT-dT-dC-3', 5'-dT-dA-dC-3', 5'-dG-dC-dC-3', 5'-dG-dG-dC-3', 5'-dG-dT-dC-3', 5'-dG-dA-dC-3', 5'-dC-dC-dC-3', 5'-dC-dG-dC-3', 5'-dC-dT-dC-3', 5'-dC-dA-dC-3' or their derivatives) mixture of monomer-building blocks, mixture of dimer-building blocks, mixture of trimer-building blocks or their combinations thereof or by any of the alternative oligonucleotide synthesis strategies that are utilizing other forms of 'bulding-blocks'.

Specifically, suitable techniques employ ssDNA-binding protein mediated recombination wherein the ssDNA-binding protein is a yeast-derived Rad51, Rad54, Rad52 or a phage-derived ssDNA-annealing protein, including Lambda Red Beta, RecT, RecA, Rad52-like, Sak, Erf, or Rad51-like or Gp2.5-like ssDNA-binding protein or their orthologous sequences.

A Lambda Red Beta, RecT, RecA, Rad52-like, Sak, Erf, or Rad51-like or Gp2.5-like ssDNA-binding protein variant shares homology to Lambda Red Beta, RecT, RecA, Rad52-like, Sak, Erf, or Rad51-like or Gp2.5-like ssDNA-binding protein, or a fragment thereof. For example, a Lambda Red Beta, RecT, RecA, Rad52-like, Sak, Erf, or Rad51-like or Gp2.5-like ssDNA-binding protein variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to wild type protein.

Specifically, the oligonucleotide integration can be triggered by the overexpression of the ssDNA-binding protein in vivo, thereby forming an ssDNA oligonucleotide-ssDNA-binding protein complex which then facilitates the integration of the oligonucleotide to its complementary PTR.

Specifically, the oligonucleotide integration can be achieved by complexing the ssDNA-binding protein and the oligonucleotide ex vivo, thereby forming an ssDNA oligonucleotide-ssDNA-binding protein complex which then facilitates the integration of the oligonucleotide to the cellular DNA.

Specifically, the oligonucleotide can be integrated into the cellular DNA by any of ssDNA-binding protein mediated recombination or bacterial homologous recombination technique, e. g. as described in pORTMAGE, *Shigella flexneri, Yersinia pseudotuberculosis, Corynebacterium glutamicum, Lactococcus lactis, Lactobacillus reuteri, Bacillus subtilis, Legionella pneumophila, Mycobacterium tuberculosis, Mycobacterium smegmatis, Pseudomonas putida*, bacteriophage recombineering technique, e. g. as described in bacteriophage λ, mycobacteriophage Giles, yeast homologous recombination technique, e. g. as described in *Saccharomyces cerevisiae*, mammalian homologous recombination technique, e. g. as described in mouse embryonic stem cells, human HT1080 cells, human HeLa cells, plant homologous recombination technique, e. g. as described in *Arabidopsis thaliana*.

Specifically, the oligonucleotide pool is a soft-randomized one, which is herein understood as covering mismatching nucleobases at each position of the SOI to an extent that is lower than 50%, preferably less than 25%, 10%, 5%, or 1%, or 0.5% or in a ratio which is lower or equal to about 0.1%.

Specifically, the oligo pool comprises oligonucleotides that are produced by a polynucleotide synthesis method that allows introduction of nucleobase mismatches compared to the SOI. Specifically, the oligo pool comprises oligonucleotides that are produced by a (e.g. chemical or biological, such as enzymatic) polynucleotide synthesis method in a way that the oligo pool contain mismatching nucleobases compared to the SOI in each position in a ratio which is lower than 50%, preferably less than 25%, 10%, 5%, or 1%, or 0.5% or in a ratio which is lower or equal to about 0.1%.

Specifically, in the pool of oligonucleotides the rate of mismatching nucleobases at every position of said SOI is less than any one of 50%, 25%, 10%, 5%, 1%, 0.5% or 0.1%.

Specifically, the oligo pool comprises oligonucleotides produced by a chemical polynucleotide synthesis method using a mixture of nucleotide building blocks that contain mismatching nucleobases compared to the SOI in each position in a ratio which is lower than 50%, preferably less than 25%, 10%, 5%, or 1%, or 0.5% or in a ratio which is lower or equal to about 0.1%.

The % of each mismatching nucleotide building block during synthesis is also refered herein as the spiking ratio.

Specifically, soft-randomization of the oligo pool results in a limited mutagenesis of oligonucleotides during synthesis, wherein the number of mutations (or the number or ratio of mismatching nucleobases compared to the SOI) within the oligonucleotide sequence is lower than 20 mutations (nucleobase alterations) per 100 nucleotides.

Specifically, the nucleobase mismatches (in particular those of mutagenizing oligonucleotides) or the point mutations (in particular those introduced into the PTR) are selected from the group consisting of at least one nucleobase or nucleotide substitution, insertion or deletion, codon substitution, or combinations thereof, preferably wherein the nucleobase mismatches are single, double or triple, consecutive mismatches.

According to specific soft randomization techniques, monomer, dimer or trimer nucleotide building block based soft-randomization, point mutations can also be a block of single, double or triple, consecutive nucleobase alterations.

Specifically, the cell library is produced by one or more rounds of in vivo mutagenesis, e.g. by homologous recombination or MAGE, each round comprising:

a) transfecting or transforming the cells with the pool of oligonucleotides in a transfection or transformation medium, e.g. by electroporation, or natural competence, or protoplast transformation, in particular under conditions that allow integration of one or more nucleotides into the SOI region of the PTR; and b) replacing the transfection or transformation medium with growth medium and incubating the cells in the growth medium, in particular under conditions allowing the cells to grow in the cell culture; and optionally repeating the steps a) and b) to increase the library diversity.

Specifically, the method comprises transfecting or transforming the host cells in a transfection or transformation medium including the oligonucleotide pool and recombining the oligonucleotides with the PTR, in particular with the SOI region of the PTR, replacing the transfection or transformation medium with growth medium, incubating the cells in the growth medium, and optionally iteratively applying the recombination and cell culture steps if necessary or desired until the sequence(s) of the oligonucleotide pool are introduced into the host cells' DNA within the host cells.

Specifically, the in vivo mutagenesis (also referred to as "ssDNA oligonucleotide mediated nucleotide integration") is performed in a cell culture.

Specifically, following at least one round of in vivo mutagenesis, a repertoire of cells is selected from the produced cell library, which repertoire is used for at least one further round of in vivo mutagenesis to further increase the diversity of the (selected) repertoire.

Specifically, the homologous recombination is employing a ssDNA-binding protein, preferably selected from the group consisting of a yeast-derived Rad51, Rad54, Rad52 or a phage-derived ssDNA-annealing protein, such as Lambda Red Beta, RecT, RecA, Rad52-like, Sak, Erf, or Rad51-like or Gp2.5-like ssDNA-binding protein or their orthologous sequences.

Specifically, the homologous recombination is performed by Lambda Red recombineering, or MAGE.

Specifically, the homologous recombination is performed in the presence of a dominant negative mutator allele of the methyl-directed mismatch repair (MMR) system, preferably wherein the dominant negative mutator allele is an E32K substitution in the MutL protein comprising the amino acid sequence identified as SEQ ID NO:215.

Specifically, the homologous recombination is performed by a pORTMAGE plasmid.

According to a specific aspect, the cell library is further tailored or focused to enrich or eliminate a group of cells characterized by at least one detectable feature.

Specifically, the group of cells is enriched or eliminated in the cell library using any of a CRISPR/Cas9 system, ZFN or TALEN.

Specifically, any one of CRISPR/Cas9 systems, ZFNs or TALENs is used to eliminate cells which do not have a desired mutation.

Specifically, the cells are transfected or transformed using the natural competence of the cell, or by any electroporation, protoplast, or chemical transformation method, or by a technique mediated by any of a peptide, lipid-vesicle, or virus technique. Suitable methods for transforming or transfecting target cells can be found in Sambrook, et al. (Molecular Cloning: A Laboratory Manual. 4th, ed., Cold Spring Harbor Laboratory, Cold Spring Harbor Laboratory Press, Cold Spring Harbor, N.Y., 2012), or in other laboratory manuals.

Specifically, the SOI is a non-coding or coding sequence or a combination thereof.

Specifically, the SOI is within a non-transcribed sequence, either upstream or downstream of a coding sequence.

Specifically, the SOI encodes or encodes a part of the Tet repressor protein.

According to a specific aspect, the SOI encodes a protein, preferably an enzyme, a ligand-binding protein, an antibody, a structural protein, a ribozyme, an RNA, e.g., regulatory RNA, or any other RNA molecule, a group of biomolecules that form a cellular pathway, a regulatory network, a metabolic pathway, a cellular subsystem, or a part of any of the foregoing.

Specifically, the SOI encodes a therapeutic polypeptide or protein, e.g. a drug-target, a drug-resistance determinant, an efflux-pump, an enzyme, an antigen, a toxin, a ligand-binding protein, an antibiotic-producing gene, a peptide, or a cytokine.

Specifically, the SOI encodes a sequence that influences drug susceptibility, preferably wherein the drug target is dihydrofolate reductase, or part of the DNA gyrase complex or the Topoisomerase complex.

Specifically, the SOI is of a drug-target gene or an efflux pump gene or a combination thereof.

Specifically, the drug is an antibiotic, an anti-cancer drug, an anti-malarial drug, or an anti-fungal drug.

According to a specific aspect, the SOI encodes or is part of a metabolic or biosynthetic pathway, preferably encoding an enzyme or regulator of such pathway.

According to a specific aspect, the SOI comprises one or more of any of ribosomal binding sites, promoter, leader sequences, introns, ribozyme, riboswitch or regulatory sequences, or part of any of the foregoing.

Specifically, the SOI is a sequence of natural origin (e.g. a wild-type intracellular sequence), or an artificial sequence, e.g. a sequence of semi-synthetic origin or a sequence with fully synthetic (de novo) origin or a chimeric sequence, or a mutated sequence or a combination thereof.

According to a specific aspect, the SOI is of a wild-type cell, or an artificial SOI which is heterologous to the cell.

Specifically, the SOI is incorporated within a mutant cell, e.g., an artificial sequence, such as a sequence of semi-synthetic origin or a sequence with fully synthetic (de novo) origin.

Specifically, the sequence with fully synthetic (de novo) origin is synthesized with any of the polynucleotide synthesis methods.

Specifically, the SOI is an artificial polynucleotide sequence e.g., which is part of a recombinant intracellular sequence containing one or more sequences which are heterologous to the host cell.

According to a specific aspect, the SOI comprises a nucleic acid sequence within a chromosome of the cell or a plasmid. Specifically, the chromosomal or plasmid SOI is heterologous to the (wild-type) host cell.

According to a specific aspect, the SOI encodes a polypeptide sequence, preferably wherein the variation covers every possible amino acid residue in said polypeptide sequence.

Specifically, the SOI encodes a metabolic or biosynthetic pathway or a part of such pathway, e.g. respective enzymes or regulators of such pathway.

Specifically, the SOI encodes a single biomolecule such as an enzyme, or a ligand-binding protein, an antibody, a structural protein, or a protein with other function, a ribozyme, a riboswitch, a regulatory RNA, or any other RNA molecule, or a group of biomolecules that form a cellular pathway, a regulatory network, a metabolic pathway, or a cellular subsystem, or a part of any of the foregoing.

Specifically, the SOI is an artificial polynucleotide sequence (e.g. which is part of a recombinant intracellular sequence containing one or more sequences which are heterologous to the host cell). Specific embodiments refer to those SOI which are heterologous to the host cell.

Specifically, the SOI is a coding polynucleotide sequence encoding a therapeutic polypeptide or protein, e.g. a drug-target, a drug-resistance determinant, an enzyme, an antibody, an antigen, a toxin, a ligand-binding protein, an antibiotic-producing gene, a peptide, and a cytokine.

Specific examples refer to a SOI which encodes an antibody, antibody fragment, or antigen-binding sequence.

Specifically, the SOI is part of the intracellular genome, or particularly any of chromosomal, episomal, plasmid, viral or bacteriophage DNA.

Specifically, the SOI is a nucleic acid sequence incorporated in a host cell chromosome or plasmid, and optionally heterologous to the host cell. Specifically, the intracellular DNA is endogenous to said cell or a mutated version thereof, or a heterologous DNA, preferably any of mammalian origin, such as of human, CHO, primate, mouse origin, or microbial, such as protozoal, bacterial, fungal or yeast, viral (or bacteriophage) or artificial DNA.

Specifically, the SOI originates from a virus, such as cDNA of a (+) RNA virus, (−) RNA virus, dsDNA virus, RNA to DNA virus, or DNA virus, or of a bacteriophage, or a cloned or engineered viral variant of any of the foregoing. In particular, the bacteriophage virus is any of a T7, T4, P1, Lambda-phage, or a cloned or engineered viral variant of any of the foregoing. Specifically, the cell is a eukaryotic or prokaryotic cell, preferably a microorganism.

Specifically, the cell is of human, rodent, preferably mouse or hamster, fungi, yeast, or bacteria origin, including wild-type or mutant cells.

Specific examples refer to host cells which are mammalian, such as human, CHO, primate, mouse; or protozoa; fungi, yeast, in particular *Saccharomyces cerevisiae*, or bacteria. Specifically, the yeast is a disease-causing or bioactive-compound producing yeast, or any of their synthetic or engineered variants.

Specifically, the cell is a recombinant host cell comprising a heterologous intracellular DNA sequence or heterologous SOL.

Protozoa for use in the methods described herein are specifically selected from the group consisting of unicellular eukaryotic organisms, including Flagellates (e.g. *Giardia lamblia*); Amoeboids (e.g. *Entamoeba histolytica*); Ciliates (e.g. *Balantidium coli*), Sporozoans (e.g. *Plasmodium*, such as *Plasmodium falciparum*).

Specifically, the cell is a bacterial cell of a bacterium which is selected from the group consisting of *Clostridium* species, Enterobacteriaceae, including Carbapenem-resistant Enterobacteriaceae (CRE) and extended spectrum β-lactamase producing Enterobacteriaceae (ESBLs), *Neisseria gonorrhoeae*, *Acinetobacter* species, *Campylobacter* species, *Pseudomonas* species, *Escherichia* species, *Salmonella* species, *Shigella* species, *Klebsiella* species, *Staphylococcus aureus*, *Mycobacterium* species, *Vibrio* species, or any of their synthetic or engineered variants.

Bacteria for use in the methods described herein are specifically selected from the group consisting of, but not limited to, the Proteobacteria phylum, including the family of Pseudomonodaceae, including the *Pseudomonas* genus and the unclassified Pseudomonads, the family of Moraxellaceae, including the *Acinetobacter* genus, Epsilonproteobacteria class, Enterobacteriaceae, including *Citrobacter, Edwardsiella, Enterobacillus, Enterobacter, Erwinia, Escherichia, Klebsiella, Pantoea, Proteus, Salmonella, Serratia, Shigella Yersinia* genus and species, Alphaproteobacteria class, including Magnetococcidae, Rickettsidae or Caulobacteridae with Rhizobiales, Betaproteobacteria class, including Burkholderiale, Niesseriales, including Niesseriaceae or a *Vibrio*, including *Vibrio natriegens*, *Vibrio cholera*, the Spirochaetes phylum, the Actinobacteria phylum, including Mycobacteriaceae and the *Mycobacterium* genus, Pasteurellaceae family, including the *Haemophilus* genus, Legionellaceae family, including *Legionella*, the Bacteroidetes phylum, including the family of Bacteroidetes and Porphyromonadaceae, or any of their synthetic or engineered variants.

Specifically, the cell is a bacterium selected from the group consisting of *Enterococcus, Staphylococcus, Klebsiella, Acinetobacter, Pseudomonas, Shigella, Salmonella, Citrobacter, Proteus, Vibrio* and *Escherichia* species, and any of their synthetic or engineered variants thereof.

Specifically, the bacterium is pathogenic to humans. Specific embodiments refer to an ESKAPE pathogen, preferably selected from the group consisting of *Enterococcus faecium, Staphylococcus aureus, Klebsiella pneumoniae, Acinetobacter baumanii, Pseudomonas aeruginosa* and *Enterobacter* species, and any of their synthetic or engineered variants thereof. ESKAPE pathogens (*Enterococcus faecium, Staphylococcus aureus, Klebsiella pneumoniae, Acinetobacter baumannii, Pseudomonas aeruginosa*, and *Enterobacter* species) are currently considered as the leading cause of nosocomial infections throughout the world.

Fungi for use in the methods described herein are specifically selected from the group consisting of *Neurospora crassa, Aspergillus* species, including *Aspergillus nidulans, Penicillium* species, including *Penicillium chrysogenum, Magnaporthe grisea*, or disease-causing or bioactive-compound producing fungi or any of their synthetic or engineered variants.

Yeasts for use in the methods described herein are specifically selected from the group consisting of, but not limited to, *Saccharomyces*, including *Saccharomyces cervisiae*, Baker's yeast, *Saccharomyces boulardii, Yarrowia lipolytica, Schizosaccharomyces pombe, Pichia* species, including *Pichia pastoris* or pathogenic yeast, including *Cryptococcus* species, *Cryptococcus neoformans, Cryptococcus gattii, Candida* species, *Candida albicans, Candida tropicalis, Candida stellatoidea, Candida glabrata, Candida krusei, Candida parapsilosis, Candida guilliermondii, Candida viswanathii, Candida lusitaniae*, and *Rhodotorula mucilaginosa*, or disease-causing or bioactive-compound producing yeast or any of their synthetic or engineered variants.

Specifically, the cell is a microorganism which is pathogenic to any of bacteria, yeast, animals, or plants. Specific examples refer to a microorganism which is pathogenic to animal, plants or human beings.

According to a specific aspect, the microorganism is susceptible or resistant to one or more drugs, wherein the type and degree of drug response is a detectable feature which may be developed by the in vivo mutagenesis method described herein.

Specifically, the cell is a drug-responsive microorganism, and the cell library encompasses a repertoire of variant cells which are drug-resistant.

Specifically, the cell is a microorganism, in particular a disease causing microorganism, preferably where the microorganism is drug-responsive, the library diversity encompasses cells which are drug-resistant, or vice versa. Specifically, the drug is an antibiotic, an anti-cancer drug, an anti-malarial drug, or an anti-fungal drug and other drugs will be readily apparent to those skilled in the art.

Specifically, the cell is part of an animal (including human beings) microbiome.

In certain embodiments, the PTR is simultaneously targeted in a series of different cells which are cultivated in the same cell culture, e.g. including the isolated native or cultured microbiome or a microbial community of an animal (including human beings), or in an environmental sample. In a specific example the method described herein is used to engineer the microbiome, e.g. to alter its composition or mutagenize drug-resistance determinants.

Specifically, the cell is a cancerous cell line or stem-cell line, an insect cell including *Drosophila melanogaster* cells, plant cells, amphibian cells including *Xenopus laevis* cells, nematode cells including *Caenorhabditis elegans* cells, or mammalian cells (such as Chinese hamster ovary cells (CHO), mouse cells, African green monkey kidney cells (COS), fetal human cells (293T) or other human cells).

Specifically, the cell is a eukaryotic cell or cell line, such as a cancerous cell line, preferably where the cell line is drug-responsive, the library diversity encompasses cells which are drug-resistant, or vice versa.

Specifically, the drug is a chemotherapeutic agent, an anti-cancer drug, an anti-malarial drug, or an anti-fungal drug. Suitable drugs are typically biologically active compounds or a mixture of compounds that have a therapeutic, prophylactic or other beneficial pharmacological or physiological effect. Examples of drugs that can be screened with the cell libraries described herein include anti-arrhythmic drugs, anticoagulants, antidiabetics, antiepileptics, antifungals, antigout, antimalarials, antimuscarinic agents, antineoplastic agents, antiprotozoal agents, thyroid and antithyroid agents, anxiolytic sedatives and neuroleptics, beta blocking agents, drugs affecting bone metabolism, cardiac inotropic agents, chelating agents, antidotes and antagonists, corticosteroids, cough suppressants, expectorants and mucolytics, dermatological agents, diuretics, gastro-intestinal agents, general and local anaesthetics, histamine H1 receptor antagonists, nitrates, vitamins, opioid analgesics, parasympathomimetics, anti-asthma agents, muscle relaxants, stimulants and anorectics, sympathomimetics, thyroid agents, xanthines, lipid regulating agents, antiinflamatory drugs, analgesics, antiarthritic drugs, antispasmodics, antidepressants, antipsychotic drugs, tranquillizers, narcotic antagonists, antiparkinsonism agents, cholinergic agonists, anticancer drugs, immunosuppressive agents, antiviral agents, antibiotic agents, appetite suppressants, antiemetics, anticholinergics, antihistamines, antimigraine agents, coronary, cerebral or peripheral vasodilators, hormonal agents, contraceptive agents, antithrombotic agents, diuretics, antihypertensive agents and cardiovascular drugs. Other drugs will be readily apparent to those skilled in the art.

Specifically, the drug is an antibiotic, which is a chemotherapeutic agent that has the capacity to inhibit the growth of or to kill, one or more organism. Antibiotics are well-known to those skilled in the art. Classes of antibiotics include, but are not limited to, aminoglycosides (e.g., amikacin, gentamicin, kanamycin, neomycin, netilmicin, streptomycin, tobramycin, paromomycin and the like), ansamycins (e.g., geldanamycin, herbimycin and the like), carbacephem (e.g., loracarbef), carbapenems (e.g., ertapenem, doripenem, imipenem/cilastatin, meropenem and the like) cephalosporins (e.g., first generation (e.g., cefadroxil, cefazolin, cefalotin, cefalexin and the like), second generation (e.g., cefaclor, cefamandole, cefoxitin, cefprozil, cefuroxime and the like), third generation (e.g., cefixime, cefdinir, cefditoren, cefoperazone, cefotaxime, cefpodoxime, ceftazidime, ceftibuten, ceftizoxime, ceftriaxone and the like), fourth generation (e.g., cefepime and the like) and fifth generation (e.g., ceftobiprole and the like)), glycopeptides (e.g., teicoplanin, vancomycin and the like), macrolides (e.g., azithromycin, clarithromycin, dirithromycin, erythromycin, roxithromycin, troleandomycin, telithromycin, spectinomycin and the like), monobatams (e.g., aztreonam and the like), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticacillin and the like), polypeptides (e.g., bacitracin, colistin, polymyxin B, PGLA, TPII and the like), quinolones (e.g., ciprofloxacin, delafloxacin, enoxacin, gatifloxacin, levofloxacin, lomefloxacin, moxifloxacin, norfloxacin, ofloxacin, trovafloxacin and the like) or other bacterial topoisomerase inhibitors (e.g. gepotidacin, GSK2140944, NBTI-5463, AM8191, VXc-486, NBTI-7, AZD0914, closthioamide, nybomycin, deoxynybomycin, QPT-1, AM8191), sulfonamides (e.g., mafenide, prontosil, sulfacetamide, sulfamethizole, sulfanilamide, sulfasalazine, sulfisoxazole, trimethoprim, trimethoprim-sulfamethoxazole and the like), tetracyclines (e.g., demeclocycline, doxycycline, minocycline, oxytetracycline, tetracycline and the like) and others (e.g., arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin, tinidazol and the like) (See, e.g., Robert Berkow (ed.) The Merck Manual of Medical Information-Home Edition. Pocket (September 1999), ISBN 0-671-02727-1) Other antibiotics will be readily apparent to those skilled in the art.

Specifically, the cell is a pathogen (disease-causing, e.g. for bacteria, yeast, mammalians), e.g. a human, animal or plant pathogen.

Specifically, the human pathogen is selected from the group consisting of *Clostridium difficile*, Enterobacteriaceae, including Carbapenem-resistant Enterobacteriaceae (CRE) and extended spectrum β-lactamase producing Enterobacteriaceae (ESBLs), *Neisseria gonorrhoeae*, including drug-resistant *Neisseria gonorrhoeae*, *Acinetobacter*, including multidrug-resistant *Acinetobacter*, *Campylobacter*, including drug-resistant *Campylobacter*, *Candida* (a fungus), including fluconazole-resistant *Candida*, *Enterococcus*, including Vancomycin-resistant *Enterococcus* (VRE), *Pseudomonas aeruginosa*, including multidrug-resistant *Pseudomonas aeruginosa*, *Salmonella*, including drug-resistant Non-typhoidal *Salmonella* and *Salmonella Typhi*, *Shigella*, including drug-resistant *Shigella*, *Staphylococcus aureus*, including methicillin-resistant *Staphylococcus aureus* (MRSA) and Vancomycin-resistant *Staphylococcus aureus* (VRSA), *Streptococcus pneumoniae*, including drug-resistant *Streptococcus pneumoniae*, *Mycobacterium tuberculosis*, including drug-resistant *Mycobacterium tuberculosis*, Group A and Group B *Streptococcus*, including Clindamycin- and/or Erythromycin-resistant *Streptococcus*, *Vibrio* species or ESKAPE pathogen, including *Enterococcus faecium, Staphylococcus aureus, Klebsiella pneumoniae, Acinetobacter baumanii, Pseudomonas aeruginosa* and *Enterobacter* species or any of their synthetic or engineered variants.

Specifically, the plant pathogen is selected from the group of *Pseudomonas syringae, Ralstonia solanacearum; Agrobacterium tumefaciens; Xanthomonas oryzae; Xanthomonas campestris; Xanthomonas axonopodis; Erwinia amylovora; Xylella fastidiosa; Dickeya dadantii and solani; Pectobacterium carotovorum, Pectobacterium atrosepticum, Clavibacter michiganensis* and *sepedonicus, Pseudomonas savastanoi, Liberibacter asiaticus*.

The invention further provides for a pool of partially overlapping ssDNA oligonucleotides which upon alignment form a continuous sequence that is complementary to at least a SOI, wherein the pool contains a diversity of mutagenizing oligonucleotides covering nucleobase mismatches at every position of said SOI and combinations of said nucleobase mismatches, wherein each mutagenizing oligonucleotide comprises at least one mismatching nucleobase, and optionally a combinations of mismatches at two or more different positions, up to 20% mismatching nucleobases, compared to the SOI.

Specifically, the mutagenizing oligonucleotides are produced by a polynucleotide synthesis method that allows introduction of nucleobase mismatches compared to the SOI, in particular at every position of the SOL.

Specifically, the polynucleotide synthesis method introduces nucleobase mismatches in the continuous sequence compared to the SOI which cover nucleobase mismatches at every position of the SOI.

Specifically, the polynucleotide synthesis method is a chemical polynucleotide synthesis method using a mixture of nucleotide building blocks, preferably employing monomer, dimer or trimer nucleotide building block based polynucleotide synthesis.

Specifically, the polynucleotide synthesis method is a H-phosphonate, phosphodiester, phosphotriester or phosphite triester synthesis method or a massively parallel oligonucleotide synthesis method, in particular wherein the massively parallel oligonucleotide synthesis method is a microarray or microfluidics-based oligonucleotide synthesis method.

Specifically, the pool of oligonucleotides is provided to ensure the rate of nucleobase mismatches at every position in the continuous sequence compared to the SOI, which is less than any one of 50%, 25%, 10%, 5%, 1%, 0.5% or 0.1%.

According to a specific aspect, the pool is used in the in vivo mutagenesis method described herein, preferably for accelerated evolution of the intracellular DNA. Specifically, the phenotype and particularly the function of the cell is changed upon such mutagenesis, such as to obtain a repertoire of cells which differ in at least one of their phenotype or functions.

According to a specific aspect, a method of producing the pool described herein is provided, in particular wherein the pool contains a diversity of mutagenizing oligonucleotides covering nucleobase mismatches at every position of said SOL.

Specifically, combinations of said nucleobase mismatches can be produced by the mutagenesis method described herein, and/or employing the pool of partially overlapping ssDNA oligonucleotides described herein, which correspond to the same position of said SOI or different positions.

Specifically, said combinations of nucleobase mismatches are through combination of mutagenizing oligonucleotides, which are oligonucleotides each characterized by any of 1, 2, or more mismatching nucleobases, or preferably by a mixture of oligonucleotides each characterized by any of 1, 2, or more mismatching nucleobases, preferably wherein the mismatching nucleobases correspond to different positions within said SOI.

The invention further provides for a cell library obtainable by the method described herein, which comprises a repertoire of variant cells wherein the library diversity is at least $10^3$, $10^4$, $10^5$, $10^6$, $10^7$, $10^8$, $10^9$, or $10^{10}$; or the library of intracellular DNA contained therein.

Specifically, the library can be further tailored or focused to enrich or eliminate a group of cells characterized by specific features. For example, the CRISPR/Cas9 system can be used to eliminate cells which do not have a desired mutation.

According to a specific aspect, the library can be screened for identifying and/or selecting cells characterized by specific features or a desired phenotype.

Specifically, the repertoire comprises variant cells which are drug-resistant.

Specifically, the cell library can be used in a method of producing variant cells which are drug-resistant.

Specifically, the risk or frequency of developing drug resistance can be determined for a specific organism, which can be measured as the ratio of cells that are drug resistant within the cell library obtainable by the mutagenesis method described herein.

According to a specific aspect, the mutagenesis method described herein, and/or the pool of partially overlapping ssDNA oligonucleotides described herein, can be used for directed evolution of intracellular DNA in a cell.

Specifically, the use is for directed evolution of a bacterial cell to develop drug resistance.

Specifically, the use is for identifying mutations in a PTR, in particular a SOI region within a PTR, which enhance drug-resistance.

Specifically, the use is to determine the risk of developing drug resistance.

In particular, the frequency of drug resistance is measured as the ratio of cells that are drug resistant within the cell library obtainable by the mutagenesis method described herein.

Specifically, the use is to provide a structure-activity relationship map, wherein the interacting residues are given by the mutations that are enhancing drug-resistance.

According to a specific aspect, a method of identifying drug resistance-conferring variants is provided, wherein the variants are produced by one or more rounds of homologous recombination, each round comprising:

a) transfecting or transforming the cells with the pool of oligonucleotides in a transfection or transformation medium without the drug; and b) replacing the transfection or transformation medium with growth medium and incubating the cells in the growth medium containing the drug; and optionally repeating the steps a) and b) to obtain drug resistant variants.

In particular, such method employs the pool of partially overlapping ssDNA oligonucleotides described herein.

FIGURES

FIG. 1: describes the nucleobase composition and the uniform distribution of nucleobase mismatches within the oligo pool of SEQ ID NO:2, in which each nucleotide position was synthesized with 0.5% spiking with each of the mismatching A, T, G, or C nucleobase at each given position. Nucleotide composition was determined by Illumina sequencing.

FIG. 2: Mutational bias within SEQ ID NO:2 oligo pool, in which each nucleotide position was synthesized with 0.5% nucleobase spiking with each of the mismatching A, T, G, or C nucleobase at each given position, as compared to the SOI.

Figure 3:
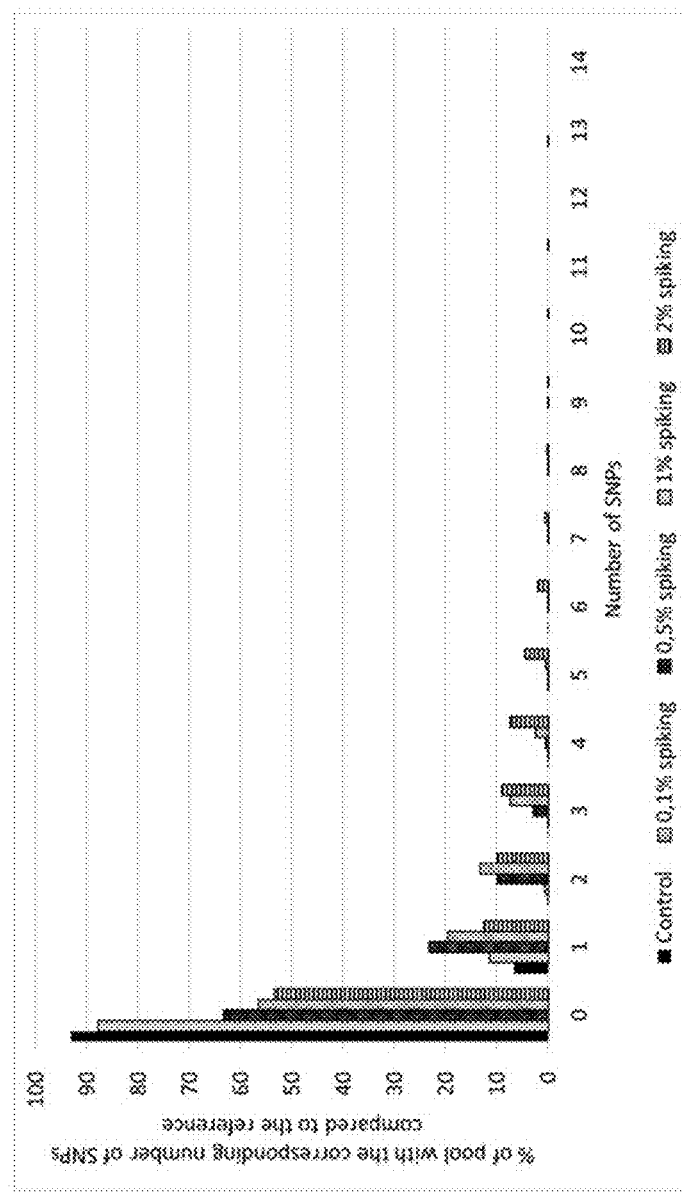

FIG. 3: The average number of mutations (SNPs) compared to the SOI within a pool of mutagenizing DNA oligonucleotides (SEQ ID NO:3) is precisely controllable by the level of nucleobase spiking during the course of DNA oligonucleotide synthesis. Control indicates results from an oligo pool which was synthesized without spiking. Values are based on Illumina HT sequencing of at least 50 000 individual oligonucleotide strands for each oligonucleotide pool.

FIG. 4: Integration of soft-randomized oligonucleotide pools (SEQ ID NO:2 and SEQ ID NO:3) at their target (PTR1 and PTR2, respectively) results in mutagenesis and the elevation of genomic mutation rate with high regional specificity to the oligonucleotide's target site. Y-axis shows the percentage of clones which contain a point mutation in the given position. SEQ ID NO:2 is at positions 1-90, SEQ ID NO:3 is at position 162-252. Apparent mutations between PTR1 and PTR2 are the results of sequencing errors.

Figure 5:
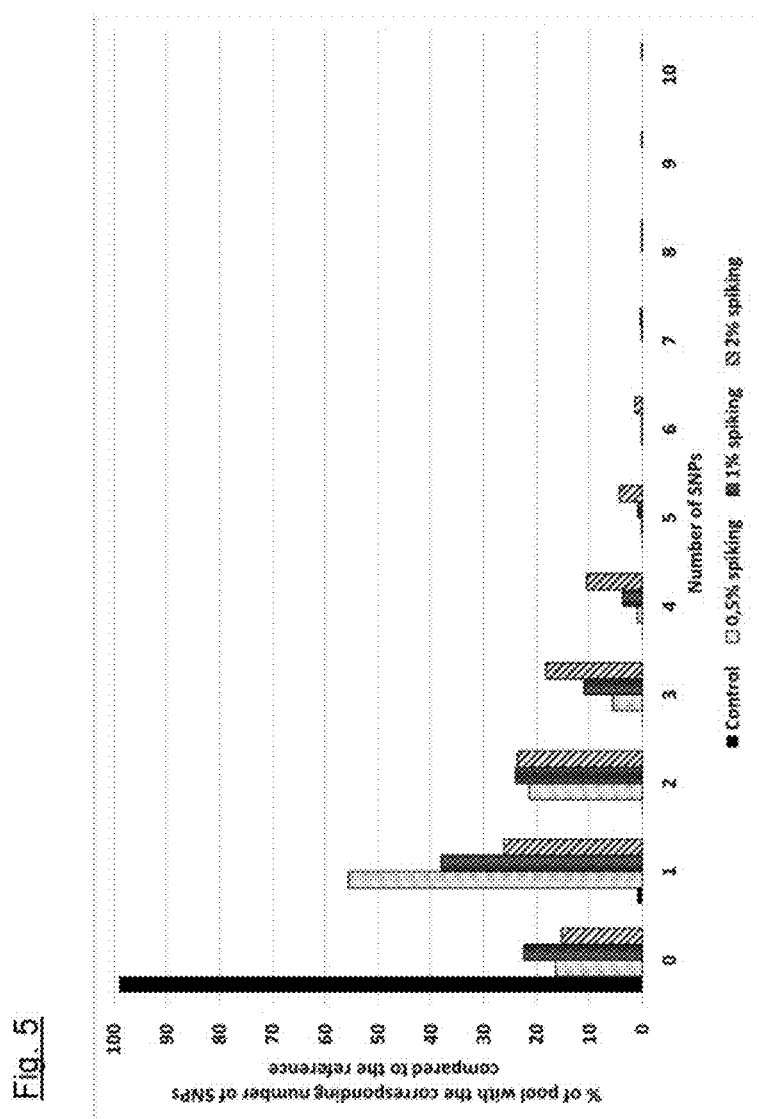

FIG. 5: The number of point mutations (Single Nucleotide Polymorphism (SNP)) observed within target site (PTR1) of SEQ ID NO:2 soft-randomized oligonucleotide pool in *Escherichia coli* K-12 is tunable by the spiking ratio of the oligonucleotide pool during the course of DNA oligonucleotide synthesis. Samples represent allelic composition after 5 consecutive integrations of the oligonucleotide pool with the corresponding spiking ratio, control represents mutagenesis with a non-spiked oligo.

FIG. 6: Nucleobase alteration bias in the cellular DNA and spectra of mutations at the PTR1 after 5 cycles of consecutive integration of a soft-randomized oligonucleotide pool (SEQ ID NO:2) in *E. coli* K-12 MG1655.

FIG. 7: Integration into the cellular DNA of a pool of overlapping, soft randomized single stranded DNA (ssDNA) oligonucleotides (SEQ ID NO:4-SEQ ID NO:11) with 0.5% nucleobase spiking with each of the mismatching A, T, G, or C nucleobases at each given position, which when aligned to each other with their overlaps form a continuous sequence resulting in a uniform mutagenesis at the entire SOI. Figure shows the percentage of mutations in the *E. coli* K-12 folA locus at each nucleotide position after 5 cycles of consecutive integration of a soft-randomized oligonucleotide pool. Here, position 1 indicates the first position of the Open Reading Frame, while negative positions belong to the promoter region. Note that position 1 on the figure is position 301 in SEQ ID NO:28 and in Table 1. Table 1: Integration into the cellular DNA of a pool of overlapping, soft randomized single stranded DNA (ssDNA) oligonucleotides (SEQ ID NO:4-SEQ ID NO:11) with 0.5% nucleobase spiking with each of the mismatching A, T, G, or C nucleobase at each given position, which when aligned to each other with their overlaps form a continuous sequence, results in a diverse combination of nucleobase mutations at their target. Mutations were determined compared to the wild-type SOI sequence with high-throughput sequencing and positions indicate nucleotide positions within the sequence of the PTR of the folA (DHFR) locus. Table indicates the most frequent 50 mutants from the mutagenized cell pool. Note that in Table 1 position 301 is position 1 in FIG. 7.

Figure 8:
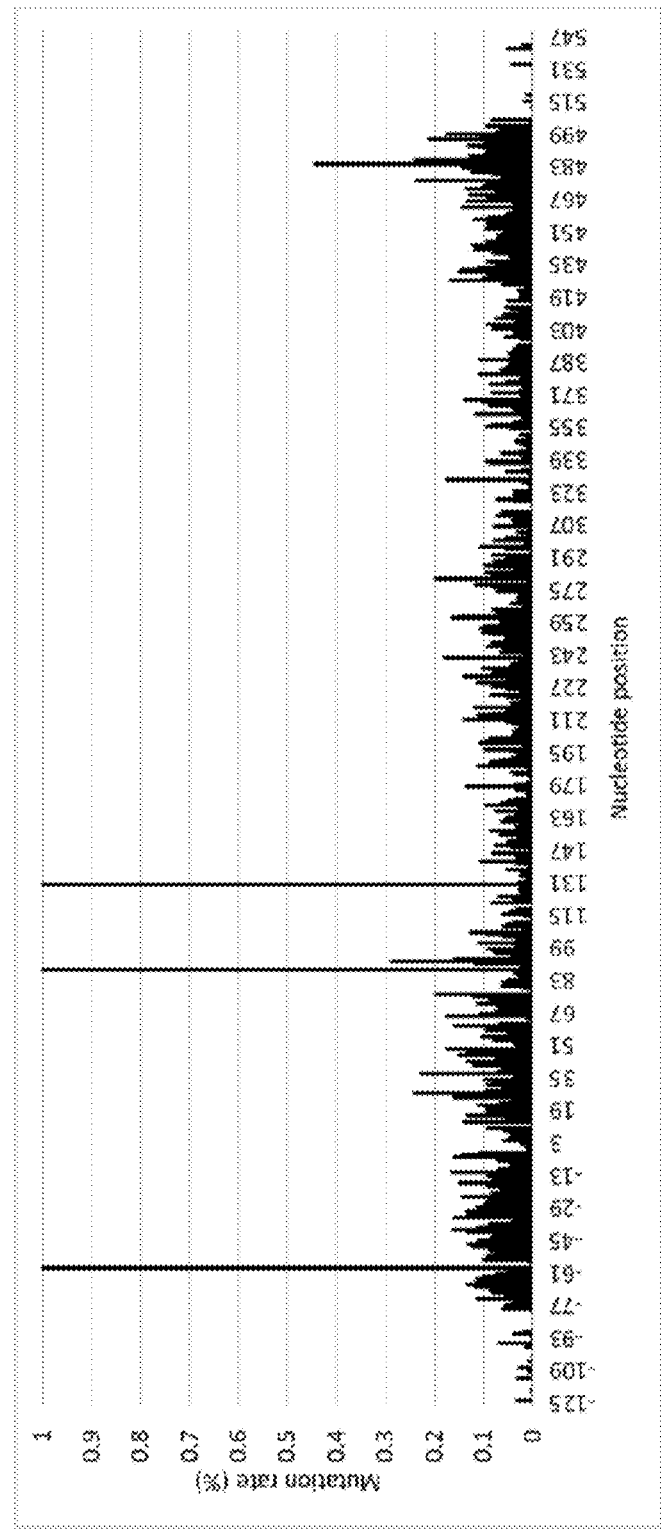

FIG. 8: Integration into the cellular DNA of a pool of overlapping, soft randomized single stranded DNA (ssDNA) oligonucleotides (SEQ ID NO:4-SEQ ID NO:11) with 0.5% nucleobase spiking with each of the mismatching A, T, G, or C nucleobases at each given position of the SOI into a SOI which differs by 3 mismatching nucleotides compared to the consensus sequence of the oligo pool and to the original SOI. The 3 mutations in the SOI are the result of a previous round of mutagenesis and selection. Still, the oligo pool results in efficient mutagenesis of the entire SOI in *E. coli* K-12 MG1655. Figure shows the mutation rate in the cellular DNA at the SOI (folA locus), compared to the wild-type SOI, after five consecutive rounds of soft-randomized oligonucleotide integration. Note that position 1 on the figure is position 301 in SEQ ID NO:28 and in Table 1.

FIG. 9: The relation between the nucleobase-monomer spiking ratio of the soft-randomized DNA oligonucleotide pool with a sequence length of 90 nucleobases, and the distribution of the number of nucleobase mismatches compared to the wild-type sequence. A hard randomized oligo pool (25% spiking ratio of each nucleobase, containing an overall 75% of mismatching nucleobases at each position) on the entire sequence length generates a pool of sequences with limited homology (<40%) to their target site, while soft randomized oligo pools (0.5-5% spiking ratio of each nucleobase) produces highly homologous sequences (>80%) towards their target with high probability (Table 2).

Figure 10:
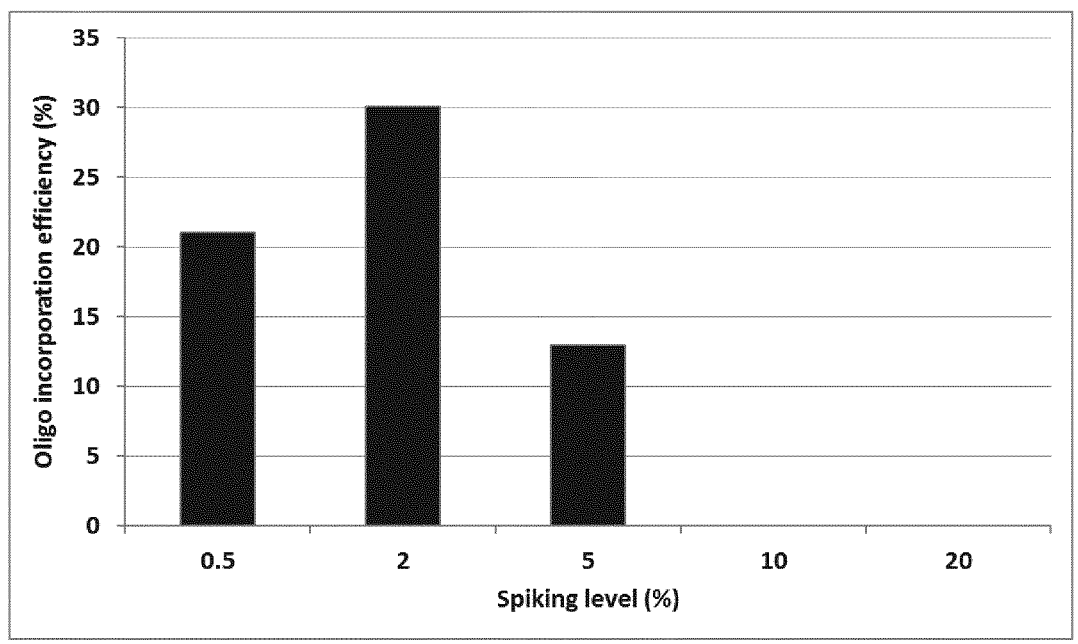

FIG. 10: The number of mismatching nucleobases is logarithmically related to the efficiency of the integration of a DNA oligonucleotide into the cellular DNA (Wang and Church 2011) (allelic-replacement (AR) efficiency), therefore increasing monomer-nucleobase spiking ratio during the synthesis of the oligonucleotide pool above 5% lowers the efficiency of integration. FIG. 10 shows the relation between the monomer-nucleobase spiking ratio of SEQ ID NO:3 oligonucleotide pool and the efficiency of integration at the SOI.

Figure 11A:
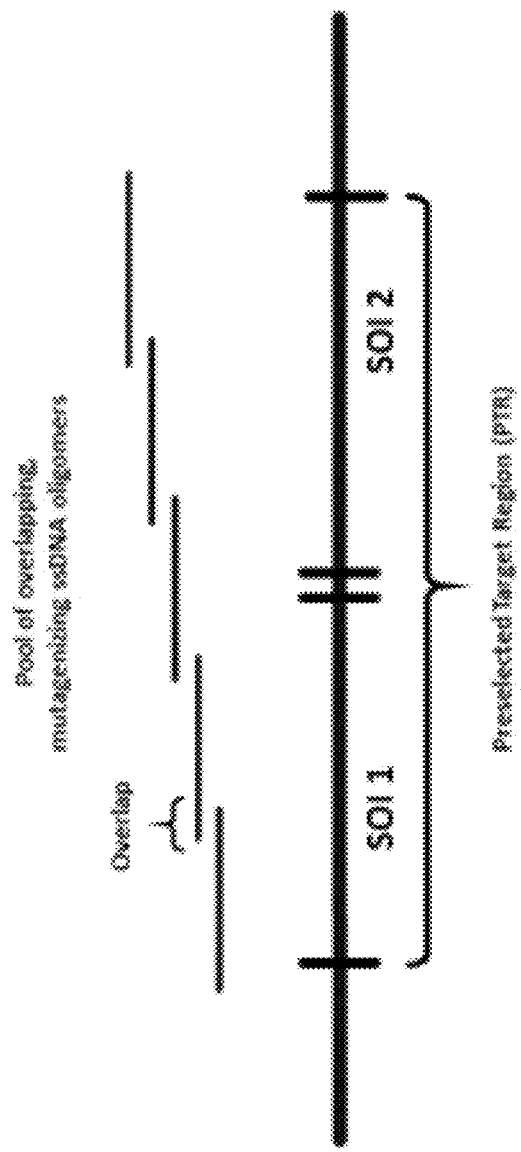
Figure 11B:
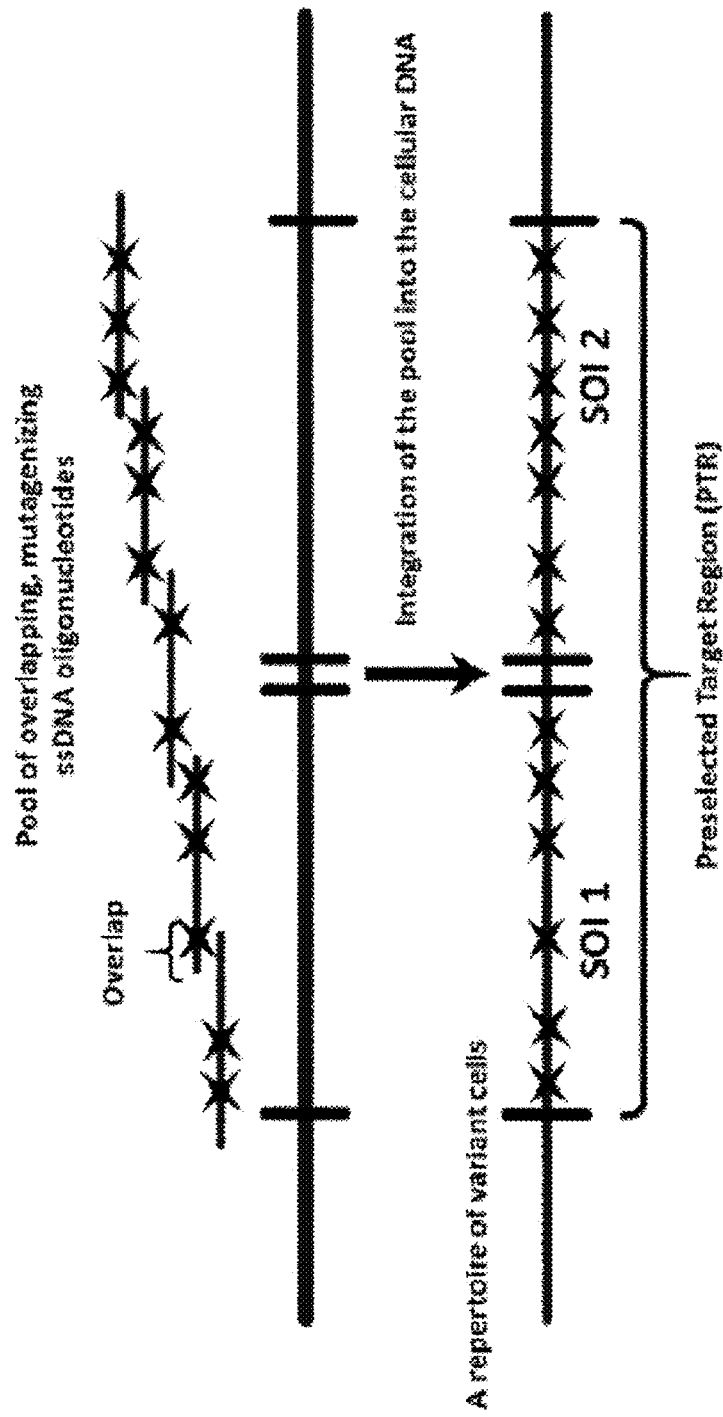

FIG. 11: Schematic representation of the mutagenesis described herein.

A: The method described herein applies a pool of overlapping single stranded DNA (ssDNA) oligonucleotides which when aligned to each other with their overlaps form a continuous sequence that is complementary to the preselected target region (PTR) and has a length that is at least the length of the PTR, which PTR comprises at least one sequence of interest (SOI).

B: In vivo mutagenesis of the sequence of interest (SOI) within a PTR is achieved by providing a pool of overlapping single stranded DNA (ssDNA) oligonucleotides which when aligned with their overlaps form a continuous sequence that is complementary to the SOI region of the PTR, wherein the pool contains a diversity of mutagenizing oligonucleotides covering nucleobase mismatches at every position of said SOI and combinations of said mismatches. FIG. 11 B represents individual oligos from the oligo pool, wherein each mutagenizing oligonucleotide comprises at least one mismatching nucleobase up to 20% mismatching nucleobases, compared to the SOI region of the PTR. Integrating the pool into said intracellular DNA induces in vivo mutagenesis of the intracellular DNA through hybridizing the oligonucleotides to the PTR and produces a cell library comprising a repertoire of variant cells which carry point mutations within said SOI region of the PTR.

Figure 12:
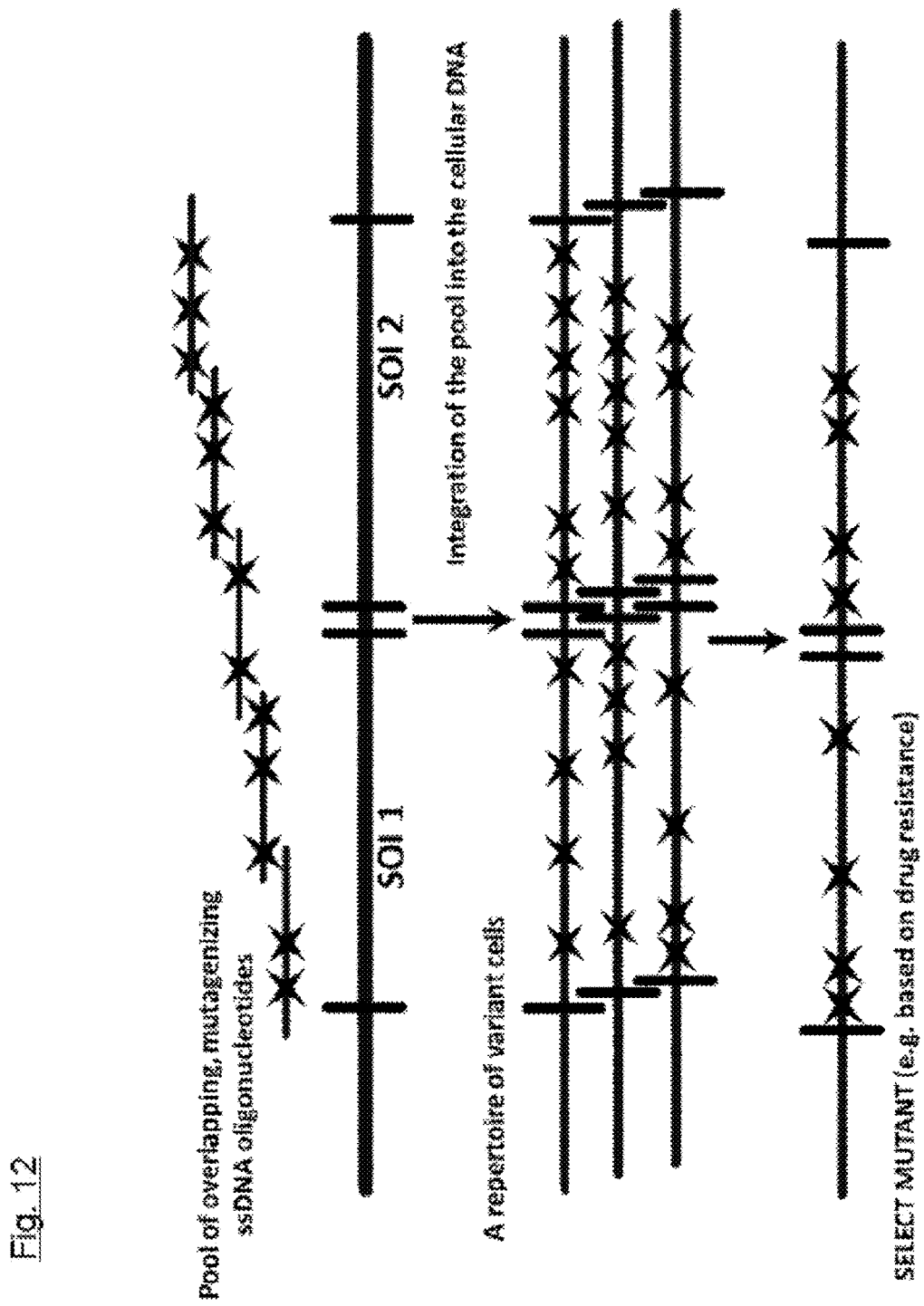

FIG. 12: Schematic representation of the workflow for selecting mutants from the library, generated by the method of invention. Exemplary SOI may comprise or consist of a nucleic acid construct comprising a nucleotide sequence encoding a cellular expression product to be evolved, e.g. drug-resistance determinants or recombinant proteins which are heterologous to the host cell. Exemplary recombinant proteins are enzymes, antibodies, antibody fragments or ligand-binding sequences. Exemplary SOIs which are non-coding nucleic acids are promoter or leader sequences, or introns, ribozyme, riboswitch or regulatory sequences or part of any thereof or within non-transcribed sequences, either upstream or downstream of a coding sequence. Selection of the mutant or mutants can be performed in vitro or in vivo, e.g. selecting a mutant based on the increased production of a recombinant protein or proteins or for resistance towards a drug or multiple drugs.

FIG. 13: Table 3: Selection of mutants from an *Escherichia coli* K-12 MG 1655 library in which the folA (DHFR) locus was mutagenized with the method of invention can identify mutants of a drug-target that confers resistance to trimethoprim. Following mutagenesis, the resulting cell libraries were exposed to 200 μg/ml trimethoprim antibiotic-stress on solid media, a concentration on which the parental *Escherichia coli* K-12 MG 1655 cannot grow. Subsequently, the genotype of around 1000 resistant mutants was determined by High-Throughput (HT) SMRT sequencing. Sequence analyses revealed that soft randomized single stranded DNA (ssDNA) oligonucleotide-mediated mutagenesis resulted in a diverse combination of complex DHFR mutants that are resistant to trimethoprim. Table indicates the most frequent mutants from the resistant cell pool. Mutational positions indicate nucleotide position within the PTR of the folA (DHFR) locus.

FIG. 14: Table 6: Single step adaptive mutational landscape of the folA regulatory and protein-coding region in *E. coli* MG1655 under mild (3 mg/L) trimethoprim selection. Single step mutational abundance data for each mapping position was used to determine the average abundance of each single step mutational event for each library (n=3). The threshold of detection was determined based on the background noise level for each biological sample. PCR and sequencing noise was quantified by assessing the Illumina MiSeq false base-call rate from non-mutagenized, wild-type folA control amplicons for each strain. The averaged background error rate at the DNA level after read quality filtering was 0.0003.

Based on error probability, amino acid mutations above the threshold value of 0.002 were marked as detected mutational hot-spots and missense amino acid mutations above the threshold value of 0.005 were marked as adaptive, resistance-conferring single step mutations. Mutations with an average DNA mutation abundance in the folA regulatory region above the threshold value of 0.002 were marked as detected mutational hot-spots and DNA mutations above the threshold value of 0.01 were marked as adaptive resistance-conferring single nucleotide polymorphisms.

Trimethoprim susceptibility was determined in MS media+casamino acid (without thiamine). Trimethoprim resistance, quantified as the 75% inhibitory concentration of trimethoprim (IC75), was calculated from the function of growth versus trimethoprim concentrations. Specifically, the IC75 value was calculated as the trimethoprim concentration at which the area under the growth curve of the given cell population was equal to one quarter of an uninhibited control. As a measure of the effect of each individual genotype, relative IC75 values for each of the corresponding mutants were determined and compared to the IC75 of the wild-type.

FIG. 15: Table 7: Frequency within the sequenced samples of resistance-conferring mutations towards ciprofloxacin. The gyrA gene of *E. coli* K-12 MG 1655 was subjected to overlapping, soft-randomized oligo pool-mediated mutagenesis, Followed by selection using ciprofloxacin (5-times of the wild-type MIC) on antibiotic-containing LB agar plates. From this agar plate over 1000 resistant mutants were selected and analyzed using Pacific Biosciences RSII Single Molecule Real-Time (SMRT) circular-consensus amplicon sequencing.

The analysis revealed that all putative resistance mutations reside solely in the protein-coding region, with clinically occurring mutations at Ser 83 and Asp 87 (and their combinations) dominating the observed mutational landscape. A novel, previously unknown resistance-conferring mutation (Gly288Asp) was also identified.

Figure 16:
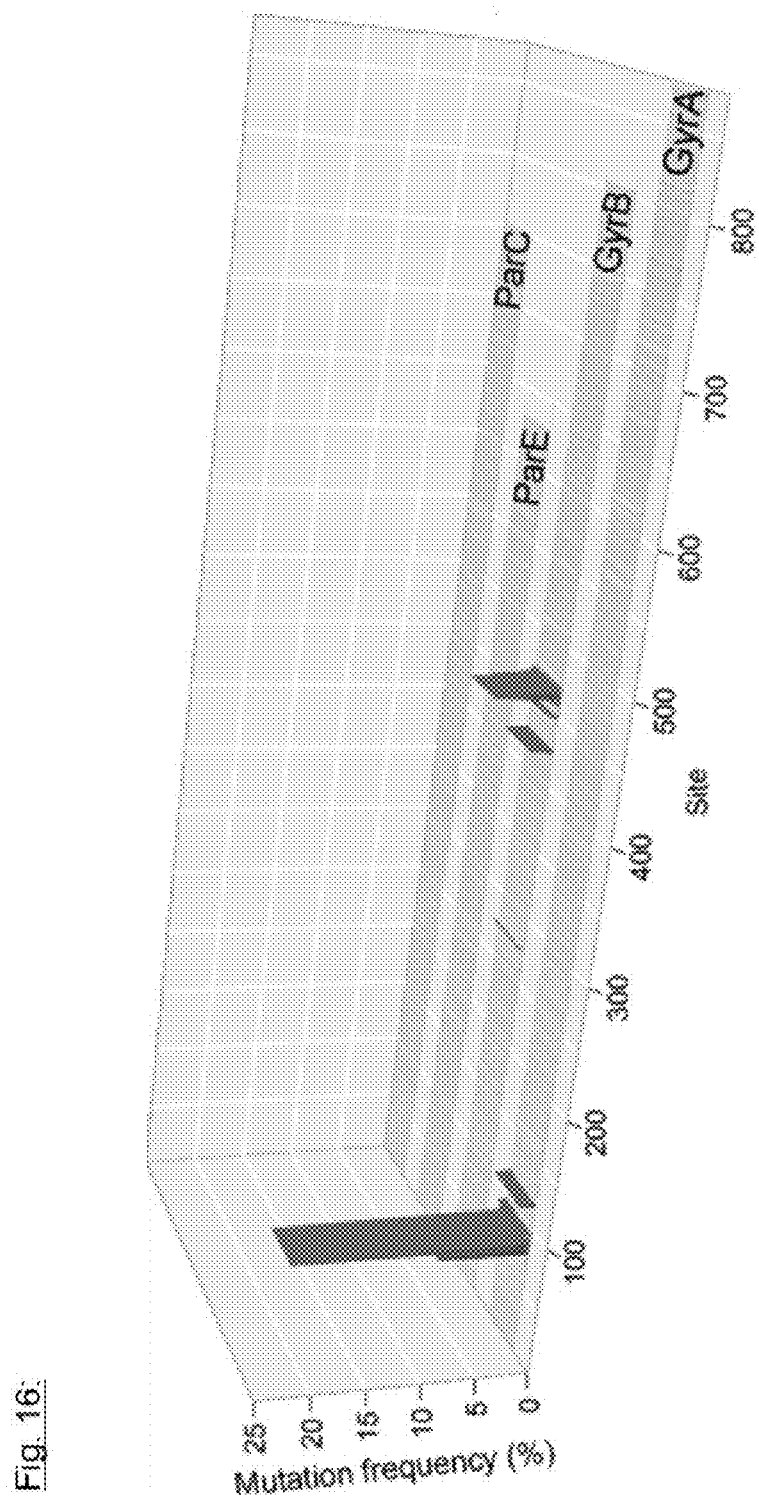

FIG. 16: Map of identified ciprofloxacin resistance-conferring mutations at the drug targets of fluoroquinolones in *E. coli* K-12 MG1655 following overlapping, soft-randomized oligo pool-mediated mutagenesis of multiple drug target-encoding genes (gyrA, gyrB, parE, parC). Figure shows mutation frequencies at detected mutational hot-spots based on simultaneous Single Molecule Real-Time (SMRT) sequencing at the gyrA, gyrB, parC and parE loci. Positions are marked with amino acid positions within the protein-coding region of the target loci. Mutational positions above a 0.5% mutation frequency cutoff are marked with dark grey bars.

Figure 17:
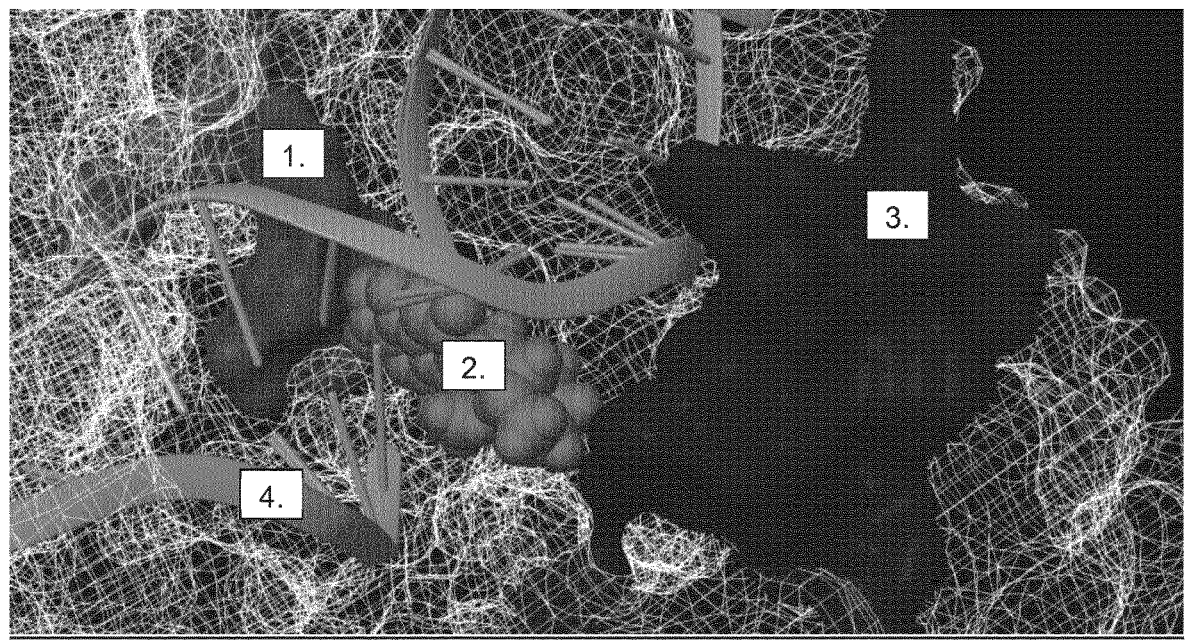

FIG. 17: Structural representation of ciprofloxacin resistance-conferring mutational hot spots of GyrA (marked as 1.) and GyrB (marked as 3.), two subunits of the DNA gyrase complex (Protein Data Bank ID: 5BS8). The figure also shows the interaction of the complex with a fluoroquinolone (marked as 2.) and dsDNA (marked as 4.). Mutated positions above the 0.5% mutation frequency cut-offs are indicated and qualified as mutational hot spots.

FIG. 18: Frequency of mutants within the sequenced samples of 5-Fluoroorotic Acid (5-FOA)-resistant *Saccharomyces cerevisiae* cells. Soft-randomized oligo pool-mediated mutagenesis of the URA3 locus was performed resulting in loss-of-function mutants of the gene, resulting in resistance to 5-FOA. Mutagenized cells were plated onto 5-FOA containing SD-agar plates, from which over 2000 resistant mutants were selected and analyzed using Pacific Biosciences RSII Single Molecule Real-Time (SMRT) circular-consensus amplicon sequencing.

FIG. 19: Mutagenesis of the gyrA PTR with the method described herein enables a miniaturized drug-resistance assay and the discovery of resistance-conferring mutants towards ciprofloxacin, an antibiotic drug. Image shows ciprofloxacin resistant *E. coli* K-12 colonies following a single cycle of oligo-mediated mutagenesis (1) besides a non-mutagenized control (2) after 24 h of incubation at 30° C. To assess the frequency of ciprofloxacin resistant mutants, 10 l of the mutagenized cell population has been plated onto a ciprofloxacin containing $LB^L$ agar plate including 20 mg/ml tetrazolium violet to stain bacterial colonies, besides 500 l of a non-mutagenized control cell suspension. Please see Example 6 for further details.

FIG. 20: Sequences referred to herein

SEQ ID NO:1: pORTMAGE2 plasmid, circular DNA

SEQ ID NO:2-11: single stranded DNA oligonucleotides

SEQ ID NO:12: SfolORM1, Soft-randomized oligonucleotide with 0.5% soft-randomization for the mutagenesis of the *S. enterica* folA PTR SEQ ID NO:13: SfolORM2, Soft-randomized oligonucleotide with 0.5% soft-randomization for the mutagenesis of the *S. enterica* folA PTR SEQ ID NO:14: SfolORM3, Soft-randomized oligonucleotide with 0.5% soft-randomization for the mutagenesis of the *S. enterica* folA PTR SEQ ID NO:15: SfolORM4, Soft-randomized oligonucleotide with 0.5% soft-randomization for the mutagenesis of the *S. enterica* folA PTR SEQ ID NO:16: SfolORM5, Soft-randomized oligonucleotide with 0.5% soft-randomization for the mutagenesis of the *S. enterica* folA PTR SEQ ID NO:17: SfolORM6, Soft-randomized oligonucleotide with 0.5% soft-randomization for the mutagenesis of the *S. enterica* folA PTR SEQ ID NO:18: SfolORM7, Soft-randomized oligonucleotide with 0.5% soft-randomization for the mutagenesis of the *S. enterica* folA PTR
SEQ ID NO:19: SfolPRM1, Soft-randomized oligonucleotide with 0.5% soft-randomization for the mutagenesis of the *S. enterica* folA PTR
SEQ ID NO:20: CfolORM1, Soft-randomized oligonucleotide with 0.5% soft-randomization for the mutagenesis of the *E. coli* CFT073 folA PTR
SEQ ID NO:21: CfolORM2, Soft-randomized oligonucleotide with 0.5% soft-randomization for the mutagenesis of the *E. coli* CFT073 folA PTR
SEQ ID NO:22: CfolORM3, Soft-randomized oligonucleotide with 0.5% soft-randomization for the mutagenesis of the *E. coli* CFT073 folA PTR
SEQ ID NO:23: CfolORM4, Soft-randomized oligonucleotide with 0.5% soft-randomization for the mutagenesis of the *E. coli* CFT073 folA PTR
SEQ ID NO:24: CfolORM5, Soft-randomized oligonucleotide with 0.5% soft-randomization for the mutagenesis of the *E. coli* CFT073 folA PTR
SEQ ID NO:25: CfolORM6, Soft-randomized oligonucleotide with 0.5% soft-randomization for the mutagenesis of the *E. coli* CFT073 folA PTR
SEQ ID NO:26: CfolORM7, Soft-randomized oligonucleotide with 0.5% soft-randomization for the mutagenesis of the *E. coli* CFT073 folA PTR
SEQ ID NO:27: CfolPRM1, Soft-randomized oligonucleotide with 0.5% soft-randomization for the mutagenesis of the *E. coli* CFT073 folA PTR
SEQ ID NO:28: The *Escherichia coli* K-12 MG1655 folA (DHFR) locus, including the folA (DHFR) PTR between nucleotide position 63-656.
SEQ ID NO:29: The *Escherichia coli* UPEC CFT073 folA (DHFR) locus, including the folA (DHFR) PTR between nucleotide position 142-734.
SEQ ID NO:30: The *Salmonella enterica* LT2 folA (DHFR) locus, including the folA (DHFR) PTR between nucleotide position 60-653.
SEQ ID NO:31-32: Barcoded primers used for the amplification of the folA PTR for HT sequencing analysis of *E. coli* K-12 MG1655.
SEQ ID NO:33-34: Barcoded primers used for the amplification of the folA PTR for HT sequencing analysis of *Salmonella enterica* LT2.
SEQ ID NO:35-36: Barcoded primers used for the amplification of the folA PTR for HT sequencing analysis of *E. coli* UPEC CFT073.
SEQ ID NO:37-75: Soft-randomized oligonucleotides with 0.5% soft-randomization for the mutagenesis of the *E. coli* K-12 MG1655 gyrA PTR.
SEQ ID NO:76-108: Soft-randomized oligonucleotides with 0.5% soft-randomization for the mutagenesis of the *E. coli* K-12 MG1655 gyrB PTR.
SEQ ID NO:109-140: Soft-randomized oligonucleotides with 0.5% soft-randomization for the mutagenesis of the *E. coli* K-12 MG1655 parC PTR.
SEQ ID NO:141-167: Soft-randomized oligonucleotides with 0.5% soft-randomization for the mutagenesis of the *E. coli* K-12 MG1655 parE PTR.
SEQ ID NO:168-214: sequences referred to in the Examples
SEQ ID NO:215-221: target gene sequences referred to in the Examples
SEQ ID NO:216-220: originating from *E. coli*
SEQ ID NO:221 originating from *S. cerevisiae*

DETAILED DESCRIPTION OF THE INVENTION

Specific terms as used throughout the specification have the following meaning. The term "cell culture" as used herein shall refer to the growth and propagation of cells in vitro, i.e. outside of a higher organism or tissue. It is particularly understood that the term shall not apply to transgenic animals or human beings. Suitable culture conditions for individual types of cells are known in the art, such as taught in Cell Culture Technology for Pharmaceutical and Cell-Based Therapies (2005). Cells may be cultured in a cell culture medium, in particular in suspension or while attached to a solid substrate.

The term "contiguous" interchangeably used with "continuous" with respect to a nucleic acid sequence is a sequential sequence of nucleic acids, for example, deoxyribonucleic acids, peptide nucleic acids, derivatives or analogs thereof, and combinations thereof.

The continuous sequence described herein is formed upon aligning the oligonucleotides of the ssDNA oligonucleotide pool to each other with overlaps. Therefore, the continuous sequence is of a hypothetical polynucleotide composed of an oligonucleotide sequence assembly joined together by their overlaps (i.e. the overlapping parts or overhangs), such that the overlaps are included in the continuous sequence only once. Upon aligning two oligonucleotide sequences with an overlap, a continuous sequence is formed which has a length that is the length of both individual oligonucleotides taken together, minus the length of the overlap. Consequently, the continuous sequence comprises a segment of each of the aligned oligonucleotides. The size of the continuous sequence described herein may vary from 60 nucleobases to up to $10^6$ nucleobases. The size of the oligonucleotide overlap can be in a size range from 2% of the length of the oligonucleotide to up to 50%. For example, to cover a SOI with 1000 nucleobase length, 14 oligonucleotides are needed, each with a length of 90 nucleotides aligning for every 72 nucleotides of the SOL.

In another example, two oligonucleotides, each of 90 bases length, may be aligned with an overlap of e.g. at least 10 bases, such that the 3' terminal sequence of at least 5 nucleobases length of the first oligonucleotide is overlapping with the 5' terminal sequence of at least 5 nucleobases length. In this case, the continuous sequence is characterized by an 85 base segment of the first oligonucleotide and an 85 base segment of the second oligonucleotide, and an overlap of 10 bases in length which originates from both, the first and the second oligonucleotide. The oligonucleotide section excluding any overlap is herein referred to as "core" region of an oligonucleotide.

In the pool of oligonucleotides described herein a series of oligonucleotides are provided wherein each of the oligonucleotides comprises a terminal sequence that is overlapping with the terminal sequence of another oligonucleotide. As an exception to the foregoing, those oligonucleotides which comprise the 5' or 3' terminus of the continuous sequence formed upon alignment are not overlapping at the respective 5' or 3' terminus.

The term "evolution" and "pattern of evolution" as used herein is understood in the following way. In an evolution process, a population of nucleic acids such as a SOI is subjected to one or more rounds of (a) replication and (b) mutation to produce a desired evolved (mutated) SOI that is different from the original SOI, or a cellular phenotype that is determined by the SOI difference. The evolution procedure may be carried out in vitro, for example, using cells in culture which are mutated by in vivo mutagenesis.

For example, a model of accelerated evolution of drug resistance arising in patients may be provided. The methods described herein may be used to accelerate evolution in cells, such that mutant microorganisms of an original microorganism may be produced. The repertoire of mutants may comprise those microorganisms that are still susceptible to a drug (alike the original microorganism), and further comprise microorganisms that have evolved as drug-resistant ones, e.g. through mutagenesis of drug-targets.

In another example the method described herein may be used to mutagenize drug-resistance determinants e.g. antibiotic-resistance determinants, e.g. antibiotic-resistance determinants that are e.g. described in the literature (McArthur et al. 2013) or identified by those skilled in the art, e.g. by functional metagenomics or by adaptive laboratory evolution, such that libraries of mutant drug-resistance determinants may be produced. In another example, multiple drug-resistance determinants may be mutagenized in the same microorganism, thereby multiplex libraries of mutant drug-resistance determinants may be produced.

Such libraries may be used to select specific library members that are displaying drug resistance (FIG. 12). Genotype of such drug-resistant variants can be determined by any of the mutational analysis methods and such variants can be further characterised by other phenotypic or genotypic assays, e.g. assayed for susceptibility towards other drugs.

In another example, a recombinant host cell may be evolved, which expresses a heterologous PTR to produce a heterologous polypeptide or protein to be mutagenized. The polypeptide or protein may be encoded by a genetic construct incorporated into the host cell and expressed by an expression cassette, wherein a promoter is typically operably linked to an encoding sequence which is heterologous to the promoter and/or the host cell. Exemplary proteins are proteases or enzymes, antibodies, antigens e.g. vaccine antigens, toxins, antigen- or ligand-binding proteins such as receptors, antibiotics, peptides, or cytokines. Specific PTR examples encode an antibody, antibody fragment, or antigen-binding sequences e.g. of antibody variable domains.

One class of preferred targets include a genome of a virus, such as cDNA of (+) RNA virus genomes or (−) RNA viruses; genome of dsDNA viruses, RNA to DNA viruses, especially HIV and HTLV, and DNA viruses, bacteriophages including T7, T4, P1, Lambda-phage or any of their cloned or engineered variants.

In another example, a model of accelerated clonal evolution of diseased cells, e.g. tumor cells is provided. The methods described herein may be used to accelerate evolution in diseased cells, such that mutant cells of an original cell may be produced. The repertoire of mutants may comprise those cells that are susceptible to a first drug (alike the original microorganism), and further comprise cells that have evolved as being resistant to a first drug, but susceptible to a second drug or drug combination, resembling second line treatment. It is specifically understood that the in vivo clonal mutagenesis described herein refers to somatic cells, excluding in vivo mutagenesis of a gamete, germ cell, gametocyte, undifferentiated stem cell, or any animal or human being.

Therefore, the methods described herein particularly can serve as a rapid, high-throughput method to evolve intracellular DNA in a cell culture, e.g. intracellular DNA which is of viral origin, genomic (including e.g. chromosomal, episomal, plasmid) origin or a heterologous (artificial) DNA that has been introduced into the host cell.

The method described herein may produce libraries or cell mutants which may serve as a tool to develop individualized or personalized treatment for a disease undergoing clonal evolution. Mutations associated with resistance may be any mutation indicating that a subclonal population will become resistant to a therapy. Therefore, the present method supports novel therapies determined by the clonal evolution in a patient in need thereof.

The pattern of evolution obtainable by the method described herein typically involves only a limited clonal diversity, e.g. wherein the mutants are characterized by only a few (lower than 10, 20, 30, 50, 100 or 500) mutations compared to the original cell, which are confined to at least one genomic section comprised in the PTR.

The pattern may be determined by any suitable evolution mapping technique, such as selecting or enriching clones from the library and subjecting the selected or enriched clones to mutation analysis, sequencing of the entire PTR with capillary sequencing or with high-throughput (HT) sequencing e.g. polony sequencing, pyrosequencing, Illumina (Solexa) sequencing, SOLiD sequencing, semiconductor sequencing, DNA nanoball sequencing, Heliscope single molecule sequencing, Single molecule real time (SMRT) sequencing, Nanopore DNA sequencing, tunnelling currents DNA sequencing, sequencing by hybridization, sequencing with mass spectrometry, Microfluidic Sanger sequencing, Microscopy-based sequencing, RNAP sequencing and determining mutations and the frequency of mutations within the pool, compared to the original sequence of nucleotides.

Specific embodiments may produce an evolutionary pattern involving mutations at each and every position or codon of the SOI region of the PTR. The repertoire of mutants may cover mutations exchanging one or more nucleobases, e.g. by any of the alternative three nucleobases exchanging the original nucleobase, or by less than the three alternative ones, such as only two or one selected nucleobase(s).

The evolutionary pattern is mainly characterized by the type and amount of mutagenizing oligonucleotides which confer specific mutations through the number, type and position of mismatching nucleobases. Also, the evolutionary pattern may be characterized by the number of mutagenesis rounds. For example, the mutagenesis method may be carried out as one or more rounds of evolution, each comprising a step of mutagenesis by integrating the mutagenizing oligonucleotides into the SOI region of the PTR, followed by a cultivation step to grow and/or replicate the mutant cells. The repertoire of mutant cells may be analyzed for the evolutionary pattern after one or more rounds of ssDNA oligonucleotide integration and mutagenesis. Additional diversity can be introduced by a further round of evolution. Thus, a population of cells in a cell library produced by the method described herein may be diversified by mutagenesis employing one or more further rounds of in vivo mutagenesis described herein, or any other conventional mutagenesis methods. In specific embodiments, further mutagenesis may be carried out on only a subpopulation of the library, e.g. suitable mutants which are provided in a fraction of the library which is produced by selecting desirable phenotypes or genotypes and fractionating the library.

For example, the number of diverse modified cells in a single round of mutagenesis with an oligonucleotide pool can be up to $2.5 \times 10^{11}$ in a single round of modification. The library size may be limited by the amount which can be transformed or transfected in one cycle. To maximize library size, various transformation strategies can be used and known by those skilled in the art, e.g. as described in Sambrook et al. (Molecular Cloning: A Laboratory Manual, Cold Spring Harbor, 1989). In one specific example, the number of transformed cells can be maximized by electroporating multiple, up to 96 or 384 or higher individually separated volumes of electrocompetent cells (e.g. in a 96-format electroporator) simultaneously with the same oligo pool.

The term "sequence of interest" (SOI) as used herein, refers to a DNA sequence which is of an intracellular DNA, which is non-coding and/or coding for a polypeptide. Specifically, the SOI is the sequence of a gene encoding a gene product, or a partial gene. Specifically, the SOI is to be evolved in an in vivo mutagenesis method as described herein. The term includes any variations or mutants of an original or parent (e.g., wild-type or naturally-occurring) SOI that are the result of an evolution process according to methods described herein.

In certain embodiments, a SOI is comprised in a nucleic acid construct comprising a nucleotide sequence encoding an enzyme to be evolved, or a metabolic or biosynthetic pathway to be evolved, or a part of the respective encoding nucleotide sequence. In another example, the SOI is comprised in a nucleic acid construct comprising a nucleotide sequence encoding a cellular expression product to be evolved, e.g. recombinant proteins which are heterologous to the host cell. Exemplary recombinant proteins are enzymes, antibodies, antibody fragments or ligand-binding sequences. Exemplary SOIs which are non-coding nucleic acid sequences are promoter or leader sequences, or introns, ribozyme, riboswitch or regulatory sequences or part of any thereof or within non-transcribed sequences, either upstream or downstream of a coding sequence.

In certain embodiments, the SOI is comprised in a nucleic acid construct comprising a heterologous nucleotide sequence that is artificial (e.g. de novo synthetized or cloned from another organism) and encodes one or more proteins and regulatory sequences, for example an operon or a metabolic pathway, whose functionality is optimized or adapted to the host organism to be efficiently functional.

The term "heterologous" as used herein with respect to a nucleotide sequence or a SOI, or an amino acid sequence or protein, refers to a compound which is either foreign, i.e. "exogenous", such as not found in nature, in a given host cell; or that is naturally found in a given host cell, e.g., is "endogenous", however, in the context of a heterologous construct, e.g. employing a heterologous nucleic acid. The heterologous nucleotide sequence as found endogenously may also be produced in an unnatural, e.g. greater than expected or greater than naturally found, amount in the cell. The heterologous nucleotide sequence, or a nucleic acid comprising the heterologous nucleotide sequence, possibly differs in sequence from the endogenous nucleotide sequence but encodes the same protein as found endogenously. Specifically, heterologous nucleotide sequences are those not found in the same relationship to a host cell in nature. Any recombinant or artificial nucleotide sequence engineered to transform a particular host cell is understood to be heterologous to the host cell. An example of a heterologous polynucleotide is a nucleotide sequence not natively associated with the gene to be expressed. A specific example of a heterologous compound is a nucleic acid comprising a SOI, to which endogenous, naturally-occurring genetic or regulatory elements of the host cell is not normally operably linked.

The term "library" as used herein shall refer to a collection of library members which are nucleic acid fragments (e.g. an oligonucleotide library) or a collection of cells (e.g. a microbial cell library). The library members share common features (such as conferred by genomic sequences), but differ in at least one mutation and/or phenotype. A library typically contains library members which are diverse, besides those that have common features. One particular type of library is a library of randomized mutants of oligonucleotides or cells, generated by random mutagenesis. A specific example would be a rationally designed (or synthetic) library, e.g. a library which comprises specifically engineered DNA fragments or oligonucleotides.

A cell library may be a library of isogenic cells (or cell lines or clones) comprising a variety of genomic mutations in a parent (originator) cell. Mutant cells of a parent cell obtained by the mutagenesis method described herein may be selected by determining the desired function of the cell with a phenotype-based selection or screening method or (genetic or functional) single cell analysis allowing the identification of single cells, containing one or more mutations or nucleobase alterations among a large population of cells.

Exemplary methods for phenotype-based selection or screening of cells from a library are based on viability of cells or survival of a microorganism library or repertoire of variant microorganisms under selective conditions, for example in the presence of a toxin or drug, such as an antibiotic. In some embodiment, selection is based on growth differences where the growth is quantified with an optical measurement or growth over time is used to enrich clones with improved growth capacity. In other cases, the enrichment or dilution of particular genotypes, originating from the growth differences, may be quantified by determining the frequency of certain genotypes in the population by one of the below-mentioned DNA sequencing-based quantification techniques. The subject of DNA sequencing may be the PTR itself, or an identification tag or barcode that is a short DNA sequence which labels each cell in the population. In another embodiment, phenotype-based selection or screening is based on the growth differences, which originate from the improved utilization of a nutrient, for example of a carbon source. In another embodiment, the improved utilization of the nutrient or chemical substance is quantified with an analytical technique, for example by the measurement of intracellular metabolite concentration, the increase of which is the improvement in the desired phenotype. In other embodiment, the phenotype-based selection and screening may involve the quantification of the catalysis of a chemical reaction, which is based on optical quantification of the reaction product or the reactants for example by detecting the signal from a fluorescence, absorbance or colorimetric assay or using mass spectrometry. In other embodiments, the phenotype-based screening or selection involves a differentiation in the binding capacity of a protein to a target molecule, for example using a binding assay to enrich variants with improved affinity to a specific ligand or using an optical assay based on for example fluorescence, absorbance or colorimetric assays.

Exemplary methods for sequencing-based screening of cells within a library are the following: SNP genotyping methods, including hybridization-based methods (e.g. molecular beacons, SNP microarrays, restriction fragment length polymorphism, PCR-based methods, including Allele-specific PCR, primer extension-, 5'-nuclease or Oligonucleotide Ligation Assay, Single strand conformation polymorphism, Temperature gradient gel electrophoresis, Denaturing high performance liquid chromatography, High-resolution Melting of the entire amplicon (HRM), SNPlex and surveyor nuclease assay; Sequencing based mutation analysis, including capillary sequencing or high-throughput sequencing of an entire PCR amplicon of the PTR (amplicon sequencing). Such high-throughput (HT) amplicon sequencing methods include, but are not restricted to polony sequencing, pyrosequencing, Illumina (Solexa) sequencing, SOLiD sequencing, semiconductor sequencing, DNA nanoball sequencing, Heliscope single molecule sequencing, Single molecule real time (SMRT) sequencing, Nanopore DNA sequencing, tunneling currents DNA sequencing, sequencing by hybridization, sequencing with mass spectrometry, Microfluidic Sanger sequencing, Microscopy-based sequencing, RNAP sequencing.

The cell library described herein is specifically characterized by a size (also referred to as library diversity) which is at least $10^3$, $10^4$, $10^5$, $10^6$, $10^7$, $10^8$, $10^9$, $10^{10}$ or $10^{11}$ library members which are characterized by different mutations or nucleobase or nucleotide alterations, e.g. a substitution, or insertion or deletion of one or more subsequent nucleotides, e.g. to change the encoded amino acid sequence. Typically, the library members differ in at least one or more point mutation at the nucleotide or amino acid level. Specifically, in some embodiment, the variation covers every possible naturally-occurring nucleobase or amino acid residue at a certain position. If the cell mutants are produced by mutagenesis of a parent cell line, a variety of isogenic cells of the same type of the parent cell line is produced.

Each library member may be individually characterized and marked by a selectable marker or a DNA sequence tag or barcode, to facilitate the selection of a library member in the library or the identification of a library member in the library. Alternatively, the genetic mutation may be determined directly by a suitable determination method, e.g. high-throughput sequencing, capillary sequencing or employing specific probes hybridizing with the mutated region, to select the cell line comprising the mutation.

It may be desirable to locate the library members in separate containers, to obtain a library of cell collections in containers. According to a specific embodiment, the library is provided in an array, e.g. a cell chip, wherein the array comprises a series of spots on a solid carrier, wherein the series of spots include a suspension of one or more cells from a cell collection. Likewise, the cell library may be indexed to nucleic acid arrays.

Such libraries may be used to select specific library members to study the interaction with a predefined substance, e.g. a chemical or biological, such as a drug, inhibitor or enhancer. Specific applications of such a library are (i) the identification of genes involved in various biological processes, such as the life cycle of a cell or responses to growth factors or growth in the presence of different chemical substances, such as drugs e.g. antibiotics, or cytokines or nutrients and energy sources, (ii) the determination of the specificity of an antibody or ligand-binding molecule or (iii) the use of a mutant cell line for the production of a biological (e.g. antibody, cytokine or industrially relevant metabolite/bioproduct, for example an RNA, a peptide or a protein molecule).

A further application may be the selection of a suitable host cell, for expressing a recombination product or for the increased expression of a recombinant product as compared to the parental cell. Cell arrays or cells in specific containers or the pooled population of cells may be employed to enable highly parallel, high throughput analyses of cell phenotypes that complement efforts for assessing cell growth and morphology, protein expression levels, and cell imaging.

The library of oligonucleotides as described herein may specifically comprise a variety of oligonucleotides to be used as template for introducing nucleobase alterations in a SOI region of a PTR. Therefore, the library described herein comprises library members suitably composed of oligonucleotides of a defined length, but different or variable in sequence, wherein the oligonucleotides are complementary to a certain region of the cellular DNA to a certain degree, such as to enable hybridization, which region is longer than the sequence of a single oligonucleotide, but is covered by at least two or more oligonucleotides which are overlapping.

Such a library is conveniently provided as a pool or mixture in a liquid (in particular aqueous) medium which is physiologically acceptable to the cell to be mutated. The pool of oligonucleotides specifically comprises at least 100, preferably at least any of $10^3$, $10^4$, $10^5$, $10^6$, $10^7$, $10^8$, $10^9$, $10^{10}$, or even more library members in the oligo pool which are oligonucleotides, each capable of hybridizing to the PTR. The library preferably comprises oligonucleotides which are artificially or chemically synthesized, or chemically modified (e.g. including peptidyl nucleic acids or phosphorothioate bond) oligonucleotides, e.g. synthesized by suitable methods well-known in the art.

The term "point mutation" or nucleobase alterations as used herein shall refer to a mutation event altering a nucleic acid or amino acid sequence at a certain location, such as by introducing or exchanging single nucleobases or amino acids or introducing gaps. A point mutation or nucleobase alterations may involve a change in one or more single or adjacent or consecutive nucleobases or amino acid residues in a sequence. In a library comprising a repertoire of mutants covering a limited diversity, the frequency of point mutations in a sequence is limited, such that the mutants share at least a certain sequence identity to a parent (or reference) sequence, which is e.g. at least any of 80%, 90%, 95%, 96%, 97%, 98%, or 99%.

According to a specific example, the diversity within a pool of oligonucleotides described herein is characterized as follows: the diversity may be determined by the number of mutations within the oligonucleotide sequence. For example, in a single oligonucleotide with a length of 90 nucleotides, the theoretical number of possible single nucleotide changes is 90×3=270 with the four naturally occurring DNA, A, T, G or C nucleotides. For two single nucleotide changes with the four naturally occurring DNA, A, T, G or C nucleotides per oligonucleotide (double mutants) the number of possible sequences is 36045. For three single nucleotide changes per oligonucleotide (triple mutants) this number is 3171960. For quadruple mutations this number is 206970390. These numbers can further increase by incorporating non-natural nucleobases within the oligonucleotide sequence.

In order to modify the cells by introducing the oligonucleotide pool into the cells, typically up to 0.1 nmol oligonucleotides for $10^{10}$ electrocompetent cells is used which equals about $6\times10^{15}$ oligonucleotide molecules for $10^{10}$ cells. Since this number is larger than the number of possible sequences with up to 4 mutations, every possible oligonucleotide sequence is represented in the oligonucleotide pool on a statistical level which has up to four mutations compared to the PTR. Considering a transformation efficiency of 40%, every possible oligonucleotide sequences up to four mutations compared to the PTR can be delivered into the target cells.

Point mutations in a nucleic acid sequence may specifically include frameshift mutations that disrupt gene function or gene expression (gene knock-outs), defined point mutations (knock-ins). The exchange in a sequence may comprise only one point mutation in an oligonucleotide or SOI sequence of the PTR described herein, thereby encoding a different amino acid, or a series of point mutations, e.g. to obtain a pattern of mutations, in particular a pattern which resembles a pattern of evolution.

In some cases, positions are distributed randomly, e.g. with either any of the possible nucleobases or amino acid residues, or chosen or selected as preferred ones to randomize the sequences.

In some cases, the sequence diversity is defined to be different between positions, such differences can be incorporated into the mutagenizing pool during the course of the mutagenizing pool generation.

The term "preselected target region" (PTR) as used herein shall refer to a target polynucleotide, which is any non-coding or coding contiguous portion of genomic sequence whether or not it is within, or associated with, a gene. The PTR described herein may e.g. include or have a polynucleotide sequence that is a SOI which is a whole gene sequence, or may include or have a SOI which is a contiguous sub-region or segment of a whole gene sequence. In the latter case, the PTR may be positioned within a whole gene.

The term "hybridization condition" as used herein refers to the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other well-known factors, such as the length of incubation time or reaction chamber dimensions may contribute to the environment.

As used herein, the term "hybridization" is intended to mean the process during which two nucleic acid sequences anneal to one another with intermolecular chemical bond (e.g. hydrogen bonds) so as to form a double strand under appropriate conditions. In some embodiments, in vivo hybridization is promoted by ssDNA-annealing proteins, such as the Beta protein of the Lambda Red system, which promote annealing of a single-stranded oligonucleotide to the cellular DNA.

The hybridization between two complementary sequences or sufficiently complementary sequences depends on the operating conditions that are used, and in particular the stringency. The stringency may be understood to denote the degree of homology; the higher the stringency, the higher percent homology between the sequences. The stringency may be defined in particular by the base composition of the two nucleic sequences, and/or by the degree of mismatching between these two nucleic sequences. By varying the conditions, e.g. salt concentration and temperature, a given nucleic acid sequence may be allowed to hybridize only with its exact complement (high stringency) or with any somewhat related sequences (low stringency). Increasing the temperature or decreasing the salt concentration may tend to increase the selectivity of a hybridization reaction.

Sequences of a certain homology or complementarity are herein described to particularly hybridize within the host cell, i.e. in vivo hybridizing. Therefore, the homology of the two nucleic acid sequences is specifically at least 70%, preferably at least 80%, preferably at least 90%, i.e. the double strand obtained during this hybridization comprises preferably at least 70%, preferably at least 80%, preferably at least 90% or 100% A-T bonds and C-G bonds.

The stringent or physiological conditions and the respective stringency can be determined by those skilled in the art, e.g. as described in Sambrook et al. (Molecular Cloning: A Laboratory Manual, Cold Spring Harbor, 1989).

By "complementary" it is meant that the nucleotide sequences of similar regions of two single stranded nucleic acids have a nucleotide base composition that allow the single-stranded regions to hybridize together in a stable, double-stranded hydrogen-bonded region under stringent hybridization or amplification conditions. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotide sequences are 100% complementary. Besides conventional bases (A, G, C, T), analogs e.g., inosine and 2'-deoxyinosine and their derivatives (e.g. 7'-deaza-2'-deoxyinosine, 2'-deaza-2'-deoxyinosine), azole- (e.g. benzimidazole, indole, 5-fluoroindole) or nitroazole analogues (e.g. 3-nitropyrrol, 5-nitroindol, 5-nitroimidazole, 4-nitropyrazole, 4-nitrobenzimidazole) and their derivatives, acyclic sugar analogues (e.g. those derived from hypoxanthine- or indazole derivatives, 3-nitroimidazole, or imidazole-4,5-dicarboxamide), 5'-triphosphates of universal base analogues (e.g. derived from indole derivatives), isocarbostyril and other hydrophobic analogues, and any of its derivatives (e.g. methylisocarbostyril, 7-propynylisocarbostyril), hydrogen bonding universal base analogues (e.g. pyrrolopyrimidin), and other chemically modified bases (such as diaminopurine, 5-methylcytosine, isoguanine, 5-methyl-isocytosine, K-2'-deoxyribose, P-2'-deoxyribose) can have different base-pairing preferences and can pair with more than one natural nucleobase with similar stringency/probability. In certain cases, the monomers are linked by phosphodiester or by peptidyl linkages or by phosphorothioate linkages.

The term "random" as used herein regarding mutagenesis shall mean a method wherein DNA mutations are randomly introduced to produce mutant genes or genomic sequences, which are also referred to as "randomized". Randomized DNA sequences may encode a series of amino acid sequences, which are termed "randomized" as well. A multitude of randomized nucleotide sequences, cells comprising such nucleotide sequences, and their expression products are conveniently compiled into a library, herein referred to as randomized library or randomized library members.

In soft randomization, in a pool of oligonucleotides each residue, or each 2 or each 3 consecutive residues is mutated to a limited extent, e.g. the occurrence of the original nucleobase (the nucleobase which is in the SOI) at a given position on the oligonucleotides in the pool (herein understood as "frequency") is bigger than the occurency or frequency of each mismatching nucleobases. In other words, the nucleobase composition in the oligo pool at each position is highly biased toward the original sequence. Both in chemical or biological synthesis of the oligonucleotide pool, the theoretical frequency of an amino acid substitution at any position depends on the quantitative ratios between the nucleotides added at particular steps during the synthesis of the oligonucleotides. Specifically, the overall frequency of the mismatching nucleobases are preferably less than 50%, 25%, 10%, 5%, or 1%, or 0.5% or in a ratio which is lower or equal to about 0.1%.

Soft randomized oligonucleotides are specifically characterized by a limited extent (frequency) of nucleobase mismatches, such that the overall sequence identity to the corresponding region within the SOI remains high, e.g. at least 80% or at least 90% or at least 95%. The theoretical frequency of point mutations at any position depends on the quantitative ratios between the nucleotides, nucleotide monomers, dimer-nucleotides (e.g. natural dimer-nucleotides, including 5'-dA-dC-3', 5'-dA-dG-3', 5'-dA-dT-3', 5'-dA-dA-3', 5'-dT-dC-3', 5'-dT-dG-3', 5'-dT-dT-3', 5'-dT-dA-3', 5'-dG-dC-3', 5'-dG-dG-3', 5'-dG-dT-3', 5'-dG-dA-3', 5'-dC-dC-3', 5'-dC-dG-3', 5'-dC-dT-3', 5'-dC-dA-3' or their derivatives) or trimer-nucleotides (e.g. natural trimer-nucleotides, including 5'-dA-dC-dA-3', 5'-dA-dG-dA-3', 5'-dA-dT-dA-3', 5'-dA-dA-dA-3', 5'-dT-dC-dA-3', 5'-dT-dG-dA-3', 5'-dT-dT-dA-3', 5'-dT-dA-dA-3', 5'-dG-dC-dA-3', 5'-dG-dG-dA-3', 5'-dG-dT-dA-3', 5'-dG-dA-dA-3', 5'-dC-dC-dA-3', 5'-dC-dG-dA-3', 5'-dC-dT-dA-3', 5'-dC-dA-dA-3', 5'-dA-dC-dT-3', 5'-dA-dG-dT-3', 5'-dA-dT-dT-3', 5'-dA-dA-dT-3', 5'-dT-dC-dT-3', 5'-dT-dG-dT-3', 5'-dT-dT-dT-3', 5'-dT-dA-dT-3', 5'-dG-dC-dT-3', 5'-dG-dG-dT-3', 5'-dG-dT-dT-3', 5'-dG-dA-dT-3', 5'-dC-dC-dT-3', 5'-dC-dG-dT-3', 5'-dC-dT-dT-3', 5'-dC-dA-dT-3', 5'-dA-dC-dG-3', 5'-dA-dG-dG-3', 5'-dA-dT-dG-3', 5'-dA-dA-dG-3', 5'-dT-dC-dG-3', 5'-dT-dG-dG-3', 5'-dT-dT-dG-3', 5'-dT-dA-dG-3', 5'-dG-dC-dG-3', 5'-dG-dG-dG-3', 5'-dG-dT-dG-3', 5'-dG-dA-dG-3', 5'-dC-dC-dG-3', 5'-dC-dG-dG-3', 5'-dC-dT-dG-3', 5'-dC-dA-dG-3', 5'-dA-dC-dC-3', 5'-dA-dG-dC-3', 5'-dA-dT-dC-3', 5'-dA-dA-dC-3', 5'-dT-dC-dC-3', 5'-dT-dG-dC-3', 5'-dT-dT-dC-3', 5'-dT-dA-dC-3', 5'-dG-dC-dC-3', 5'-dG-dG-dC-3', 5'-dG-dT-dC-3', 5'-dG-dA-dC-3', 5'-dC-dC-dC-3', 5'-dC-dG-dC-3', 5'-dC-dT-dC-3', 5'-dC-dA-dC-3' or their derivatives) which are admixed during the synthesis of the oligonucleotides. The ratio of each alternative base, dimer-base or trimer base to the original base is understood as the spiking ratio. A low spiking ratio means that the nucleotide building blocks predominantly used in the synthesis of the oligonucleotide is the original nucleotides, nucleotide monomers, dimer-nucleotides or trimer-nucleotides of the SOI.

If the monomer-nucleotide ratio is 0.5% with natural nucleosides (deoxyadenosine, deoxythymidine, deoxyguanosine, and deoxycytidine), the three natural, alternative monomer-nucleotides are admixed during the synthesis of the oligonucleotides in this ratio to the nucleotide that is in the SOI at that position, i.e. the ratio of the four nucleotides is 98.5%:0.5%:0.5%:0.5%, resulting in a mutation frequency of about 1.5% at each position. For a spiking ratio of 25%, which is the level of hard-randomization, e.g. which is marked with an IUPAC nucleotide code of N, all 4 nucleotides are mixed in a ratio of 25% each. Accordingly, the percentage of the mismatching nucleotides in the oligo pool is 75% in each position in case of a polynucleotide synthesis that involves four nucleotide building blocks).

If the dimer-nucleotide spiking ratio is 0.1%, the 15 natural, alternative dimer-nucleotides are admixed in this ratio to the dimer-nucleotide that is in the SOI at that position, i.e. the ratio of the 16 dimer-nucleotides is 98.5%: 0.1%:0.1%:0.1%:0.1%:0.1%:0.1%:0.1%:0.1%:0.1%:0.1%:0.1%:0.1%:0.1%:0.1%:0.1%.

If the trimer-nucleotide spiking ratio is 0.024%, the alternative 63 trimer precursors are mixed in this ratio to the trimer-nucleotide that is in the SOI at that position, i.e. the ratio of the 64 trimer-nucleotides is 98.5%:0.024%:0.024%: 0.024%:0.024%:0.024%:0.024%:0.024%:0.024%:0.024%: 0.02 4%:0.024%:0.024%:0.024%:0.024%:0.024%:0.024%: 0.024%:0.024%:0.024%:0.024%: 0.024%:0.024%:0.024%: 0.024%:0.024%:0.024%:0.024%:0.024%:0.024%: 0.0 24%:0.024%:0.024%:0.024%:0.024%:0.024%:0.024: 0.024%:0.024%:0.024%:0.024%:0.024%:0.024%:0.024%: 0.024%:0.024%:0.024%:0.024%:0.024%:0.024%: 0.024%:0 0.024%:0.024%:0.024%:0.024%:0.024%: 0.024%:0.024%:0.024%:0.024%:0.024%:0.02 4%:0.024%.

The number of resulting point mutations in the PTR reflects the number of nucleotide positions where the oligonucleotide differs from the SOI (herein referred to as mismatches). This number can vary e.g. between 1 and 30, preferably between 1 and 20, more preferably between 1 and 10.

Such soft randomized DNA oligonucleotides can be synthesized on any of the DNA synthesizers with any of the DNA synthesis chemistries including the H-phosphonate, phosphodiester, phosphotriester or phosphite triester synthesis methods or any of the large-scale, massively parallel oligonucleotide synthesis methods.

Such soft randomized DNA oligonucleotides can be synthesized e.g. on an AB13900 DNA synthesizer according to the following, modified phosphoramidite chemistry-based protocol: Controlled pore glass (CPG) was used as a solid support and the following synthesis cycles were applied: I.) Deprotection was achieved with trichloroacetic acid (TCA) in dichloromethane (DCM). II.) Incoming phosphoramidite, dissolved in anhydrous acetonitrile and premixed with the other amidites in the defined spiking ratio, was coupled by activation with 5-ethylthio-1-H-tetrazole. III.) Capping was done with acetic anhydride in anhydrous tetrahydrofuran (THF), N-methyl-imidazole and pyridine containing anhydrous THF solution. IV.) The oxidation step was accomplished with iodine (5 g per Liter of pyridine:water: THF=0.5:2:97.5 mixture). Cycles were repeated until the final DNA position and DNA strands were cleaved from the solid support with concentrated ammonia (containing triethylamine). Crude oligonucleotides were purified by reverse-phase high-performance liquid chromatography (HPLC). After concentration from HPLC fractions, the dimethoxytrityl (5'-DMTr) protecting group was removed using a Poly-Pak column (Glen Research) according to the manufacturer's protocol.

Table 2 (FIG. 9) shows the distribution of the numbers of point mutations (mismatching nucleobases compared to the SOI) with different phosphoramidite-monomer spiking ratios.

The term "homologous" as used herein is meant that a first nucleic acid sequence has a degree of identity with a second nucleic acid sequence (e.g. a wild-type SOI or locus) with which it is to be recombined, which identity is at least about 70%, at least about 80%, preferably at least about 90%, over a nucleic acid region, e.g. a region of homology within a SOI, or an ssDNA oligonucleotide, which is designed to undergo mutagenesis by a homologous recombination technique. The degree of required identity may depend on the length of the homologous sequence. The shorter the homologous sequence, the higher the percentage homology may be used to perform homologous recombination.

"Percent (%) identity" with respect to a nucleotide sequence is defined as the percentage of nucleotides in a candidate DNA sequence that is identical with the nucleotides in the DNA sequence, after aligning the sequence and introducing gaps, if necessary, to achieve the maximum percent sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "single stranded DNA oligonucleotide", also referred to as "ssDNA oligonucleotide" or simply "oligonucleotide" or "oligo", shall refer to an oligonucleotide which is a linear polymer of nucleotide monomers. Monomers making up oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, wobble base pairing, or the like. ssDNA oligonucleotides described herein typically range in size between 40 and 200. Whenever an oligonucleotide is represented by a sequence of letters (upper or lower case), such as "ATGC," it will be understood that the nucleotides are in 5'->3' order from left to right and that "A" denotes deoxyadenosine, "T" denotes deoxythymidine, "G" denotes deoxyguanosine, and "C" denotes deoxycytidine. Besides conventional nucleotides (A, G, C, T), modified nucleotides e.g. K-2'-deoxyribose, P-2'-deoxyribose, 2'-deoxyinosine, 2'-deoxyxanthosine or nucleotides with nucleobase analogs may be used e.g., inosine, or 5-methylisocytosine, or 3-nitropyrrole, 5-nitroindole, pyrrolidine, 4-nitroimidazole, 4-nitropyrazole, 4-nitrobenzimidazole, 4-aminobenzimidazole, 5-nitroindazole, 3-nitroimidazole, 5-aminoindole, benzimidazole, 5-fluoroindole, indole, methylisocarbostyril, pyrrolopyrimidine 7-propynylisocarbostryril. The terminology and atom numbering conventions follow those disclosed in Strachan and Read, Human Molecular Genetics 2 (Wiley-Liss, New York, 1999). Usually oligonucleotides comprise the four natural nucleosides (e.g. deoxyadenosine, deoxycytidine, deoxyguanosine, deoxythymidine for DNA or their ribose counterparts for RNA) linked by phosphodiester or by peptidyl linkages or by phosphorothioate linkages; however, they may also comprise non-natural nucleotide analogs, e.g. including modified bases, sugars, or internucleosidic linkages.

In some embodiments, the single stranded oligonucleotide pools are produced using chemical synthesis methods, e.g. by synthesizing the oligonucleotide sequence from monomer-phophoramidites, dimer-phosphoramidites (Neuner, Cortese, and Monaci 1998) or trimer-phosphoramidites (Sondek and Shortle 1992), mixture of monomer-phosphoramidites, mixture of dimer-phosphoramidites, mixture of trimer-phosphoramidites or their combination thereof.

In some embodiments, the oligonucleotides are produced and purified from naturally-occurring sources, or synthesized in vivo, within the cell undergoing in vivo mutagenesis using any of a variety of well-known enzymatic methods e.g. as described in Farzadfard et al. (2014). Specifically, enzymes that synthesize soft-randomized oligonucleotide pools include, but are not limited to low fidelity DNA polymerase proteins or low fidelity reverse transciptase proteins which incorporate mismatching nucleotides during synthesis with high frequency. Alternatively, mismatching nucleotides are incorporated into the oligos with a higher frequency by the DNA polymerases or reverse transcriptases due to the presence of chemical substances, which are well-known to those skilled in the art.

The term "mutagenizing oligonucleotide" as used herein shall refer to the ssDNA oligonucleotide which comprises at least one mismatching nucleobase compared to a cellular DNA sequence with which it is to be recombined. Upon integrating the mutagenizing oligonucleotide into the PTR, the point mutation can be introduced into the cellular DNA sequence, which corresponds to the mismatching nucleobase and its position. Non-mutagenizing oligonucleotides are herein referred to those which have 100% sequence identity to the cellular DNA sequence. Upon integrating the non-mutagenizing oligonucleotide into the PTR, there is no point mutation introduced.

In certain embodiments, the mutagenizing oligonucleotide can undergo processing, partial degradation or enzymatic chew-back or modification within the cell, this process can generate variants of the same mutagenizing oligonucleotide within the target cell and these variants can create different modifications. In one example these processed oligonucleotides can lead to the partial recombination of the oligonucleotide at its target.

Specifically, the mutagenizing oligonucleotide can undergo complete or partial integration at its target, whereas the partial refers to a case where the 10%, 20%, 30%, 50% or more percentage of the sequence, and the corresponding mutations on it become incorporated.

The term "ssDNA oligonucleotide mediated nucleotide integration" used herein shall refer to a reaction between nucleotide sequences having corresponding sites containing a similar nucleotide sequence (i.e., homologous sequences) through which the molecules can interact (recombine) to form a new, recombinant nucleic acid sequence. The sites of similar nucleotide sequence are each referred to herein as a "homologous sequence". Generally, the frequency of recombination increases as the length of the homology sequence increases. Thus, while ssDNA oligonucleotide mediated nucleotide integration can occur between two nucleic acid sequences that are less than identical, the recombination frequency (or efficiency) declines as the divergence between the two sequences increases. Recombination may be accomplished using one homology sequence on each of two molecules to be combined, thereby generating a "single-crossover" recombination product. Alternatively, two or more homology sequences may be placed on molecules to be recombined. Recombination between two homology sequences on the donor with two homology sequences on the target generates a "double-crossover" recombination product. An exemplary method employs homologous recombination.

Recombination described herein may be performed by a variety of techniques (e.g. MAGE, CAGE, CRISPR/Cas9, BuDs, ZFNs, TALEs, TALENs or ssDNA-binding protein mediated recombination wherein the ssDNA-binding protein is a yeast-derived Rad51, Rad54, Rad52 or a phage-derived ssDNA-annealing protein, including Lambda Red beta, RecT, RecA, Rad52-like, Sak, Erf, or Rad51-like or Gp2.5-like ssDNA-binding protein or any of their orthologous sequences from other organisms).

In specific embodiments, the integration of the oligo pool is performed by homologous recombination.

Specifically, the homologous recombination-mediated integration of the oligo pool is performed by ssDNA-binding protein mediated recombination wherein the ssDNA-binding protein is a yeast-derived Rad51, Rad54, Rad52 or a phage-derived ssDNA-annealing protein, including Lambda Red beta, RecT, RecA, Rad52-like, Sak, Erf, or Rad51-like or Gp2.5-like ssDNA-binding protein or any of their orthologous sequences from other organisms.

In specific embodiments, the integration of the oligo pool is performed by a pORTMAGE procedure.

MAGE refers to multiplex automated genome engineering, and generally includes introducing multiple nucleic acid sequences into one or more cells such that the entire cell culture approaches a state involving a set of changes to a genome or targeted region. The method can be used to generate one specific configuration of alleles or can be used for combinatorial exploration of designed alleles optionally including additional random, or non-designed, changes. This can be used with any of a variety of devices that allow the cyclic addition of many different DNAs in parallel in random or specific order, with or without use of one or more selectable markers.

ssDNA-binding protein mediated recombination, homologous recombination and MAGE-based methods typically include introducing multiple oligonucleotides into a cell including the steps transforming or transfecting cells using transformation medium or transfection medium including a pool of oligonucleotides comprising mutagenizing oligonucleotides, replacing the transformation medium or transfection medium with growth medium, incubating the cell in the growth medium, and repeating the steps if necessary or desired until multiple nucleic acid mutations have been introduced into the cell. The pool of oligonucleotides may have a diversity of different random or non-random mutations at the location of the SOI and the desired mutagenesis. Cells are transfected or transformed with a variety of oligonucleotides leading to the formation of a diverse genomic and cellular library of mutants. The diversity of the library can be increased by increasing the number of transformation or transfection cycles. Specifically, multiple mutations are generated in the cellular chromosome or in a genome.

Increasing the number of cycles of mutagenesis generally increases the diversity of the library. In particular embodiments, a library is prepared by one or more cycles of MAGE, for example, at least any of 1, 2, 3, 4, 5, 6, 7, 8, 9, 10, 11, 12, 13, 14, 15, or more cycles, with or without intervening cycles of selection. Further methods of mutagenesis, selection, fractionating and/or creating sub-populations of the library may be carried out to improve genetic diversity.

MAGE particularly employs a highly efficient lambda phage red recombination system (the λRed System) which is a process by which the genome of a cell is reprogrammed to perform desired functions via a form of accelerated, directed evolution. The λRed System includes $\beta$, $\gamma$, and exo genes, whose products are called Beta, Gam, and Exo, respectively. Gam inhibits the host RecB,C,D exonuclease and the SbcC,D nuclease activities, so that exogenously added linear DNA is not degraded. The Exo protein is a dsDNA-dependent exonuclease that binds to the terminus of each strand while degrading the other strand in a 5' to 3' direction. Beta binds to the resulting ssDNA overhangs, ultimately pairing them with a complementary chromosomal DNA target. The λRed System has been widely utilized for specific gene inactivation in *E. coli, Salmonella, Citrobacter* and *Shigella* species, and for introducing small biological tags or single genes into these chromosomes.

During MAGE cycling described herein, Beta proteins recombine oligonucleotides designed to target key genomic regions for highly specific mutations. Deleting or impairing a mismatch repair system in the cell may further improve recombination efficiency by avoiding or down-modulating the mismatch repair machinery. Specifically, the cell or microorganism is a MAGE-competent cell or organism, which is optionally mismatch-repair deficient.

Methods of making transgenic organisms are generally specific to each host organism and are known in the art. For example, DNA cassettes can be introduced into a known intergenic region of the genome of bacteria using λRed recombination.

At each round of transformation, without wishing to be bound by theory, protein Beta binds to, protects, and promotes strand annealing of the ssDNA oligonucleotides. This may occur in the lagging strand during DNA replication where the oligonucleotides are thus incorporated into the duplicated genome. After each cycle of transformation, genetic diversity is greatly increased in focused genomic regions according to the targeted design of the oligonucleotide pool. After a certain number of cycles of transformation, selection or screening is performed for the desired genomic characteristic and the process is repeated. Therefore, the process may be conducted in a continuous fashion.

According to a specific example, randomized MAGE (rMAGE) mutagenesis employing randomized, artificial oligonucleotides is herein described.

rMAGE can target multiple, predefined genomic regions, can cover long, continuous loci, can have broad, controllable mutagenesis spectra for each nucleotide position, can allow unprecedented mutation rate of the target sequences, can enable multiple rounds of evolution in a fast and efficient manner, and can be applicable to a range of host species. Additionally, rMAGE can simultaneously minimise off-target mutation rate and is cost-effective.

According to a specific example described herein, rMAGE is employed based on pORTMAGE (Nyerges et al. 2016) and soft-randomization-based DNA synthesis.

pORTMAGE is herein defined as follows: a broad-host vector-based system which provides controllable expression for single-stranded DNA binding protein and a protein for the down-regulation of the methyl-directed mismatch repair (MMR) of the host organism and allows for allelic replacement, integration of ssDNA oligos and oligo-pools into the genome or to episomal or plasmid DNA.

pORTMAGE, e.g. the one stated as SEQ ID NO:1, expresses the λ Red recombinase enzymes Beta, Gam, and Exo allowing both dsDNA and ssDNA-mediated allelic replacement. pORTMAGE further expresses a dominant negative mutator allele, specifically an E32K amino acid mutant variant of the *Escherichia coli* MutL protein, a member of the methyl-directed mismatch repair (MMR) system of the host organism. Expression of both λ Red recombinase enzymes, as well as the dominant negative mutator allele of mutL is controlled by the λ phage-derived c1857 repressor. The c1857 repressor is temperature sensitive, meaning that it is fully functional at 30° C., while non-functional when the temperature is raised to 42° C. This allows repression of transcription of the said regulated genes at the lower temperature, while transcription is able to occur when raising the temperature of the cell cultures. Limiting the higher temperature (and therefore expression of the genes) to the period of time needed for allelic replacement allows for highly efficient targeted mutagenesis to the genome and also the inhibition of unwanted mutations that occur when the MMR system is disabled.

pORTMAGE allows for efficient ssDNA-mediated allelic replacement, MAGE, oligo pool integration without requiring prior modification of the host genome, without off-target mutagenesis, and within an expanded set of host organisms. This approach shortens the time-frame of genome editing and allows for exploration of sequence space within previously untapped species.

Based on the observed negative correlation between the number of mismatching nucleobases within an oligo and its integration efficiency during MAGE (Wang and Church 2011), soft-randomization of the targeting oligo (Hermes et al. 1989) could extend the locus undergoing mutagenesis by a single oligo pool. In soft-randomized (spiked) DNA oligonucleotide synthesis, through the precise tuning of nucleotide composition in a synthetic DNA oligonucleotide, each possible allelic variant at every nucleotide position within a synthetized pool of oligos is represented. Meanwhile, the number of mutations compared to the SOI is constrained and defined by the extent of soft-randomization (also defined as the spiking ratio) within each individual sequence (Hall et al. 2001) to allow for efficient integration (Table 2) and FIG. 10.

Unexpectedly, it was found that in this manner, incorporating pools of soft-randomized (spiked) DNA oligonucleotides can extend the locus undergoing mutagenesis up to the length of the entire incorporating oligo (FIG. 4).

Multiplexed integration of multiple adjacent oligos can further extend the mutagenized regions to fully cover multiple loci (FIGS. 11 A and B). Multiplexed integration of multiple adjacent, overlapping oligos can further extend the mutagenized regions to fully cover and uniformly mutagenize multiple loci (FIG. 7 and FIG. 8).

According to a specific example, the maximum number of modified cells that is achievable in one round of rMAGE mutagenesis under certain conditions is $2.5 \times 10^{11}$ variants. The representable diversity within such a generated cell library can be between 1 and up to $10^{12}$ variants (mutants) depending on the spiking ratio, the number of modified cells and the size of the PTR, in particular the SOI region of the PTR, to be mutated.

When the nucleotide monomer spiking ratio is 0.5%, many oligonucleotides may have the same mutations. Thus, the actual diversity in the oligonucleotide pool and in the cellular DNA after modification may be lower than what may be considered as a transformation limit upon electroporation (e.g. $2 \times 10^{11}$ cells) and may be about $10^8$, if the size of the SOI is 72 nucleobases. The longer the SOI, the higher this diversity may be. For a 1000 nucleobase long SOI, this number can be $1.4 \times 10^9$, if 14 overlapping oligonucleotides are needed to cover the full length of the SOI.

Based on such calculations, for e.g. the full representation of up to the combination of 3 mutations is possible with uniform mutational distribution, if the SOI is no longer than about 1000 nucleobases.

If a full representation of the mutations is not required (or a lower mutation rate), a longer SOI can be mutated.

The foregoing description will be more fully understood with reference to the following examples. Such examples are, however, merely representative of methods of practicing one or more embodiments of the present invention and should not be read as limiting the scope of invention.

EXAMPLES

Example 1: Introduction of Soft-Randomized Oligonucleotides into the Genomic DNA of Three Different Bacterial Species To demonstrate that soft-randomized oligonucleotide pools can mutagenize efficiently by ssDNA-mediated Lambda Red recombineering with a pORTMAGE protocol, ssDNA oligonucleotide pools with different randomization levels were incorporated into the genomes of three different bacterial species. In order to characterize the performance and kinetics of mutagenesis in a uniform manner across species, the same "exogenous" DNA seguence, a landing-pad assay was used in all species, which eliminates target-sequence-based bias across different genetic backgrounds (Nyerges et al. 2014). *E. coli* K-12 MG1655 (Source: *E. coli* Genome Project, University of Wisconsin-Madison), as well as the clinically important *Salmonella enterica* (Source: American Type Culture Collection 700720) and the biotechnologically relevant organism *Citrobacter freundii* (Source: American Type Culture Collection 8090) were selected as model organisms. Two 90 bp loci (PTR1 and PTR2, respectively) within the landing pad sequence were targeted using two pools of spiked oligonucleotides (SEQ ID NO:2 and SEQ ID NO:3, respectively) and a standard pORTMAGE procedure. Note that in this example the target site of the two oligo pools do not overlap. This example tests the incorporation of random oligos only.

To this aim, first, two sets of DNA oligonucleotides (SEQ ID NO:2 and SEQ ID NO:3) with equimolar monomer-nucleotide (A, T, G or C) spiking levels of 0, 0.1, 0.5, 2, 5, 10, and 20% were synthesized for the targeted mutagenesis of the Landing pad's two sites, PTR1 and PTR2, respectively.

Synthesis of these monomer-nucleotide spiked oligonucleotides was performed on an AB13900 DNA synthesizer, according to a modified phosphoramidite chemistry-based protocol: Controlled pore glass (CPG) was used as a solid support (3000 Å pore size and 10-25 µmol/g loading) and the following synthesis cycles were applied: I.) Deprotection was achieved with 3% (w/v) trichloroacetic acid (TCA) in dichloromethane (DCM). II.) Incoming monomer-nucleotide (A, T, G or C) phosphoramidite, dissolved in 0.055 M concentration in anhydrous acetonitrile and pre-mixed with the other three spiking monomer-nucleotide (A, T, G or C) amidites in the defined spiking ratio, was coupled by activation with 5-ethylthio-1-H-tetrazole. III.) Capping was done with 10% (v/v) acetic anhydride in anhydrous tetrahydrofuran (THF) and 16% (v/v) N-methyl-imidazole and 10% (v/v) pyridine containing anhydrous THF solution. IV.) The oxidation step was accomplished with iodine (5 g per Liter of pyridine:water:THF=0.5:2:97.5 mixture). Cycles were repeated until the $90^{th}$ position and DNA strands were cleaved from the solid support with concentrated ammonia. Crude oligonucleotides were purified by reverse-phase high-performance liquid chromatography (HPLC). After concentration from HPLC fractions, the dimethoxytrityl (5'-DMTr) protecting group was removed using a PolyPak column (Glen Research) according to the manufacturer's protocol.

Base composition at each position within the oligonucleotide sequence was determined by high-throughput (HT) Illumina sequencing according to the following procedure: Oligonucleotides were made double stranded by annealing each to their reverse complement and 5'-end labeled with T4 polynucleotide kinase. Following cleanup with AMPure XP magnetic beads (Beckman Coulter), library preparation and sequencing was performed using the NEBNext DNA Library Prep Master Mix Set for Illumina (New England Biolabs) according to the manufacturer's instructions.

Sequencing was done using a MiSeq Reagent Kit v2 for a 250 bp PE sequencing run on a MiSeq (Ilumina) and each position was covered with at least $10^5$ reads. Sequencing confirmed soft-randomization across the sequence of the oligo pool, (FIG. 1 and FIG. 3). Mutation rate and in turn, the number of mutations per each individual oligo was precisely adjustable by the spiking ratio (FIG. 3). The spectra of mutations showed a bias-less generation of all mutational possibilities (FIG. 2).

Oligonucleotide incorporation was carried out with a pORTMAGE protocol as follows: cells were grown in Lysogeny-Broth-Lennox (LB$^L$) media (10 g of tryptone, 5 g of yeast extract, 5 g of sodium chloride per 1 L of water) with the appropriate antibiotic and 40 µl of the electrocompetent cell suspension was mixed with the corresponding oligonucleotide pool at a 2.5 µM final concentration. Electroporation can be done on a BTX (Harvard Apparatus) CM-630 Exponential Decay Wave Electroporation System in 1 mm gap electroporation cuvettes (parameters of electroporation: 1.8 kV, 200Ω, 25 µF). Immediately after electroporation, cells were suspended in 5 ml TB media (24 g yeast extract, 12 g tryptone, 9.4 g $K_2HPO_4$, and 2 g $KH_2PO_4$ per 1 L of water) to allow for cells to recover. The cells could later be transferred to larger volumes for further growth and cycling. Cells were either subjected to additional pORTMAGE cycles by growing to mid-log phase and preparing electrocompetent cells again, or allowed to reach stationary phase for storage for subsequent phenotypic or genotypic analysis.

It was found that soft-randomized oligos could incorporate at the two predefined genomic loci and genomically replicate the chemically-encoded diversity at the targeted positions (FIG. 4, FIG. 5, FIG. 6).

The observed pattern of the unbiased integration of the central nucleotide positions, with a sudden drop at the terminal bases at each end (FIG. 4) indicated processing of targeting oligos over the course of genomic integration, hypothesized previously in E. coli (Li et al. 2013). This oligo processing resulted in the removal of up-to 9 terminal nucleobases. Unexpectedly, this pattern was found conserved in E. coli, in Salmonella enterica and in Citrobacter freundii and most probably it is conserved across species.

To characterize the effect of spiking level on the efficiency of integration, as well as the resulting mutagenesis of the target sequence, oligos of various randomization levels were tested. DNA oligonucleotides with spiking levels of 0, 0.1, 0.5, 1, 2, 5, 10, and 20% were incorporated into the target regions. As expected, spiking levels correlated with the number of mutations in the target sequence (FIG. 5). Also, there was a negative correlation between the level of randomization and the integration efficiency of a given oligo above a spiking ratio of 2% (FIG. 10). A 0.5% spiking ratio was found to result in an average of 1 mutation per 90 nucleotides. The level of sequence diversification (library size, a proxy of mutation rate) was tunable by the number of the consecutive cycles of the pORTMAGE protocol, while the mean number of mutational events within each library member was adjustable by the spiking ratio of the synthetic oligo sequences (FIG. 5).

Performing 5 consecutive cycles of the pORTMAGE protocol with medium-level (2%) spiking resulted in an over $10^6$-fold mutation rate increase at the PTR and the generation of up to 10 mutations within the 90 bp target compared to wild-type. Mutagenesis of non-targeted regions remained consistent with the background mutation rate tested with a rifampicin resistance fluctuation test (see description of the protocol in example 3). The experiments revealed that rMAGE can efficiently and specifically mutagenize with soft-randomized oligos two targeted genomic PTRs in three different bacterial species.

Example 2: Introducing rMAGE Mutational Libraries into PTRs Encoded in Three Different Bacterial Species in Order to Generate a Large Number of Allelic Variants with a Low Number of Randomly Distributed Mutations The mutagenesis method described herein was applied to introduce mostly single mutations into the drug target of trimethoprim. Clinical and laboratory studies demonstrated that under prolonged trimethoprim pressure, evolution of antimicrobial resistance proceeds dominantly through mutations in folA, encoding trimethoprim's target, dihydrofolate reductase (DHFR) (Toprak et al. 2011). As resistance-conferring mutations have been detected both in the regulatory (Flensburg and Sköld 1987) and in the DHFR structural regions of folA (Watson, Liu, and Ollis 2007), both loci were targeted for mutagenesis with overlapping soft-randomized oligonucleotide pools. Soft-randomized oligos were designed to cover the entire folA (DHFR) locus in E. coli K-12 MG1655 (Source: E. coli Genome Project, University of Wisconsin-Madison, sequence of PTR is SEQ ID NO:28: position 220-813.), in E. coli UPEC CFT073 (Source: E. coli Genome Project, University of Wisconsin-Madison, sequence of PTR is SEQ ID NO:29: position 220-813, Salmonella enterica LT2 (Source: American Type Culture Collection 700720, sequence of PTR is SEQ ID NO:30: position 220-813.), in which mutations have been previously observed to confer trimethoprim resistance. Synthesis of the corresponding monomer-nucleotide soft-randomized oligonucleotides (oligos) was performed on an AB13900 DNA synthesizer, according to a modified phosphoramidite chemistry-based protocol as it is described in Example 1.

Each of these oligos were designed to have an 18 nucleotide overlap with each adjacent one, as it has been observed (FIG. 4) that 5' and 3' ssDNA degradation and the removal of mismatching nucleobases can occur after the Okazaki-fragment-like integration of ssDNA molecules within the replication fork. This has resulted in the removal of up-to 9 terminal nucleobases and this pattern was found to be conserved across species. This ssDNA processing was permitted by using phosphodiester internucleotide linkages within the oligos. An overlap of 18 nucleobases ensures that all positions will have an equally high probability of mutagenesis. The regulatory (promoter) region was targeted with a single soft-randomized oligo construct.

Mutagenesis was performed based on the previously described pORTMAGE protocol (Nyerges et al. 2016) with the corresponding oligonucleotide pools (SEQ ID:4-SEQ ID NO:11 for E. coli K-12 MG 1655; SEQ ID NO:12-SEQ ID NO:19 for Salmonella enterica serovar Typhimurium; SEQ ID NO:20-SEQ ID NO:27 for E. coli CFT073 UPEC (Source: American Type Culture Collection 700928)) with a spiking level of 0.5%. Since only a single round of rMAGE mutagenesis was carried out, a large fraction of the mutagenized alleles expected to have a single mutation only. Specifically, the mutagenesis cycles were carried out by 0.5 µl of each of the 8 soft-randomized overlapping oligos, covering the folA (DHFR) region. The 4 µl oligo samples were electroporated into the competent cells which were then suspended in 5 ml fresh TB media to allow for recovery at 30° C. for 1 hour under continuous agitation. An extra 5 ml $LB^L$ media was then added along with the appropriate antibiotic to maintain the pORTMAGE plasmid.

Determination of allele composition at the target site was achieved by amplicon HT sequencing of the PTR. From the aliquoted frozen populations recovered after 1 mutagenesis cycle, cellular DNA was extracted from $\sim 2 \times 10^9$ cells using GenElute™ Bacterial Genomic DNA kit (Sigma-Aldrich) for subsequent Illumina High-Throughput (HT) amplicon sequencing. For amplicon sequencing, the PTR was amplified with PCR by corresponding PCR primer pairs, Primer1 TCATTGTAATGCGGCGAGTCCA (SEQ ID NO:31) and Primer2 AAGCGGCGGCGTCTTAAACA (SEQ ID NO:32) for E. coli K-12 MG1655, PRIMER3 ACCCGAGGT-CAAACCGTCAATC (SEQ ID NO:33) and Primer 4 CGC-TACGCTTATCAGGCCTACA (SEQ ID NO:34) for Salmonella enterica serovar Typhimurium; PRIMER5 GATGAACCGGAAACGAAACCC (SEQ ID NO:35) and PRIMER6 TGCAGTCATGATCTCGTGCTCCT (SEQ ID NO:36) for *E. coli* CFT073 UPEC. PCR amplicons were subjected to NEBNext dsDNA Fragmentase (New England Biolabs) treatment, followed by fragment purification, end repair, dA tailing and ligation according to the manufacturer's instructions. Library preparation and sequencing was done using a MiSeq Reagent Kit v2 for a 250-bp PE sequencing run on a MiSeq (Illumina). The resulting sequences were compared to the sequence of the PTR using CLC Genomics Workbench Tool (CLC Bio, Version 9.0). Paired-end reads were first trimmed and quality trim with an error probability threshold of 0.001 (Phred Q value of 30) was carried out. Sequence analyses were used to confirm that the mutagenesis resulted in a uniform distribution of mutations along the whole PTR including the overlapping regions of the oligos.

Example 3: Consecutive rMAGE Mutagenesis Cycles with PTRs which Encode an Antibiotic Resistance Gene in Three Different Bacterial Species to Map Combinations of Resistance Mutations Since high level trimethoprim resistance frequently involves multiple mutations within the target protein of the antibiotic trimethoprim, the folA gene was mutagenized to generate higher-order mutational combinations. 5 consecutive rounds of soft-randomized oligo pool-mediated mutagenesis were carried out using a pooled set of overlapping, soft-randomized oligos, simultaneously targeting all nucleotide positions of the folA regulatory and structural regions in *E. coli* K-12 MG1655 (Source: *E. coli* Genome Project, University of Wisconsin-Madison, sequence of PTR is SEQ ID NO:28: position 220-813.), in *E. coli* UPEC CFT073 (Source: *E. coli* Genome Project, University of Wisconsin-Madison, sequence of PTR is SEQ ID NO:29: position 142-734, *Salmonella enterica* LT2 (Source: American Type Culture Collection 700720, sequence of PTR is SEQ ID NO:30: position 60-653.).

To introduce combinatorial mutational libraries into these PTRs, cells were subjected to five cycles of folA-targeted soft-randomized, overlapping oligo pool-mediated mutagenesis with the corresponding oligonucleotide pools ((SEQ ID:4-SEQ ID NO:11 for *E. coli* K-12 MG 1655; SEQ ID NO:11-SEQ ID NO:19 for *Salmonella enterica* serovar *Typhimurium*; SEQ ID NO:20-SEQ ID NO:27 for *E. coli* CFT073 UPEC (Source: American Type Culture Collection 700928) with a spiking ratio of 0.5%. The mutagenesis cycles were carried out as it is described in Example 2, except that following 1 cycle of rMAGE mutagenesis, the cells were either subjected to additional mutagenesis cycles by growing to mid-log phase and preparing electrocompetent cells again, or allowed to reach stationary phase and aliquoted into 1 ml portions to which 0.5 ml 50% glycerol was added. The aliquoted samples were then frozen and stored at −80° C. for subsequent phenotypic and/or genotypic analysis. From the aliquoted frozen populations recovered after each mutagenesis cycle, cellular DNA was extracted from ~2×10$^9$ cells using GenElute™ Bacterial Genomic DNA kit (Sigma-Aldrich) for subsequent Illumina (described in Example 2) amplicon sequencing. Sequence analyses were used to confirm that the mutagenesis resulted in a uniform distribution of mutations along the whole PTR including the overlapping regions of the oligos (FIG. 7, Table 1).

Following mutagenesis, the resulting cell libraries were exposed to various trimethoprim concentrations (3 μg/ml, 50 μg/ml and 200 μg/ml) on agar plates and grown at 30° C. for 48 hours and the fraction of resistant cells was determined.

Trimethoprim resistance, quantified as trimethoprim IC75 values, were determined for selected isolates. IC75 values were calculated from the function of growth versus trimethoprim concentrations in MS media. As a measure of the effect of each individual genotype, relative trimethoprim IC75 value change for each of the corresponding mutant was determined, compared to the IC75 value of the wild-type, parental strain. Specifically, the IC75 value was calculated as the trimethoprim concentration at which growth-rate of the given cell population was equal to one quarter of the uninhibited growth-rate of a wild-type control.

Library composition analysis was achieved by high throughput (HT) sequencing of the antibiotic-selected folA (DHFR) libraries: approximately 1000 resistant colonies per plate for Pacific Biosciences RSII SMRT circular-consensus amplicon sequencing (CCS) were scraped off from plates in 5 ml MS media, from which 0.5 ml was used to extract pooled cellular DNA (using GeneElute Bacterial Genomic DNA Kit, Sigma). For amplicon sequencing, the PTR was amplified with the corresponding PCR primers, Primer1 TCATTGTAATGCGGCGAGTCCA (SEQ ID NO:31) and Primer2 AAGCGGCGGCGTCTTAAACA (SEQ ID NO:32) for *E. coli* K-12 MG1655 PRIMER3 ACCCGAGGT-CAAACCGTCAATC (SEQ ID NO:33) and Primer 4 CGC-TACGCTTATCAGGCCTACA (SEQ ID NO:34) for *Salmonella enterica* serovar *Typhimurium*; PRIMER5 GATGAACCGGAAACGAAACCC (SEQ ID NO:35) and PRIMER6 TGCAGTCATGATCTCGTGCTCCT (SEQ ID NO:36) for *E. coli* CFT073 UPEC and the amplicons were purified and subjected to sequencing for >30× rounds to reach an average circular-consensus error rate of >Q40. PacBio CCS reads were imported to CLC Genomics Workbench Tool (CLC Bio, Version 9.0). Reads with any ambiguous nucleotide as well as reads shorter than 500 bases were discarded. Each read was individually mapped against the PTR. Variant calling was performed at a base call error probability threshold of 0.1.

Library composition analysis revealed that mutagenesis resulted in a high fraction of resistant clones under mild trimethoprim stress. HT sequence analyses revealed that rMAGE resulted in a diverse combination of complex DHFR mutants (FIG. 13 (Table 3). MIC measurements showed that the combination of resistance mutations achieved by rMAGE mutagenesis resulted in an over 1500-fold increase in trimethoprim resistance in selected isolates (Table 4))

To determine off-target mutation frequencies in *E. coli* K-12 MG1655 at the untargeted rpoB locus, the 5 cycle rMAGE populations were assessed for resistance to rifampicin. For this assay, starter cultures were grown overnight at 30° C. in LB$^L$ made from the frozen cultures of the 5-cycle rMAGE population. The starter cultures were diluted 1000-fold into 6 parallel samples in 1 ml LB$^L$ media and grown overnight at 30° C. The 1 ml samples were then harvested and plated onto LB$^L$ agar plates containing 100 μg/ml rifampicin, and grown at 30° C. for 48 hours. Total cell numbers were determined by plating appropriate dilutions onto LB$^L$ plates and growing overnight at 30° C. Mutation frequencies were determined by the fraction of average resistant cells from the average total cell number.

TABLE 4

| Strain ID | folA regulatory mutation | folA structural mutation (Amino Acid change) | Trimethoprim IC75 value (μg/ml) | Relative Trimethoprim IC75 change |
|---|---|---|---|---|
| E. coli MG1655 1 | C-58T | A26T, L28R, P39R | 1162 | 1549 |
| E. coli MG1655 2 | C-58T | A26T, L28R, P39R | 1162 | 1549 |
| E. coli MG1655 3 | C-58T | A26T, L28R, P39R | 1346 | 1795 |
| E. coli MG1655 4 | C-58T | A26T, L28R, P39R | 1254 | 1672 |
| E. coli MG1655 5 | C-58T | A26T, L28R, P39R | 1162 | 1549 |
| E. coli MG1655 6 | C-58T | A26T, L28R, P39R | 1254 | 1672 |
| E. coli MG1655 7 | C-58T | L28R | 448 | 597 |
| E. coli MG1655 8 | C-58T, T-74A | L28R, N147D | 448 | 597 |
| E. coli MG1655 9 | C-58T | L28R | 610 | 691 |
| E. coli MG1655 10 | C-58T | L28R | 610 | 691 |
| E. coli MG1655 11 | C-58T | L28R | 518 | 691 |
| E. coli MG1655 12 | C-43T, C-58T | A26D, L28R, H45R | 794 | 936 |
| E. coli CFT073 UPEC 1 | — | L28R, R98P | 426 | 568 |
| E. coli CFT073 UPEC 2 | — | L28R, R98P | 426 | 568 |
| E. coli CFT073 UPEC 3 | — | L28R, R98P | 426 | 568 |
| E. coli CFT073 UPEC 4 | — | L28R, R98P | 353 | 470 |
| E. coli CFT073 UPEC 5 | — | L28R, R98P | 488 | 650 |
| E. coli CFT073 UPEC 6 | A-8G | L28R, A26T, H45R | Not Determined | NA |
| E. coli CFT073 UPEC 7 | — | L28R, R98P | Not Determined | NA |
| E. coli CFT073 UPEC 8 | — | L28R, R98P, S150N, E157Q | Not Determined | NA |
| E. coli CFT073 UPEC 9 | — | L28R, A26T | Not Determined | NA |
| E. coli CFT073 UPEC 10 | C-58T | L28R | Not Determined | NA |
| E. coli CFT073 UPEC 11 | C-38T, G-32A | L28R | Not Determined | NA |
| E. coli CFT073 UPEC 12 | C-58T | L28R, H45Y | Not Determined | NA |
| Salmonella enterica 1 | C-60T, G-28C | R98P, F153S | 610 | 813 |
| Salmonella enterica 2 | C-60T, G-28C | R98P, F153S | 610 | 813 |
| Salmonella enterica 3 | C-60T, G-28C | R98P, F153S | 610 | 813 |
| Salmonella enterica 4 | C-60T, G-28C | R98P, F153S | 426 | 568 |
| Salmonella enterica 5 | C-60T, G-28C | R98P, F153S | 610 | 813 |
| Salmonella enterica 6 | C-60T, G-28C | R98P, F153S | 610 | 813 |
| Salmonella enterica 7 | C-60T, G-28C | R98P, F153S | 610 | 813 |
| Salmonella enterica 8 | C-60T, G-28C | R98P, F153S | 610 | 813 |
| Salmonella enterica 9 | C-60T | E17D, L28R | 1162 | 1549 |
| Salmonella enterica 10 | C-60T, T-76G | L28R | 794 | 1059 |
| Salmonella enterica 11 | C-60T, T-70A | L28R | 288 | 383 |
| Salmonella enterica 12 | C-60T | A26D, L28R | 383 | 510 |

Importantly, only a slight bias could be observed in this library of cells with regards to the types of mutations generated. Some of the detected mutations and combinations thereof have been previously detected in laboratory studies and trimethoprim resistant clinical isolates. Notably, the achieved antibiotic resistance levels (defined herein as the IC75 value (trimethoprim concentration at which growth-rate of the given isolate was equal to one quarter of the uninhibited growth-rate of the wild-type parental strain) by the individual isolates of UPEC were comparable or higher than the clinically occurring trimethoprim concentration within the urinary tract (Wisell, Kahlmeter, and Giske 2008).

Example 4: Multi-Round Directed Evolution of a PTR that Encodes an Antibiotic Resistance Gene in Three Different Bacterial Species To demonstrate that the mutagenesis method described herein can be applied in consecutive rounds of mutagenesis and selection (multi-round in vivo directed evolution), an E. coli K-12 MG 1655 DHFR variant with three mutations (C-58A; G90C (FolA:Trp30Cys); C132G) was mutagenized using the soft-randomized oligo pool that had been previously used to target the wild-type folA (DHFR) gene in example 3. In this allelic DHFR variant, three mutations had been fixed in the prior round of overlapping, soft-randomized oligo pool-mediated mutagenesis and subsequent selection on mild trimethoprim concentration described in Examle 3.

This question is relevant for directed evolution, as one would expect that the overlapping, soft-randomized oligo set, designed for the wild-type sequence may revert the pre-existing mutations and hinder the recombination of mutations from the previous round of mutagenesis when the same oligo pool is used as in the first round of mutagenesis. Thus, five rMAGE cycles were carried out using the wild-type PTR targeting, soft-randomized oligo pool (SEQ ID:4-SEQ ID NO:11) on the previously described E. coli K-12 MG 1655 DHFR variant with the 3 mutations. The resulting library was analysed by amplicon HT sequencing of the PTR as it is described in Example 2. Sequence randomization was successful across the whole length of the target sequence (FIG. 8). No substantial decrease in the level of nucleotide variation was observed in the DHFR variant with the only exception being the nucleotides adjacent to the three pre-existing mutations.

Highly trimethoprim-sensitive variants were selected on MS+casamino acid (-thiamine) agar plates containing 1000 μg/ml trimethoprim. Individual resistant clones were then isolated for further genotype and trimethoprim susceptibility analysis as described in Example 3. Analysis revealed that mutagenesis generated a diverse set of highly trimethoprim-resistant variants of the genomically encoded FolA with increased sequence divergence compared to the parental allele, simultaneously retaining earlier mutations:

TABLE 5

| Strain ID | folA regulatory mutation | Amino acid change | Relative Trimethoprim IC75 change |
|---|---|---|---|
| 8 | C-58A | A26S, L28R, W30C | >7300 |
| 11 | C-58A | A26T, L28R, W30C | >7300 |

TABLE 5-continued

| Strain ID | folA regulatory mutation | Amino acid change | Relative Trimethoprim IC75 change |
|---|---|---|---|
| 12 | C-58A | A26T, L28R, M88L | 3300-4000 |
| 23 | C-58A | A26T, L28R | 2000-2600 |

This feature has particular relevance, as it shortens the time-frame for an evolutionary cycle and enables the generation of many parallel adaptive evolutionary paths in the same mutagenesis sample without the need of a new oligo design for each of the parental alleles.

Together, these results indicate that soft-randomized, overlapping oligo pool-mediated mutagenesis could generate multi-step adaptive evolutionary trajectories towards folA (DHFR) alleles that can show high-level trimethoprim resistance, phenotypes which are inaccessible via single mutational events.

Example 5: Discovery of Drug Resistance-Conferring Protein Variants

To demonstrate that the mutagenesis method described herein can discover drug-resistant bacterial variants, E. coli K-12 MG 1655 (Source: E. coli Genome Project, University of Wisconsin-Madison) DHFR (FolA, SEQ ID NO:216) was subjected to overlapping, soft-randomized oligo pool-mediated mutagenesis. Specifically, a single round of rMAGE mutagenesis cycle was carried out according to the protocol described in Example 2 with the equimolar mixture of SEQ ID:4-SEQ ID NO:11. The resulting mutants were then subjected to mild trimethoprim selection pressure (4-times the wild-type trimethoprim minimum inhibitory concentration (MIC)) and the genotypes of resistant clones were determined with amplicon HT sequencing of the PTR as described in Example 2. Clones with more than one mutation were excluded from further analysis, thus focusing on the adaptive single-step mutational landscape. Sequence analysis detected a large number of FolA mutations that confer resistance against trimethoprim (FIG. 14 (Table 6)). Analysis of these mutations, including previously not-described mutations 15F, A7T, G97S, and R98P (with positions referring to the amino acid position of the FolA protein) individually confirmed their resistance-conferring phenotypes.

Example 6: A Miniaturised Drug Resistance-Assay to Analyse Resistance Against Antibiotics To demonstrate that overlapping, soft-randomized oligo pool-mediated mutagenesis dramatically increases mutagenesis specifically at a user-defined resistance determinant and thereby accelerate the discovery of mutations that confer resistance to a drug, gyrA was analysed, GyrA (SEQ ID NO:217) encodes the A subunit of DNA gyrase, which is targeted by topoisomerase-targeting drugs including the fluoroquinolone antibiotic ciprofloxacin (D. C. Hooper et al. 1987).

Resistance-conferring mutations towards ciprofloxacin, one of the most frequently used fluoroquinolone antibiotic (D. C. Hooper et al. 1987) were investigated. To this aim, E. coli K-12 MG 1655 gyrA was subjected to overlapping, soft-randomized oligo pool-mediated mutagenesis. Specifically, five cycles of gyrA-targeted soft-randomized, overlapping oligo pool-mediated mutagenesis were carried out according to the protocol described in Example 2 with SEQ ID NO:37-SEQ ID NO:75. These overlapping, soft-randomized oligos cover the entire promoter and protein-coding regions (SEQ ID NO:37-SEQ ID NO:75) of gyrA. Following mutagenesis, 10 µL of the resulting cell library was subjected to ciprofloxacin stress (5-times of the wild-type MIC) on ciprofloxacin-containing $LB^L$ agar plates. From this agar plate 1000 resistant mutants were selected. Selection-experiments were performed in triplicates.

Pacific Biosciences RSII Single Molecule Real-Time (SMRT) circular-consensus amplicon sequencing was applied to determine the sequences of these resistant mutants. 200 ng of the isolated genomic DNA from the pooled colonies served as a template for Phusion High-Fidelity PCR with the corresponding species and sample specific barcoded primer pairs (SEQ ID NO:168-SEQ ID NO:175 to prepare barcoded amplicon libraries. PCR reactions were performed in 50 LI volumes with the following settings: 98° C. 3 min, 18-22 cycles of (98° C. 20 sec; 63° C. 30 sec; 72° C. 90 sec), with a final extension of 5 min at 72° C. To avoid overamplification and amplicon-chimera formation, PCR reactions were stopped at mid-exponential phase (based on the semi-quantitative measurement of the PCR product) and amplicons were purified using a Zymo DNA Clean and Concentrator Kit (Zymo Research). Barcoded amplicons were then mixed at an equimolar ratio and sequencing libraries were prepared and sequenced on Pacific Biosciences RSII SMRTcells.

To analyse sequencing data, sequencing reads were imported to CLC Genomics Workbench Tool (CLC Bio, Version 9.0). Reads with any ambiguous nucleotides as well as reads shorter than 80% of the target region were discarded. Each read was individually mapped against its target sequence (on the Escherichia coli K-12 MG1655 (NCBI Reference Sequence: NC_000913.3 genome) using CLC considering only those alignments that displayed at least 90% sequence similarity over at least 80% of the length of the query read. Single nucleotide variants for each mapped read were then called together with any associated amino acid change within the protein coding region of the reference. Variant calling was performed at a base call error probability threshold of 0.1.

HT sequence analysis of these samples with Pacific Biosciences RSII SMRT circular-consensus amplicon sequencing analysis revealed that all resistance mutations reside solely in the protein-coding region. Clinically occurring mutations at the Quinolone Resistance Determining Region (QRDR) of gyrA (Piddock 1999) and their combinations dominated the observed mutational landscape (FIG. 15 (Table 7)) and novel mutations were also discovered.

Therefore, within a single screen performed with 10 µl of the mutagenized cell library, the assay performed with the mutagenesis method described herein was able to detect ciprofloxacin resistance mutations that are frequently observed in the clinic and also revealed novel ones.

Example 7: Experimental Evolution of Multimeric Protein Complexes Enables the Analysis of Drug-Target Interaction Improvement of complex traits, such as those encoded in protein complexes and biosynthetic pathways, demands directed co-evolution of genetically interacting genes that are frequently coded at distinct loci in the genome. To demonstrate that the mutagenesis method described herein can perform co-evolution at distinct protein domains and enable drug-target interaction analyses, mutagenesis at the DNA gyrase complex and the DNA topoisomerase IV complex was performed. These four proteins are encoded at 4 distinct locations on the *E. coli* chromosome.

All four constituents were mutagenized along the full lengths of their corresponding protein-coding DNA regions in their native genomic context. Accordingly, a single round of rMAGE mutagenesis was performed in *E. coli* K-12 MG1655, using SEQ ID NO:37-SEQ ID NO:167.

Notably, in Gram-negative bacteria (such as *E. coli*), ciprofloxacin's primary drug target is the DNA gyrase complex (David C. Hooper and Jacoby 2015). However, ciprofloxacin also has lower binding affinity to the homologous DNA topoisomerase IV complex (Khodursky, Zechiedrich, and Cozzarelli 1995). Therefore, mutagenesis at the target sites was assayed by a ciprofloxacin frequency-of-resistance assay. Specifically, the resulting mutants were subjected to mild ciprofloxacin stress (i.e. at a dosage two-fold higher than the wild-type MIC) on LB agar plates, and the number of resistant variants were determined.

Selection experiments revealed that mutagenesis resulted in ciprofloxacin resistant variants at a frequency of $10^{-4}$. In parallel, resistant variants from non-mutagenised, control cell populations appeared at a frequency of $1.83*10^{-7}$, thus demonstrating the accelerated mutagenesis of the drug's resistance-determinant with the overlapping oligo pools.

Following selection, the genotypes of 3000 resistant clones were determined from the mutagenized cell population by using HT amplicon sequencing.

Pacific Biosciences RSII Single Molecule Real-Time (SMRT) circular-consensus amplicon sequencing was applied to determine the sequences of these multimeric Topoisomerase IV libraries. 200 ng of the isolated genomic DNA served as template for Phusion High-Fidelity PCR with the corresponding species and sample specific barcoded primer pairs (SEQ ID NO:168-SEQ ID NO:175 for gyrA (SEQ ID NO:217), SEQ ID NO:176-SEQ ID NO:183 for gyrB (SEQ ID NO:218), SEQ ID NO:184-SEQ ID NO:191 for parC (SEQ ID NO:219), and SEQ ID NO:192-SEQ ID NO:199 for parE (SEQ ID NO:220)) to prepare barcoded amplicon libraries. PCR reactions were performed in 50 ml volumes with the following settings: 98° C. 3 min, 18-22 cycles of (98° C. 20 sec; 63° C. 30 sec; 72° C. 90 sec), with a final extension of 5 min at 72° C. PCR reactions were stopped at mid-exponential phase (based on the semi-quantitative measurement of the PCR product) and amplicons were purified using a Zymo DNA Clean and Concentrator Kit (Zymo Research). Barcoded amplicons were then mixed at an equimolar ratio and sequencing libraries were prepared and sequenced on Pacific Biosciences RSII SMRTcells. These Pacific Biosciences CCS reads were imported to CLC Genomics Workbench Tool (CLC Bio, Version 9.0). Reads with any ambiguous nucleotide, as well as reads shorter than 80% of the target region, were discarded. Each read was individually mapped against its target sequence (on the *Escherichia coli* K-12 MG1655 (NCBI Reference Sequence: NC_000913.3 genome) using CLC considering only those alignments that displayed at least 90% sequence similarity over at least 80% of the length of the query read. Single nucleotide variants for each mapped read were then called together with any associated amino acid change within the protein coding region of the reference. Variant calling was performed at a base call error probability threshold of 0.1.

Sequence analysis indicated mutagenesis at multiple target loci and, as expected, the overwhelming majority of the identified alleles carried single mutations only. Mutations were detected in gyrA and gyrB. Most notably, the analysis revealed a region on the GyrB protein that was mutated in 22.4% of the analyzed alleles (FIG. 16).

To compare the position of the resistance-conferring mutations to the binding site of fluoroquinolones on the DNA gyrase complex, the observed mutational hot-spots above a 0.5% mutation frequency were plotted on the crystal structure of the DNA gyrase complex from *Mycobacterium tuberculosis* (Protein Data Bank: 5BS8). These drug-protein interaction analyses demonstrated that this protein region is in close proximity of the drug and may interact with ciprofloxacin (FIG. 17). FIG. 17 displays the ciprofloxacin resistance determining regions of GyrA (1.) and GyrB (3.), two subunits of the DNA gyrase complex. The figure also shows the interaction of the complex with a fluoroquinolone (2.) and dsDNA (4.).

Example 8: Overlapping, Soft-Randomized Olio Pool-Mediated Mutagenesis on a Genomic Tar Et in Yeast For the efficient mutagenesis with the method described herein a functioning recombineering system is provided in the given host. Based on the conserved functionality of oligo-mediated recombineering in prokaryotic and eukaryotic hosts (Houlleberghs et al. 2016) (Rios et al. 2012) (Moerschell, Tsunasawa, and Sherman 1988) (DiCarlo et al. 2013), overlapping, soft-randomized oligo pool-mediated mutagenesis is not restricted to engineer bacteria and can be deployed to mutagenize eukaryotic hosts, e.g. the model organism and industrial production host *Saccharomyces cerevisiae*, a yeast.

To demonstrate the portability of overlapping, soft-randomized oligo pool-mediated mutagenesis to *Saccharomyces cerevisiae*, the incorporation of overlapping, soft-randomized oligos was characterized using a similar protocol as in *E. coli*. To perform mutagenesis without necessitating additional genomic modifications and thus keeping the flexibility of the prokaryotic, pORTMAGE-based approach, the wild-type yeast homologous recombination system was employed to set-up overlapping, soft-randomized oligo pool-mediated mutagenesis. As the target, the endogenous URA3 gene in *Saccharomyces cerevisiae* BY4741 URA3+ (SEQ ID NO:221), encoding orotidine 5-phosphate decarboxylase was chosen. Loss-of-function URA3 mutants can be readily selected based on their 5-Fluoroorotic Acid (5-FOA)-resistant phenotype on 5-FOA containing agar plates (DiCarlo et al. 2013). Therefore, mutagenesis was assayed as the fraction of resistant cells towards 5-FOA in diversified cell populations compared with the frequency of an unmutagenized control. Using 11 overlapping spiked oligo pools (SEQ ID NO:200-SEQ ID NO:210), a single overlapping, soft-randomized oligo pool-mediated mutagenesis cycle was performed.

Specifically, overlapping, soft-randomized oligos for *S. cerevisiae* URA3 were designed to target the non-coding strand of URA3 (YEL021W, SEQ ID NO:221). Spiked oligonucleotides were synthesized as described in Example 1. Yeast-mutagenesis was performed by delivering oligonucleotides to *S. cerevisiae* BY4741 URA3+ cells by electroporation. Briefly, electrocompetent cells were prepared from 200 ml cell culture and resuspended in ice-cold electroporation buffer. 200 µl of this cell suspension was mixed with 5.5 µl 100 µM oligo mixture (0.5 µl, 50 µmole of each individual oligo, 11 total). Electroporation was performed on a BTX CM-630 system (2.5 kV, 200 Ω, 25 µF) in 2 mm gap electroporation cuvettes. Immediately after electroporation, cells were suspended in 8 ml of YPD-Sorbitol media (91.8 g sorbitol, 20 g bacto-pepton, 10 g yeast extract, 20 g glucose per 1 l of water) to allow for cell recovery for 1 hour at 30° C. under continuous shaking, 250 rpm. Cells were then collected by centrifugation and resuspended in 100 ml YPD (20 g bacto-pepton, 10 g yeast extract, 20 g glucose per 1 l of water). Cells were grown for 12 hours at 30° C. under continuous shaking at 250 rpm. As the next step, URA3 mutagenesis was assessed by measuring 5-fluoroorotic acid (5-FOA) resistance frequency. In the presence of 5-FOA, the active orotidine 5'-phosphate decarboxylase, encoded by URA3, converts 5-FOA into the toxic 5-fluorouracil and causes cell death. Therefore, by determining the fraction of 5-FOA resistant cells, mutagenesis that resulted in loss-of-function mutations in URA3 (DiCarlo et al. 2013) was assayed.

Untreated control and oligo-mutagenized cell populations were assessed for resistance on 5-fluoroorotic acid (5-FOA) containing SD agar plates (5 g ammonium sulphate, 1.7 g yeast nitrogen base, 20 g glucose, 20 g bacto-agar, 1 g 5-FOA and 2 g of the following drop-out supplement (0.5 g adenine, 2 g alanine, 2 g arginine, 2 g asparagine, 2 g aspartic acid, 2 g cysteine, 2 g glutamine, 2 g glutamic acid, 2 g glycine, 2 g histidine, 2 g inositol, 2 g isoleucine, 10 g leucine, 2 g lysine, 2 g methionine, 0.2 g para-amino benzoic acid, 2 g phenylalanine, 2 g proline, 2 g serine, 2 g threonine, 2 g tryptophan, 2 g tyrosine, 2 g uracil, 2 g valine) in 1000 ml). Appropriate dilutions of the cell libraries were plated on 5-FOA containing SD agar plates. Plates were incubated for 3 days at 30° C. Resistance frequencies were determined by the fraction of average 5-FOA resistant cells from the average total cell number, determined by plating appropriate dilutions onto SD agar plates without 5-FOA.

Soft-randomized oligo pool-mediated mutagenesis resulted in a 77-fold upregulation of the fraction of resistant cells as compared to the background level. The resulting mutants were then isolated and the genotypes of resistant cells were determined using HT amplicon sequencing of the 5-FOA resistant cell libraries. From each parallel experiment, 300 individual 5-FOA resistant colonies were picked up from SD+5-FOA plates and spotted onto a new agar plate. After 48 hours at 30° C., 300 resistant colonies were scraped off into 2 ml sterile distilled water from which 0.5 ml was used to extract genomic DNA according to a glass bead lysis protocol as described previously (Szamecz et al. 2014). Finally, the purified gDNA was dissolved in 100 µl nuclease-free water. Selection experiments were performed in triplicates.

PCR amplicons for HT sequencing on Pacific Biosciences RSII were prepared by amplifying the URA3 locus from pooled genomic DNA libraries from 3 parallel selection experiments. 500 ng of the isolated genomic DNA served as template for URA3-specific PCRs (SEQ ID NO:211-SEQ ID NO:212 for wild-type controls, SEQ ID NO:213-SEQ ID NO:214 for mutagenized cells) with the corresponding primers in Q5 Mix (Q5 High-Fidelity 2× Master Mix, NEB) PCR reactions according to the manufacturer's protocol. To avoid overamplification, 23 PCR cycles (1 min at 98° C.; 23× (15 seconds at 98° C., 25 seconds at 53° C., 35 seconds at 72° C.); 1 min 72° C.) were carried out and reactions were stopped at mid-exponential phase. PCR products were then run on 1% agarose gel and isolated from the gel using Zymoclean Gel DNA Recovery Kit and eluted in 18 µl 1× TE buffer. Eluted amplicons were mixed equimolarly and the sample was sequenced on a single SMRT cell on Pacific Biosciences RS II. Reads were filtered on SMRT Portal (SMRT Analysis version 2.3.0.1). Mutational and nucleotide composition analysis for each sample was performed with a custom Python script.

Sequence analysis revealed that overlapping, soft-randomized oligo pool-mediated mutagenesis generated diverse mutations and their combinations at the target site, many of which, as expected, resulted in inactivation of the URA3 function (FIG. 18).

In light of the emerging role of *Saccharomyces cerevisiae* as an eukaryotic chassis for synthetic biology and biotechnology (Dai et al. 2015), the mutagenesis method described herein would thus have a broad range of applications. We can expect applications ranging from the optimization of large-scale DNA construction, from genes to entire synthetic genomes (Vickers 2016) (Richardson et al. 2017), to the directed evolution of yeast bio-synthetic processes for the better production a high-value bio-products.

DISCUSSION

In summary, these examples show that the in vivo mutagenesis method described herein has the capacity to simultaneously mutagenize multiple predefined DNA sequences with extensive sizes across a variety of bacterial species and in yeasts.

Through the precise tuning of nucleotide composition in each synthetic DNA oligomer, the mutational bias is tightly controlled and each possible mutation and their combinations are represented within the synthesized oligo pool. Meanwhile, the number of mutations is constrained within each individual oligo sequence, by distributing the mutations within the oligo pool with a soft randomization approach. The limited number of mismatches to the target sequence allows for efficient genomic integration of the oligos, while the overlapping design allows for random and uniformly distributed mutagenesis for extended targets. The applicability of this strategy to mutagenize an entire genomic PTR was demonstrated in *Escherichia coli, Salmonella enterica, Citrobacter freundii* and *Saccharomyces cerevisiae*. Mutation rate was precisely controllable by the spiking ratio of soft-randomization during the course of chemical DNA synthesis and reached over $10^6$-times the wild-type mutation rate. The efficiency of overlapping, soft-randomized oligo pool-mediated mutagenesis has been shown in *E. coli* K-12 MG1655, *E. coli* CFT073 UPEC and *Salmonella enterica*. It also comprehensively mapped and compared adaptive mutational trajectories towards trimethoprim and ciprofloxacin resistance.

The protocol is also extremely cost-effective: in conjunction with microarray-derived, spiked oligonucleotides, it can theoretically randomize up-to $6.4 \times 10^6$ basepairs of continuous target DNA for approximately 5000 USD, 210-fold longer than alternative methods at the same price.

These results pave the way towards high-throughput in vivo exploration of fitness landscapes of endogenous genes and gene networks. Beyond in vivo deep mutational scanning and the exploration of adaptive trajectories towards clinical drugs (e.g. antibiotics), soft-randomized oligonucleotide mediated mutagenesis is useful for metabolic and enzyme engineering in a large set of species, including previously untapped, clinically and biotechnologically relevant hosts.

REFERENCES

Amiram, Miriam, Adrian D. Haimovich, Chenguang Fan, Yane-Shih Wang, Hans-Rudolf Aerni, Ioanna Ntai, Daniel W. Moonan, et al. 2015. "Evolution of Translation Machinery in Recoded Bacteria Enables Multi-Site Incorporation of Nonstandard Amino Acids." *Nature Biotechnology* 33 (12): 1272-79. doi:10.1038/nbt.3372.

Biedenbach, D. J., S. K. Bouchillon, M. Hackel, L. A. Miller, N. E. Scangarella-Oman, C. Jakielaszek, and D. F. Sahm. 2016. "In Vitro Activity of Gepotidacin, a Novel Triazaacenaphthylene Bacterial Topoisomerase Inhibitor, against a Broad Spectrum of Bacterial Pathogens." *Antimicrobial Agents and Chemotherapy* 60 (3): 1918-23. doi:10.1128/AAC.02820-15.

Bonde, Mads T., Sriram Kosuri, Hans J. Genee, Kira Sarup-Lytzen, George M. Church, Morten O. A. Sommer, and Harris H. Wang. 2014. "Direct Mutagenesis of Thousands of Genomic Targets Using Microarray-Derived Oligonucleotides." *ACS Synthetic Biology*. doi:10.1021/sb5001565.

Coussement, Pieter, Jo Maertens, Joeri Beauprez, Wouter Van Bellegem, and Marjan De Mey. 2014. "One Step DNA Assembly for Combinatorial Metabolic Engineering." *Metabolic Engineering* 23: 70-77. doi:10.1016/j.ymben.2014.02.012.

Dai, Zhubo, Yi Liu, Juan Guo, Luqi Huang, and Xueli Zhang. 2015. "Yeast Synthetic Biology for High-Value Metabolites." *FEMS Yeast Research* 15 (1): 1-11. doi: 10.1111/1567-1364.12187.

DiCarlo, James E., Andrew J. Conley, Merja Penttilä, Jussi Jäntti, Harris H. Wang, and George M. Church. 2013. "Yeast Oligo-Mediated Genome Engineering (YOGE)." *ACS Synthetic Biology*. doi:10.1021/sb400117c.

Diner, Elie J., and Christopher S. Hayes. 2009. "Recombineering Reveals a Diverse Collection of Ribosomal Proteins L4 and L22 That Confer Resistance to Macrolide Antibiotics." *Journal of Molecular Biology* 386 (2): 300-315. doi:10.1016/j.jmb.2008.12.064.

Enzymes, pathways and organisms for making a polymerizable monomer by whole cell bioprocess. 2016. Accessed October 19. http://www.google.com/patents/WO2001068803A2.

Farrell, D. J., H. S. Sader, P. R. Rhomberg, N. E. Scangarella-Oman, and R. K.

Flamm. 2017. "In Vitro Activity of Gepotidacin (GSK2140944) against *Neisseria Gonorrhoeae*." *Antimicrobial Agents and Chemotherapy* 61 (3): e02047-16. doi:10.1128/AAC.02047-16.

Flensburg, J., and O. Sköld. 1987. "Massive Overproduction of Dihydrofolate Reductase in Bacteria as a Response to the Use of Trimethoprim." *European Journal of Biochemistry* 162 (3): 473-76.

Gallagher, Ryan R., Zhe Li, Aaron O. Lewis, and Farren J. Isaacs. 2014. "Rapid Editing and Evolution of Bacterial Genomes Using Libraries of Synthetic DNA." *Nature Protocols* 9 (10): 2301-16. doi:10.1038/nprot.2014.082.

Gao, Xiaolian, Eric LeProust, Hua Zhang, Onnop Srivannavit, Erdogan Gulari, Peilin Yu, Ciro Nishiguchi, Qin Xiang, and Xiaochuan Zhou. 2001. "A Flexible Light-Directed DNA Chip Synthesis Gated by Deprotection Using Solution Photogenerated Acids." *Nucleic Acids Research* 29 (22): 4744-50. doi:110.1093/nar/29.22.4744.

Hall, Bradley, John M. Micheletti, Pooja Satya, Krystal Ogle, Jack Pollard, and Andrew D. Ellington. 2001. "Design, Synthesis, and Amplification of DNA Pools for In Vitro Selection." In *Current Protocols in Molecular Biology*. John Wiley & Sons, Inc. http://onlinelibrary.wiley.com/doi/10.1002/0471142727.mb2402s88/abstract.

Hermes, Jeffrey D., Shirish M. Parekh, Stephen C. Blacklow, Hubert Koster, and Jeremy R. Knowles. 1989. "A Reliable Method for Random Mutagenesis: The Generation of Mutant Libraries Using Spiked Oligodeoxyribonucleotide Primers." *Gene* 84 (1): 143-51. doi:10.1016/0378-1119(89)90148-0.

Hooper, D. C., J. S. Wolfson, E. Y. Ng, and M. N. Swartz. 1987. "Mechanisms of Action of and Resistance to Ciprofloxacin." *The American Journal of Medicine* 82 (4A): 12-20.

Hooper, David C., and George A. Jacoby. 2015. "Mechanisms of Drug Resistance: Quinolone Resistance." *Annals of the New York Academy of Sciences* 1354 (September): 12-31. doi:10.1111/nyas.12830.

Houlleberghs, Hellen, Marleen Dekker, Hildo Lantermans, Roos Kleinendorst, Hendrikus Jan Dubbink, Robert M. W. Hofstra, Senno Verhoef, and Hein Te Riele. 2016. "Oligonucleotide-Directed Mutagenesis Screen to Identify Pathogenic Lynch Syndrome-Associated MSH2 DNA Mismatch Repair Gene Variants." *Proceedings of the National Academy of Sciences of the United States of America* 113 (15): 4128-33. doi:10.1073/pnas.1520813113.

Khodursky, A. B., E. L. Zechiedrich, and N. R. Cozzarelli. 1995. "Topoisomerase IV Is a Target of Quinolones in *Escherichia Coli*." *Proceedings of the National Academy of Sciences of the United States of America* 92 (25): 11801-5.

Kow, Yoke W., Gaobin Bao, Jason W. Reeves, Sue Jinks-Robertson, and Gray F. Crouse. 2007. "Oligonucleotide Transformation of Yeast Reveals Mismatch Repair Complexes to Be Differentially Active on DNA Replication Strands." *Proceedings of the National Academy of Sciences of the United States of America* 104 (27): 11352-57. doi:10.1073/pnas.0704695104.

LeProust, Emily M., Bill J. Peck, Konstantin Spirin, Heather Brummel McCuen, Bridget Moore, Eugeni Namsaraev, and Marvin H. Caruthers. 2010. "Synthesis of High-Quality Libraries of Long (150mer) Oligonucleotides by a Novel Depurination Controlled Process." *Nucleic Acids Research* 38 (8): 2522-40. doi:10.1093/nar/gkq163.

Li, Xin-tian, Lynn C. Thomason, James A. Sawitzke, Nina Costantino, and Donald L.

Court. 2013. "Bacterial DNA Polymerases Participate in Oligonucleotide Recombination." *Molecular Microbiology* 88 (5): 906-20. doi:10.1111/mmi.12231.

McArthur, Andrew G., Nicholas Waglechner, Fazmin Nizam, Austin Yan, Marisa A. Azad, Alison J. Baylay, Kirandeep Bhullar, et al. 2013. "The Comprehensive Antibiotic Resistance Database." *Antimicrobial Agents and Chemotherapy* 57 (7): 3348-57. doi:10.1128/AAC.00419-13.

Methods and compositions for cellular and metabolic engineering. 2016. Accessed October 19. http://www.google.com/patents/U.S. Pat. No. 6,391,640.

Moerschell, R P, S Tsunasawa, and F Sherman. 1988. "Transformation of Yeast with Synthetic Oligonucleotides." *Proceedings of the National Academy of Sciences of the United States of America* 85 (2): 524-28.

Neuner, P, R Cortese, and P Monaci. 1998. "Codon-Based Mutagenesis Using Dimer-Phosphoramidites." *Nucleic Acids Research* 26 (5): 1223-27.

Nordwald, Erik M., Andrew Garst, Ryan T Gill, and Joel L Kaar. 2013. "Accelerated Protein Engineering for Chemical Biotechnology via Homologous Recombination." *Current Opinion in Biotechnology* 24 (6): 1017-22. doi: 10.1016/j.copbio.2013.03.003.

Nyerges, Ákos, Bálint Csörgö, István Nagy, Balázs Bálint, Péter Bihari, Viktória Lázár, Gábor Apjok, et al. 2016. "A Highly Precise and Portable Genome Engineering Method Allows Comparison of Mutational Effects across Bacterial Species." *Proceedings of the National Academy of Sciences* 113 (9): 2502-7. doi:10.1073/pnas.1520040113.

Nyerges, Ákos, Bálint Csörgö, István Nagy, Dóra Latinovics, Béla Szamecz, György Pósfai, and Csaba Pál. 2014. "Conditional DNA Repair Mutants Enable Highly Precise Genome Engineering." *Nucleic Acids Research*, February, gku105. doi:10.1093/nar/gku105.

Piddock, Laura J. V. 1999. "Mechanisms of Fluoroquinolone Resistance: An Update 1994-1998." *Drugs* 58 (2): 11-18. doi:10.2165/00003495-199958002-00003.

Richardson, Sarah M., Leslie A. Mitchell, Giovanni Stracquadanio, Kun Yang, Jessica S. Dymond, James E. DiCarlo, Dongwon Lee, et al. 2017. "Design of a Synthetic Yeast Genome." *Science* 355 (6329): 1040-44. doi:10.1126/science.aaf4557.

Rios, Xavier, Adrian W. Briggs, Danos Christodoulou, Josh M. Gorham, Jonathan G. Seidman, and George M. Church. 2012. "Stable Gene Targeting in Human Cells Using Single-Strand Oligonucleotides with Modified Bases." *PLoS ONE* 7 (5): e36697. doi:10.1371/journal.pone.0036697.

Savage, Victoria J., Cédric Charrier, Anne-Marie Salisbury, Emmanuel Moyo, Henry Forward, Nathan Chaffer-Malam, Richard Metzger, et al. 2016. "Biological Profiling of Novel Tricyclic Inhibitors of Bacterial DNA Gyrase and Topoisomerase IV." *The Journal of Antimicrobial Chemotherapy* 71 (7): 1905-13. doi:10.1093/jac/dkw061.

Sondek, J., and D. Shortle. 1992. "A General Strategy for Random Insertion and Substitution Mutagenesis: Substoichiometric Coupling of Trinucleotide Phosphoramidites." *Proceedings of the National Academy of Sciences* 89 (8): 3581-85. doi:10.1073/pnas.89.8.3581.

Szamecz, Béla, Gábor Boross, Dorottya Kalapis, Károly Kovács, Gergely Fekete, Zoltán Farkas, Viktória Lázár, et al. 2014. "The Genomic Landscape of Compensatory Evolution." *PLOS Biology* 12 (8): e1001935. doi:10.1371/journal.pbio.1001935.

Toprak, Erdal, Adrian Veres, Jean-Baptiste Michel, Remy Chait, Daniel L Hartl, and Roy Kishony. 2011. "Evolutionary Paths to Antibiotic Resistance under Dynamically Sustained Drug Selection." *Nature Genetics* 44 (1): 101-5. doi:10.1038/ng.1034.

Vickers, Claudia E. 2016. "The Minimal Genome Comes of Age." *Nature Biotechnology* 34 (6): 623-24. doi:10.1038/nbt.3593.

Wang, Harris H., and George M. Church. 2011. "Multiplexed Genome Engineering and Genotyping Methods." In *Methods in Enzymology*, 498:409-26. Elsevier. http://linkinghub.elsevier.com/retrieve/pii/B9780123851208000188.

Wang, Harris H., Farren J. Isaacs, Peter A. Carr, Zachary Z. Sun, George Xu, Craig R. Forest, and George M. Church. 2009. "Programming Cells by Multiplex Genome Engineering and Accelerated Evolution." *Nature* 460 (7257): 894-98. doi:10.1038/nature08187.

Watson, Morgan, Jian-Wei Liu, and David Ollis. 2007. "Directed Evolution of Trimethoprim Resistance in *Escherichia Coli.*" *The FEBS Journal* 274 (10): 2661-71. doi:10.1111/j.1742-4658.2007.05801.x.

Wisell, Karin Tegmark, Gunnar Kahlmeter, and Christian G. Giske. 2008. "Trimethoprim and Enterococci in Urinary Tract Infections: New Perspectives on an Old Issue." *The Journal of Antimicrobial Chemotherapy* 62 (1): 35-40. doi:10.1093/jac/dkn 147.

Yu, Daiguan, James A. Sawitzke, Hilary Ellis, and Donald L. Court. 2003. "Recombineering with Overlapping Single-Stranded DNA Oligonucleotides: Testing a Recombination Intermediate." *Proceedings of the National Academy of Sciences* 100 (12): 7207-12. doi:10.1073/pnas.1232375100.

---

The invention claimed is:

1. A method of in vivo mutagenesis of a preselected target region (PTR) of an intracellular DNA within a cell culture, which PTR comprises at least one sequence of interest (SOI) which is at least 250 nucleobases long, the method comprising:
   a) providing a pool of partially overlapping single stranded DNA (ssDNA) oligonucleotides which are non-complementary in their overlaps and which align to a continuous sequence that is complementary to the SOI, wherein the pool contains a diversity of mutagenizing single stranded oligonucleotides covering nucleobase mismatches at every position of said SOI and combination of said nucleobase mismatches, wherein each mutagenizing oligonucleotide is hybridizing with the PTR and comprises at least one mismatching nucleobase up to 20% mismatching nucleobases, compared to the SOI;
   b) integrating the pool into said intracellular DNA by homologous recombination and inducing in vivo mutagenesis of the intracellular DNA through hybridizing the oligonucleotides to the PTR, thereby producing a cell library comprising a repertoire of variant cells covering point mutations in said PTR at every position and combinations of said point mutations within said PTR, wherein the cell library comprises at least $10^6$ library members which are characterized by different mutations.

2. The method of claim 1, wherein at least 0.1% of the oligonucleotides contained in said pool are mutagenizing oligonucleotides.

3. The method of claim 1, wherein a majority of the mutagenizing oligonucleotides comprises less than 20 mismatching nucleobases or less than 6 codon substitutions per 100 nucleobases.

4. The method of claim 1, wherein each of the ssDNA oligonucleotides has a length of 40-200 nucleotides.

5. The method of claim 1, wherein each of the overlapping oligonucleotides comprises an overlap which is up to 50% of the oligonucleotide length.

6. The method of claim 1, wherein each of the overlapping oligonucleotides comprises an overlap of at least 5 nucleotides up to 20 nucleotides at the 5' and/or 3' ends.

7. The method of claim 1, wherein the pool comprises oligonucleotides that are produced by a polynucleotide synthesis method that allows introduction of nucleobase mismatches compared to the SOT.

8. The method of claim 7, wherein in the pool of oligonucleotides the rate of nucleobase mismatches at every position of said SOI is less than 50%.

9. The method of claim 1, wherein the nucleobase mismatches are selected from the group consisting of a nucleobase or nucleotide substitution, insertion, or deletion, a codon substitution, or combinations thereof.

10. The method of claim 1, wherein the cell library is produced by one or more rounds of in vivo mutagenesis, each round comprising:

a) transfecting or transforming cells of the cell culture with the pool of oligonucleotides in a transfection or transformation medium; and
b) replacing the transfection or transformation medium with growth medium and incubating the cells in the growth medium; and optionally repeating the steps a) and b) to increase the library diversity.

11. The method of claim 10, wherein following at least one round of in vivo mutagenesis, a repertoire of cells is selected from the produced cell library, and wherein the repertoire is used for at least one further round of in vivo mutagenesis to increase the diversity of the repertoire.

12. The method of claim 10, wherein the cells are transfected or transformed using the natural competence of the cell, or by an electroporation, protoplast, or chemical transformation method, or by a technique mediated by any of a peptide, a lipid-vesicle, or a virus.

13. The method of claim 1, wherein the cell library is further tailored or focused to enrich or eliminate a group of cells characterized by at least one detectable feature.

14. The method of claim 1, wherein said repertoire of variant cells covers point mutations which are randomly distributed within said PTR.

15. The method of claim 1, wherein the SOI is a non-coding sequence or a combination of non-coding and coding sequences.

16. The method of claim 1, wherein the SOI encodes a protein, a ribozyme, a riboswitch, an RNA, or a group of biomolecules that form a cellular pathway, a regulatory network, a metabolic pathway, a cellular subsystem, or a part of any of the foregoing.

17. The method of claim 1, wherein the SOI encodes or is part of a metabolic or biosynthetic pathway.

18. The method of claim 1, wherein the SOI comprises one or more of any of a ribosomal binding site, promoter, leader sequence, introns, ribozyme, riboswitch or regulatory sequence, or part of any of the foregoing.

19. The method of claim 1, wherein the SOI comprises a nucleic acid sequence within a chromosome or a plasmid of a cell.

20. The method of claim 19, wherein the cell is of human, rodent, fungi, or bacteria origin, including wild-type or mutant cells.

21. The method of claim 19, wherein the cell is a microorganism.

22. The method of claim 21, wherein the microorganism is a bacterium from a genus selected from the group consisting of *Enterococcus, Staphylococcus, Klebsiella, Acinetobacter, Pseudomonas, Shigella, Salmonella, Citrobacter, Proteus, Vibrio* and *Escherichia*, and any of their synthetic or engineered variants thereof.

23. The method of claim 19, wherein the cell is a drug-responsive microorganism, and the cell library encompasses a repertoire of variant cells which are drug-resistant.

24. A cell library obtainable by the method of claim 1, wherein the library comprises a repertoire of variant cells having a diversity of at least $10^7$.

25. The cell library of claim 24, wherein the repertoire comprises variant cells which are drug-resistant.

26. The method of claim 1, wherein the SOI is a coding sequence.

* * * * *

SEQUENCE LISTING

```
<160> NUMBER OF SEQ ID NOS: 221

<210> SEQ ID NO 1
<211> LENGTH: 8096
<212> TYPE: DNA
<213> ORGANISM: Artificial sequence
<220> FEATURE:
<223> OTHER INFORMATION: Plasmid

<400> SEQUENCE: 1
cagctgtctc ttatacacat ctccgctgtg ctttcagtgg atttcggata acagaaaggc      60
cgggaaatac ccagcctcgc tttgtaacgg agtagacgaa agtgattgcg cctacccgga     120
tattatcgtg aggatgctca tcgccatttc actcatcttt cagggctttt atcgccggat     180
gtaaatcaac agattgtaac agaccacccg gcggcgtttt cacaagttgc ggacataacc     240
gttccacgtc cgccagcagg gttatggcct gtgccattga ccactgcgca tgttcgctca     300
tcagatttcg tgcaatccac tgcgcaatat tgccaggttc gaatacggac tgcttcgcca     360
ggtagcctat cagttcagga atcaagattt gtaaattttg ttggcgtaag ggtaaaggca     420
ctgccctgat ggtcacatgc tgtgcatctg actggaaatc aatacccaat tccgccaggg     480
cagactgcgc tttttctaat gccgattttt cttcggcaga aactttttagc cgcaacggaa     540 tcagcagcgg ctgggcgcaa acgggcgctt cacccggcgt caattgtgcc tgacgcagcc     600
```

```
aacgttctgc cactggcaag gataaaagtg aaatgttgcc gtcgcgctcc agcaacgcac      660
agtcggaatg gacgatagtc agtacccgac caaaactctg actgttcgcc gcaagtgcag      720
gttcctgcgg ttccggcgct tttaattttt gcatcggcgc gggcgtttgc aaaagctggc      780
gatacacttc accttgctgt ttctggtagc ctggctgcgc attcggccag ggggcagccg      840
gacgactgcc tgatgctggc gcaggagtgt agcgcggagc taccggctca cgagctgccg      900
gttctgcaaa gtgattgcgc cccgccgcca cgcggttttc cggaatggaa cgcggtgcag      960
gttggggttc atcgtccagc ggtagcggcg tttccagttg ctgttgtagc acgctcagca     1020
cgccctgata gataaaatca tgcaccagac gcgactgatg gaaacgcact tcgtgtttgg     1080
cggggtgcac gttgacgtcc acctgatgtg ggtcgatctc cagatacaac acaaatgccg     1140
gttgctgatc ggcccccagt ttgtcttcgc aggcctggcg gatcgcgtga ttgatcaggc     1200
gatcgcgcat catgcgaccg ttcacgtagc aatactgaat ttctgccagt gcgggcgtgg     1260
tgtgatttgg atcggccacc cagccgcgta gcgtgagatc gccgtgttgc cattcaatcg     1320
ccagcgcttg ttcaagaaaa gcggtgccgc aaatcgcgcc taagcgccgt tcttttttgcc     1380 cgccttccgg cactgcgcgg tactgacgca caattttacc gttatgcgac aggttgatcg     1440
tgacgtcgaa acgcgccagc gcaatgcggc ggatgatctc atcaatgtgg ttaaattcgg     1500
ttttctcggt gcgcaggaat ttgcgccgcg ccggggtgtt gtagaacaga tccagcacct     1560
ccagcgtcgt cccacagga tgcgccgccg gttttaccgt cacgttcata tcgcgccctt      1620
cggcataggc ctgccaggct tcctgctgtt ctgcggtgcg tgaagtgagc gtcaggcggg     1680
aaaccgaact gatactcgcc agcgcctcac cgcgaaagcc caggctgata atggcttcga     1740
gatcgtccag agaggcgatt ttactggtgg catgacgagc cagcgccagc gccagctcat     1800
cttttttgat accgcagccg ttatcacgaa tgcggataag tttcgcccca ccgcgttcga     1860
tatcaatatc gatacgcgtc gcacctgcat cgaggctgtt tttcactagt tctttgacta     1920
ccgacgcagg tcgctcgacc acctcacctg cggcaatctg gttcgccagt gtgtgccggta     1980 agacctgaat tggcatttttg taatcctcct ctctcatcgc cattgctccc caaatacaaa     2040
accaatttca gccagtgcct cgtccatttt ttcgatgaac tccggcacga tctcgtcaaa     2100
actcgccatg tactttttcat cccgctcaat cacgacataa tgcaggcctt cacgcttcat     2160
acgcgggtca tagttggcaa agtaccaggc attttttcgc gtcacccaca tgctgtactg     2220
cacctgggcc atgtaagctg actttatggc ctcgaaacca ccgagccgga acttcatgaa     2280
atcccgggag gtaaacgggc atttcagttc aaggccgttg ccgtcactgc ataaaccatc     2340
gggagagcag gcggtacgca ctttcgtc gcgatagatg atcggggatt cagtaacatt       2400
cacgccggaa gtaaattcaa acagggttct ggcgtcgttc tcgtactgtt ttccccaggc     2460
cagtgcttta gcgttaactt ccggagccac accggtgcaa acctcagcaa gcagggtgtg     2520
gaagtaggac atttttcatgt caggccactt ctttccggag cggggttttg ctatcacgtt     2580
gtgaacttct gaagcggtga tgacgccgag ccgtaatttg tgccacgcat cttcccctg     2640 ttcgacagct ctcacatcga tcccggtacg ctgcaggata atgtccggtg tcatgctgcc     2700
accttctgct ctgcggcttt ctgtttcagg aatccaagag cttttactgc ttcggcctgt     2760
gtcagttctg acgatgcacg aatgtcgcgg cgaaatatct gggaacagag cggcaataag     2820
tcgtcatccc atgttttatc cagggcgatc agcagagtgt taatctcctg catggtttca     2880
tcgttaaccg gagtgatgtc gcgttccggc tgacgttctg cagtgtatgc agtatttccg     2940
acaatgcgct cggcttcatc cttgtcatag ataccagcaa atccgaaggc cagacgggca     3000
```

```
cactgaatca tggctttatg acgtaacatc cgtttgggat gcgactgcca cggccccgtg    3060
atttctctgc cttcgcgagt tttgaatggt tcgcggcggc attcatccat ccattcggta    3120
acgcagatcg gatgattacg gtccttgcgg taaatccggc atgtacagga ttcattgtcc    3180
tgctcaaagt ccatgccatc aaactgctgg ttttcattga tgatgcggga ccagccatca    3240
acgcccacca ccggaacgat gccattctgc ttatcaggaa aggcgtaaat ttctttcgtc    3300
cacggattaa ggccgtactg gttggcaacg atcagtaatg cgatgaactg cgcatcgctg    3360
gcatcacctt taaatgccgt ctggcgaaga gtggtgatca gttcctgtgg gtcgacagaa    3420
tccatgccga cacgttcagc cagcttccca gccagcgttg cgagtgcagt actcattcgt    3480 tttataccte tgaatcaata tcaacctggt ggtgagcaat ggtttcaacc atgtaccgga    3540
tgtgttctgc catgcgctcc tgaaactcaa catcgtcatc aaacgcacgg gtaatggatt    3600
ttttgctggc cccgtggcgt tgcaaatgat cgatgcatag cgattcaaac aggtgctggg    3660
gcaggccttt tccatgtcg tctgccagtt ctgcctcttt ctcttcacgg gcgagctgct    3720
ggtagtgacg cgcccagctc tgagcctcaa gacgatcctg aatgtaataa gcgttcatgg    3780
ctgaactcct gaaatagctg tgaaaatatc gcccgcgaaa tgccgggctg attagtaatc    3840
cggaatcgca cttacggcca atgcttcgtt tcgtatcaca caccccaaag ccttctgctt    3900
tgaatgctgc ccttcttcag ggcttaattt ttaagagcgt caccttcatg gtggtcagtg    3960
cgtcctgctg atgtgctcag tatcaccgcc agtggtattt atgtcaacac cgccagagat    4020
aatttatcac cgcagatggt tatctgtatg tttttttatat gaatttatt tttgcagggg    4080 ggcattgttt ggtaggtgag agatctgaat tgctatgttt agtgagttgt atctatttat    4140
ttttcaataa atacaattgg ttatgtgttt tgggggcgat cgtgaggcaa agaaaacccg    4200
gcgctgaggc cgggttaaga gttggtagct cttgatccgg caaacaaacc accgctggta    4260
gcggtggttt ttttgtttgc aagcagcaga ttacgcgcag aaaaaaagga tctcaagaag    4320
atcctttgat cttttctacg gggtctgacg ctcagtggaa cgaaaactca cgttaaggga    4380
ttttggtcat gagattatca aaaaggatct cacctagat cctttttaaat taaaaatgaa    4440 gttttaaatc aatctaaagt atatatgagt aaacttggtc tgacagttac caatgcttaa    4500
tcagtgaggc acctatctca gcgatctgtc tatttcgttc atccatagtt gcctgactcc    4560
ccgtcgtgta gataactacg atacgggagg gcttaccatc tggccccagt gctgcaatga    4620
taccgcgaga cccacgctca ccggctccag atttatcagc aataaaccag ccagccggaa    4680
gggccgagcg cagaagtggt cctgcaactt tatccgcctc catccagtct attaattgtt    4740
gccgggaagc tagagtaagt agttcgccag ttaatagttt gcgcaacgtt gttgccattg    4800
ctacaggcat cgtggtgtca cgctcgtcgt ttggtatggc ttcattcagc tccgttccc    4860 aacgatcaag gcgagttaca tgatccccca tgttgtgcaa aaaagcggtt agctccttcg    4920
gtcctccgat cgttgtcaga agtaagttgg ccgcagtgtt atcactcatg gttatggcag    4980
cactgcataa ttctcttact gtcatgccat ccgtaagatg cttttctgtg actggtgagt    5040
actcaaccaa gtcattctga gaatagtgta tgcggcgacc gagttgctct tgcccggcgt    5100
caatacggga taataccgcg ccacatagca gaactttaaa agtgctcatc attggaaaac    5160
gttcttcggg gcgaaaactc tcaaggatct taccgctgtt gagatccagt tcgatgtaac    5220
ccactcgtgc acccaactga tcttcagcat cttttacttt caccagcgtt tctgggtgag    5280
caaaaacagg aaggcaaaat gccgcaaaaa agggaataag ggcgacacgg aaatgttgaa    5340
```

-continued

```
tactcatact cttccttttt caatattatt gaagcattta tcagggttat tgtctcatga    5400
gcggatacat atttgaatga attcaaccat ttactatgtt atgttctgag gggagtgaaa    5460
attcccctaa ttcgatgaag attcttgctc aattgttatc agctatgcgc cgaccagaac    5520
accttgccga tcagccaaac gtctcttcag gccactgact agcgataact tccccacaa    5580
cggaacaact ctcattgcat gggatcattg gtactgtgg gtttagtggt tgtaaaaaca    5640
cctgaccgct atccctgatc agtttcttga aggtaaactc atcacccca gtctggcta    5700
tgcagaaatc acctggctca acagcctgct cagggtcaac gagaattaac attccgtcag    5760
gaaagcttgg cttggagcct gttggtgcgg tcatggaatt accttcaacc tcaagccaga    5820
atgcagaatc actggctttt ttggttgtgc ttacccatct ctccgcatca cctttggtaa    5880
aggttctaag ctcaggtgag aacatccctg cctgaacatg agaaaaaaca gggtactcat    5940
actcacttct aagtgacggc tgcatactaa ccgcttcata catctcgtag atttctctgg    6000
cgattgaagg gctaaattct tcaacgctaa ctttgagaat ttttgtaagc aatgcggcgt    6060
tataagcatt taatgcattg atgccattaa ataaagcacc aacgcctgac tgccccatcc    6120
ccatcttgtc tgcgacagat tcctgggata agccaagttc atttttcttt ttttcataaa    6180
ttgctttaag gcgacgtgcg tcctcaagct gctcttgtgt taatggtttc tttttttgtgc   6240
tcatacgtta aatctatcac cgcaagggat aaatatctaa caccgtgcgt gttgactatt    6300
ttacctctgg cggtgataat ggttgcatgt actaaggagg ttgtatggaa caacgagatg    6360
tgtataagag acagctggcc tgcccctccc ttttggtgtc caaccggctc gacggggca    6420
gcgcaaggcg gtgcctccgg cgggccactc aatgcttgag tatactcact agactttgct    6480
tcgcaaagtc gtgaccgcct acggcggctg cggcgcccta cgggcttgct ctccgggctt    6540
cgccctgcgc ggtcgctgcg ctcccttgcc agcccgtgga tatgtggacg atggccgcga    6600
gcggccaccg gctggctcgc ttcgctcggc ccgtggacaa ccctgctgga caagctgatg    6660
gacaggctgc gcctgcccac gagcttgacc acagggattg cccaccggct acccagcctt    6720
cgaccacata cccaccggct ccaactgcgc ggcctgcggc cttgccccat caattttttt    6780
aattttctct ggggaaaagc ctccggcctg cggcctgcgc gcttcgcttg ccggttggac    6840
accaagtgga aggcgggtca aggctcgcgc agcgaccgcg cagcggcttg gccttgacgc    6900
gcctggaacg acccaagcct atgcgagtgg gggcagtcga agggcgaagc ccgcccgcct    6960
gcccccgag cctcacggcg gcgagtgcgg gggttccaag ggggcagcgc caccttgggc    7020
aaggccgaag gccgcgcagt cgatcaacaa gccccgagg ggccactttt tgccggaggg    7080
ggagccgcgc cgaaggcgtg ggggaacccc gcagggtgc ccttctttgg gcaccaaaga    7140
actagatata gggcgaaatg cgaaagactt aaaaatcaac aacttaaaaa aggggggtac    7200
gcaacagctc attgcggcac cccccgcaat agctcattgc gtaggttaaa gaaaatctgt    7260
aattgactgc cacttttacg caacgcataa ttgttgtcgc gctgccgaaa agttgcagct    7320
gattgcgcat ggtgccgcaa ccgtgcggca ccctaccgc atggagataa gcatggccac    7380
gcagtccaga gaaatcggca ttcaagccaa gaacaagccc ggtcactggg tgcaaacgga    7440
acgcaaagcg catgaggcgt gggccgggct tattgcgagg aaacccacgg cggcaatgct    7500
gctgcatcac ctcgtggcgc agatgggcca ccagaacgcc gtggtggtca gccagaagac    7560
actttccaag ctcatcggac gttctttgcg gacggtccaa tacgcagtca aggacttggt    7620
ggccgagcgc tggatctccg tcgtgaagct caacggcccc gcaccgtgt cggcctacgt    7680
ggtcaatgac cgcgtggcgt ggggccagcc ccgcgaccag ttgcgcctgt cggtgttcag    7740
```

```
tgccgccgtg gtggttgatc acgacgacca ggacgaatcg ctgttggggc atggcgacct      7800
gcgccgcatc ccgaccctgt atccgggcga gcagcaacta ccgaccggcc ccggcgagga      7860
gccgcccagc cagcccggca ttccgggcat ggaaccagac ctgccagcct tgaccgaaac      7920
ggaggaatgg gaacggcgcg ggcagcagcg cctgccgatg cccgatgagc cgtgttttct      7980
ggacgatggc gagccgttgg agccgccgac acgggtcacg ctgccgcgcc ggtagcactt      8040
gggttgcgca gcaacccgta agtgcgctgt ccagactat cggctgtacc gcctcg           8096

<210> SEQ ID NO 2
<211> LENGTH: 90
<212> TYPE: DNA
<213> ORGANISM: Artificial sequence
<220> FEATURE:
<223> OTHER INFORMATION: Oligonucleotides

<400> SEQUENCE: 2
ttgagatgtt agataggcac catactcact tttgcccttt agaagqggaa agctggcaag       60 attttttacg taataacgct aaaagtttta                                        90

<210> SEQ ID NO 3
<211> LENGTH: 90
<212> TYPE: DNA
<213> ORGANISM: Artificial sequence
<220> FEATURE:
<223> OTHER INFORMATION: Oligonucleotides

<400> SEQUENCE: 3
ttagataaaa gtaaagtgat taacagcgca ttagagctgc ttaatgaggt cggaatcgaa       60
ggtttaacaa cccgtaaact cgcccagaag                                        90

<210> SEQ ID NO 4
<211> LENGTH: 90
<212> TYPE: DNA
<213> ORGANISM: Artificial sequence
<220> FEATURE:
<223> OTHER INFORMATION: Oligonucleotides

<400> SEQUENCE: 4
atcggcaggc aggttccacg gcatggcgtt ttccatgccg ataacgcgat ctaccgctaa       60
cgccgcaatc agactgatca ttgagatttc                                        90

<210> SEQ ID NO 5
<211> LENGTH: 90
<212> TYPE: DNA
<213> ORGANISM: Artificial sequence
<220> FEATURE:
<223> OTHER INFORMATION: Oligonucleotides

<400> SEQUENCE: 5
accgattgat tcccaggtat ggcggcccat aatcacgggt ttatttaagg tgttgcgttt       60
aaaccaggcg agatcggcag gcaggttcca                                        90

<210> SEQ ID NO 6
<211> LENGTH: 90
<212> TYPE: DNA
<213> ORGANISM: Artificial sequence
<220> FEATURE:
<223> OTHER INFORMATION: Oligonucleotides

<400> SEQUENCE: 6
```

```
cacccacgtt acgcgatcgt ccgtacccgg ttgactgctg aggataatat ttttgcgtcc    60
tggcaacgga cgaccgattg attcccaggt                                     90
```

<210> SEQ ID NO 7
<211> LENGTH: 90
<212> TYPE: DNA
<213> ORGANISM: Artificial sequence
<220> FEATURE:
<223> OTHER INFORMATION: Oligonucleotides

<400> SEQUENCE: 7

```
aacgcgaccg ccgccaatca ccatgatttc tggtacgtca ccacacgccg cgatggcttc    60
atccaccgac ttcacccacg ttacgcgatc                                     90
```

<210> SEQ ID NO 8
<211> LENGTH: 90
<212> TYPE: DNA
<213> ORGANISM: Artificial sequence
<220> FEATURE:
<223> OTHER INFORMATION: Oligonucleotides

<400> SEQUENCE: 8

```
ggtgtcgcct tccacttctg cgtcgatatg cgtcagatac agttttttgcg cttttggcaa   60 gaactgttca taaacgcgac cgccgccaat                                     90
```

<210> SEQ ID NO 9
<211> LENGTH: 90
<212> TYPE: DNA
<213> ORGANISM: Artificial sequence
<220> FEATURE:
<223> OTHER INFORMATION: Oligonucleotides

<400> SEQUENCE: 9

```
gttctgcgca tcagcatcgt ggaattcgct gaataccgat tcccagtcat ccggctcgta    60
atccgggaaa tgggtgtcgc cttccacttc                                     90
```

<210> SEQ ID NO 10
<211> LENGTH: 90
<212> TYPE: DNA
<213> ORGANISM: Artificial sequence
<220> FEATURE:
<223> OTHER INFORMATION: Oligonucleotides

<400> SEQUENCE: 10

```
gcatccggcg ctagccgtaa attctataca aaattaccgc cgctccagaa tctcaaagca    60
atagctgtga gagttctgcg catcagcatc                                     90
```

<210> SEQ ID NO 11
<211> LENGTH: 90
<212> TYPE: DNA
<213> ORGANISM: Artificial sequence
<220> FEATURE:
<223> OTHER INFORMATION: Oligonucleotides

<400> SEQUENCE: 11

```
actgatcatt gagatttccc gataaaaaaa attgtcgcca ctatacgtaa agcgtaaacc    60
gtcgtcgact ggtgcgagga tgatgttgag                                     90
```

<210> SEQ ID NO 12
<211> LENGTH: 90
<212> TYPE: DNA
<213> ORGANISM: Artificial sequence

```
<220> FEATURE:
<223> OTHER INFORMATION: Oligonucleotides

<400> SEQUENCE: 12
atcggcaggc aggttccacg gcatggcgtt ttccataccg atgacgcgat ccaccgctaa      60
cgccgcaatc agactgatca ttaattattt                                       90

<210> SEQ ID NO 13
<211> LENGTH: 90
<212> TYPE: DNA
<213> ORGANISM: Artificial sequence
<220> FEATURE:
<223> OTHER INFORMATION: Oligonucleotides

<400> SEQUENCE: 13
tccgatggac tcccaggtgt gacgtcccat gacgacaggt ttatttaacg tgttacgttt      60
aaaccaggcg agatcggcag gcaggttcca                                       90

<210> SEQ ID NO 14
<211> LENGTH: 90
<212> TYPE: DNA
<213> ORGANISM: Artificial sequence
<220> FEATURE:
<223> OTHER INFORMATION: Oligonucleotides

<400> SEQUENCE: 14
cacccactgc acgcgatcgt cggtgcctgg ctggctgctg ataacaatat ttttacgtcc      60
cggtaagggg cgtccgatgg actcccaggt                                       90

<210> SEQ ID NO 15
<211> LENGTH: 90
<212> TYPE: DNA
<213> ORGANISM: Artificial sequence
<220> FEATURE:
<223> OTHER INFORMATION: Oligonucleotides

<400> SEQUENCE: 15
cacgcgcccg ccgccaatga ccataatttc cggcgcatcg ccgcaagcgg caatcgcctc      60
atcgacagac ttcacccact gcacgcgatc                                       90

<210> SEQ ID NO 16
<211> LENGTH: 90
<212> TYPE: DNA
<213> ORGANISM: Artificial sequence
<220> FEATURE:
<223> OTHER INFORMATION: Oligonucleotides

<400> SEQUENCE: 16
ggtatcgcct tcgacttccg catcaatatg cgtcagataa agcttctgcg cctttggcag      60
gaactgctcg tacacgcgcc cgccgccaat                                       90

<210> SEQ ID NO 17
<211> LENGTH: 90
<212> TYPE: DNA
<213> ORGANISM: Artificial sequence
<220> FEATURE:
<223> OTHER INFORMATION: Oligonucleotides

<400> SEQUENCE: 17
attctgcgcg tcggcatcgt gaaactcact gaataccgat tcccagtcat ccggttcata      60
atccggaaaa tgggtatcgc cttcgacttc                                       90
```

<210> SEQ ID NO 18
<211> LENGTH: 90
<212> TYPE: DNA
<213> ORGANISM: Artificial sequence
<220> FEATURE:
<223> OTHER INFORMATION: Oligonucleotides

<400> SEQUENCE: 18
taaggcgttt cgccgccatc cggcactaca gcgttaacga cgctccagaa tctcgaaaca    60
atagctgtga gaattctgcg cgtcggcatc                                    90

<210> SEQ ID NO 19
<211> LENGTH: 90
<212> TYPE: DNA
<213> ORGANISM: Artificial sequence
<220> FEATURE:
<223> OTHER INFORMATION: Oligonucleotides

<400> SEQUENCE: 19
actgatcatt aattatttcc tgatacaaaa aaaattgccg ccactatacg taaagcgcaa    60
tctttcgtcg actgacgaaa agaggatgag                                    90

<210> SEQ ID NO 20
<211> LENGTH: 90
<212> TYPE: DNA
<213> ORGANISM: Artificial sequence
<220> FEATURE:
<223> OTHER INFORMATION: Oligonucleotides

<400> SEQUENCE: 20
atcggcaggc aggttccacg gcatggcgtt ttccatgccg ataacgcgat ctaccgctaa    60
cgccgcaatc agactgatca ttgagatttc                                    90

<210> SEQ ID NO 21
<211> LENGTH: 90
<212> TYPE: DNA
<213> ORGANISM: Artificial sequence
<220> FEATURE:
<223> OTHER INFORMATION: Oligonucleotides

<400> SEQUENCE: 21
accgatggat tcccaggtat ggcggcccat aatcacgggt ttatttaaag tgttgcgttt    60
aaaccaggcg agatcggcag gcaggttcca                                    90

<210> SEQ ID NO 22
<211> LENGTH: 90
<212> TYPE: DNA
<213> ORGANISM: Artificial sequence
<220> FEATURE:
<223> OTHER INFORMATION: Oligonucleotides

<400> SEQUENCE: 22
cacccacgtt acgcgatcgt ccgtacccgg ttgactgctg aggataatat ttttgcgtcc    60
tggcaacgga cgaccgatgg attcccaggt                                    90

<210> SEQ ID NO 23
<211> LENGTH: 90
<212> TYPE: DNA
<213> ORGANISM: Artificial sequence
<220> FEATURE:
<223> OTHER INFORMATION: Oligonucleotides

<400> SEQUENCE: 23

```
aacgcgaccg ccgccaatca ccatgatttc tggtacgtca ccacacgccg caatggcttc    60
atccaccgac ttcacccacg ttacgcgatc                                     90

<210> SEQ ID NO 24
<211> LENGTH: 90
<212> TYPE: DNA
<213> ORGANISM: Artificial sequence
<220> FEATURE:
<223> OTHER INFORMATION: Oligonucleotides

<400> SEQUENCE: 24
ggtgtcgcct tccacttccg cgtcgatatg cgtcagatac agttttttgcg ctttcggcag   60 gaactgctca taaacgcgac cgccgccaat                                     90

<210> SEQ ID NO 25
<211> LENGTH: 90
<212> TYPE: DNA
<213> ORGANISM: Artificial sequence
<220> FEATURE:
<223> OTHER INFORMATION: Oligonucleotides

<400> SEQUENCE: 25
gttctgcgca tcggcatcgt ggaattcgct gaataccgat tcccagtcat ccggctcgta    60
atccgggaaa tgggtgtcgc cttccacttc                                     90

<210> SEQ ID NO 26
<211> LENGTH: 90
<212> TYPE: DNA
<213> ORGANISM: Artificial sequence
<220> FEATURE:
<223> OTHER INFORMATION: Oligonucleotides

<400> SEQUENCE: 26
gtatcagtga tgccggaatt ctaatataca aaattaccgc cgctccagaa tctcaaagca    60
atagctgtga gagttctgcg catcggcatc                                     90

<210> SEQ ID NO 27
<211> LENGTH: 90
<212> TYPE: DNA
<213> ORGANISM: Artificial sequence
<220> FEATURE:
<223> OTHER INFORMATION: Oligonucleotides

<400> SEQUENCE: 27
actgatcatt gagatttccc gataaaaaaa attgtcgcca ctatacgtaa agcgtaaacc    60
gtcgtcgact ggtgcgagga tgatgttgag                                     90

<210> SEQ ID NO 28
<211> LENGTH: 1080
<212> TYPE: DNA
<213> ORGANISM: Escherichia coli

<400> SEQUENCE: 28
ggaccgcgaa catctgtcat taattcaacg catggctgg cagggaaccg aagaaggtaa     60
acataccggc aacatggcgg atgaaccgga acgaaaccc tcatcctaat aaagagtgac    120
gtaaatcaca ctttacagct aactgtttgt ttttgtttca ttgtaatgcg gcgagtccag   180
ggagagagcg tggactcgcc agcagaatat aaaattttcc tcaacatcat cctcgcacca   240
gtcgacgacg gtttacgctt tacgtatagt ggcgacaatt ttttttatcg ggaaatctca   300
```

| | |
|---|---|
| atgatcagtc tgattgcggc gttagcggta gatcgcgtta tcggcatgga aaacgccatg | 360 |
| ccgtggaacc tgcctgccga tctcgcctgg tttaaacgca acaccttaaa taaacccgtg | 420 |
| attatgggcc gccatacctg ggaatcaatc ggtcgtccgt tgccaggacg caaaaatatt | 480 |
| atcctcagca gtcaaccggg tacggacgat cgcgtaacgt gggtgaagtc ggtggatgaa | 540 |
| gccatcgcgg cgtgtggtga cgtaccagaa atcatggtga ttggcggcgg tcgcgtttat | 600 |
| gaacagttct tgccaaaagc gcaaaaactg tatctgacgc atatcgacgc agaagtggaa | 660 |
| ggcgacaccc atttcccgga ttacgagccg gatgactggg aatcggtatt cagcgaattc | 720 |
| cacgatgctg atgcgcagaa ctctcacagc tattgctttg agattctgga gcggcggtaa | 780 |
| ttttgtatag aatttacggc tagcgccgga tgcgacgccg gtcgcgtctt atccggcctt | 840 |
| cctatatcag gctgtgttta agacgccgcc gcttcgccca atccttatg ccggttcgac | 900 |
| ggctggacaa atactgtttt atcttcccag cgcaggcagg ttaatgtacc accccagcag | 960 |
| cagccggtat ccagcgcgta tataccttcc ggcgtacctt tgccctccag cgatgcccag | 1020 |
| tgaccaaagg cgatgctgta ttcttcagcg acagggccag gaatcgcaaa ccacggtttc | 1080 |

<210> SEQ ID NO 29
<211> LENGTH: 948
<212> TYPE: DNA
<213> ORGANISM: Escherichia coli

<400> SEQUENCE: 29

| | |
|---|---|
| agaccgtgaa catctgtcat taattcaacg acatggctgg cagggaaccg aagaagggaa | 60 |
| acatactggc aatatggcgg atgaaccgga acgaagccc tcatcctaat aaagagtgac | 120 |
| gtaaatcacg ctttacagct aactgtttgt ttttgtttca ttgtaatgcg gcgagtccag | 180 |
| ggagagagcg tggactcgcc agcagaatat aaaattttcc tcaacatcat cctcgcacca | 240 |
| gtcgacgacg gtttacgctt tacgtatagt ggcgacaatt ttttttatcg ggaaatctca | 300 |
| atgatcagtc tgattgcggc gttagcggta gatcgcgtta tcggcatgga aaacgccatg | 360 |
| ccgtggaacc tgcctgccga tctcgcctgg tttaaacgca acactttaaa taaacccgtg | 420 |
| attatgggcc gccatacctg ggaatccatc ggtcgtccgt tgccaggacg caaaaatatt | 480 |
| atcctcagca gtcaaccggg tacggacgat cgcgtaacgt gggtgaagtc ggtggatgaa | 540 |
| gccattgcgg cgtgtggtga cgtaccagaa atcatggtga ttggcggcgg tcgcgtttat | 600 |
| gagcagttcc tgccgaaagc gcaaaaactg tatctgacgc atatcgacgc ggaagtggaa | 660 |
| ggcgacaccc atttcccgga ttacgagccg gatgactggg aatcggtatt cagcgaattc | 720 |
| cacgatgccg atgcgcagaa ctctcacagc tattgctttg agattctgga gcggcggtaa | 780 |
| ttttgtatat tagaattccg gcatcactga tacgtcaga tatccgtgta tactagacgt | 840 |
| ataaattgta caggagcacg agatcatgac tgcaaaacgt accacacaaa gtgtgaccgt | 900 |
| caccgtcgac cgtgagttag tcaatcgcgc tcgtgatgca ggcttaaa | 948 |

<210> SEQ ID NO 30
<211> LENGTH: 1079
<212> TYPE: DNA
<213> ORGANISM: Salmonella enterica

<400> SEQUENCE: 30

| | |
|---|---|
| gagcatctgt cgttgattca gcgccacggc tggcagggaa cggctgaggg caaacattcc | 60 |
| ggggaggtcg ccgatgaacc cgaggtcaaa ccgtcaatct aaagtaaaaa atgtgatgtt | 120 |
| ctgcaaactt tactgctaat tggctgttttt tgaactactg taatgctggc gctccacatc | 180 |

|  |  |  |  | |
|---|---|---|---|---|
| aaatgagtgg | cgtcgccagc | agaacgaaaa | attttcgtgc tcatcctctt ttcgtcagtc | 240 |
| gacgaaagat | tgcgctttac | gtatagtggc | ggcaattttt tttgtatcag gaaataatta | 300 |
| atgatcagtc | tgattgcggc | gttagcggtg | gatcgcgtca tcggtatgga aaacgccatg | 360 |
| ccgtggaacc | tgcctgccga | tctcgcctgg | tttaaacgta acacgttaaa taaacctgtc | 420 |
| gtcatgggac | gtcacacctg | ggagtccatc | ggacgcccct taccgggacg taaaaatatg | 480 |
| ttatcagcag | ccagccaggc | accgacgatc | gcgtgcagtg ggtgaagtct gtcgatgagg | 540 |
| cgattgccgc | ttgcggcgat | gcgccggaaa | ttatggtcat tggcggcggg cgcgtgtacg | 600 |
| agcagttcct | gccaaaggcg | cagaagcttt | atctgacgca tattgatgcg gaagtcgaag | 660 |
| gcgataccca | ttttccggat | tatgaaccgg | atgactggga atcggtattc agtgagtttc | 720 |
| acgatgccga | cgcgcagaat | tctcacagct | attgtttcga gattctggag cgtcgttaac | 780 |
| gctgtagtgc | cggatggcgg | cgaaacgcct | tatccggcct actcttgagc cagatgtcgc | 840 |
| cagatgtagg | cctgataagc | gtagcgccat | caggcataaa cctatcaggc gttgaccgct | 900 |
| tcgccttcgc | ccatatccat | ctggcggttt | gacggctgca caaaatactg tttatcttcc | 960 |
| cagcgtaaac | aggtcaactc | cccgccccag | cagcagccgg tatccagcgc gtaaatacct | 1020 |
| tccggcgtcc | ctttcccttc | cagcgacgcc | cagtgcccga acgcaatact gtaagcctc | 1079 |

<210> SEQ ID NO 31
<211> LENGTH: 22
<212> TYPE: DNA
<213> ORGANISM: Artificial sequence
<220> FEATURE:
<223> OTHER INFORMATION: Primers

<400> SEQUENCE: 31
tcattgtaat gcggcgagtc ca                                            22

<210> SEQ ID NO 32
<211> LENGTH: 20
<212> TYPE: DNA
<213> ORGANISM: Artificial sequence
<220> FEATURE:
<223> OTHER INFORMATION: Primers

<400> SEQUENCE: 32
aagcggcggc gtcttaaaca                                               20

<210> SEQ ID NO 33
<211> LENGTH: 22
<212> TYPE: DNA
<213> ORGANISM: Artificial sequence
<220> FEATURE:
<223> OTHER INFORMATION: Primers

<400> SEQUENCE: 33
acccgaggtc aaaccgtcaa tc                                            22

<210> SEQ ID NO 34
<211> LENGTH: 22
<212> TYPE: DNA
<213> ORGANISM: Artificial sequence
<220> FEATURE:
<223> OTHER INFORMATION: Primers

<400> SEQUENCE: 34
cgctacgctt atcaggccta ca                                            22

<210> SEQ ID NO 35
<211> LENGTH: 21
<212> TYPE: DNA
<213> ORGANISM: Artificial sequence
<220> FEATURE:
<223> OTHER INFORMATION: Primers

<400> SEQUENCE: 35
gatgaaccgg aaacgaaacc c                                          21

<210> SEQ ID NO 36
<211> LENGTH: 23
<212> TYPE: DNA
<213> ORGANISM: Artificial sequence
<220> FEATURE:
<223> OTHER INFORMATION: Primers

<400> SEQUENCE: 36
tgcagtcatg atctcgtgct cct                                        23

<210> SEQ ID NO 37
<211> LENGTH: 90
<212> TYPE: DNA
<213> ORGANISM: Artificial sequence
<220> FEATURE:
<223> OTHER INFORMATION: Oligonucleotides

<400> SEQUENCE: 37
gtcgctcatc taaccgctat ccctctactg tatcccggat tcaaaggtcg caaattataa    60
cacagccgcg cagtttgagg taaacctata                                    90

<210> SEQ ID NO 38
<211> LENGTH: 90
<212> TYPE: DNA
<213> ORGANISM: Artificial sequence
<220> FEATURE:
<223> OTHER INFORMATION: Oligonucleotides

<400> SEQUENCE: 38
cgacatcgca taatccagat aggagctctt cagctcttcc tcaatgttga ccggtgtaat    60
ttctctcgca aggtcgctca tctaaccgct                                    90

<210> SEQ ID NO 39
<211> LENGTH: 90
<212> TYPE: DNA
<213> ORGANISM: Artificial sequence
<220> FEATURE:
<223> OTHER INFORMATION: Oligonucleotides

<400> SEQUENCE: 39
ggcgtaaagt acgcgacggt gtaccggctt caggccatct cggacatctg gcagcgcacg    60
gccaacaatg accgacatcg cataatccag                                    90

<210> SEQ ID NO 40
<211> LENGTH: 90
<212> TYPE: DNA
<213> ORGANISM: Artificial sequence
<220> FEATURE:
<223> OTHER INFORMATION: Oligonucleotides

<400> SEQUENCE: 40
accgattacg tcaccaacga cacgggcaga ttttttatag gctttgttcc agtcattgcc    60
tagtacgttc atggcgtaaa gtacgcgacg                                    90

<210> SEQ ID NO 41
<211> LENGTH: 90
<212> TYPE: DNA
<213> ORGANISM: Artificial sequence
<220> FEATURE:
<223> OTHER INFORMATION: Oligonucleotides

<400> SEQUENCE: 41
acgcagcgag aatggctgcg ccatgcggac gatcgtgtca tagaccgccg agtcaccatg    60
gggatggtat ttaccgatta cgtcaccaac                                    90

<210> SEQ ID NO 42
<211> LENGTH: 90
<212> TYPE: DNA
<213> ORGANISM: Artificial sequence
<220> FEATURE:
<223> OTHER INFORMATION: Oligonucleotides

<400> SEQUENCE: 42
cgtataacgc attgccgccg cagagtcgcc gtcgatagaa ccgaagttac cctgaccgtc    60
taccagcata taacgcagcg agaatggctg                                    90

<210> SEQ ID NO 43
<211> LENGTH: 90
<212> TYPE: DNA
<213> ORGANISM: Artificial sequence
<220> FEATURE:
<223> OTHER INFORMATION: Oligonucleotides

<400> SEQUENCE: 43
atcaacgaaa tcgaccgtct cttttcgag atcggccatc agttcatggg caatttcgc     60 cagacggatt tccgtataac gcattgccgc                                    90

<210> SEQ ID NO 44
<211> LENGTH: 90
<212> TYPE: DNA
<213> ORGANISM: Artificial sequence
<220> FEATURE:
<223> OTHER INFORMATION: Oligonucleotides

<400> SEQUENCE: 44
agaaccgttc accagcaggt taggaatttt ggttggcatg acgtccggaa ttttttccgt    60
gccgtcatag ttatcaacga aatcgaccgt                                    90

<210> SEQ ID NO 45
<211> LENGTH: 90
<212> TYPE: DNA
<213> ORGANISM: Artificial sequence
<220> FEATURE:
<223> OTHER INFORMATION: Oligonucleotides

<400> SEQUENCE: 45
cagacaaccg ttgatgactt ccgtcaggtt gtgcggcggg atgttggttg ccatacctac    60
ggcgataccg gaagaaccgt tcaccagcag                                    90

<210> SEQ ID NO 46
<211> LENGTH: 90
<212> TYPE: DNA
<213> ORGANISM: Artificial sequence
<220> FEATURE:
<223> OTHER INFORMATION: Oligonucleotides

```
<400> SEQUENCE: 46
cgtcgggaag tccggccccg ggatgtgttc catcagccct tcaatgctga tgtcttcatc    60
atcaatatac gccagacaac cgttgatgac                                     90

<210> SEQ ID NO 47
<211> LENGTH: 90
<212> TYPE: DNA
<213> ORGANISM: Artificial sequence
<220> FEATURE:
<223> OTHER INFORMATION: Oligonucleotides

<400> SEQUENCE: 47
gcggatatac accttgccgc gaccggtacg gtaagcttct tcaataccgc gacgaccgtt    60
aatgattgcc gccgtcggga agtccggccc                                     90

<210> SEQ ID NO 48
<211> LENGTH: 90
<212> TYPE: DNA
<213> ORGANISM: Artificial sequence
<220> FEATURE:
<223> OTHER INFORMATION: Oligonucleotides

<400> SEQUENCE: 48
ctgatacgga atttcgtgga cgataatggt ttcacgaccg gttttggcgt caacttccac    60
ttctgcgcga gcgcggatat acaccttgcc                                     90

<210> SEQ ID NO 49
<211> LENGTH: 90
<212> TYPE: DNA
<213> ORGANISM: Artificial sequence
<220> FEATURE:
<223> OTHER INFORMATION: Oligonucleotides

<400> SEQUENCE: 49
cgcgctgatg ccttccacgc gttttttcttt taccagttcc gcaatcttct cgatcaggcg    60
cgctttgttt acctgatacg gaatttcgtg                                     90

<210> SEQ ID NO 50
<211> LENGTH: 90
<212> TYPE: DNA
<213> ORGANISM: Artificial sequence
<220> FEATURE:
<223> OTHER INFORMATION: Oligonucleotides

<400> SEQUENCE: 50
aacttcaccg accgcatcgc gtttcacttc aatcacgatg cgcataccgt ctttgtcaga    60
ctcgtcacgc agcgcgctga tgccttccac                                     90

<210> SEQ ID NO 51
<211> LENGTH: 90
<212> TYPE: DNA
<213> ORGANISM: Artificial sequence
<220> FEATURE:
<223> OTHER INFORMATION: Oligonucleotides

<400> SEQUENCE: 51
atggtgcaat gccaccatgt tgataccgaa agaaacctgc aactgggtct gggagtagag    60
gttgttgagc acaacttcac cgaccgcatc                                     90

<210> SEQ ID NO 52
<211> LENGTH: 90
```

```
<212> TYPE: DNA
<213> ORGANISM: Artificial sequence
<220> FEATURE:
<223> OTHER INFORMATION: Oligonucleotides

<400> SEQUENCE: 52
ggtcaccact tcacggcggt gacgaacaaa cgccgcgatg atgtctttca ggttcatgat    60
cttcggctga ccatggtgca atgccaccat                                    90

<210> SEQ ID NO 53
<211> LENGTH: 90
<212> TYPE: DNA
<213> ORGANISM: Artificial sequence
<220> FEATURE:
<223> OTHER INFORMATION: Oligonucleotides

<400> SEQUENCE: 53
cagcgccacg gctaatgctt caaggatatg agcacgatcg cgagctttac gcagttcgaa    60
aatagtacga cgggtcacca cttcacggcg                                    90

<210> SEQ ID NO 54
<211> LENGTH: 90
<212> TYPE: DNA
<213> ORGANISM: Artificial sequence
<220> FEATURE:
<223> OTHER INFORMATION: Oligonucleotides

<400> SEQUENCE: 54
aaccagcgca gttttcgctt ctgcaggcgt cggcgcatga cggatcagtt cgatgatcgg    60
gtcgatgttc gccagcgcca cggctaatgc                                    90

<210> SEQ ID NO 55
<211> LENGTH: 90
<212> TYPE: DNA
<213> ORGANISM: Artificial sequence
<220> FEATURE:
<223> OTHER INFORMATION: Oligonucleotides

<400> SEQUENCE: 55
ttccggacgc gcagcatcgt cgccagcacg ttcgagcatc gcggcaacgt tgcccagctg    60
ccacggatta gcaaccagcg cagttttcgc                                    90

<210> SEQ ID NO 56
<211> LENGTH: 90
<212> TYPE: DNA
<213> ORGANISM: Artificial sequence
<220> FEATURE:
<223> OTHER INFORMATION: Oligonucleotides

<400> SEQUENCE: 56
cagaatcgcc tgagcttgct gttcggtcag gtagtacaga ccatcacgca cgccgaactc    60
tggctccagc cattccggac gcgcagcatc                                    90

<210> SEQ ID NO 57
<211> LENGTH: 90
<212> TYPE: DNA
<213> ORGANISM: Artificial sequence
<220> FEATURE:
<223> OTHER INFORMATION: Oligonucleotides

<400> SEQUENCE: 57
atccagcagc tctttgtatt cgtcgagcag tttttcgtgc tcaagaccgg tcagtttctg    60
```
caaacgcaga tccagaatcg cctgagcttg                                            90

<210> SEQ ID NO 58
<211> LENGTH: 90
<212> TYPE: DNA
<213> ORGANISM: Artificial sequence
<220> FEATURE:
<223> OTHER INFORMATION: Oligonucleotides

<400> SEQUENCE: 58
ctccagctct tcacggatca cttccatcag acgatcggcg ctaccaagaa tacgcaacag           60
ttccgcgatc tgatccagca gctctttgta                                            90

<210> SEQ ID NO 59
<211> LENGTH: 90
<212> TYPE: DNA
<213> ORGANISM: Artificial sequence
<220> FEATURE:
<223> OTHER INFORMATION: Oligonucleotides

<400> SEQUENCE: 59
ttccaggttg atgtctgcgc tgttggcggt gatttcagta cgacgtttgt caccgaactg           60
ttcacgaacc agctccagct cttcacggat                                            90

<210> SEQ ID NO 60
<211> LENGTH: 90
<212> TYPE: DNA
<213> ORGANISM: Artificial sequence
<220> FEATURE:
<223> OTHER INFORMATION: Oligonucleotides

<400> SEQUENCE: 60
agaaagcggc tgatacttaa cgtagccctg gtgagagagc gtcacgacca catcttcctg           60
ggtgatcaga tcttccaggt tgatgtctgc                                            90

<210> SEQ ID NO 61
<211> LENGTH: 90
<212> TYPE: DNA
<213> ORGANISM: Artificial sequence
<220> FEATURE:
<223> OTHER INFORMATION: Oligonucleotides

<400> SEQUENCE: 61
gtcgataaag tcttcttctt taatacgtgc ggcagattta cctttcccgc cacgacgctg           60
cgcttcgtat tcagaaagcg gctgatactt                                            90

<210> SEQ ID NO 62
<211> LENGTH: 90
<212> TYPE: DNA
<213> ORGANISM: Artificial sequence
<220> FEATURE:
<223> OTHER INFORMATION: Oligonucleotides

<400> SEQUENCE: 62
tttcatcgaa tagacgcgac cacggctgga gaagcacaga atatggtcgt gagtgttcgc           60
caccagcagt cggtcgataa agtcttcttc                                            90

<210> SEQ ID NO 63
<211> LENGTH: 90
<212> TYPE: DNA
<213> ORGANISM: Artificial sequence
<220> FEATURE:
<223> OTHER INFORMATION: Oligonucleotides

<400> SEQUENCE: 63
ctgctccagc ggcagcaggt tgacgatcgg acgaccgcgc gcgccacgag tggcttccgg    60
caactgataa actttcatcg aatagacgcg                                     90

<210> SEQ ID NO 64
<211> LENGTH: 90
<212> TYPE: DNA
<213> ORGANISM: Artificial sequence
<220> FEATURE:
<223> OTHER INFORMATION: Oligonucleotides

<400> SEQUENCE: 64
agcggtcgcc atgaagactt tcacgccttc ttcaaactcg gtcactggca ggatcgcagt    60
gatacgttcg tcctgctcca gcggcagcag                                     90

<210> SEQ ID NO 65
<211> LENGTH: 90
<212> TYPE: DNA
<213> ORGANISM: Artificial sequence
<220> FEATURE:
<223> OTHER INFORMATION: Oligonucleotides

<400> SEQUENCE: 65
tttgatcgcc actttaccgg cggtacgcag acggttgaac tcggtgagga cagttttctt    60
cacggtaccg ttagcggtcg ccatgaagac                                     90

<210> SEQ ID NO 66
<211> LENGTH: 90
<212> TYPE: DNA
<213> ORGANISM: Artificial sequence
<220> FEATURE:
<223> OTHER INFORMATION: Oligonucleotides

<400> SEQUENCE: 66
agcggagaac agcattactt cgtcttcgcc gctggtcagg tcaacgccga tcagctcatc    60
gccgtcaacc agtttgatcg ccactttacc                                     90

<210> SEQ ID NO 67
<211> LENGTH: 90
<212> TYPE: DNA
<213> ORGANISM: Artificial sequence
<220> FEATURE:
<223> OTHER INFORMATION: Oligonucleotides

<400> SEQUENCE: 67
accgcgaaca ccggtggtgt tgcagcccat cgcacggaca gaagactctt taaagcgcac    60
cactttacct tcagcggaga acagcattac                                     90

<210> SEQ ID NO 68
<211> LENGTH: 90
<212> TYPE: DNA
<213> ORGANISM: Artificial sequence
<220> FEATURE:
<223> OTHER INFORMATION: Oligonucleotides

<400> SEQUENCE: 68
tgcggtgagg attgcgccat cgccacgagg cacgatcaga gagacgactt tatcgccttc    60
acctaagcga ataccgcgaa caccggtggt                                     90

<210> SEQ ID NO 69

<211> LENGTH: 90
<212> TYPE: DNA
<213> ORGANISM: Artificial sequence
<220> FEATURE:
<223> OTHER INFORMATION: Oligonucleotides

<400> SEQUENCE: 69
aacccctttc gtcgcacgcg acttggttgg gtattccgcc actgcggtac gtttaccgta    60
accgttttgc gttgcggtga ggattgcgcc                                    90

<210> SEQ ID NO 70
<211> LENGTH: 90
<212> TYPE: DNA
<213> ORGANISM: Artificial sequence
<220> FEATURE:
<223> OTHER INFORMATION: Oligonucleotides

<400> SEQUENCE: 70
gatctggtcg cagtcatcta cctgtaccgc gccaacaact aaaccgttac gttcggtaac    60
cttgatggag ataacccctt tcgtcgcacg                                    90

<210> SEQ ID NO 71
<211> LENGTH: 90
<212> TYPE: DNA
<213> ORGANISM: Artificial sequence
<220> FEATURE:
<223> OTHER INFORMATION: Oligonucleotides

<400> SEQUENCE: 71
ggtgttacgg cccacgatgc tgatttccga aacgcgagta cgtaccagcg taccggcatc    60
ggtgatcatc atgatctggt cgcagtcatc                                    90

<210> SEQ ID NO 72
<211> LENGTH: 90
<212> TYPE: DNA
<213> ORGANISM: Artificial sequence
<220> FEATURE:
<223> OTHER INFORMATION: Oligonucleotides

<400> SEQUENCE: 72
aaccggttca gcaacacgtt gcagacccac tacgttttca tcttccgcag tacggatgag    60
gatcacgccc tgggtgttac ggcccacgat                                    90

<210> SEQ ID NO 73
<211> LENGTH: 90
<212> TYPE: DNA
<213> ORGANISM: Artificial sequence
<220> FEATURE:
<223> OTHER INFORMATION: Oligonucleotides

<400> SEQUENCE: 73
gtccacttcc ggagcgattt catcgtcccc ttccgcggca ctgccgtcga tggtatccag    60
atcttcctcg tcaaccggtt cagcaacacg                                    90

<210> SEQ ID NO 74
<211> LENGTH: 90
<212> TYPE: DNA
<213> ORGANISM: Artificial sequence
<220> FEATURE:
<223> OTHER INFORMATION: Oligonucleotides

<400> SEQUENCE: 74
attcaaacaa gggagatagc tcccttttgg catgaagaag taaaattatt cttcttctgg    60

```
ctcgtcgtca acgtccactt ccggagcgat                                     90
```

<210> SEQ ID NO 75
<211> LENGTH: 90
<212> TYPE: DNA
<213> ORGANISM: Artificial sequence
<220> FEATURE:
<223> OTHER INFORMATION: Oligonucleotides

<400> SEQUENCE: 75

```
ttacgcaccg catccagccc tttcaggact ttgatactgg aggagtcata agaattcgac    60
atcaacgttt ctcgctcatt tatacttggg                                     90
```

<210> SEQ ID NO 76
<211> LENGTH: 90
<212> TYPE: DNA
<213> ORGANISM: Artificial sequence
<220> FEATURE:
<223> OTHER INFORMATION: Oligonucleotides

<400> SEQUENCE: 76

```
tctaccacct cgaataccat gtggtgcaga ccggtgccgt catccgtgtc gccgatatac    60
atacccgggc gcttacgcac cgcatccagc                                     90
```

<210> SEQ ID NO 77
<211> LENGTH: 90
<212> TYPE: DNA
<213> ORGANISM: Artificial sequence
<220> FEATURE:
<223> OTHER INFORMATION: Oligonucleotides

<400> SEQUENCE: 77

```
acagagttat cggcgtgaat ggtgacgata atttctttac agtgacccgc gagcgcttcg    60
tcgatagcgt tatctaccac ctcgaatacc                                     90
```

<210> SEQ ID NO 78
<211> LENGTH: 90
<212> TYPE: DNA
<213> ORGANISM: Artificial sequence
<220> FEATURE:
<223> OTHER INFORMATION: Oligonucleotides

<400> SEQUENCE: 78

```
acttccgccg ccgatacgcc ctcttccggg tgaataccgg tcggaatgcc gcgcccgtca    60
tcctgtacag agacagagtt atcggcgtga                                     90
```

<210> SEQ ID NO 79
<211> LENGTH: 90
<212> TYPE: DNA
<213> ORGANISM: Artificial sequence
<220> FEATURE:
<223> OTHER INFORMATION: Oligonucleotides

<400> SEQUENCE: 79

```
ccgtgcagac cgccggacac tttataggag ttatcgtcaa atttaccgcc tgcgtgcaga    60
acggtcatga tcacttccgc cgccgatacg                                     90
```

<210> SEQ ID NO 80
<211> LENGTH: 90
<212> TYPE: DNA
<213> ORGANISM: Artificial sequence
<220> FEATURE:

<223> OTHER INFORMATION: Oligonucleotides

<400> SEQUENCE: 80

| tgaattttac cctcgcgctg gataaccagc tccagttttt gcgacagggc gtttactacc | 60 |
| gaaacaccaa cgccgtgcag accgccggac | 90 |

<210> SEQ ID NO 81
<211> LENGTH: 90
<212> TYPE: DNA
<213> ORGANISM: Artificial sequence
<220> FEATURE:
<223> OTHER INFORMATION: Oligonucleotides

<400> SEQUENCE: 81

| gtgccggttt tttcagtctc gccggtaacc gccagcgggg cctgcggtac accgtgttcg | 60 |
| tagatctgac ggtgaatttt accctcgcgc | 90 |

<210> SEQ ID NO 82
<211> LENGTH: 90
<212> TYPE: DNA
<213> ORGANISM: Artificial sequence
<220> FEATURE:
<223> OTHER INFORMATION: Oligonucleotides

<400> SEQUENCE: 82

| ttcgccagaa tttcatattc gaactcggtc acattggtga aggtttcgag gctgggccag | 60 |
| aaacgcacca tggtgccggt tttttcagtc | 90 |

<210> SEQ ID NO 83
<211> LENGTH: 90
<212> TYPE: DNA
<213> ORGANISM: Artificial sequence
<220> FEATURE:
<223> OTHER INFORMATION: Oligonucleotides

<400> SEQUENCE: 83

| tctttgccgt cgcgcttgtc gcgcagacga atggaaacgc cggagttgag gaacgacaac | 60 |
| tcacgcagac gtttcgccag aatttcatat | 90 |

<210> SEQ ID NO 84
<211> LENGTH: 90
<212> TYPE: DNA
<213> ORGANISM: Artificial sequence
<220> FEATURE:
<223> OTHER INFORMATION: Oligonucleotides

<400> SEQUENCE: 84

| tggatcggcg ttttgttctt gttcagatat tcaacgaacg ccttgatgcc gccttcatag | 60 |
| tggaagtggt cttctttgcc gtcgcgcttg | 90 |

<210> SEQ ID NO 85
<211> LENGTH: 90
<212> TYPE: DNA
<213> ORGANISM: Artificial sequence
<220> FEATURE:
<223> OTHER INFORMATION: Oligonucleotides

<400> SEQUENCE: 85

| ccatcgttcc actgcaacgc cacttcgacg ccaataccgt cttttcagt ggagaagtag | 60 |
| aagatattcg ggtggatcgg cgttttgttc | 90 |

```
<210> SEQ ID NO 86
<211> LENGTH: 90
<212> TYPE: DNA
<213> ORGANISM: Artificial sequence
<220> FEATURE:
<223> OTHER INFORMATION: Oligonucleotides

<400> SEQUENCE: 86
aagcctgcca ggtgagtacc gccgtcacgc tgcggaatgt tgttggtaaa gcagtagatg      60
ttttcctgga agccatcgtt ccactgcaac                                      90

<210> SEQ ID NO 87
<211> LENGTH: 90
<212> TYPE: DNA
<213> ORGANISM: Artificial sequence
<220> FEATURE:
<223> OTHER INFORMATION: Oligonucleotides

<400> SEQUENCE: 87
ctgactttgg cttttttgct gtagccttct ttgtccatgt aggcgttcag ggtacgggtc      60
atcgccgcac ggaagcctgc caggtgagta                                      90

<210> SEQ ID NO 88
<211> LENGTH: 90
<212> TYPE: DNA
<213> ORGANISM: Artificial sequence
<220> FEATURE:
<223> OTHER INFORMATION: Oligonucleotides

<400> SEQUENCE: 88
gagaatttcg ggtccggcac tttcacggaa acgaccgcaa tcaggccttc acgcgcatcg      60
tcaccggtgg cgctgacttt ggcttttttg                                      90

<210> SEQ ID NO 89
<211> LENGTH: 90
<212> TYPE: DNA
<213> ORGANISM: Artificial sequence
<220> FEATURE:
<223> OTHER INFORMATION: Oligonucleotides

<400> SEQUENCE: 89
agcagttcgt tcatctgctg ttcaaccgcc gatttcacct cagaagaaac cagtttgtct      60
ttggtctggg aggagaattt cgggtccggc                                      90

<210> SEQ ID NO 90
<211> LENGTH: 90
<212> TYPE: DNA
<213> ORGANISM: Artificial sequence
<220> FEATURE:
<223> OTHER INFORMATION: Oligonucleotides

<400> SEQUENCE: 90
gcacgggcag catcgataat tttgccaacc acgattttcg cgtcggttgg gttttccagc      60
aggtattctg ccagcagttc gttcatctgc                                      90

<210> SEQ ID NO 91
<211> LENGTH: 90
<212> TYPE: DNA
<213> ORGANISM: Artificial sequence
<220> FEATURE:
<223> OTHER INFORMATION: Oligonucleotides

<400> SEQUENCE: 91
```
cccggcaggc cgctaagtc gagcgcacct ttacggcggg tcatttcacg cgcgcgacgc    60
gccgcttcac gggcacgggc agcatcgata    90

<210> SEQ ID NO 92
<211> LENGTH: 90
<212> TYPE: DNA
<213> ORGANISM: Artificial sequence
<220> FEATURE:
<223> OTHER INFORMATION: Oligonucleotides

<400> SEQUENCE: 92
cccgcggagt cccttccac caggtacagt tcggaaagcg ccggatcgcg ttcctggcag    60
tctgccagtt tgcccggcag gcccgctaag    90

<210> SEQ ID NO 93
<211> LENGTH: 90
<212> TYPE: DNA
<213> ORGANISM: Artificial sequence
<220> FEATURE:
<223> OTHER INFORMATION: Oligonucleotides

<400> SEQUENCE: 93
acgttgagga ttttacccctt cagcggcaga atcgcctggt tcttgcggtt acgcccctgc    60
ttcgcagagc cgcccgcgga gtccccttcc    90

<210> SEQ ID NO 94
<211> LENGTH: 90
<212> TYPE: DNA
<213> ORGANISM: Artificial sequence
<220> FEATURE:
<223> OTHER INFORMATION: Oligonucleotides

<400> SEQUENCE: 94
ccacagccaa gcgcggtgat aagcgtcgcc acttcctgag aagagagcat cttatcgaag    60
cgcgctttct cgacgttgag gattttaccc    90

<210> SEQ ID NO 95
<211> LENGTH: 90
<212> TYPE: DNA
<213> ORGANISM: Artificial sequence
<220> FEATURE:
<223> OTHER INFORMATION: Oligonucleotides

<400> SEQUENCE: 95
acgtccgcat cggtcatgat gatgatgctg tgataacgca gtttgtccgg gttgtactcg    60
tcacgaccga taccacagcc aagcgcggtg    90

<210> SEQ ID NO 96
<211> LENGTH: 90
<212> TYPE: DNA
<213> ORGANISM: Artificial sequence
<220> FEATURE:
<223> OTHER INFORMATION: Oligonucleotides

<400> SEQUENCE: 96
ccgcgttcaa cgatttccgg catctgacga tagaagaagg tcaacagcag cgtacgaatg    60
tgcgagccgt cgacgtccgc atcggtcatg    90

<210> SEQ ID NO 97
<211> LENGTH: 90
<212> TYPE: DNA
<213> ORGANISM: Artificial sequence
<220> FEATURE:
<223> OTHER INFORMATION: Oligonucleotides

<400> SEQUENCE: 97
tcgtctttaa tgtactgttc ctgcttgcct ttcttcactt tgtacagcgg cggctgagcg    60
atgtagacgt gaccgcgttc aacgatttcc    90

<210> SEQ ID NO 98
<211> LENGTH: 90
<212> TYPE: DNA
<213> ORGANISM: Artificial sequence
<220> FEATURE:
<223> OTHER INFORMATION: Oligonucleotides

<400> SEQUENCE: 98
ggtgcactgg cgttggtgtg cagcgttgcg ccgtccagcg cgatagagat ctggtactga    60
tccatcgctt cgtcgtcttt aatgtactgt    90

<210> SEQ ID NO 99
<211> LENGTH: 90
<212> TYPE: DNA
<213> ORGANISM: Artificial sequence
<220> FEATURE:
<223> OTHER INFORMATION: Oligonucleotides

<400> SEQUENCE: 99
atacgattga tcattttctg cgtcgcgttg tactcagata ccagtttctc taacgcttcg    60
ccagccaatg ccggtgcact ggcgttggtg    90

<210> SEQ ID NO 100
<211> LENGTH: 90
<212> TYPE: DNA
<213> ORGANISM: Artificial sequence
<220> FEATURE:
<223> OTHER INFORMATION: Oligonucleotides

<400> SEQUENCE: 100
gaaaggtcag cttccgtcaa cgtcggctga tagataagct ctttcagcat tgctttcgga    60
taacgacgct ccatacgatt gatcattttc    90

<210> SEQ ID NO 101
<211> LENGTH: 90
<212> TYPE: DNA
<213> ORGANISM: Artificial sequence
<220> FEATURE:
<223> OTHER INFORMATION: Oligonucleotides

<400> SEQUENCE: 101
ctgccgtgct gttctttgtc gttcagttcg ctgaccagcg cgttcaccca gcgggtaacg    60
gtctgctcat cagaaaggtc agcttccgtc    90

<210> SEQ ID NO 102
<211> LENGTH: 90
<212> TYPE: DNA
<213> ORGANISM: Artificial sequence
<220> FEATURE:
<223> OTHER INFORMATION: Oligonucleotides

<400> SEQUENCE: 102
tgggtacgca cgcgaacaat cggctcgaac aggttttgct cagcattggt gtgaacatca    60
aacttccact ggctgccgtg ctgttctttg    90

-continued

<210> SEQ ID NO 103
<211> LENGTH: 90
<212> TYPE: DNA
<213> ORGANISM: Artificial sequence
<220> FEATURE:
<223> OTHER INFORMATION: Oligonucleotides

<400> SEQUENCE: 103
agcgtgcaga tacgacgata ttcgccaccg gtgataaact cgtgatccag cggatagtca    60
gtatccacac cgtgggtacg cacgcgaaca                                    90

<210> SEQ ID NO 104
<211> LENGTH: 90
<212> TYPE: DNA
<213> ORGANISM: Artificial sequence
<220> FEATURE:
<223> OTHER INFORMATION: Oligonucleotides

<400> SEQUENCE: 104
gctaccggct gacgacgctc gccacgttcg ataaacgcat cttcttccag caagccacgc    60
agtttctcac ccagcgtgca gatacgacga                                    90

<210> SEQ ID NO 105
<211> LENGTH: 90
<212> TYPE: DNA
<213> ORGANISM: Artificial sequence
<220> FEATURE:
<223> OTHER INFORMATION: Oligonucleotides

<400> SEQUENCE: 105
cctttataac gctggatgga gaggccgcga cgggactctt tcaccagcca gtccagcgcc    60
tgctcgaagc tggctaccgg ctgacgacgc                                    90

<210> SEQ ID NO 106
<211> LENGTH: 90
<212> TYPE: DNA
<213> ORGANISM: Artificial sequence
<220> FEATURE:
<223> OTHER INFORMATION: Oligonucleotides

<400> SEQUENCE: 106
acgcgcagca tacgacgact ttccgggtcc atagtggttt cccacagctg ttccgggttc    60
atctcgccca gacctttata acgctggatg                                    90

<210> SEQ ID NO 107
<211> LENGTH: 90
<212> TYPE: DNA
<213> ORGANISM: Artificial sequence
<220> FEATURE:
<223> OTHER INFORMATION: Oligonucleotides

<400> SEQUENCE: 107
cggcgcggtt caacggcgtc gcccatcagc gtggtgaaca actggtcggc agcaatcgca    60
tctttaacgg taacgcgcag catacgacga                                    90

<210> SEQ ID NO 108
<211> LENGTH: 90
<212> TYPE: DNA
<213> ORGANISM: Artificial sequence
<220> FEATURE:
<223> OTHER INFORMATION: Oligonucleotides

<400> SEQUENCE: 108

```
gcacgctcgc atggttagcg ccattaaata tcgatattcg ccgctttcag ggcgttctct    60
tcaataaacg cacggcgcgg ttcaacggcg                                     90

<210> SEQ ID NO 109
<211> LENGTH: 90
<212> TYPE: DNA
<213> ORGANISM: Artificial sequence
<220> FEATURE:
<223> OTHER INFORMATION: Oligonucleotides

<400> SEQUENCE: 109
gtagtttaag taggcgtttt ccgtaaattc atgtagcgca aggcgctctg ccatatcgct    60
cattaattct gattcctcaa cttattcgcc                                     90

<210> SEQ ID NO 110
<211> LENGTH: 90
<212> TYPE: DNA
<213> ORGANISM: Artificial sequence
<220> FEATURE:
<223> OTHER INFORMATION: Oligonucleotides

<400> SEQUENCE: 110
aatgcggcgc tgaacaggtt tcagaccatc accaataaac ggcaacgcac ggtccatgat    60
cacgtacatg gagtagttta agtaggcgtt                                     90

<210> SEQ ID NO 111
<211> LENGTH: 90
<212> TYPE: DNA
<213> ORGANISM: Artificial sequence
<220> FEATURE:
<223> OTHER INFORMATION: Oligonucleotides

<400> SEQUENCE: 111
gtcaccgacg gtacgggccg atttttaaa tttggcgctg gcattcaggc ccagttcaga    60
catcgcatac acaatgcggc gctgaacagg                                     90

<210> SEQ ID NO 112
<211> LENGTH: 90
<212> TYPE: DNA
<213> ORGANISM: Artificial sequence
<220> FEATURE:
<223> OTHER INFORMATION: Oligonucleotides

<400> SEQUENCE: 112
gaacggttgc gccatcagga ccatcgcttc ataacaggcg ctatcgccgt gcggatggta    60
tttacccagt acgtcaccga cggtacgggc                                     90

<210> SEQ ID NO 113
<211> LENGTH: 90
<212> TYPE: DNA
<213> ORGANISM: Artificial sequence
<220> FEATURE:
<223> OTHER INFORMATION: Oligonucleotides

<400> SEQUENCE: 113
tgccgcgaac gatttcggat cgtccggcgc gccccagttc ccctgaccat caaccagcgg    60
ataacggtaa gagaacggtt gcgccatcag                                     90

<210> SEQ ID NO 114
<211> LENGTH: 90
<212> TYPE: DNA
```

```
<213> ORGANISM: Artificial sequence
<220> FEATURE:
<223> OTHER INFORMATION: Oligonucleotides

<400> SEQUENCE: 114
agccgtcccc tgccccagct cgctcaatag cagctcggaa tatttcgaca accgggattc    60
ggtgtaacgc attgccgcga acgatttcgg                                     90

<210> SEQ ID NO 115
<211> LENGTH: 90
<212> TYPE: DNA
<213> ORGANISM: Artificial sequence
<220> FEATURE:
<223> OTHER INFORMATION: Oligonucleotides

<400> SEQUENCE: 115
caaaatgttt ggcagacggg caggtagcat tttcggctcc tgcaaagtgc cgtcgaagtt    60
tggcacccag tcagccgtcc cctgccccag                                     90

<210> SEQ ID NO 116
<211> LENGTH: 90
<212> TYPE: DNA
<213> ORGANISM: Artificial sequence
<220> FEATURE:
<223> OTHER INFORMATION: Oligonucleotides

<400> SEQUENCE: 116
agccacttca cgcaggttat gcggtggaat atcggtcgcc atgccgacgg caataccggt    60
ggtgccgtta agcaaaatgt ttggcagacg                                     90

<210> SEQ ID NO 117
<211> LENGTH: 90
<212> TYPE: DNA
<213> ORGANISM: Artificial sequence
<220> FEATURE:
<223> OTHER INFORMATION: Oligonucleotides

<400> SEQUENCE: 117
cggcccctgc acgatatcca gcagctgatc gagcgtggtt ttcggctggt cgattaatgc    60
gattgccgcc tgagccactt cacgcaggtt                                     90

<210> SEQ ID NO 118
<211> LENGTH: 90
<212> TYPE: DNA
<213> ORGANISM: Artificial sequence
<220> FEATURE:
<223> OTHER INFORMATION: Oligonucleotides

<400> SEQUENCE: 118
accacgtccg ttctcgtaga ttttacggat ctcggcgcgc gaagtgataa tttccgcttc    60
agtcggataa tccggcccct gcacgatatc                                     90

<210> SEQ ID NO 119
<211> LENGTH: 90
<212> TYPE: DNA
<213> ORGANISM: Artificial sequence
<220> FEATURE:
<223> OTHER INFORMATION: Oligonucleotides

<400> SEQUENCE: 119
aacctgatgc ggcaatgcgc tgataaccac cgcgccatct tctttcttcc acaccgcgcg    60
catacgcact gaaccacgtc cgttctcgta                                     90
```

<210> SEQ ID NO 120
<211> LENGTH: 90
<212> TYPE: DNA
<213> ORGANISM: Artificial sequence
<220> FEATURE:
<223> OTHER INFORMATION: Oligonucleotides

<400> SEQUENCE: 120
agatcgtcaa ccatcggcag cttttgttg cgcatttgcg cagcaatttg ctccagtacg      60
cgcgcacctg aaacctgatg cggcaatgcg                                      90

<210> SEQ ID NO 121
<211> LENGTH: 90
<212> TYPE: DNA
<213> ORGANISM: Artificial sequence
<220> FEATURE:
<223> OTHER INFORMATION: Oligonucleotides

<400> SEQUENCE: 121
tccatatcca cgcggttgga acgcggcaca atcaccaggc gggtcgggtt ctcgtggtca      60
gattcatcgc gcagatcgtc aaccatcggc                                      90

<210> SEQ ID NO 122
<211> LENGTH: 90
<212> TYPE: DNA
<213> ORGANISM: Artificial sequence
<220> FEATURE:
<223> OTHER INFORMATION: Oligonucleotides

<400> SEQUENCE: 122
ccgatcatat taaggttaat acgatagctc ttttccagat cggtggtagc gaagaggtgg      60
ttcatcacct gatccatatc cacgcggttg                                      90

<210> SEQ ID NO 123
<211> LENGTH: 90
<212> TYPE: DNA
<213> ORGANISM: Artificial sequence
<220> FEATURE:
<223> OTHER INFORMATION: Oligonucleotides

<400> SEQUENCE: 123
gtatcgcggc ggaacaccag ccattcggag aggatttcca gcaggttttt caccgccgga      60
cgaccatcca gaccgatcat attaaggtta                                      90

<210> SEQ ID NO 124
<211> LENGTH: 90
<212> TYPE: DNA
<213> ORGANISM: Artificial sequence
<220> FEATURE:
<223> OTHER INFORMATION: Oligonucleotides

<400> SEQUENCE: 124
accagcaaac cttcgaggat atgcaggcgc ttgaggactt tctccagacg atagttcagt      60
cggcggcgca cggtatcgcg gcggaacacc                                      90

<210> SEQ ID NO 125
<211> LENGTH: 90
<212> TYPE: DNA
<213> ORGANISM: Artificial sequence
<220> FEATURE:
<223> OTHER INFORMATION: Oligonucleotides

<400> SEQUENCE: 125
gacatcagcg ccggtttcgg ttcatcttca ttacgaatga tctcaatcac ttcgtcgata    60
ttgagaaacg ccaccagcaa accttcgagg                                     90

<210> SEQ ID NO 126
<211> LENGTH: 90
<212> TYPE: DNA
<213> ORGANISM: Artificial sequence
<220> FEATURE:
<223> OTHER INFORMATION: Oligonucleotides

<400> SEQUENCE: 126
tccagtttgg caagatgacg cagtttcagt tcgaggatcg cttccgcctg ggtttccgta    60
aggccaaacc gcgacatcag cgccggtttc                                     90

<210> SEQ ID NO 127
<211> LENGTH: 90
<212> TYPE: DNA
<213> ORGANISM: Artificial sequence
<220> FEATURE:
<223> OTHER INFORMATION: Oligonucleotides

<400> SEQUENCE: 127
gaagccaaaa tgccctgcaa ctggtcgcgc tcttttttcca gttcactctg ctcaccgcga    60
atcttcatct cttccagttt ggcaagatga                                     90

<210> SEQ ID NO 128
<211> LENGTH: 90
<212> TYPE: DNA
<213> ORGANISM: Artificial sequence
<220> FEATURE:
<223> OTHER INFORMATION: Oligonucleotides

<400> SEQUENCE: 128
cgacgatcgt caccgtaggc ttgcgcgtct gcctgcagtt ctttcttcag caggttattc    60
attttacgct cggaagccaa aatgccctgc                                     90

<210> SEQ ID NO 129
<211> LENGTH: 90
<212> TYPE: DNA
<213> ORGANISM: Artificial sequence
<220> FEATURE:
<223> OTHER INFORMATION: Oligonucleotides

<400> SEQUENCE: 129
gtgacaggtt cagacggcag catgtcgtgc tcgctcatcg ctttcgcttc ttcgcgttcc    60
tgcaacggcg aacgacgatc gtcaccgtag                                     90

<210> SEQ ID NO 130
<211> LENGTH: 90
<212> TYPE: DNA
<213> ORGANISM: Artificial sequence
<220> FEATURE:
<223> OTHER INFORMATION: Oligonucleotides

<400> SEQUENCE: 130
taattcaggc ccggcgcgtc gatatcatgg cctttagcgc tgcgtaccca gcccatctgc    60
gacagcacaa tggtgacagg ttcagacggc                                     90

<210> SEQ ID NO 131
<211> LENGTH: 90

<212> TYPE: DNA
<213> ORGANISM: Artificial sequence
<220> FEATURE:
<223> OTHER INFORMATION: Oligonucleotides

<400> SEQUENCE: 131
gtggaatcaa caaacactac cggttggttg ctcttacctt tcaccgccgc tttgaagcta    60
tcacccgctt tataattcag gcccggcgcg    90

<210> SEQ ID NO 132
<211> LENGTH: 90
<212> TYPE: DNA
<213> ORGANISM: Artificial sequence
<220> FEATURE:
<223> OTHER INFORMATION: Oligonucleotides

<400> SEQUENCE: 132
ttgccggtga gcggctcgcc ctgaccacgc gccgacggca gcgtaatcgg gtcaatggca    60
tagctacgac cggtggaatc aacaaacact    90

<210> SEQ ID NO 133
<211> LENGTH: 90
<212> TYPE: DNA
<213> ORGANISM: Artificial sequence
<220> FEATURE:
<223> OTHER INFORMATION: Oligonucleotides

<400> SEQUENCE: 133
gccatcagca gtttctgatc gtcgctttcc atcagcatat ggtcaacggt cgccccaggc    60
ggcaacgtta atttgccggt gagcggctcg    90

<210> SEQ ID NO 134
<211> LENGTH: 90
<212> TYPE: DNA
<213> ORGANISM: Artificial sequence
<220> FEATURE:
<223> OTHER INFORMATION: Oligonucleotides

<400> SEQUENCE: 134
aaagccttac ctgcacggtt acgcgccacc agatcgttaa aggtgcagac gaaaccgtaa    60
cccgcatcgg aagccatcag cagtttctga    90

<210> SEQ ID NO 135
<211> LENGTH: 90
<212> TYPE: DNA
<213> ORGANISM: Artificial sequence
<220> FEATURE:
<223> OTHER INFORMATION: Oligonucleotides

<400> SEQUENCE: 135
gccagcagca tatcggaagc atcttcaatc accaccggcg gcataacatg gcattttcc    60 ggtaaggtga tcaaagcctt acctgcacgg    90

<210> SEQ ID NO 136
<211> LENGTH: 90
<212> TYPE: DNA
<213> ORGANISM: Artificial sequence
<220> FEATURE:
<223> OTHER INFORMATION: Oligonucleotides

<400> SEQUENCE: 136
ttgcctttgc ccttcgacag ctgcggcaga tcacttaccg ggaacatcaa catacggcct    60
gcctgagtga ttgccagcag catatcggaa                                       90

<210> SEQ ID NO 137
<211> LENGTH: 90
<212> TYPE: DNA
<213> ORGANISM: Artificial sequence
<220> FEATURE:
<223> OTHER INFORMATION: Oligonucleotides

<400> SEQUENCE: 137
ggcagaacgt acaattgcgc cagaccatct tctccacgcg cggcttctgc cgatggaatg      60
ttgataatct tgttgccttt gcccttcgac                                      90

<210> SEQ ID NO 138
<211> LENGTH: 90
<212> TYPE: DNA
<213> ORGANISM: Artificial sequence
<220> FEATURE:
<223> OTHER INFORMATION: Oligonucleotides

<400> SEQUENCE: 138
actttctgta actcttccgg gcgcagttta attttgcgtt tcccaacatg aatggtcagc      60
gtgctttgcg gcggcagaac gtacaattgc                                      90

<210> SEQ ID NO 139
<211> LENGTH: 90
<212> TYPE: DNA
<213> ORGANISM: Artificial sequence
<220> FEATURE:
<223> OTHER INFORMATION: Oligonucleotides

<400> SEQUENCE: 139
gagtcgatct caacacgatc gatacgctgc aaaccgcgca tcaacgtacc gcggcgtcca     60
cgttcgccag tgactttctg taactcttcc                                      90

<210> SEQ ID NO 140
<211> LENGTH: 90
<212> TYPE: DNA
<213> ORGANISM: Artificial sequence
<220> FEATURE:
<223> OTHER INFORMATION: Oligonucleotides

<400> SEQUENCE: 140
tgcaagcggg aggaaacagc gccctccccg gcatattact cttcgctatc accgctgctg     60
gcacggcgag gagagtcgat ctcaacacga                                      90

<210> SEQ ID NO 141
<211> LENGTH: 90
<212> TYPE: DNA
<213> ORGANISM: Artificial sequence
<220> FEATURE:
<223> OTHER INFORMATION: Oligonucleotides

<400> SEQUENCE: 141
cggcgaaccg gctcaagccc ggtgagtacc tcaatggcat cagcgttata agtttgcgtc     60
atggtttaag ttagtaattc gagttgatcg                                      90

<210> SEQ ID NO 142
<211> LENGTH: 90
<212> TYPE: DNA
<213> ORGANISM: Artificial sequence
<220> FEATURE:
<223> OTHER INFORMATION: Oligonucleotides

<400> SEQUENCE: 142
tccacactgt tatcaatgac ttcttgcccc aaatggttag ggcgagtggt atcggtatac    60
atccccggac ggcggcgaac cggctcaagc                                    90

<210> SEQ ID NO 143
<211> LENGTH: 90
<212> TYPE: DNA
<213> ORGANISM: Artificial sequence
<220> FEATURE:
<223> OTHER INFORMATION: Oligonucleotides

<400> SEQUENCE: 143
tcaataactt ctaacgactg gtcagcatgt aaaataacgt ccacgcgttt tgcgtgaccc    60
gccagtgctt catccacact gttatcaatg                                    90

<210> SEQ ID NO 144
<211> LENGTH: 90
<212> TYPE: DNA
<213> ORGANISM: Artificial sequence
<220> FEATURE:
<223> OTHER INFORMATION: Oligonucleotides

<400> SEQUENCE: 144
cggcaaagaa tcagttcaac cgccggtaca ccctcttccg ggtgaatatc caccggcatc    60
ccgcgcccat cgtcaataac ttctaacgac                                    90

<210> SEQ ID NO 145
<211> LENGTH: 90
<212> TYPE: DNA
<213> ORGANISM: Artificial sequence
<220> FEATURE:
<223> OTHER INFORMATION: Oligonucleotides

<400> SEQUENCE: 145
gaaatcccca cgccatgcag gccgccagag aactggtaat ttttgttaga gaatttaccg    60
cctgcatgca gacggcaaag aatcagttca                                    90

<210> SEQ ID NO 146
<211> LENGTH: 90
<212> TYPE: DNA
<213> ORGANISM: Artificial sequence
<220> FEATURE:
<223> OTHER INFORMATION: Oligonucleotides

<400> SEQUENCE: 146
aaggcgatgt tataaacctg accatcgcgg cgcacgttaa cttctacgcg cttcgacagg    60
gcgttaacca ccgaaatccc cacgccatgc                                    90

<210> SEQ ID NO 147
<211> LENGTH: 90
<212> TYPE: DNA
<213> ORGANISM: Artificial sequence
<220> FEATURE:
<223> OTHER INFORMATION: Oligonucleotides

<400> SEQUENCE: 147
acactggtac cagtattgcg tttaccgcaa gtgccgacaa cctgtaaatc ctgcacctttt    60 tcgccatttt caaaggcgat gttataaacc                                    90

<210> SEQ ID NO 148

```
<211> LENGTH: 90
<212> TYPE: DNA
<213> ORGANISM: Artificial sequence
<220> FEATURE:
<223> OTHER INFORMATION: Oligonucleotides

<400> SEQUENCE: 148
ttcagcacat gcgtcaggcg tgaaacagaa aatcgcgggc tgtcaaagaa ggtttcatcc    60
ggccagaagt gcacactggt accagtattg                                     90

<210> SEQ ID NO 149
<211> LENGTH: 90
<212> TYPE: DNA
<213> ORGANISM: Artificial sequence
<220> FEATURE:
<223> OTHER INFORMATION: Oligonucleotides

<400> SEQUENCE: 149
cagcgttgtt cggtattgtt gatctcatct ttaaaagtga tctcaacgcc agggcacaat    60
accgctttgg ctttcagcac atgcgtcagg                                     90

<210> SEQ ID NO 150
<211> LENGTH: 90
<212> TYPE: DNA
<213> ORGANISM: Artificial sequence
<220> FEATURE:
<223> OTHER INFORMATION: Oligonucleotides

<400> SEQUENCE: 150
ggtttttccg gcagcgtcgg cagaccattt accgcttccg ccaggtaatc attcagaccg    60
tcctgatagc accagcgttg ttcggtattg                                     90

<210> SEQ ID NO 151
<211> LENGTH: 90
<212> TYPE: DNA
<213> ORGANISM: Artificial sequence
<220> FEATURE:
<223> OTHER INFORMATION: Oligonucleotides

<400> SEQUENCE: 151
tcaccgcctt ccggcagcca cagtagcgcc cagtccacag cttcagtatc accagcgaaa    60
ttaccgataa acggttttc cggcagcgtc                                      90

<210> SEQ ID NO 152
<211> LENGTH: 90
<212> TYPE: DNA
<213> ORGANISM: Artificial sequence
<220> FEATURE:
<223> OTHER INFORMATION: Oligonucleotides

<400> SEQUENCE: 152
tgacgcagac cattaacatg ggtaccgccc tgcatcgttg ggataaggtt gacgtagctt    60
tcggtcagca gttcaccgcc ttccggcagc                                     90

<210> SEQ ID NO 153
<211> LENGTH: 90
<212> TYPE: DNA
<213> ORGANISM: Artificial sequence
<220> FEATURE:
<223> OTHER INFORMATION: Oligonucleotides

<400> SEQUENCE: 153
gccgacagct ttacaccgcg cggcagaata ttgcggtatt cacagaactc acgcatcgcg    60
```

```
tccaacaggc cctgacgcag accattaaca                                      90
```

<210> SEQ ID NO 154
<211> LENGTH: 90
<212> TYPE: DNA
<213> ORGANISM: Artificial sequence
<220> FEATURE:
<223> OTHER INFORMATION: Oligonucleotides

<400> SEQUENCE: 154

```
gtctgcccgg caaactgcgg atcctgcatt tttactgaca gcacataggc gcagcgatcc     60
cagatatctt ccgccgacag ctttacaccg                                      90
```

<210> SEQ ID NO 155
<211> LENGTH: 90
<212> TYPE: DNA
<213> ORGANISM: Artificial sequence
<220> FEATURE:
<223> OTHER INFORMATION: Oligonucleotides

<400> SEQUENCE: 155

```
cacaggataa aggcatcttt caccacgcca gaaacgaatg ccgcgcattg acgcgaagag     60
agacgctctt tcgtctgccc ggcaaactgc                                      90
```

<210> SEQ ID NO 156
<211> LENGTH: 90
<212> TYPE: DNA
<213> ORGANISM: Artificial sequence
<220> FEATURE:
<223> OTHER INFORMATION: Oligonucleotides

<400> SEQUENCE: 156

```
cgcatacggc gctgggcgct ggaaatcgcc atctccgcca gcagttcagc cgcctgaacg     60
ttctggttca gccacaggat aaaggcatct                                      90
```

<210> SEQ ID NO 157
<211> LENGTH: 90
<212> TYPE: DNA
<213> ORGANISM: Artificial sequence
<220> FEATURE:
<223> OTHER INFORMATION: Oligonucleotides

<400> SEQUENCE: 157

```
gtacaatcag ccagtttgcc aggcaacgcc gggccgctgg tcagcttttt acgcaccact     60
tttttggccg cacgcatacg gcgctgggcg                                      90
```

<210> SEQ ID NO 158
<211> LENGTH: 90
<212> TYPE: DNA
<213> ORGANISM: Artificial sequence
<220> FEATURE:
<223> OTHER INFORMATION: Oligonucleotides

<400> SEQUENCE: 158

```
gcctgcttgg cagatccgcc tgcggagtca ccttccacaa ggaacagctc ggtacggtta     60
aggtcctgcg cggtacaatc agccagtttg                                      90
```

<210> SEQ ID NO 159
<211> LENGTH: 90
<212> TYPE: DNA
<213> ORGANISM: Artificial sequence
<220> FEATURE:

<223> OTHER INFORMATION: Oligonucleotides

<400> SEQUENCE: 159
tcggaagaga cttcccaggt gttaaggatc ttacctttca gtggcatgat cgcctgatat    60
tcgcgatcgc gcgcctgctt ggcagatccg    90

<210> SEQ ID NO 160
<211> LENGTH: 90
<212> TYPE: DNA
<213> ORGANISM: Artificial sequence
<220> FEATURE:
<223> OTHER INFORMATION: Oligonucleotides

<400> SEQUENCE: 160
agatcgtcgc tgtcaggatc gataccgatc gctaccgaaa tatcgtgcac ttcctgcgaa    60
gccagcactt cgtcggaaga gacttcccag    90

<210> SEQ ID NO 161
<211> LENGTH: 90
<212> TYPE: DNA
<213> ORGANISM: Artificial sequence
<220> FEATURE:
<223> OTHER INFORMATION: Oligonucleotides

<400> SEQUENCE: 161
agcgtggcaa tgtgcagacc atcagagtcc gcatccgcga ggatacagat tttgccataa    60
cgaagctggc tcagatcgtc gctgtcagga    90

<210> SEQ ID NO 162
<211> LENGTH: 90
<212> TYPE: DNA
<213> ORGANISM: Artificial sequence
<220> FEATURE:
<223> OTHER INFORMATION: Oligonucleotides

<400> SEQUENCE: 162
ggtggcagtg cgacgtaaac gtgaccgtgt ttcaccaacg cgcggaaatg ttttacgaac    60
aaagcgcaga gcagcgtggc aatgtgcaga    90

<210> SEQ ID NO 163
<211> LENGTH: 90
<212> TYPE: DNA
<213> ORGANISM: Artificial sequence
<220> FEATURE:
<223> OTHER INFORMATION: Oligonucleotides

<400> SEQUENCE: 163
tcaagtacgc cctctttctc ttcttccgtc agcgcgtaat aaacctcttt cccgagatca    60
atacggtaga gcggtggcag tgcgacgtaa    90

<210> SEQ ID NO 164
<211> LENGTH: 90
<212> TYPE: DNA
<213> ORGANISM: Artificial sequence
<220> FEATURE:
<223> OTHER INFORMATION: Oligonucleotides

<400> SEQUENCE: 164
tgcatcgggt tcatttcccc cagacccttta aaacgctgga cgttcggctt gcctttcttg    60
cgttttaatt gctcaagtac gccctctttc    90

```
<210> SEQ ID NO 165
<211> LENGTH: 90
<212> TYPE: DNA
<213> ORGANISM: Artificial sequence
<220> FEATURE:
<223> OTHER INFORMATION: Oligonucleotides

<400> SEQUENCE: 165
tgatcgtctt catcatcgat agtcaactgc accagacggc gagtgttcgg atcaagcgtg      60
gtttcgcgca attgcatcgg gttcatttcc                                      90

<210> SEQ ID NO 166
<211> LENGTH: 90
<212> TYPE: DNA
<213> ORGANISM: Artificial sequence
<220> FEATURE:
<223> OTHER INFORMATION: Oligonucleotides

<400> SEQUENCE: 166
tcttgcaacc agttgcggcg atcttccgag cgtttcttcg ccagcagcat atccatcatc      60
gcgtcagtac gctgatcgtc ttcatcatcg                                      90

<210> SEQ ID NO 167
<211> LENGTH: 90
<212> TYPE: DNA
<213> ORGANISM: Artificial sequence
<220> FEATURE:
<223> OTHER INFORMATION: Oligonucleotides

<400> SEQUENCE: 167
cttgtttgcc cggccatcct gaccgggcaa tgttctttcc tttaaacctc aatctccgcc      60
atgtcgcctt tctcttgcaa ccagttgcgg                                      90

<210> SEQ ID NO 168
<211> LENGTH: 58
<212> TYPE: DNA
<213> ORGANISM: Artificial sequence
<220> FEATURE:
<223> OTHER INFORMATION: Primers

<400> SEQUENCE: 168
gtcgagttga tccatggtct tgcgagcgac tctatcggca cttctactcc gtaattgg       58

<210> SEQ ID NO 169
<211> LENGTH: 56
<212> TYPE: DNA
<213> ORGANISM: Artificial sequence
<220> FEATURE:
<223> OTHER INFORMATION: Primers

<400> SEQUENCE: 169
tgacacagac gcataggatc gatagagtcg ctcgcaagcg gaaagcagtg ctattg         56

<210> SEQ ID NO 170
<211> LENGTH: 58
<212> TYPE: DNA
<213> ORGANISM: Artificial sequence
<220> FEATURE:
<223> OTHER INFORMATION: Primers

<400> SEQUENCE: 170
gtcgagttga tccatggtct tgcgagcgac tctatcggca cttctactcc gtaattgg       58

<210> SEQ ID NO 171
```

<211> LENGTH: 56
<212> TYPE: DNA
<213> ORGANISM: Artificial sequence
<220> FEATURE:
<223> OTHER INFORMATION: Primers

<400> SEQUENCE: 171
tgacacagac gcataggatc gagcgcagat gctgtcagcg gaaagcagtg ctattg    56

<210> SEQ ID NO 172
<211> LENGTH: 58
<212> TYPE: DNA
<213> ORGANISM: Artificial sequence
<220> FEATURE:
<223> OTHER INFORMATION: Primers

<400> SEQUENCE: 172
gtcgagttga tccatggtct ctgcgcagta cgtgcaggca cttctactcc gtaattgg    58

<210> SEQ ID NO 173
<211> LENGTH: 56
<212> TYPE: DNA
<213> ORGANISM: Artificial sequence
<220> FEATURE:
<223> OTHER INFORMATION: Primers

<400> SEQUENCE: 173
tgacacagac gcataggatc atgtagtagt gagcatagcg gaaagcagtg ctattg    56

<210> SEQ ID NO 174
<211> LENGTH: 58
<212> TYPE: DNA
<213> ORGANISM: Artificial sequence
<220> FEATURE:
<223> OTHER INFORMATION: Primers

<400> SEQUENCE: 174
gtcgagttga tccatggtct gagatacgct gcagtcggca cttctactcc gtaattgg    58

<210> SEQ ID NO 175
<211> LENGTH: 56
<212> TYPE: DNA
<213> ORGANISM: Artificial sequence
<220> FEATURE:
<223> OTHER INFORMATION: Primers

<400> SEQUENCE: 175
tgacacagac gcataggatc gagcgcagat gctgtcagcg gaaagcagtg ctattg    56

<210> SEQ ID NO 176
<211> LENGTH: 58
<212> TYPE: DNA
<213> ORGANISM: Artificial sequence
<220> FEATURE:
<223> OTHER INFORMATION: Primers

<400> SEQUENCE: 176
gtcgagttga tccatggtct tgcgagcgac tctatcgaat atgctgaggt gctggaac    58

<210> SEQ ID NO 177
<211> LENGTH: 58
<212> TYPE: DNA
<213> ORGANISM: Artificial sequence
<220> FEATURE:
<223> OTHER INFORMATION: Primers

<400> SEQUENCE: 177

-continued tgacacagac gcataggatc gatagagtcg ctcgcacggg atgataattg cggattgc    58

<210> SEQ ID NO 178
<211> LENGTH: 58
<212> TYPE: DNA
<213> ORGANISM: Artificial sequence
<220> FEATURE:
<223> OTHER INFORMATION: Primers

<400> SEQUENCE: 178
gtcgagttga tccatggtct tgcgagcgac tctatcgaat atgctgaggt gctggaac    58

<210> SEQ ID NO 179
<211> LENGTH: 58
<212> TYPE: DNA
<213> ORGANISM: Artificial sequence
<220> FEATURE:
<223> OTHER INFORMATION: Primers

<400> SEQUENCE: 179
tgacacagac gcataggatc gagcgcagat gctgtccggg atgataattg cggattgc    58

<210> SEQ ID NO 180
<211> LENGTH: 58
<212> TYPE: DNA
<213> ORGANISM: Artificial sequence
<220> FEATURE:
<223> OTHER INFORMATION: Primers

<400> SEQUENCE: 180
gtcgagttga tccatggtct ctgcgcagta cgtgcagaat atgctgaggt gctggaac    58

<210> SEQ ID NO 181
<211> LENGTH: 58
<212> TYPE: DNA
<213> ORGANISM: Artificial sequence
<220> FEATURE:
<223> OTHER INFORMATION: Primers

<400> SEQUENCE: 181
tgacacagac gcataggatc atgtagtagt gagcatcggg atgataattg cggattgc    58

<210> SEQ ID NO 182
<211> LENGTH: 58
<212> TYPE: DNA
<213> ORGANISM: Artificial sequence
<220> FEATURE:
<223> OTHER INFORMATION: Primers

<400> SEQUENCE: 182
gtcgagttga tccatggtct gagatacgct gcagtcgaat atgctgaggt gctggaac    58

<210> SEQ ID NO 183
<211> LENGTH: 58
<212> TYPE: DNA
<213> ORGANISM: Artificial sequence
<220> FEATURE:
<223> OTHER INFORMATION: Primers

<400> SEQUENCE: 183
tgacacagac gcataggatc gagcgcagat gctgtccggg atgataattg cggattgc    58

<210> SEQ ID NO 184
<211> LENGTH: 57
<212> TYPE: DNA

```
<213> ORGANISM: Artificial sequence
<220> FEATURE:
<223> OTHER INFORMATION: Primers

<400> SEQUENCE: 184
gtcgagttga tccatggtct tgcgagcgac tctatcgcac cgctgattcc tatctac        57

<210> SEQ ID NO 185
<211> LENGTH: 57
<212> TYPE: DNA
<213> ORGANISM: Artificial sequence
<220> FEATURE:
<223> OTHER INFORMATION: Primers

<400> SEQUENCE: 185
tgacacagac gcataggatc gatagagtcg ctcgcagttc gatgctgtca ccatgtc        57

<210> SEQ ID NO 186
<211> LENGTH: 57
<212> TYPE: DNA
<213> ORGANISM: Artificial sequence
<220> FEATURE:
<223> OTHER INFORMATION: Primers

<400> SEQUENCE: 186
gtcgagttga tccatggtct tgcgagcgac tctatcgcac cgctgattcc tatctac        57

<210> SEQ ID NO 187
<211> LENGTH: 57
<212> TYPE: DNA
<213> ORGANISM: Artificial sequence
<220> FEATURE:
<223> OTHER INFORMATION: Primers

<400> SEQUENCE: 187
tgacacagac gcataggatc gagcgcagat gctgtcgttc gatgctgtca ccatgtc        57

<210> SEQ ID NO 188
<211> LENGTH: 57
<212> TYPE: DNA
<213> ORGANISM: Artificial sequence
<220> FEATURE:
<223> OTHER INFORMATION: Primers

<400> SEQUENCE: 188
gtcgagttga tccatggtct ctgcgcagta cgtgcagcac cgctgattcc tatctac        57

<210> SEQ ID NO 189
<211> LENGTH: 57
<212> TYPE: DNA
<213> ORGANISM: Artificial sequence
<220> FEATURE:
<223> OTHER INFORMATION: Primers

<400> SEQUENCE: 189
tgacacagac gcataggatc atgtagtagt gagcatgttc gatgctgtca ccatgtc        57

<210> SEQ ID NO 190
<211> LENGTH: 57
<212> TYPE: DNA
<213> ORGANISM: Artificial sequence
<220> FEATURE:
<223> OTHER INFORMATION: Primers

<400> SEQUENCE: 190
gtcgagttga tccatggtct gagatacgct gcagtcgcac cgctgattcc tatctac        57
```

<210> SEQ ID NO 191
<211> LENGTH: 57
<212> TYPE: DNA
<213> ORGANISM: Artificial sequence
<220> FEATURE:
<223> OTHER INFORMATION: Primers

<400> SEQUENCE: 191
tgacacagac gcataggatc gagcgcagat gctgtcgttc gatgctgtca ccatgtc    57

<210> SEQ ID NO 192
<211> LENGTH: 57
<212> TYPE: DNA
<213> ORGANISM: Artificial sequence
<220> FEATURE:
<223> OTHER INFORMATION: Primers

<400> SEQUENCE: 192
gtcgagttga tccatggtct tgcgagcgac tctatccatc accctgacgt tgagatg    57

<210> SEQ ID NO 193
<211> LENGTH: 56
<212> TYPE: DNA
<213> ORGANISM: Artificial sequence
<220> FEATURE:
<223> OTHER INFORMATION: Primers

<400> SEQUENCE: 193
tgacacagac gcataggatc gatagagtcg ctcgcactgg aacgcaccaa tggaag    56

<210> SEQ ID NO 194
<211> LENGTH: 57
<212> TYPE: DNA
<213> ORGANISM: Artificial sequence
<220> FEATURE:
<223> OTHER INFORMATION: Primers

<400> SEQUENCE: 194
gtcgagttga tccatggtct tgcgagcgac tctatccatc accctgacgt tgagatg    57

<210> SEQ ID NO 195
<211> LENGTH: 56
<212> TYPE: DNA
<213> ORGANISM: Artificial sequence
<220> FEATURE:
<223> OTHER INFORMATION: Primers

<400> SEQUENCE: 195
tgacacagac gcataggatc gagcgcagat gctgtcctgg aacgcaccaa tggaag    56

<210> SEQ ID NO 196
<211> LENGTH: 57
<212> TYPE: DNA
<213> ORGANISM: Artificial sequence
<220> FEATURE:
<223> OTHER INFORMATION: Primers

<400> SEQUENCE: 196
gtcgagttga tccatggtct ctgcgcagta cgtgcacatc accctgacgt tgagatg    57

<210> SEQ ID NO 197
<211> LENGTH: 56
<212> TYPE: DNA
<213> ORGANISM: Artificial sequence
<220> FEATURE:

<223> OTHER INFORMATION: Primers

<400> SEQUENCE: 197
tgacacagac gcataggatc atgtagtagt gagcatctgg aacgcaccaa tggaag          56

<210> SEQ ID NO 198
<211> LENGTH: 57
<212> TYPE: DNA
<213> ORGANISM: Artificial sequence
<220> FEATURE:
<223> OTHER INFORMATION: Primers

<400> SEQUENCE: 198
gtcgagttga tccatggtct gagatacgct gcagtccatc accctgacgt tgagatg         57

<210> SEQ ID NO 199
<211> LENGTH: 56
<212> TYPE: DNA
<213> ORGANISM: Artificial sequence
<220> FEATURE:
<223> OTHER INFORMATION: Primers

<400> SEQUENCE: 199
tgacacagac gcataggatc gagcgcagat gctgtcctgg aacgcaccaa tggaag          56

<210> SEQ ID NO 200
<211> LENGTH: 90
<212> TYPE: DNA
<213> ORGANISM: Artificial sequence
<220> FEATURE:
<223> OTHER INFORMATION: Oligonucleotides

<400> SEQUENCE: 200
agataaatca tgtcgaaagc tacatataag gaacgtgctg ctactcatcc tagtcctgtt      60
gctgccaagc tatttaatat catgcacgaa                                       90

<210> SEQ ID NO 201
<211> LENGTH: 90
<212> TYPE: DNA
<213> ORGANISM: Artificial sequence
<220> FEATURE:
<223> OTHER INFORMATION: Oligonucleotides

<400> SEQUENCE: 201
tttaatatca tgcacgaaaa gcaaacaaac ttgtgtgctt cattggatgt tcgtaccacc      60
aaggaattac tggagttagt tgaagcatta                                       90

<210> SEQ ID NO 202
<211> LENGTH: 90
<212> TYPE: DNA
<213> ORGANISM: Artificial sequence
<220> FEATURE:
<223> OTHER INFORMATION: Oligonucleotides

<400> SEQUENCE: 202
gagttagttg aagcattagg tcccaaaatt tgtttactaa aaacacatgt ggatatcttg      60
actgattttt ccatggaggg cacagttaag                                       90

<210> SEQ ID NO 203
<211> LENGTH: 90
<212> TYPE: DNA
<213> ORGANISM: Artificial sequence
<220> FEATURE:
<223> OTHER INFORMATION: Oligonucleotides

<400> SEQUENCE: 203
atggagggca cagttaagcc gctaaaggca ttatccgcca agtacaattt tttactcttc    60
gaagacagaa aatttgctga cattggtaat                                     90

<210> SEQ ID NO 204
<211> LENGTH: 90
<212> TYPE: DNA
<213> ORGANISM: Artificial sequence
<220> FEATURE:
<223> OTHER INFORMATION: Oligonucleotides

<400> SEQUENCE: 204
tttgctgaca ttggtaatac agtcaaattg cagtactctg cgggtgtata cagaatagca    60
gaatgggcag acattacgaa tgcacacggt                                     90

<210> SEQ ID NO 205
<211> LENGTH: 90
<212> TYPE: DNA
<213> ORGANISM: Artificial sequence
<220> FEATURE:
<223> OTHER INFORMATION: Oligonucleotides

<400> SEQUENCE: 205
attacgaatg cacacggtgt ggtgggccca ggtattgtta gcggtttgaa gcaggcggcg    60
gaagaagtaa caaaggaacc tagaggcctt                                     90

<210> SEQ ID NO 206
<211> LENGTH: 90
<212> TYPE: DNA
<213> ORGANISM: Artificial sequence
<220> FEATURE:
<223> OTHER INFORMATION: Oligonucleotides

<400> SEQUENCE: 206
aaggaaccta gaggcctttt gatgttagca gaattgtcat gcaagggctc cctagctact    60
ggagaatata ctaagggtac tgttgacatt                                     90

<210> SEQ ID NO 207
<211> LENGTH: 90
<212> TYPE: DNA
<213> ORGANISM: Artificial sequence
<220> FEATURE:
<223> OTHER INFORMATION: Oligonucleotides

<400> SEQUENCE: 207
aagggtactg ttgacattgc gaagagcgac aaagattttg ttatcggctt tattgctcaa    60
agagacatgg gtggaagaga tgaaggttac                                     90

<210> SEQ ID NO 208
<211> LENGTH: 90
<212> TYPE: DNA
<213> ORGANISM: Artificial sequence
<220> FEATURE:
<223> OTHER INFORMATION: Oligonucleotides

<400> SEQUENCE: 208
ggaagagatg aaggttacga ttggttgatt atgacacccg gtgtgggttt agatgacaag    60
ggagacgcat gggtcaaca gtatagaacc                                      90

<210> SEQ ID NO 209

```
<211> LENGTH: 90
<212> TYPE: DNA
<213> ORGANISM: Artificial sequence
<220> FEATURE:
<223> OTHER INFORMATION: Oligonucleotides

<400> SEQUENCE: 209
ggtcaacagt atagaaccgt ggatgatgtg gtctctacag gatctgacat tattattgtt    60
ggaagaggac tatttgcaaa gggaagggat                                     90

<210> SEQ ID NO 210
<211> LENGTH: 90
<212> TYPE: DNA
<213> ORGANISM: Artificial sequence
<220> FEATURE:
<223> OTHER INFORMATION: Oligonucleotides

<400> SEQUENCE: 210
tttgcaaagg gaagggatgc taaggtagag ggtgaacgtt acagaaaagc aggctgggaa    60
gcatatttga gaagatgcgg ccagcaaaac                                     90

<210> SEQ ID NO 211
<211> LENGTH: 41
<212> TYPE: DNA
<213> ORGANISM: Escherichia coli

<400> SEQUENCE: 211
gctcgtcgcg cgcacagttg aagaaacatg aaattgccca g                        41

<210> SEQ ID NO 212
<211> LENGTH: 40
<212> TYPE: DNA
<213> ORGANISM: Escherichia coli

<400> SEQUENCE: 212
tgtgcgcgcg acgagccgag attcccgggt aataactgat                          40

<210> SEQ ID NO 213
<211> LENGTH: 41
<212> TYPE: DNA
<213> ORGANISM: Artificial sequence
<220> FEATURE:
<223> OTHER INFORMATION: Mutant DNA

<400> SEQUENCE: 213
acacacagac tgtgaggttg aagaaacatg aaattgccca g                        41

<210> SEQ ID NO 214
<211> LENGTH: 40
<212> TYPE: DNA
<213> ORGANISM: Artificial sequence
<220> FEATURE:
<223> OTHER INFORMATION: Mutant DNA

<400> SEQUENCE: 214
ctcacagtct gtgtgtcgag attcccgggt aataactgat                          40

<210> SEQ ID NO 215
<211> LENGTH: 615
<212> TYPE: PRT
<213> ORGANISM: Escherichia coli

<400> SEQUENCE: 215

Met Pro Ile Gln Val Leu Pro Pro Gln Leu Ala Asn Gln Ile Ala Ala
```

-continued

```
  1               5                  10                 15
Gly Glu Val Val Glu Arg Pro Ala Ser Val Val Lys Glu Leu Val Lys
          20                  25                 30
Asn Ser Leu Asp Ala Gly Ala Thr Arg Ile Asp Ile Asp Ile Glu Arg
          35                  40                 45
Gly Gly Ala Lys Leu Ile Arg Ile Arg Asp Asn Gly Cys Gly Ile Lys
 50                  55                  60
Lys Asp Glu Leu Ala Leu Ala Leu Ala Arg His Ala Thr Ser Lys Ile
 65                  70                  75                  80
Ala Ser Leu Asp Asp Leu Glu Ala Ile Ile Ser Leu Gly Phe Arg Gly
          85                  90                  95
Glu Ala Leu Ala Ser Ile Ser Ser Val Ser Arg Leu Thr Leu Thr Ser
         100                 105                 110
Arg Thr Ala Glu Gln Gln Glu Ala Trp Gln Ala Tyr Ala Glu Gly Arg
         115                 120                 125
Asp Met Asn Val Thr Val Lys Pro Ala Ala His Pro Val Gly Thr Thr
130                  135                 140
Leu Glu Val Leu Asp Leu Phe Tyr Asn Thr Pro Ala Arg Arg Lys Phe
145                  150                 155                 160
Leu Arg Thr Glu Lys Thr Glu Phe Asn His Ile Asp Glu Ile Ile Arg
                 165                 170                 175
Arg Ile Ala Leu Ala Arg Phe Asp Val Thr Ile Asn Leu Ser His Asn
                 180                 185                 190
Gly Lys Ile Val Arg Gln Tyr Arg Ala Val Pro Glu Gly Gly Gln Lys
                 195                 200                 205
Glu Arg Arg Leu Gly Ala Ile Cys Gly Thr Ala Phe Leu Glu Gln Ala
         210                 215                 220
Leu Ala Ile Glu Trp Gln His Gly Asp Leu Thr Leu Arg Gly Trp Val
225                  230                 235                 240
Ala Asp Pro Asn His Thr Thr Pro Ala Leu Ala Glu Ile Gln Tyr Cys
                 245                 250                 255
Tyr Val Asn Gly Arg Met Met Arg Asp Arg Leu Ile Asn His Ala Ile
                 260                 265                 270
Arg Gln Ala Cys Glu Asp Lys Leu Gly Ala Asp Gln Pro Ala Phe
         275                 280                 285
Val Leu Tyr Leu Glu Ile Asp Pro His Gln Val Asp Val Asn Val His
         290                 295                 300
Pro Ala Lys His Glu Val Arg Phe His Gln Ser Arg Leu Val His Asp
305                  310                 315                 320
Phe Ile Tyr Gln Gly Val Leu Ser Val Leu Gln Gln Leu Glu Thr
                 325                 330                 335
Pro Leu Pro Leu Asp Asp Glu Pro Gln Pro Ala Pro Arg Ser Ile Pro
                 340                 345                 350
Glu Asn Arg Val Ala Ala Gly Arg Asn His Phe Ala Glu Pro Ala Ala
                 355                 360                 365
Arg Glu Pro Val Ala Pro Arg Tyr Thr Pro Ala Pro Ala Ser Gly Ser
         370                 375                 380
Arg Pro Ala Ala Pro Trp Pro Asn Ala Gln Pro Gly Tyr Gln Lys Gln
385                  390                 395                 400
Gln Gly Glu Val Tyr Arg Gln Leu Leu Gln Thr Pro Ala Pro Met Gln
                 405                 410                 415
Lys Leu Lys Ala Pro Glu Pro Gln Glu Pro Ala Leu Ala Ala Asn Ser
                 420                 425                 430
```

```
Gln Ser Phe Gly Arg Val Leu Thr Ile Val His Ser Asp Cys Ala Leu
        435                 440                 445

Leu Glu Arg Asp Gly Asn Ile Ser Leu Leu Ser Leu Pro Val Ala Glu
    450                 455                 460

Arg Trp Leu Arg Gln Ala Gln Leu Thr Pro Gly Glu Ala Pro Val Cys
465                 470                 475                 480

Ala Gln Pro Leu Leu Ile Pro Leu Arg Leu Lys Val Ser Ala Glu Glu
                485                 490                 495

Lys Ser Ala Leu Glu Lys Ala Gln Ser Ala Leu Ala Glu Leu Gly Ile
            500                 505                 510

Asp Phe Gln Ser Asp Ala Gln His Val Thr Ile Arg Ala Val Pro Leu
        515                 520                 525

Pro Leu Arg Gln Gln Asn Leu Gln Ile Leu Ile Pro Glu Leu Ile Gly
    530                 535                 540

Tyr Leu Ala Lys Gln Ser Val Phe Glu Pro Gly Asn Ile Ala Gln Trp
545                 550                 555                 560

Ile Ala Arg Asn Leu Met Ser Glu His Ala Gln Trp Ser Met Ala Gln
                565                 570                 575

Ala Ile Thr Leu Leu Ala Asp Val Glu Arg Leu Cys Pro Gln Leu Val
            580                 585                 590

Lys Thr Pro Pro Gly Gly Leu Leu Gln Ser Val Asp Leu His Pro Ala
        595                 600                 605

Ile Lys Ala Leu Lys Asp Glu
    610             615

<210> SEQ ID NO 216
<211> LENGTH: 480
<212> TYPE: DNA
<213> ORGANISM: Escherichia coli

<400> SEQUENCE: 216
atgatcagtc tgattgcggc gttagcggta gatcgcgtta tcggcatgga aaacgccatg      60
ccgtggaacc tgcctgccga tctcgcctgg tttaaacgca acaccttaaa taaacccgtg     120
attatgggcc gccatacctg gaatcaatc ggtcgtccgt tgccaggacg caaaatatt      180 atcctcagca gtcaaccggg tacggacgat cgcgtaacgt gggtgaagtc ggtggatgaa     240
gccatcgcgg cgtgtggtga cgtaccagaa atcatggtga ttggcggcgg tcgcgtttat     300
gaacagttct tgccaaaagc gcaaaaactg tatctgacgc atatcgacgc agaagtggaa     360
ggcgacaccc atttcccgga ttacgagccg atgactgggg aatcggtatt cagcgaattc     420
cacgatgctg atgcgcagaa ctctcacagc tattgctttg agattctgga gcggcggtaa     480

<210> SEQ ID NO 217
<211> LENGTH: 2628
<212> TYPE: DNA
<213> ORGANISM: Escherichia coli

<400> SEQUENCE: 217
atgagcgacc ttgcgagaga aattacaccg gtcaacattg aggaagagct gaagagctcc      60
tatctggatt atgcgatgtc ggtcattgtt ggccgtgcgc tgccagatgt ccgagatggc     120
ctgaagccgg tacaccgtcg cgtactttac gccatgaacg tactaggcaa tgactggaac     180
aaagcctata aaaatctgc ccgtgtcgtt ggtgacgtaa tcggtaaata ccatccccat     240
ggtgactcgg cggtctatga cacgatcgtc cgcatggcgc agccattctc gctgcgttat     300
```

```
atgctggtag acggtcaggg taacttcggt tctatcgacg gcgactctgc ggcggcaatg    360
cgttatacgg aaatccgtct ggcgaaaatt gcccatgaac tgatggccga tctcgaaaaa    420
gagacggtcg atttcgttga taactatgac ggcacggaaa aaattccgga cgtcatgcca    480
accaaaattc ctaacctgct ggtgaacggt tcttccggta tcgccgtagg tatggcaacc    540
aacatcccgc cgcacaacct gacggaagtc atcaacggtt gtctggcgta tattgatgat    600
gaagacatca gcattgaagg gctgatggaa cacatcccgg ggccggactt cccgacggcg    660
gcaatcatta acggtcgtcg cggtattgaa gaagcttacc gtaccggtcg cggcaaggtg    720
tatatccgcg ctcgcgcaga agtggaagtt gacgccaaaa ccggtcgtga accattatc     780
gtccacgaaa ttccgtatca ggtaaacaaa gcgcgcctga tcgagaagat tgcggaactg    840
gtaaaagaaa aacgcgtgga aggcatcagc gcgctgcgtg acgagtctga caaagacggt    900
atgcgcatcg tgattgaagt gaaacgcgat gcggtcggtg aagttgtgct caacaacctc    960
tactcccaga cccagttgca ggtttctttc ggtatcaaca tggtggcatt gcaccatggt   1020
cagccgaaga tcatgaacct gaaagacatc atcgcgcgcg ttgttcgtca ccgccgtgaa   1080
gtggtgaccc gtcgtactat tttcgaactg cgtaaagctc gcgatcgtgc tcatatcctt   1140
gaagcattag ccgtggcgct ggcgaacatc gacccgatca tcgaactgat ccgtcatgcg   1200
ccgacgcctg cagaagcgaa aactgcgctg gttgctaatc cgtggcagct gggcaacgtt   1260
gccgcgatgc tcgaacgtgc tggcgacgat gctgcgcgtc cggaatggct ggagccagag   1320
ttcggcgtgc gtgatggtct gtactacctg accgaacagc aagctcaggc gattctggat   1380
ctgcgtttgc agaaactgac cggtcttgag cacgaaaaac tgctcgacga atacaaagag   1440
ctgctggatc agatcgcgga actgttgcgt attcttggta gcgccgatcg tctgatggaa   1500
gtgatccgtg aagagctgga gctggttcgt gaacagttcg gtgacaaacg tcgtactgaa   1560
atcaccgcca acagcgcaga catcaacctg gaagatctga tcacccagga agatgtggtc   1620
gtgacgctct ctcaccaggg ctacgttaag tatcagccgc tttctgaata cgaagcgcag   1680
cgtcgtggcg ggaaaggtaa atctgccgca cgtattaaag aagaagactt tatcgaccga   1740
ctgctggtgg cgaacactca cgaccatatt ctgtgcttct ccagccgtgg tcgcgtctat   1800
tcgatgaaag tttatcagtt gccggaagcc actcgtggcg cgcgcggtcg tccgatcgtc   1860
aacctgctgc cgctggagca ggacgaacgt atcactgcga tcctgccagt gaccgagttt   1920
gaagaaggcg tgaaagtctt catggcgacc gctaacggta ccgtgaagaa aactgtcctc   1980
accgagttca accgtctgcg taccgccggt aaagtggcga tcaaactggt tgacggcgat   2040
gagctgatcg gcgttgacct gaccagcggc gaagacgaag taatgctgtt ctccgctgaa   2100
ggtaaagtgg tgcgctttaa agagtcttct gtccgtgcga tgggctgcaa caccaccggt   2160
gttcgcggta ttcgcttagg tgaaggcgat aaagtcgtct ctctgatcgt gcctcgtggc   2220
gatggcgcaa tcctcaccgc aacgcaaaac ggttacggta acgtaccgcg agtggcggaa   2280
tacccaacca agtcgcgtgc gacgaaaggg gttatctcca tcaaggttac cgaacgtaac   2340
ggtttagttg ttggcgcggt acaggtagat gactgcgacc agatcatgat gatcaccgat   2400
gccggtacgc tggtacgtac tcgcgtttcg gaaatcagca tcgtgggccg taacacccag   2460
ggcgtgatcc tcatccgtac tgcggaagat gaaaacgtag tgggtctgca acgtgttgct   2520
gaaccggttg acgaggaaga tctggatacc atcgacggca gtgccgcgga aggggacgat   2580
gaaatcgctc cggaagtgga cgttgacgac gagccagaag aagaataa                2628
```

<210> SEQ ID NO 218
<211> LENGTH: 2415
<212> TYPE: DNA
<213> ORGANISM: Escherichia coli

<400> SEQUENCE: 218

```
atgtcgaatt cttatgactc ctccagtatc aaagtcctga aagggctgga tgcggtgcgt      60
aagcgcccgg gtatgtatat cggcgacacg gatgacggca ccggtctgca ccacatggta     120
ttcgaggtgg tagataacgc tatcgacgaa gcgctcgcgg gtcactgtaa agaaattatc     180
gtcaccattc acgccgataa ctctgtctct gtacaggatg acgggcgcgg cattccgacc     240
ggtattcacc cggaagaggg cgtatcggcg gcggaagtga tcatgaccgt tctgcacgca     300
ggcggtaaat ttgacgataa ctcctataaa gtgtccggcg gtctgcacgg cgttggtgtt     360
tcggtagtaa acgccctgtc gcaaaaactg gagctggtta ccagcgcga gggtaaaatt     420 caccgtcaga tctacgaaca cggtgtaccg caggccccgc tggcggttac cggcgagact     480
gaaaaaaccg gcaccatggt gcgtttctgg cccagcctcg aaaccttcac caatgtgacc     540
gagttcgaat atgaaattct ggcgaaacgt ctgcgtgagt tgtcgttcct caactccggc     600
gtttccattc gtctgcgcga caagcgcgac ggcaaagaag accttccaa ctatgaaggc     660 ggcatcaagg cgttcgttga atatctgaac aagaacaaaa cgccgatcca cccgaatatc     720
ttctacttct ccactgaaaa agacggtatt ggcgtcgaag tggcgttgca gtggaacgat     780
ggcttccagg aaaacatcta ctgctttacc aacaacattc gcagcgtga cggcggtact     840 cacctggcag gcttccgtgc ggcgatgacc cgtaccctga acgcctacat ggacaaagaa     900
ggctacagca aaaaagccaa agtcagcgcc accggtgacg atgcgcgtga aggcctgatt     960
gcggtcgttt ccgtgaaagt gccggacccg aaattctcct cccagaccaa agacaaactg    1020
gtttcttctg aggtgaaatc ggcggttgaa cagcagatga cgaactgct ggcagaatac    1080 ctgctggaaa acccaaccga cgcgaaaatc gtggttggca aaattatcga tgctgcccgt    1140
gcccgtgaag cggcgcgtcg cgcgcgtgaa atgacccgcc gtaaaggtgc gctcgactta    1200
gcgggcctgc cgggcaaact ggcagactgc caggaacgcg atccggcgct ttccgaactg    1260
tacctggtgg aaggggactc cgcgggcggc tctgcgaagc aggggcgtaa ccgcaagaac    1320
caggcgattc tgccgctgaa gggtaaaatc ctcaacgtcg agaaagcgcg cttcgataag    1380
atgctctctt tcaggaagt ggcgacgctt atcaccgcgc ttggctgtgg atcggtcgt     1440 gacgagtaca cccggacaa actgcgttat cacagcatca tcatgac cgatgcggac    1500 gtcgacggct cgcacattcg tacgctgctg ttgaccttct tctatcgtca gatgccggaa    1560
atcgttgaac gcggtcacgt ctacatcgct cagccgccgc tgtacaaagt gaagaaaggc    1620
aagcaggaac agtacattaa agacgacgaa gcgatggatc agtaccagat ctctatcgcg    1680
ctggacggcg caacgctgca caccaacgcc agtgcaccgg cattggctgg cgaagcgtta    1740
gagaaactgg tatctgagta caacgcgacg cagaaaatga tcaatcgtat ggagcgtcgt    1800
tatccgaaag caatgctgaa agagcttatc tatcagccga cgttgacgga agctgacctt    1860
tctgatgagc agaccgttac ccgctggggtg aacgcgctgg tcagcgaact gaacgacaaa    1920
gaacagcacg gcagccagtg aagtttgat gttcacacca tgctgagca aaacctgttc    1980 gagccgattg ttcgcgtgcg tacccacggt gtggatactg actatccgct ggatcacgag    2040
tttatcaccg gtgcgaata tcgtcgtatc tgcacgctgg gtgagaaact gcgtggcttg    2100
ctggaagaag atgcgtttat cgaacgtggc gagcgtcgtc agccggtagc cagcttcgag    2160
```

```
caggcgctgg actggctggt gaaagagtcc cgtcgcggcc tctccatcca gcgttataaa    2220
ggtctgggcg agatgaaccc ggaacagctg tgggaaacca ctatggaccc ggaaagtcgt    2280
cgtatgctgc gcgttaccgt taaagatgcg attgctgccg accagttgtt caccacgctg    2340
atgggcgacg ccgttgaacc gcgccgtgcg tttattgaag agaacgccct gaaagcggcg    2400
aatatcgata tttaa                                                    2415
```

<210> SEQ ID NO 219
<211> LENGTH: 2259
<212> TYPE: DNA
<213> ORGANISM: Escherichia coli

<400> SEQUENCE: 219

```
atgagcgata tggcagagcg ccttgcgcta catgaattta cggaaaacgc ctacttaaac      60
tactccatgt acgtgatcat ggaccgtgcg ttgccgttta ttggtgatgg tctgaaacct     120
gttcagcgcc gcattgtgta tgcgatgtct gaactgggcc tgaatgccag cgccaaattt     180
aaaaaatcgg cccgtaccgt cggtgacgta ctgggtaaat accatccgca cggcgatagc     240
gcctgttatg aagcgatggt cctgatggcg caaccgttct cttaccgtta tccgctggtt     300
gatggtcagg ggaactgggg cgcgccggac gatccgaaat cgttcgcggc aatgcgttac     360
accgaatccc ggttgtcgaa atattccgag ctgctattga gcgagctggg cagggacg      420 gctgactggg tgccaaactt cgacggcact ttgcaggagc cgaaaatgct acctgcccgt     480
ctgccaaaca ttttgcttaa cggcaccacc ggtattgccg tcggcatggc gaccgatatt     540
ccaccgcata acctgcgtga agtggctcag gcggcaatcg cattaatcga ccagccgaaa     600
accacgctcg atcagctgct ggatatcgtg caggggccgg attatccgac tgaagcggaa     660
attatcactt cgcgcgccga gatccgtaaa atctacgaga acgacgtgg ttcagtgcgt     720 atgcgcgcgg tgtggaagaa agaagatggc gcggtggtta tcagcgcatt gccgcatcag     780
gtttcaggtg cgcgcgtact ggagcaaatt gctgcgcaaa tgcgcaacaa aaagctgccg     840
atggttgacg atctgcgcga tgaatctgac cacgagaacc cgacccgcct ggtgattgtg     900
ccgcgttcca accgcgtgga tatggatcag gtgatgaacc acctcttcgc taccaccgat     960
ctggaaaaga gctatcgtat taaccttaat atgatcggtc tggatggtcg tccggcggtg    1020 aaaaaccctgc tggaaatcct ctccgaatgg ctggtgttcc gccgcgatac cgtgcgccgc    1080
cgactgaact atcgtctgga gaaagtcctc aagcgcctgc atatcctcga aggtttgctg    1140
gtggcgtttc tcaatatcga cgaagtgatt gagatcattc gtaatgaaga tgaaccgaaa    1200
ccggcgctga tgtcgcggtt tggccttacg gaaacccagg cggaagcgat cctcgaactg    1260
aaactgcgtc atcttgccaa actggaagag atgaagattc gcggtgagca gagtgaactg    1320 gaaaagagc gcgaccagtt gcagggcatt ttggcttccg agcgtaaaat gaataacctg    1380
ctgaagaaag aactgcaggc agacgcgcaa gcctacggtg acgatcgtcg ttcgccgttg    1440
caggaacgcg aagaagcgaa agcgatgagc gagcacgaca tgctgccgtc tgaacctgtc    1500
accattgtgc tgtcgcagat gggctgggta cgcagcgcta aaggccatga tatcgacgcg    1560
ccgggcctga attataaagc gggtgatagc ttcaaagcgg cggtgaaagg taagagcaac    1620
caaccggtag tgtttgttga ttccaccggt cgtagctatg ccattgaccc gattacgctg    1680
ccgtcggcgc gtggtcaggg cgagccgctc accggcaaat taacgttgcc gcctggggcg    1740
accgttgacc atatgctgat ggaaagcgac gatcagaaac tgctgatggc ttccgatgcg    1800
ggttacggtt tcgtctgcac ctttaacgat ctggtggcgc gtaaccgtgc aggtaaggct    1860
```

```
ttgatcacct taccggaaaa tgcccatgtt atgccgccgg tggtgattga agatgcttcc    1920
gatatgctgc tggcaatcac tcaggcaggc cgtatgttga tgttcccggt aagtgatctg    1980
ccgcagctgt cgaagggcaa aggcaacaag attatcaaca ttccatcggc agaagccgcg    2040
cgtggagaag atggtctggc gcaattgtac gttctgccgc cgcaaagcac gctgaccatt    2100
catgttggga aacgcaaaat taaactgcgc ccggaagagt tacagaaagt cactggcgaa    2160
cgtggacgcc gcggtacgtt gatgcgcggt ttgcagcgta cgatcgtgt tgagatcgac    2220 tctcctcgcc gtgccagcag cggtgatagc gaagagtaa                          2259
```

<210> SEQ ID NO 220
<211> LENGTH: 1893
<212> TYPE: DNA
<213> ORGANISM: Escherichia coli

<400> SEQUENCE: 220

```
atgacgcaaa cttataacgc tgatgccatt gaggtactca ccgggcttga gccggttcgc      60
cgccgtccgg ggatgtatac cgataccact cgccctaacc atttggggca agaagtcatt     120
gataacagtg tggatgaagc actggcgggt cacgcaaaac gcgtggacgt tattttacat     180
gctgaccagt cgttagaagt tattgacgat gggcgcggga tgccggtgga tattcacccg     240
gaagagggta taccggcggt tgaactgatt cttttgccgtc tgcatgcagg cggtaaattc     300
tctaacaaaa attaccagtt ctctggcggc ctgcatggcg tggggatttc ggtggttaac     360
gccctgtcga agcgcgtaga agttaacgtg cgccgcgatg gtcaggttta taacatcgcc     420
tttgaaaatg gcgaaaaggt gcaggattta caggttgtcg gcacttgcgg taaacgcaat     480
actggtacca gtgtgcactt ctggccggat gaaaccttct ttgacagccc gcgattttct     540
gtttcacgcc tgacgcatgt gctgaaagcc aaagcggtat tgtgccctgg cgttgagatc     600
acttttaaag atgagatcaa caataccgaa caacgctggt gctatcagga cggtctgaat     660
gattacctgg cggaagcggt aaatggtctg ccgacgctgc cggaaaaacc gtttatcggt     720
aatttcgctg gtgatactga agctgtggac tgggcgctac tgtggctgcc ggaaggcggt     780
gaactgctga ccgaaagcta cgtcaacctt atcccaacga tgcagggcgg tacccatgtt     840
aatggtctgc gtcagggcct gttggacgcg atgcgtgagt tctgtgaata ccgcaatatt     900
ctgccgcgcg gtgtaaagct gtcggcggaa gatatctggg atcgctgcgc ctatgtgctg     960
tcagtaaaaa tgcaggatcc gcagtttgcc gggcagacga agagcgtctc tcttcgcgt     1020 caatgcgcgc cattcgtttc tggcgtggtg aaagatgcct ttatcctgtg gctgaaccag    1080
aacgttcagg cggctgaact gctggcggag atggcgattt ccagcgccca cgccgtatg    1140 cgtgcggcca aaaagtggt gcgtaaaaag ctgaccagcg gccggcgtt gcctggcaaa    1200 ctggctgatt gtaccgcgca ggaccttaac cgtaccgagc tgttccttgt ggaaggtgac    1260
tccgcaggcg gatctgccaa gcaggcgcgc gatcgcgaat atcaggcgat catgccactg    1320
aaaggtaaga tccttaacac ctgggaagtc tcttccgacg aagtgctggc ttcgcaggaa    1380
gtgcacgata tttcggtagc gatcggtatc gatcctgaca cgacgatct gagccagctt    1440 cgttatggca aaatctgtat cctcgcggat gcggactctg atggtctgca cattgccacg    1500
ctgctctgcg ctttgttcgt aaaacatttc cgcgcgttgg tgaaacacgg tcacgtttac    1560
gtcgcactgc caccgctcta ccgtattgat ctcgggaaag aggtttatta cgcgctgacg    1620
gaagaagaga aagagggcgt acttgagcaa ttaaaacgca agaaaggcaa gccgaacgtc    1680
```

```
cagcgtttta aaggtctggg ggaaatgaac ccgatgcaat tgcgcgaaac cacgcttgat    1740
ccgaacactc gccgtctggt gcagttgact atcgatgatg aagacgatca gcgtactgac    1800
gcgatgatgg atatgctgct ggcgaagaaa cgctcggaag atcgccgcaa ctggttgcaa    1860
gagaaaggcg acatggcgga gattgaggtt taa                                 1893

<210> SEQ ID NO 221
<211> LENGTH: 804
<212> TYPE: DNA
<213> ORGANISM: Saccharomyces cerevisiae

<400> SEQUENCE: 221
atgtcgaaag ctacatataa ggaacgtgct gctactcatc ctagtcctgt tgctgccaag      60
ctatttaata tcatgcacga aaagcaaaca aacttgtgtg cttcattgga tgttcgtacc     120
accaaggaat tactggagtt agttgaagca ttaggtccca aaatttgttt actaaaaaca     180
catgtggata tcttgactga tttttccatg gagggcacag ttaagccgct aaaggcatta     240
tccgccaagt acaatttttt actcttcgaa gacagaaaat ttgctgacat tggtaataca     300
gtcaaattgc agtactctgc gggtgtatac agaatagcag aatgggcaga cattacgaat     360
gcacacggtg tggtgggccc aggtattgtt agcggtttga agcaggcggc ggaagaagta     420
acaaaggaac ctagaggcct tttgatgtta gcagaattgt catgcaaggg ctccctagct     480
actggagaat atactaaggg tactgttgac attgcgaaga gcgacaaaga ttttgttatc     540
ggctttattg ctcaaagaga catgggtgga agagatgaag gttacgattg gttgattatg     600
acacccggtg tgggtttaga tgacaaggga gacgcattgg gtcaacagta tagaaccgtg     660
gatgatgtgg tctctacagg atctgacatt attattgttg gaagaggact atttgcaaag     720
ggaagggatg ctaaggtaga gggtgaacgt tacagaaaag caggctggga agcatatttg     780
agaagatgcg gccagcaaaa ctaa                                           804
```